US007834021B2

(12) United States Patent
Xue et al.

(10) Patent No.: US 7,834,021 B2
(45) Date of Patent: Nov. 16, 2010

(54) 3-AMINOPYRROLIDINE DERIVATIVES AS MODULATORS OF CHEMOKINE RECEPTORS

(75) Inventors: Chu-Biao Xue, Hockessin, DE (US); Brian W. Metcalf, Moraga, CA (US); Ganfeng Cao, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 100 days.

(21) Appl. No.: 10/535,795

(22) PCT Filed: Nov. 26, 2003

(86) PCT No.: PCT/US03/37946

§ 371 (c)(1),
(2), (4) Date: Apr. 21, 2006

(87) PCT Pub. No.: WO2004/050024

PCT Pub. Date: Jun. 17, 2004

(65) Prior Publication Data

US 2006/0252751 A1 Nov. 9, 2006

Related U.S. Application Data

(60) Provisional application No. 60/429,605, filed on Nov. 27, 2002, provisional application No. 60/463,976, filed on Apr. 18, 2003.

(51) Int. Cl.
C07D 239/00 (2006.01)
A01N 43/54 (2006.01)
(52) U.S. Cl. ........................................ 514/256; 544/242
(58) Field of Classification Search ................. None
See application file for complete search history.

(56) References Cited

U.S. PATENT DOCUMENTS

| 4,353,734 A | 10/1982 | Seres et al. |
| 4,785,119 A | 11/1988 | Hojo et al. |
| 5,770,573 A | 6/1998 | Arrhenius et al. |
| 6,313,117 B1 | 11/2001 | Bekkali et al. |
| 6,326,372 B1 | 12/2001 | Evans et al. |
| 6,362,177 B1 | 3/2002 | Shiota et al. |
| 6,410,566 B1 | 6/2002 | Shiota et al. |
| 6,451,842 B1 | 9/2002 | Shiota et al. |
| 7,307,086 B2 | 12/2007 | Xue et al. |
| 2002/0094989 A1 | 7/2002 | Hale et al. |
| 2005/0192302 A1 | 9/2005 | Xue et al. |
| 2005/0261310 A1 | 11/2005 | Xue et al. |
| 2006/0004018 A1 | 1/2006 | Xue et al. |
| 2006/0020133 A1 | 1/2006 | Xue et al. |
| 2006/0111404 A1* | 5/2006 | Xue et al. ............ 514/343 |
| 2007/0149532 A1 | 6/2007 | Xue |

FOREIGN PATENT DOCUMENTS

| JP | 10-298180 | 11/1998 |
| JP | 2004-83511 | 3/2004 |
| WO | 95/08533 | 3/1995 |
| WO | WO 97/44329 | 11/1997 |
| WO | WO 98/57641 A1 | 12/1998 |
| WO | WO 99/25686 | 5/1999 |
| WO | 00/26186 | 5/2000 |
| WO | WO 00/59502 | 10/2000 |
| WO | WO 00/69432 | 11/2000 |
| WO | WO 00/69815 | 11/2000 |
| WO | WO 01/10439 | 2/2001 |
| WO | WO 01/19816 | 3/2001 |
| WO | WO 01/28987 A1 | 4/2001 |
| WO | WO 02/034716 | 5/2002 |
| WO | WO 02/076945 | 10/2002 |
| WO | WO 03/092586 | 11/2003 |
| WO | WO 03/093231 | 11/2003 |
| WO | WO 03/093266 | 11/2003 |
| WO | WO 2004/020584 | 3/2004 |
| WO | 2004/026836 | 4/2004 |
| WO | WO 2004/041161 | 5/2004 |
| WO | WO 2004/041163 | 5/2004 |
| WO | WO 2004/041279 | 5/2004 |
| WO | WO 2004/041777 | 5/2004 |
| WO | WO 2004/042351 | 5/2004 |
| WO | WO 2004/050024 A2 | 6/2004 |

(Continued)

OTHER PUBLICATIONS

Helsley et al., J. Med. Chem (1968), vol. 11, p. 1034-1037.*

(Continued)

*Primary Examiner*—Golam M. M. Shameem
*Assistant Examiner*—Sun Jae Y Loewe
(74) *Attorney, Agent, or Firm*—Fish & Richardson P.C.

(57) ABSTRACT

The present invention relates to 3-aminopyrrolidine derivatives of the formula I:

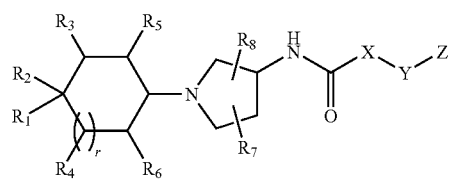

(wherein $R_1$, $R_2$, $R_3$, $R_4$, $R_5$, $R_6$, $R_7$, $R_8$, X, Y and X are as defined herein) which are useful as modulators of chemokine receptor activity. In particular, these compounds are useful as modulators of chemokine receptors and more specifically as a modulator of the CCR2 and/or CCR5 receptor. The compounds and compositions of the invention may bind to chemokine receptors, e.g., the CCR2 and/or CCR5 chemokine receptors, and are useful for treating diseases associated with chemokine, e.g., CCR2 and/or CCR5, activity, such as atherosclerosis, restenosis, lupus, organ transplant rejection and rheumatoid arthritis.

4 Claims, No Drawings

FOREIGN PATENT DOCUMENTS

| | | |
|---|---|---|
| WO | WO 2005/044264 | 5/2005 |
| WO | WO 2005/044795 | 5/2005 |
| WO | WO 2005/067502 | 7/2005 |
| WO | WO 2005/070133 | 8/2005 |
| WO | WO 2005/072361 | 8/2005 |
| WO | WO 2006/073592 | 7/2006 |

OTHER PUBLICATIONS

Tak, P.P., "Chemokine inhibition in inflammatory arthritis", Best Practice & Research Clinical Rheumatology, vol. 20, No. 5, 929-939, 2006.*
Reape et al., "Chemokines and atherosclerosis", Atherosclerosis, 147, 1999, 213-225.*
Yang et al., "Discovery of 3,5-bis(trifluoromethyl)benzyl L-arylglycinamide based potent CCR2 antagonists", Bioorganic &Medicinal Chemistry Letters, 16, 2006, 3735-3739.*
Butora et al., "3-amino-1-alkyl-cyclopentane carboxamides as small molecule antagonists of the human and murine CC chemokine receptor 2", Bioorganic&Medicinal Chemistry Letters, 2007, doi:10.1016/j.bmcl.2007.04.053.*
http://en.wikipedia.org/wiki/Prodrug (1 Page Only).*
Han et al., "Targeted Prodrug Design to Optimize Drug Delivery", AAPS PharmSci, 2000, 2(1), article 6. DOI 10.1208/ps020106 (17 Pages).*
http://en.wikipedia.org/wiki/Levodopa (4 Pages).*
Chawla et al., "Challenges in Polymorphism of Pharmaceuticals", Crips vol. 5, No1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Moalem et al., "Immune and inflammatory mechanisms in neuropathic pain", Brain Research Reviews 51 (2006), 240-264.*
Treatment options for neuropathic pain, http://www.spine-health.com/topics/conserv/neuropaintr/neuropaintr01.html (1 Page).*
Simon et al., "HIV/AIDS epidemiology, pathogenesis, prevention, and treatment", www.thelancet.com, vol. 368, Aug. 5, 2006, p. 489-504.*
Perez, "Current and future trends in the appication of HPLC-MS to metabolite0identification studies", Drug Discovery Today, vol. 12, No. 5/6, Mar. 2007, p. 249-256.*
Sundberg, "Implication of polymorphic cygochrome p450-dependent drug metabolism for drug development", Drug Metabolism and Disposition, vol. 29, No. 4, part 2, p. 570-573.*
Define:Disease treatment-Google Search (1 Page).*
MedlinePlus Medical Encyclopedia: Metabolite (1 Page).*
Pyelonephritis, Glomerulonephritis, Interstitial & Lupus Nephritis Symptoms (8 pages), http://nativeremedies.com/ailment/nephritis-kidney-inflammation-info.html.*
IGA Nephropathy (5 pages), http://kidney.niddk.nih.gov/kudiseases/pubs/iganephropathy/.*
Membranoproliferative Glomerulonephritis (4 pages), http://www.clinicaltrials.gov/ct2/show/NCT00275613?term=glomerulonephritis&rank=8.*
Treatment of Primary Glomerulonephritis (2 pages), http://content.nejm.org/cgi/content/full/337/17/1250.*
Incyte CCR2 Antagonist Program (13 pages).*
Hot Targets_ CCR2 in Inflammatory Disease (7 pages), http://www.pharmaweek.com/Exclusive_Content/1_19.asp.*
MS Pipeline, http://mspipeline.wordpress.com/ (2009).*
http://en.wikipedia.org/wiki/Prodrug (2007).*
http://en.wikipedia.org/wiki/Levodopa (2007).*
Treatment options for neuropathic pain, http://www.spine-health.com/topics/conserv/neuropaintr/neuropaintr01.html (2006).*
Sundberg, "Implication of polymorphic cygochrome p450-dependent drug metabolism for drug development", Drug Metabolism and Disposition, vol. 29, No. 4, part 2, p. 570-573 (2005).*
define:Disease treatment-Google Search (2007).*
MedlinePlus Medical Encyclopedia: Metabolite (2007).*
Pyelonephritis, Glomerulonephritis, Interstitial & Lupus Nephritis Symptoms (2008), http://nativeremedies.com/ailment/nephritis-kidney-inflammation-info.html.*
IGA Nephropathy (2008), http://kidney.niddk.nih.gov/kudiseases/pubs/iganephropathy/.*
Membranoproliferative Glomerulonephritis (2006), http://www.clinicaltrials.gov/ct2/show/NCT00275613?term=glomerulonephritis&rank=8.*
Treatment of Primary Glomerulonephritis (2008), http://content.nejm.org/cgi/content/full/337/17/1250.*
Incyte CCR2 Antagonist Program (2006).*
Hot Targets_CCR2 in Inflammatory Disease (2008), http://www.pharmaweek.com/Exclusive_Content/1_19.asp.*
Database CASPLUS on STN (Columbus, OH) No. 136:200479, Kitajima et al., "Preparation of Proline Derivatives as Dipeptidyl Peptidase IV Inhibitors and use thereof as Drugs," (2002).
Database CASPLUS on STN (Columbus, OH) No. 141:295848, Goodfellow et at, "Preparation of bis(3-aminopyrrolidin-1-yl)methanones as melanin-concentrating hormone receptor antagonists for treatment of obesity and other disorders," (2004).
Greene, *Protective Groups in Organic Synthesis*, Ch. 7 "Protection for the Amino Group," pp. 218-219, p. 232, and p. 236 (1982) Wiley-Interscience.
Bundgaard, "Design of prodrugs'," p. 27 and p. 33 (1986).
Van Vliet, Wikstrom, Pugsley, Heffner and Wise, Derivatives of Nemonapride (YM-09151-2) . . . Chapter 6, pp. 139-149.
Weisberg, S. P. et al., "CCR2 modulates inflammatory and metabolic effects of high-fat feeding." *J. Clin. Invest.* (2006) 116(1), pp. 115-124; Epub 2005, Dec 8.
Non-Final Office action mailed Oct. 31, 2007 in connection with U.S. Appl. No. 11/014,322.
Response to Office Action dated Dec. 6, 2007 in connection with U.S. Appl. No. 11/014,322.
Final Office Action mailed Aug. 19, 2008 in connection with U.S. Appl. No. 11/014,322.
Non-Final Office action mailed May 17, 2007 in connection with U.S. Appl. No. 11/167,329.
Response to Office Action dated Aug. 16, 2007 in connection with U.S. Appl. No. 11/167,329.
Final Office Action mailed Nov. 2, 2007 in connection with U.S. Appl. No. 11/167,329.
Response to Final Office Action dated Feb. 2, 2008 in connection with U.S. Appl. No. 11/167,329.
Non-Final Office Action mailed Apr. 1, 2008 in connection with U.S. Appl. No. 11/167,329.
Non-Final Office Action mailed May 16, 2007 in connection with U.S. Appl. No. 11/167,816.
Response to Non-Final Office Action dated Aug. 16, 2007 in connection with U.S. Appl. No. 11/167,816.
Final Office Action mailed Nov. 21, 2007 in connection with U.S. Appl. No. 11/167,816.
Response to Final Office Action dated Mar. 21, 2008 in connection with U.S. Appl. No. 11/167,816.
Notice of Allowance mailed Jun. 25, 2008 in connection with U.S. Appl. No. 11/167,816.
Non-Final Office Action mailed Aug. 22, 2007 in connection with U.S. Appl. No. 11/613,330.
Response to Office Action dated Jan. 22, 2008 in connection with U.S. Appl. No. 11/613,330.
Final Office Action mailed May 30, 2008 in connection with U.S. Appl. No. 11/613,330.
Non-Final Office Action mailed Jan. 17, 2008 in connection with U.S. Appl. No. 11/104,041.
Reply to Office Action of Jan. 17, 2008 dated May 6, 2008 in connection with U.S. Appl. No. 11/104,041.
Non-Final Office Action mailed Jul. 24, 2008 in connection with U.S. Appl. No. 11/104,041.
Brodmerkel, C.M., et al., J. Immunol. 2005, 175(8), 5370-8.
Hensley, G.C., et al., J. Med. Chem. (1968), 11, 1034-1037.
Search Report for Taiwan application No. 094141007, dated Dec. 23, 2008 (1 page).
Examination Report for corresponding European application No. 03790120.4, dated Jul. 16, 2009 (5 pages).

Search Report for corresponding Georgia application No. AP2003008862, dated Jun. 2, 2009 (2 pages).
International Preliminary Report on Patentability of the International Searching Authority in International Application No. PCT/US2005/042115, mailed May 22, 2007 (4 pages).
Akahoshi et al., "Expression of Monocyte Chemotactic and Activating Factor in Rheumatoid Arthritis," Arthritis Rheum., 36:762-771 (1993).
Alam et al., "Monocyte Chemotactic and Activating Factor Is a Potent Histamine-releasing Factor for Basophils," J. Clin. Invest., 89:723-728 (1992).
Allavena et al., "Induction of natural killer cell migration by monocyte chemotactic protein-1, -2 and -3," Eur. J. Immunol , 24:3233-3236 (1994).
Aukrust et al., "Elevated Circulating Levels of C-C chemokines in Patients With Congestive Heart Failure," Circulation, 97:1136-1143 (1998).
Baggiolini et al., "Interleukin-8 and Related Chemotactic Cytokines-CXC and CC Chemokines," and Adv. Immunol , 55:97-179 (1994).
Bischoff et al., "Monocyte Chemotactic Protein 1 Is a Potent Activator of Human Basophils," J. Exp. Med., 175:1271-1275 (1992).
Boring et al., "Impaired Monocyte Migration and Reduced Type 1 (Th1) Cytokine Responses in C-C Chemokine Receptor 2 Knockout Mice," J. Clin. Invest., 100:2552-2561 (1997).
Boring et al., "Decreased lesion formation in CCR2 mice reveals a role for chemokines in the initiation of atherosclerosis," Nature, 394:894-897 (1998).
Butcher, "Leucocyte-Endothelial Cell Recognition: Three (or more) Steps to Specificity and Diversity," Cell 67:1033-1036 (1991).
Carr et al., "Monocyte chemoattractant protein 1 acts as a T-lymphocyte chemoattractant," Proc. Natl. Acad. Sci. USA, 91:3652-3656 (1994).
Charo et al., "Molecular cloning and functional expression of two monocyte chemoattractant protein 1 receptors reveals alternative splicing of the carboxyl-terminal tails," Proc. Natl. Acad. Sci. USA, 91:2752-2756 (1994).
Combadiere et al., "Cloning and Functional Expression of a Human Eosinophil CC Chemokine Receptor," J Biol. Chem., 270:16491-16494 (1995).
Conti et al., "Will MCP-1 and RANTES Take Center Stage in Inflammatory Diseases Including Asthma?" Allergy and Asthma Proc., 19:121-123 (1998).
Collins et al., "Molecular Rearrangemetns. XXIX. Exo/Endo Stereospecificity of Substituted Classical Norbornyl Cations. A Reassessment of "Hot" Carbonium Ions," J. Org. Chem. 37:4358-4366 (1972).
Collins et al., "Molecular Rearrangements. XXII. The Mechanism of Hydride Shift during Hydrolyses of Certain Substituted Norbornyl Tosylates," J. Am. Chem. Soc. 89:1652-1661 (1967).
Gao et al., "Impaired Host Defense, Hematopoiesis, Granulomatous Inflammation and Type 1-Type 2 Cytokine Balance in Mice Lacking CC Chemokine Receptor 1," J. Exp. Med., 185:1959-1968 (1997).
Gerard et al., "Targeted Disruption of the l3-Chemokine Receptor CCR1 Protects against Pancreatitis-associated Lung Injury," J. Clin. Invest., 100:2022-2027 (1997).
Gesualdo et al., "Monocyte recruitment in cryoglobulinemic membranoproliferative glomerulonephritis: A pathogenetic role for monocyte chemotactic peptide-1," Kidney Int., 51:155-163 (1997).
Gillitzer et al., "MCP-1 mRNA Expression in Basal Keratinocytes of Psoriatic Lesions," J. Invest. Dermatol., 101:127-131 (1993).
Gong, "An Antagonist of Monocyte Chemoattractant Protein 1 (MCP-1) Inhibits Arthritis in the MRL-lpr Mouse Model," J. Exp. Med., 186:131-137 (1997).
Gonzalo et al., "The Coordinated Action of CC Chemokines in the Lung Orchestrates Allergic Inflammation and Airway Hyper-responsiveness," J. Exp. Med., 188:157-167 (1998).
Grimm et al., "Enhanced expression and production of monocyte chemoattractant protein-1 in inflammatory bowel disease mucosa," J. Leukoc. Biol., 59:804-812 (1996).
Gu et al., "Absence of Monocyte Chemoattractant Protein-1 Reduces Atherosclerosis in Low Density Lipoprotein Receptor-Deficient Mice," Mol. Cell, 2:275-281 (1998).

Guzman et al., "Monocyte Chemotactic Protein Antibody Inhibits Restenosis in the Rabbit Atherosclerotic Model," Abstracts from the 66th Scientific Sessions Georgia World Congress Center, Atlanta, Georgia. Nov. 8-11, Circulation, 1993, 88 (suppl.), I-371.
Hayes et al., "Human Vascular Smooth Muscle Cells Express Receptors for CC Chemokines," Arterioscler. Thromb. Vasc. Biol., 18:397-403 (1998).
Hesselgesser et al., "Identification and Characterization of Small Molecule Functional Antagonists of the CCR1 Chemokine Receptor," J Biol. Chem. 273(25):15687-15692 (1998).
Holgate, "Release of Rantes, MIP-1a, and MCP-1 into Asthmatic Airways Following Endobronchial Allergen Challenge," Am. J. Respir. Crit. Care Med., 156:1377-1383 (1997).
Holmes et al., "Structure and Functional Expression of a Human Interleukin-8 Receptor," Science 253:1278-1280 (1991).
Horuk, "Molecular properties of the chemokine receptor family," Trends Pharm. Sci., 15:159-165 (1994).
Jiang et al., "Monocyte Chemoattractant Protein-1 Regulates Adhesion Molecule Expression and Cytokine Production in Human Monocytes," J. Immunol., 148:2423-2428 (1992).
Jolicoeur et al., "Increased Expression of Monocyte Chemotactic Protein-1 in the Endometrium of Women with Endometriosis," Am. J. Pathol., 152:125-133 (1998).
Karina et al., "Monocyte chemotactic and activating factor/monocyte chemoattractant protein (MCAF/MCP-1) in bronchoalveolar lavage fluid from patients with atopic asthma and chronic bronchitis," J. Invest. Allergol. Clin. Immunol , 7(4):254-259 (1997).
Karpus et al., "MIP-1αand MCP-1 differentially regulate acute and relapsing autoimmune encephalomyelitis as well as Th1/Th2 lymphocyte differentiation," J. Leukoc. Biol., 62:681-687 (1997).
Kimura et al., "Alleviation of Monocrotaline-Induced Pulmonary Hypertension by Antibodies to Monocyte Chemotactic and Activating Factor/Monocyte Chemoattractant Protein-1," Lab. Invest., 78(5):571-581 (1998).
Koch et al., "Enhanced Production of Monocyte Chemoattractant Protein-1 in Rheumatoid Arthritis," J. Clin. Invest., 90:772-779 (1992).
Kuna et al., "Monocyte Chemotactic and Activating Factor Is a Potent Histamine-releasing Factor for Human Basophils," J. Exp. Med., 175:489-493 (1992).
Kurihara et al., "Defects in Macrophage Recruitment and Host Defense in Mice Lacking the CCR2 Chemokine Receptor," J. Exp. Med., 186(10):1757-1762 (1997).
Kuziel et al., "Severe reduction in leukocyte adhesion and monocyte extravasation in mice deficient in CC chemokine receptor 2," Proc. Natl. Acad. Sci., USA, 94:12053-12058 (1997).
Lahrtz et al., "Chemotactic activity on mononuclear cells in the cerebrospinal fluid of patients with viral meningitis is mediated by interferon-γ inducible protein-10 and monocyte chemotactic protein-1," Eur. J. Immunol , 27:2484-2489 (1997).
Lawrence and Springer, "Leukocytes Roll on a Selectin at Physiologic Flow Rates: Distinction from and Prerequisite for Adhesion through Integrins," Cell 65:859-873 (1991).
Lloyd et al., "Rantes and Monocyte Chemoattractant Protein-1 (MCP-1) Play an Important Role in the Inflammatory Phase of Crescentic Nephritis, but Only MCP-1 Is Involved in Crescent Formation and Interstitial Fibrosis," J. Exp. Med., 185:1371-1380 (1997).
Lloyd et al., "The role of chemokines in tissue inflammation and autoimmunity in renal diseases," Curr. Opin. Nephrol. Hypertens., 7:281-287 (1998).
Loetscher et al., "Monocyte chemotactic proteins MCP-1, MCP-2, and MCP-3 are major attractants for human CD4[+] and CD8[+] T lymphocytes," FASEB J., 8:1055-1060 (1994).
Loetscher et al., "Activation of NK Cells by CC Chemokines," J. Immunol , 156:322-327 (1996).
Lu et al., "Abnormalities in Monocyte Recruitment and Cytokine Expression in Monocyte Chemoattractant Protein 1-deficient Mice," J. Exp. Med., 187:601-608 (1998).
Lucchesini et al., "Synthesis of 4-Unsubstituted Isothiazoles," Heterocycles, 29:97-102 (1989).
Lukacs, "Differential Recruitment of Leukocyte Populations and Alteration of Airway Hyperreactivity by C-C Family Chemokines in Allergic Airway Inflammation," J. Immunol , 158:4398-4404 (1997).

Luster, "Chemokines - Chemotactic Cytokines that Mediate Inflammation," New Eng. J Med., 338:436-445 (1998).
MacDermott et al., "The Central Role of Chemokines (Chemotactic Cytokines) in the Immunopathogenesis of Ulcerative Colitis and Crohn's Disease," Inflammatory Bowel Diseases, 4(1):54-67 (1998).
Marra et al., "Increased Expression of Monocyte Chemotactic Protein-1 during Active Hepatic Fibrogenesis," Am. J. Pathol., 152:423-430 (1998).
Matsushima et al., "Purification and characterization of a novel monocyte chemotactic and activating factor produced by a human myelomonocytic cell line," J. Exp. Med. 169:1485-1490 (1989).
McManus et al., "MCP-1, MCP-2 and MCP-3 expression in multiple sclerosis lesions: an immunohistochemical and in situ hybridization study," J. Neuroimmunol. 86:20-29 (1998).
Murphy et al., "Cloning of complementary DNA encoding a functional human interleukin-8 receptor," Science, 253:1280-1283 (1991).
Murphy, "The molecular biology of leukocyte chemoattractant receptors," Ann. Rev. Immunol , 12:593-633 (1994).
Nelken et al., "Monocyte chemoattractant protein-1 in human atheromatous plaques," J. Clin. Invest., 88:1121-1127 (1991).
Neote et al., "Molecular cloning, functional expression, and signaling characteristics of a C-C Chemokine receptor," Cell, 72:415-425 (1993).
Niu Shin et al., "Pharmacological characterization of INCB3344, a small molecule antagonist of human CCR2," Biochem. Biophys. Res. Commun., 387:251-255 (2009).
Noris et al., "Monocyte chemoattractant protein-1 is excreted in excessive amounts in the urine of patients with lupus nephritis," Lab. Invest., 73(6):804-809 (1995).
Ogata et al., "The role of monocyte chemoattractant protein-1 (MCP-1) in the pathogenesis of collagen-induced arthritis in rats," J. Pathol., 182:106-114 (1997).
Oppenheim et al., "Properties of the novel proinflammatory supergene "intercrine" cytokine family," Annu. Rev. Immunol., 9:617-648 (1991).
Povarny et al., "Stereo- and regioselective oxymercuration—demercuration of bicycle [3.2.1]oct-2- ene skeleton," Tetrahedron Left., 25(12):1311-1312 (1984).
Power et al., "Molecular cloning and functional expression of a novel CC Chemokine receptor cDNA from a human basoshilic cell line," J. Biol. Chem., 270:19495-19500 (1995).
Rand et al , "Inhibition of T cell recruitment and cutaneous delayed-type hypersensitivity-induced inflammation with antibodies to monocyte chemoattractant protein-1," Am. J. Pathol., 148(3):855-864 (1996).
Ransohoff et al., "Do chemokines mediate leukocyte recruitment in post-traumatic CNS inflammation?" Trends Neurosci., 21:154-159 (1998).
Reinecker et al., "Monocyte-chemoattractant protein 1 gene expression in intestinal epithelial cells and inflammatory bowel disease mucosa," Gastroenterology, 108:40-50 (1995).
Robinson et al., "Chemokine expression in rheumatoid arthritis (RA): evidence of RANTES and macrophage inflammatory protein (MIP)-1β production by synovial T cells," Clin. Exp. Immunol., 101:398-407 (1995).
Robinson et al., "A Chemokine Receptor Antagonist Inhibits Experimental Breast Tumor Growth," Cancer Research, 63:8360-8365 (2003).
Rollins et al., "Recombinant human MCP-1/JE induces chemotaxis, calcium flux, and the respiratory burst in human monocytes," Blood, 78:1112-1116 (1991).
Rollins et al., "Cloning and expression of JE, a gene inducible by platelet-derived growth factor and whose product has cytokine-like properties," Proc. Natl. Acad. Sci., USA 85:3738-3742 (1988).
Rollins, "Chemokines," Blood, 90:909-928 (1997).
Rosen et al., "Design, synthesis, and properties of (4S)-7-(4-Amino-2-substituted-pyrrolidin-1-yl)quinolone-3-carboxylic acids," J. Med. Chem., 31:1598-1611 (1988).
Rovin et al., "Chemotactic factors and renal inflammation," Am. J. Kidney. Dis., 31(6):1065-1084 (1998).
Saitoh et al., "Urinary levels of monocyte chemoattractant protein (MCP)-1 and disease activity in patients with IgA nephropathy," J. Clin. Lab. Anal., 12:1-5 (1998).
Salkowski et al., "Pulmonary and hepatic gene expression following cecal ligation and puncture: monophosphoryl lipid A prophylaxis attenuates sepsis-induced cytokine and chemokine expression and neutrophil infiltration," Infect. Immun., 66(8):3569-3578 (1998).
Samson et al., "Molecular cloning and functional expression of a new human CC-Chemokine receptor gene," Biochemistry, 35:3362-3367 (1996).
Sandosham et al., "Stannylation in the electrophilic 2- and 4/6-pyrimidine position and the use of stannylpyrimidines in coupling and tin-lithium exchange reations," Tetrahedron, 50:275-284 (1994).
Schall and Bacon, "Chemokines, leukocyte trafficking, and inflammation," Curr. Opin. Immunol., 6:865-873 (1994).
Schimmer et al., "Streptococcal cell wall-induced arthritis: requirements for IL-1, IL-10, IFN-γ, and monocyte chemoattractant protein-1," J. Immunol , 160:1466-1471 (1998).
Schrier et al., "Role of chemokines and cytokines in a reactivation model of arthritis in rats induced by injection with streptococcal cell walls," J. Leukoc. Biol., 63(3):359 (1998).
Seino et al., "Expression of leukocyte chemotactic cytokines in myocardial tissue," Cytokine, 7(3):301-304 (1995).
Sousa et al., "Increased expression of the monocyte chemoattractant protein-1 in bronchial tissue from asthmatic subjects," Am. J. Respir., Cell Mol. Biol., 10:142-147 (1994).
Springer, "Adhesion receptors of the immune system," Nature, 346:425-434 (1990).
Sugiyama et al., "Chemokines in the bronchoalveolar lavage fluid of patients with sarcoidosis," Internal Medicine, 36:856-860 (1997).
Takeya et al., "Detection of monocyte chemoattractant protein-1 in human atherosclerotic lesions by an anti-monocyte chemoattractant protein-1 monoclonal antibody," Hum. Pathol., 24:534-539 (1993).
Vaddi et al., "Regulation of monocyte integrin expression by β-family chemokines," J. Immunol., 153:4721-4732 (1994).
Valente et al., "Purification of a monocyte chemotatic factor secreted by nonhuman primate vascular cells in culture," Biochemistry, 27:4162-4168 (1998).
Wada et al., "Monitoring urinary levels of monocyte chemotactic and activating factor reflects disease activity of lupus nephritis," Kidney Int., 49:761-767 (1996).
Wada et al., Intervention of crescentic glomerulonephritis by antibodies to monocyte chemotactic and activating factor (MCAF/MCP-1) FASEB J., 10:1418-1425 (1996).
Wang et al., "Synthesis of 2-substituted (±)-(2R,3R,5R)-Tetrahydrofuran-3,5-dicarboxylic acid derivatives," J. Org. Chem., 66:2052-2056 (2001).
Wong et al., "Evidence for RANTES, monocyte chemotactic protein-1, and macrophage inflammatory protein-1β expression in Kawasaki disease," J. Rheumatol., 24:1179-1185 (1997).
Yamagami et al., "cDNA cloning and functional expression of a human monocyte chemoattractant protein 1 receptor," Biochem. Biophys. Res. Commun., 202(2):1156-1162 (1994).
Yla-Herttuala et al., "Expression of monocyte chemoattractant protein 1 in macrophage-rich areas of human and rabbit atherosclerotic lesions," Proc. Natl. Acad. Sci. USA, 88:5252-5256 (1991).
Yokoyama et al., "Urinary levels of chemokines (MCAF/MCP, IL-8) reflect distinct disease activities and phases of human IgA nephropathy," J. Leukoc. Biol., 63(4):493-499 (1998).
Yoshimura et al., "Purification and amino acid analysis of two human monocyte chemoattractants produced by phytohemagglutinin-stimulated human blood mononuclear leukocytes," J. Immunol , 142:1956-1962 (1989).
Zeyneloglu et al., "The effect of monocyte chemotactic protein 1 in intraperitoneal adhesion formation in a mouse model," Am. J. Obstet. Gynecol., 179:438-443 (1998).
Zeyneloglu et al., "The role of monocyte chemotactic protein-1 in intraperitoneal adhesion formation," Human Reproduction, 13(5):1194-1199 (1998).

* cited by examiner

3-AMINOPYRROLIDINE DERIVATIVES AS MODULATORS OF CHEMOKINE RECEPTORS

CROSS-REFERENCE TO RELATED APPLICATIONS

This application is a national stage application of PCT International Application PCT/US2003/037946, filed Nov. 26, 2003, which claims priority to U.S. Provisional Patent Applications 60/429,605, filed Nov. 27, 2002 and 60/463,976, filed Apr. 18, 2003, respectively.

FIELD OF THE INVENTION

The instant invention is directed to chemokine receptor modulators, e.g., antagonists, and their use as medicinal agents. The present invention further relates to novel compounds and medical methods of treatment of inflammation, and other disorders especially those associated with lymphocyte or monocyte accumulation such as rheumatoid arthritis, lupus, graft versus host diseases and/or transplant rejection. More particularly, the present invention relates to 3-aminopyrrolidine derivatives and their use as modulators of chemokine receptors.

More specifically, the instant invention relates to new anti-inflammatory and immunomodulatory bioactive compounds and pharmaceutical compositions thereof that act via antagonism of the CCR2 receptor, (also known as the MCP-1 receptor), and therefore leading to the inhibition of Monocyte Chemoattractant Protein-1 (MCP-1). The new compounds are 3-aminopyrrolidine derivatives. The invention further relates to novel compounds for use in the compositions, to processes for their preparation, to intermediates useful in their preparation and to their use as therapeutic agents.

The chemokine receptor modulators/antagonists of the invention may be effective as therapeutic agents and/or preventive agents for diseases such as atherosclerosis, asthma, pulmonary fibrosis, myocarditis, ulcerative colitis, psoriasis, asthma, ulcerative colitis, nephritis (nephropathy), multiple sclerosis, lupus, systemic lupus erythematosus, hepatitis, pancreatitis, sarcoidosis, organ transplantation, Crohn's disease, endometriosis, congestive heart failure, viral meningitis, cerebral infarction, neuropathy, Kawasaki disease, and sepsis in which tissue infiltration of blood leukocytes, such as monocytes and lymphocytes, play a major role in the initiation, progression or maintenance of the disease.

The present invention also provides immunomodulatory bioactive compounds and pharmaceutical compositions thereof that act via antagonism of the CCR5 receptor.

BACKGROUND OF THE INVENTION

The migration and transport of leukocytes from blood vessels into diseased tissues appears to be a critical component to the initiation of normal disease-fighting inflammatory responses. The process, also known as leukocyte recruitment, is also related to the onset and progression of life-threatening inflammatory, as well as debilitating autoimmune diseases. The resulting pathology of these diseases derives from the attack of the body's immune system defenses on normal tissues. Accordingly, preventing and blocking leukocyte recruitment to target tissues in inflammatory and autoimmune disease would be a highly effective approach to therapeutic intervention.

The different classes of leukocyte cells that are involved in cellular immune responses include monocytes, lymphocytes, neutrophils, eosinophils and basophils. In most cases, lymphocytes are the leukocyte class that initiates, coordinates, and maintains chronic inflammatory responses, and thus are generally the most important class of cells to block from entering inflammatory sites. Lymphocytes attract monocytes to the tissue sites, which, collectively with lymphocytes, are responsible for most of the actual tissue damage that occurs in inflammatory disease. Infiltration of the lymphocytes and/or monocytes is known to lead to a wide range of chronic, autoimmune diseases, and also organ transplant rejection. These diseases include, but are not limited to, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *pemphigus vulgaris, p. foliacious, p. erythematosis*), glomerulonephritides, vasculitides, hepatitis, diabetes, allograft rejection, and graft-versus-host disease.

The process, by which leukocytes leave the bloodstream and accumulate at inflammatory sites, and start a disease, has at least three steps which have been described as (1) rolling, (2) activation/firm adhesion and (3) transendothelial migration [Springer, T. A., Nature 346:425433 (1990); Lawrence and Springer, Cell 65:859-873 (1991); Butcher, E. C., Cell 67:1033-1036 (1991)]. The second step is mediated at the molecular level by chemoattractant receptors. Chemoattractant receptors on the surface of leukocytes then bind chemoattractant cytokines which are secreted by cells at the site of damage or infection. Receptor binding activates leukocytes, increases the adhesiveness of the adhesion molecules that mediate transendothelial migration, and promotes directed migration of the cells toward the source of the chemoattractant cytokine.

Chemotactic cytokines (leukocyte chemoattractant/activating factors) also known as chemokines, also known as intercrines and SIS cytokines are a group of inflammatory/immunomodulatory polypeptide factors, of molecular weight 6-15 kDa, that are released by a wide variety of cells such as macrophages, monocytes, eosinophils, neutrophiles, fibroblasts, vascular endothelial cells, smooth muscle cells, and mast cells, at inflammatory sites (reviewed in Luster, New Eng. J Med., 338, 436-445 (1998) and Rollins, Blood, 90, 909-928 (1997)). Also, chemokines has been described in Oppenheim, J. J. et al., Annu. Rev. Immunol., 9:617-648 (1991); Schall and Bacon, Curr. Opin. Immunol., 6:865-873 (1994); Baggiolini, M., et al., and Adv. Immunol., 55:97-179 (1994). Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent (CC family) or separated by one amino acid (CXC family). These differences correlate with the organization of the two subfamilies into separate gene clusters. Within each gene cluster, the chemokines typically show sequence similarities between 25 to 60%. The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485; Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol., 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489). In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vasc. Biol., 1998, 18, 397; Takeya, M. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Kochi. A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., at al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Cytokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24, 1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), Asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), I-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1(9-76), has been also reported to inhibit arthritis in the mouse model (see Gong, J.-H., J. Exp., 4ed., 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

The published literature indicate that chemokines such as MCP-1 and MIP-1α attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54).

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is now known that these receptors are G protein-coupled seven-transmembrane receptors present on various leukocyte populations. So far, at least five CXC chemokine receptors (CXCR1-CXCR5) and eight CC chemokine receptors (CCR1-CCR8) have been identified. For example IL-8 is a ligand for CXCR1 and CXCR2, MIP-1α is that for CCR1 and CCR5, and MCP-1 is that for CCR2A and CCR2B (for reference, see for example, Holmes, W. E., et al., Science 1991, 253, 1278-1280; Murphy P. M., et al., Science, 253, 1280-1283; Neote, K. et al, Cell, 1993, 72, 415425; Charo, I. F., et al., Proc. Natl. Acad. Sci. USA, 1994, 91, 2752-2756; Yamagami, S., et al., Biochem. Biophys. Res. Commun., 1994, 202, 1156-1162; Combadier, C., et al., The Journal of Biological Chemistry, 1995, 270, 16491-16494, Power, C. A., et al., J. Biol. Chem., 1995, 270, 19495-19500; Samson, M., et al., Biochemistry, 1996, 35, 3362-3367; Murphy, P. M., Annual Review of Immunology, 1994, 12, 592-633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552).

Accordingly, drugs which inhibit the binding of chemokines such as MCP-1 and/or MIP-1α to these receptors, e.g., chemokine receptor antagonists, may be useful as pharmaceutical agents which inhibit the action of chemokines such as MCP-1 and/or MIP-1α on the target cells, but the prior art is silent regarding 3-aminopyrrolidine derivatives having such pharmacological effects. The identification of compounds that modulate the function of CCR2 and/or CCR5 represents an excellent drug design approach to the development of pharmacological agents for the treatment of inflammatory conditions and diseases associated with CCR2 and/or CCR5 activation, such as rheumatoid arthritis, lupus and other inflammatory diseases. The present invention provides a long felt need in the field of chemokine receptor modulators and antagonists.

OBJECTS OF THE INVENTION

With the foregoing in mind, it is an important object of the present invention to provide chemokine receptor antagonists and chemokine receptor modulators for treating rheumatoid arthritits.

Another main object of the invention is to provide chemokine receptor antagonists and their use as medicinal agents.

An additional object of the invention is to provide chemokine receptor modulators and their use as medicinal agents.

A further object of the present invention is to provide 3-aminopyrrolidine derivatives.

Another object of the invention relates to novel compounds and medical methods of treatment of inflammation.

A still further object of the invention provides new anti-inflammatory and immunomodulatory bioactive compounds and pharmaceutical compositions thereof that act via antagonism of the CCR2 receptor.

An additional object of the invention provides 3-aminopyrrolidine derivatives and their use as modulators of chemokine receptors.

A still additional object of the invention provides 3-aminopyrrolidine derivatives and their use in treating and preventing atherosclerosis and restenosis.

A further object of the invention provides 3-aminopyrrolidine derivatives and their use as modulators of the CCR5 receptor.

Another main object of the invention provides 3-aminopyrrolidine bioactive compounds and pharmaceutical compositions thereof that act via antagonism of the CCR5 receptor.

Other objects and embodiments of the present invention will be discussed below. However, it is important to note that many additional embodiments of the present invention not described in this specification may nevertheless fall within the spirit and scope of the present invention and/or the claims.

SUMMARY OF THE INVENTION

The present invention provides, in its broadest embodiment, compounds having the formula I:

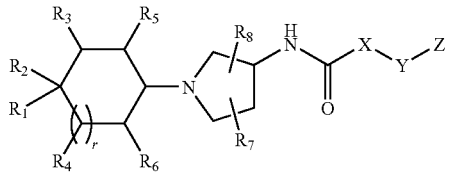

its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

X is selected from the group consisting of aryl, mono or poly substituted aryl, heterocycle heteroaryl, mono or poly substituted heteroaryl, carbocycle, mono or poly substituted carbocycle $(CR_9R_{10})$, wherein n=0-5;

Y is a bond, or is selected from the group consisting of oxygen, sulfur, nitrogen, amide bond, thioamide bond, sulfonamide, ketone, —CHOH—, CHO-alkyl-, oxime, or a urea;

Z is selected from the group consisting of carbocycle, an aryl, heterocycle or a heteroaryl with 0-3 $R_{11}$ substituents wherein $R_{11}$ is independently selected from the group consisting of: halogen, alkyl, alkenyl, alkynyl, alkoxy, alkoxyalkyl, alkylthioalkyl, thioalkyl, mono-, di- or trihaloalkyl, mono-, di- or trihaloalkoxy, nitro, amino, mono- or di-substituted amino, mono- or di-substituted aminoalkyl, carboxyl, esterified carboxyl, carboxamido, mono- or di-substituted substituted sufonamide, alkylcarbonyl, cyclic alkylsulfonyl, arylsulfonyl, heteroarylsulfonyl, alkylcarbonyl, cyclic alkylcarbonyl, arylcarbonyl, heteroarylcarbonyl, thiocarboxamido, cyano, and $R_{11a}$-aryl or $R_{11a}$-heteroaryl wherein $R_{11a}$ is H, halogen, OH, amino, mono- or di-substituted amino, mono-, di- or tri-haloalkyl, alkoxy, mono-, di- or tri-haloalkoxy, carboxamide, sulfonamide, carbamate, urea or cyano;

$R_1$ is independently selected from the group consisting of: a carbocycle, heterocycle, aryl, heteroaryl, arylalkyl, heteroarylalkyl, arylalkenyl, heteroarylalkenyl, arylalkynyl, hetero-arylalkynyl, arylaminocarbonyl, heteroarylaminocarbonyl, arylcarboxamido, heteroaryl-carboxamido, arylureido, heteroarylureido, aryloxy, heteroaryloxy, arylalkoxy, heteroarylalkoxy, arylamino or heteroarylamino and wherein said carbocycle, heterocycle, aryl, arylalkyl, heteroaryl or heteroarylalkyl, groups may be substituted with 0-3 $R_{1a}$ substituents wherein $R_{1a}$ is independently selected from the group consisting of: halogen, alkyl, alkenyl, alkynyl, alkoxy, alkoxyalkyl, alkylthioalkyl, hydroxyalkyl, mono-, di- or trihaloalkyl, mono-, di- or trihalo-alkoxy, nitro, amino, mono- or di-substituted amino, mono- or di-substituted aminoalkyl, aminocarbonyl, mono- or di-substituted aminocarbonyl, cyclic aminocarbonyl, aminosulfonyl, mono- or di-substituted aminosulfonyl, alkylcarbonyl, cyclic alkylcarbonyl, arylcarbonyl, hetero-arylcarbonyl, alkylsulfonyl, cyclic alkylsulfonyl, arylsulfonyl, heteroarylsulfonyl, carboxylic acid, esterified carboxylic acid, alkylcarbonylamino, cyclic alkylcarbonylamino, aryl-carbonylamino, heteroarylcarbonylamino, cyano, arylalkyl, heteroarylalkyl, aryloxyalkyl, heteroaryloxyalkyl, arylthioalkyl, heteroarylthioalkyl, carbamate, mono- or di-substituted carbamate, $R_{1b}$-aryl or $R_{1b}$-heteroaryl wherein $R_{1b}$ is H, halogen, OH, amino, mono- or di-substituted amino, mono-, di- or tri-haloalkyl, alkoxy, mono-, di- or tri-haloalkoxy, hydroxyalkyl, alkoxyalkyl, aminoalkyl, mono- or di-substituted aminoalkyl, carboxamide, sulfonamide, carbamate, urea or cyano;

$R_2$ is independently selected from the group consisting of: H, amino, mono- or di-substituted amino, OH, carboxyl, esterified carboxyl, carboxamide, N-monosusbstituted carboxamide, and N,N-disubstituted carboxamide, cyano, alkyl, alkenyl, alkynyl, cycloalkyl, cycloalkenyl, alkoxy, thioalkyl, mono-, di- or trihaloalkyl, halogen, aryl or heteroaryl;

optionally $R_1$ and $R_2$ can be bonded to each other to form a spirocycle;

$R_3$, $R_4$, $R_5$, and $R_6$ are independently selected form the group consisting of: H, amino, OH, alkyl, haloalkyl, dihaloalkyl, trihaloalkyl, alkenyl, alkyl, aryl, heteroaryl, arylalkyl, heteroarylalkyl, alkoxy and thioalkyl, optionally $R_1$ and $R_3$ can be cyclized to form a carbocycle or heterocycle having 0-3 $R_a$ substituents wherein $R_a$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido, cyano, mono, disubstituted, or polysusbstituted aryl and heterocycle optionally containing 0-3 $R_b$ wherein $R_b$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido and cyano;

optionally $R_3$ and $R_4$ or $R_5$ and $R_6$ are cyclized to form a bridged bicyclic system having an ethylene bridge;

optionally $R_3$ and $R_6$ are cyclized to form a bridged bicyclic system having a methylene group or an ethylene group or a heteroatom selected form the group consisting of N, O and S;

$R_7$ and $R_8$ are independently selected from the group consisting of hydrogen, $C_1$-$C_8$ alkyl, optionally $C_1$-$C_8$ alkyl can be interrupted by oxygen or sulfur; alkoxy, mono-, di- or trihaloalkyl, mono-, di- or trihaloalkoxy, alkoxyalkyl, aryloxy, heteroaryloxy, arylalkoxy, heteroarylalkoxy, aryloxyalkyl, heteroaryloxyalkyl, arylalkoxyalkyl or heteroarylalkoxyalkyl;

optionally $R_7$ and $R_8$ can be cyclized to form a spirocarbocycle or spiroheterocycle;

$R_9$ and $R_{10}$ are independently selected from the group consisting of H, OH, amino, alkoxy, mono- or disubstituted amino, alkyl, alkenyl, alkynyl, aryl, arylalkyl, heteroaryl, heteroarylalkyl, a carbocycle, or a heterocycle;

optionally $R_9$ and $R_{10}$ can be cyclized to form a carbocycle or heterocycle; and r=0-3.

The present invention also provides compounds of formula II:

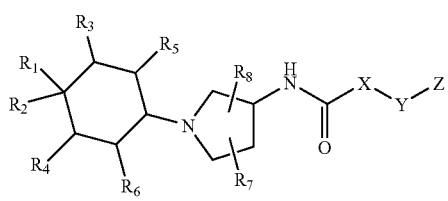

wherein X, Y, Z, and $R_1$, $R_2$, $R_3$, $R_4$, $R_5$, $R_6$, $R_7$, and $R_8$ are described in full detail below with regard to the description of the preferred embodiments; for the sake of summary suffice it to say that each of the substituent groups is defined as a more preferred subset of the corresponding substituent group as defined for the formula I compounds.

The instant invention is also directed to a compound of the formula III:

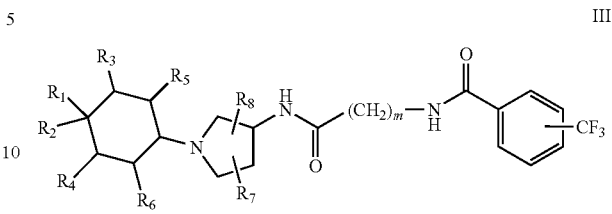

wherein $R_1$, $R_2$, $R_3$, $R_4$, $R_5$, $R_6$, $R_7$, and $R_8$ and m are described in full detail below with regard to the description of the preferred embodiments; for the sake of summary suffice it to say that each of the substituent groups is defined as a more preferred subset of the corresponding substituent group as defined for the formula I compounds.

The instant invention also relates to pharmaceutical compositions which comprise anti-inflammatory and/or immunomodulatory compounds of formula I, II and III as shown above, that act via antagonism of the CCR2 receptor, (also known as the MCP-1 receptor), therefore inhibiting the Monocyte Chemoattractant Protein-1 (MCP-1).

The instant invention is also directed to pharmaceutical compositions which comprise anti-inflammatory and/or immunomodulatory compounds of formula I, II and III as shown above, that act via antagonism of the CCR5 receptor (also known as the MCP-1 receptor), therefore inhibiting the Monocyte Chemoattractant Protein-1 (MCP-1).

The present invention is also directed to compounds of formula I, II and III which are modulators of CCR2 chemokine receptor function and are useful in the prevention or treatment of inflammatory conditions and diseases such as rheumatoid arthritis, allergic diseases, psoriasis, atopic dermatitis, lupus and asthma.

The present invention also describes compounds of formula I, II and III which are modulators of CCR5 chemokine receptor function and are useful in the prevention or treatment of inflammatory conditions and diseases such as rheumatoid arthritis, allergic diseases, psoriasis, atopic dermatitis, lupus and asthma The invention further relates to a method for modulation of chemokine receptor activity in a mammal comprising the administration of an effective amount of a compound of formula I or II and III.

The invention is also provides pharmaceutical compositions comprising compounds selected from the group of formula I, II and III and the use of these compounds and compositions in the prevention or treatment of diseases in which CCR2 chemokine receptors are involved.

The invention further provides pharmaceutical compositions comprising compounds selected from the group of formula I, II and III and the use of these compounds and compositions in the prevention or treatment of diseases in which CCR5 chemokine receptors are involved.

The invention additionally provides a method for the treatment of inflammation, rheumatoid arthritis, lupus, systemic lupus erythematosus, atherosclerosis, restenosis, immune disorders, and transplant rejection in a mammal in need thereof comprising administering to such mammal a therapeutically effective amount of a pharmaceutical composition containing a compound according to formula I, II and III in admixture with a pharmaceutically acceptable excipient, diluent, or carrier.

DESCRIPTION OF THE PREFERRED EMBODIMENTS

The present invention is directed to compounds having the following chemical structure I and II:

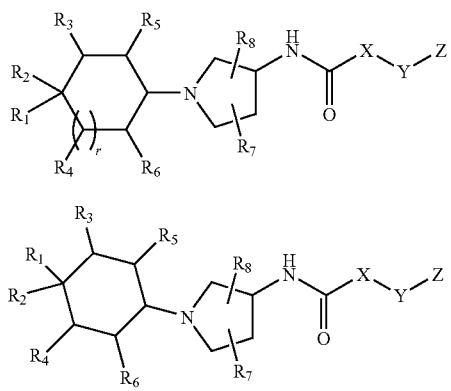

its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

X is selected from the group consisting of aryl, mono or poly substituted aryl, heterocycle heteroaryl, mono or poly substituted heteroaryl, carbocycle, mono or poly substituted carbocycle $(CR_9R_{10})_n$ herein n=0-5;

Y is a bond, or is selected from the group consisting of oxygen, sulfur, nitrogen, amide bond, thioamide bond, sulfonamide, ketone, —CHOH—, —CHO-alkyl-, oxime, or a urea;

Z is selected from the group consisting of carbocycle, an aryl, heterocycle or a heteroaryl with 0-3 $R_{11}$ substituents wherein $R_{11}$ is independently selected from the group consisting of: halogen, alkyl, alkenyl, alkynyl, alkoxy, alkoxyalkyl, alkylthioalkyl, thioalkyl, mono-, di- or trihaloalkyl, mono-, di- or trihaloalkoxy, nitro, amino, mono- or di-substituted amino, mono- or di-substituted aminoalkyl, carboxyl, esterified carboxyl, carboxamido, mono- or di-substituted carboxamido, carbamate, mono- or di-substituted carbamate, sulfonamide, mono-or di-substituted sufonamide, alkylcarbonyl, cyclic alkylsulfonyl, arylsulfonyl, heteroarylsulfonyl, alkylcarbonyl, cyclic alkylcarbonyl, arylcarbonyl, heteroarylcarbonyl, thiocarboxamido, cyano, and $R_{11a}$-aryl or $R_{11a}$-heteroaryl wherein $R_{11a}$ is H, halogen, OH, amino, mono- or di-substituted amino, mono-, di- or tri-haloalkyl, alkoxy, mono-, di- or tri-haloalkoxy, carboxamide, sulfonamide, carbamate, urea or cyano;

$R_1$ is independently selected from the group consisting of: a carbocycle, heterocycle, aryl, heteroaryl, arylalkyl, heteroarylalkyl, arylalkenyl, heteroarylalkenyl, arylalkynyl, hetero-arylalkynyl, arylaminocarbonyl, heteroarylaminocarbonyl, arylcarboxamido, heteroaryl-carboxamido, arylureido, heteroarylureido, aryloxy, heteroaryloxy, arylalkoxy, heteroarylalkoxy, arylamino or heteroarylamino and wherein said carbocycle, heterocycle, aryl, arylalkyl, heteroaryl or heteroarylalkyl, groups may be substituted with 0-3 $R_{1a}$ substituents wherein $R_{1a}$ is independently selected from the group consisting of: halogen, alkyl, alkenyl, alkynyl, alkoxy, alkoxyalkyl, alkylthioalkyl, hydroxyalkyl, mono-, di- or trihaloalkyl, mono-, di- or trihalo-alkoxy, nitro, amino, mono- or di-substituted amino, mono- or di-substituted aminoalkyl, aminocarbonyl, mono- or di-substituted aminocarbonyl, cyclic aminocarbonyl, aminosulfonyl, mono- or di-substituted aminosulfonyl, alkylcarbonyl, cyclic alkylcarbonyl, arylcarbonyl, hetero-arylcarbonyl, alkylsulfonyl, cyclic alkylsulfonyl, arylsulfonyl, heteroarylsulfonyl, carboxylic acid, esterified carboxylic acid, alkylcarbonylamino, cyclic alkylcarbonylamino, aryl-carbonylamino, heteroarylcarbonylamino, cyano, arylalkyl, heteroarylalkyl, aryloxyalkyl, heteroaryloxyalkyl, arylthioalkyl, heteroarylthioalkyl, carbamate, mono- or di-substituted carbamate, $R_{1b}$-aryl or $R_{1b}$-heteroaryl wherein $R_{1b}$ is H, halogen, OH, amino, mono- or di-substituted amino, mono-, di- or tri-haloalkyl, alkoxy, mono-, di- or tri-haloalkoxy, hydroxyalkyl, alkoxyalkyl, aminoalkyl, mono- or di-substituted aminoalkyl, carboxamide, sulfonamide, carbamate, urea or cyano;

$R_2$ is independently selected from the group consisting of: H, amino, mono- or di-substituted amino, OH, carboxyl, esterified carboxyl, carboxamide, N-monosusbstituted carboxamide, and N,N-disubstituted carboxamide, cyano, alkyl, alkenyl, alkynyl, cycloalkyl, cycloalkenyl, alkoxy, thioalkyl, mono-, di- or trihaloalkyl, halogen, aryl or heteroaryl;

optionally $R_1$ and $R_2$ can be bonded to each other to form a spirocycle;

$R_3$, $R_4$, $R_5$, and $R_6$ are independently selected form the group consisting of: H, amino, OH, alkyl, haloalkyl, dihaloalkyl, trihaloalkyl, alkenyl, alkynyl, aryl, heteroaryl, arylalkyl, heteroarylalkyl, alkoxy, mono-, di- or trihaloalkoxy, and thioalkyl;

optionally $R_1$ and $R_3$ can be cyclized to form a carbocycle or heterocycle having 0-3 $R_a$ substituents wherein $R_a$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido, cyano, mono, disubstituted, or polysusbstituted aryl and heterocycle optionally containing 0-3 $R_b$ wherein $R_b$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido and cyano;

optionally $R_3$ and $R_4$ or $R_5$ and $R_6$ are cyclized to form a bridged bicyclic system having an ethylene bridge;

optionally $R_3$ and $R_6$ are cyclized to form a bridged bicyclic system having a methylene group or an ethylene group or a heteroatom selected form the group consisting of N, O and S;

$R_7$ and $R_8$ are independently selected from the group consisting of hydrogen, $C_1$-$C_8$ alkyl, optionally $C_1$-$C_8$ alkyl can be interrupted by oxygen or sulfur; alkoxy, mono-, di- or trihaloalkyl, mono-, di- or trihaloalkoxy, alkoxyalkyl, aryloxy, heteroaryloxy, arylalkoxy, heteroarylalkoxy, aryloxyalkyl, heteroaryloxyalkyl, arylalkoxyalkyl or heteroarylalkoxyalkyl;

optionally $R_7$ and $R_8$ can be cyclized to form a spirocarbocycle or spiroheterocycle;

$R_9$ and $R_{10}$ are independently selected from the group consisting of H, OH, amino, alkoxy, mono- or disubstituted amino, alkyl, alkenyl, alkynyl, aryl, arylalkyl, heteroaryl, heteroarylalkyl, a carbocycle, or a heterocycle;

optionally $R_9$ and $R_{10}$ can be cyclized to form a carbocycle or heterocycle; and r=0-3.

The instant invention is also directed to a compound of the formula III:

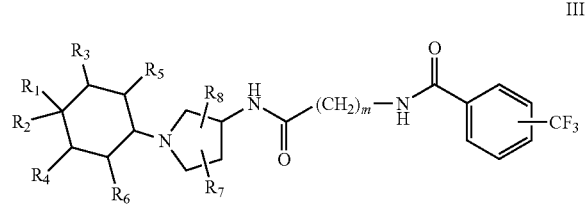

its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

$R_1$ is independently selected from the group consisting of: a carbocycle, heterocycle, aryl, heteroaryl, arylalkyl, heteroarylalkyl, arylalkenyl, heteroarylalkenyl, arylalkynyl, hetero-arylalkynyl, arylaminocarbonyl, heteroarylaminocarbonyl, arylcarboxamido, heteroaryl-carboxamido, arylureido, heteroarylureido, aryloxy, heteroaryloxy, arylalkoxy, heteroarylalkoxy, arylamino or heteroarylamino and wherein said carbocycle, heterocycle, aryl, arylalkyl, heteroaryl or heteroarylalkyl, groups may be substituted with 0-3 $R_{1a}$ substituents wherein $R^{1a}$ is independently selected from the group consisting of: halogen, alkyl, alkenyl, alkynyl, alkoxy, alkoxyalkyl, alkylthioalkyl, hydroxyalkyl, mono-, di- or trihaloalkyl, mono-, di- or trihalo-alkoxy, nitro, amino, mono- or di-substituted amino, mono- or di-substituted aminoalkyl, aminocarbonyl, mono- or di-substituted aminocarbonyl, cyclic aminocarbonyl, aminosulfonyl, mono- or di-substituted aminosulfonyl, alkylcarbonyl, cyclic alkylcarbonyl, arylcarbonyl, hetero-arylcarbonyl, alkylsulfonyl, cyclic alkylsulfonyl, arylsulfonyl, heteroarylsulfonyl, carboxylic acid, esterified carboxylic acid, alkylcarbonylamino, cyclic alkylcarbonylamino, aryl-carbonylamino, heteroarylcarbonylamino, cyano, arylalkyl, heteroarylalkyl, aryloxyalkyl, heteroaryloxyalkyl, arylthioalkyl, heteroarylthioalkyl, carbamate, mono- or di-substituted carbamate, $R_{1b}$-aryl or $R_{1b}$-heteroaryl wherein $R_{1b}$ is H, halogen, OH, amino, mono- or di-substituted amino, mono-, di- or tri-haloalkyl, alkoxy, mono-, di- or tri-haloalkoxy, hydroxyalkyl, alkoxyalkyl, aminoalkyl, mono- or di-substituted aminoalkyl, carboxamide, sulfonamide, carbamate, urea or cyano;

$R_2$ is independently selected from the group consisting of: H, amino, mono- or di-substituted amino, OH, carboxyl, esterified carboxyl, carboxamide, N-monosusbstituted carboxamide, and N,N-disubstituted carboxamide, cyano, alkyl, alkenyl, alkynyl, cycloalkyl, cycloalkenyl, alkoxy, thioalkoxy, mono-, di- or trihaloalkyl, halogen, aryl or heteroaryl;

optionally $R_1$ and $R_2$ can be bonded to each other to form a spirocycle;

$R_3$, $R_4$, $R_5$, and $R_6$ are independently selected form the group consisting of: H, amino, OH, alkyl, haloalkyl, dihaloalkyl, trihaloalkyl, alkenyl, alkynyl, aryl, heteroaryl, arylalkyl, heteroarylalkyl, alkoxy and thioalkyl, optionally $R_1$ and $R_3$ can be cyclized to form a carbocycle or heteroaryl having 0-3 $R_a$ substituents wherein $R_a$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido, cyano, mono, disubstituted, or polysusbstituted aryl and heterocycle optionally containing 0-3 $R_b$ wherein $R_b$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido and cyano;

optionally $R_3$ and $R_4$ or $R_5$ and $R_6$ are cyclized to form a bridged bicyclic system having an ethylene bridge;

optionally $R_3$ and $R_6$ are cyclized to form a bridged bicyclic system having a methylene group or an ethylene group or a heteroatom selected form the group consisting of N, O and S;

$R_7$ and $R_8$ are independently selected from the group consisting of hydrogen, $C_1$-$C_8$ alkyl, optionally $C_1$-$C_8$ alkyl can be interrupted by oxygen or sulfur; alkoxy, mono-, di- or trihaloalkyl, mono-, di- or trihaloalkoxy, alkoxyalkyl, aryloxy, heteroaryloxy, arylalkoxy, heteroarylalkoxy, aryloxyalkyl, heteroaryloxyalkyl, arylalkoxyalkyl or heteroarylalkoxyalkyl;

optionally $R_7$ and $R_8$ can be cyclized to form a spirocarbocycle or spiroheterocycle;

and m=0-5.

As defined above, with respect to compounds of the formula I and II, X is selected from the group consisting of aryl, mono or poly substituted aryl, heterocycle, heteroaryl, mono or poly substituted heteroaryl, carbocycle, mono or poly substituted carbocycle $(CR_9R_{10})_n$ wherein n=0-5. The term aryl groups is intended to include aromatic carbocylic groups such as phenyl, biphenylyl, indenyl, naphthyl and fused aromatic to heterocyclic such as 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 1-isoquinolinyl, 4-quinolinyl, 1-isoindolyl, 3-isoindolyl, and acridinyl. The term heterocyclic is intended to include aromatic and non-aromatic rings, for example containing from 3 to 20, preferably from 4 to 10 ring atoms, at least one of which is a heteroatom such as oxygen, sulphur, phosphorus or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl. Other examples include non-aromatic heterocyclic rings which are non-aromatic carbocyclic rings which include one or more heteroatoms such as nitrogen, oxygen or sulfur in the ring. The ring can be five, six, seven or eight-membered. Examples include 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thio-morpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl. In the instances where X and Z have the same meaning, then the identical definitions apply to their definitions. Additionally, when the heteroaryl or heterocyclic groups are nitrogen containing heterocycles, the nitrogen may be modified to exist in the form of the N→O⁻ (N oxides) and such oxides are intended to be included within the scope of the instant invention. In the cases of sulfur containing heterocycles, the sulfur oxides are also intended to be included within the scope of the present invention.

The substituents in the aryl groups, arylalkyl groups, heteroaryl groups, heteroarylakyl groups and heterocyclic groups of the invention are selected from the group consisting of halogen, alkyl, alkoxy, monohaloalkoxy, dihaloalkoxy, trihaloalkoxy, thioalkyl and monohaloalkyl, dihaloalkyl, trihaloalkyl, nitro, amino, carboxyl, esterified carboxyl, carboxamide, thiocarboxamido and cyano. More in particular the substituents can also be selected from the group consisting of trifluoromethyl, $C_{1-4}$ alkyl, halo, trifluoromethoxy, fluoromethoxy, difluoromethoxy, $C_{1-5}$ alkoxy, $C_{1-5}$ alkanoyl, $C_{1-5}$ alkanoyloxy, $C_{1-5}$ alkylamino, di($C_{1-5}$ alkyl)-amino, $C_{1-5}$ alkanoylamino, nitro, carboxy, carbamoyl, $C_{1-5}$ alkoxycarbonyl, thiol, $C_{1-5}$, sulphon-amido, carbamoyl $C_{1-5}$ alkyl, N—($C_{1-5}$ alkyl)carbamoyl $C_{1-5}$ alkyl, N—($C_{1-5}$ alkyl)$_2$ carbamoyl-$C_{1-5}$ alkyl, hydroxy $C_{1-5}$ alkyl or $C_{1-5}$ alkoxy $C_{1-4}$ alkyl.

The terms halo or halogen, by themselves or as part of another substituent, mean, unless otherwise stated, a fluorine, chlorine, bromine, or iodine atom. Similarly, terms such as haloalkyl, are meant to include monohaloalkyl and polyhaloalkyl. For example, the term halo($C_1$-$C_4$)alkyl is mean to include trifluoromethyl, 2,2,2-trifluoroethyl, 4-chlorobutyl, 3-bromopropyl, and the like.

The term alkyl when used either alone or as a suffix includes straight chain and branched structures such as primary alkyl groups, secondary alkyl groups and tertiary alkyl groups. These groups may contain up to 15, preferably up to 8 and more preferably up to 4 carbon atoms. Similarly the terms alkenyl and alkynyl refer to unsaturated straight or branched structures containing for example from 2 to 12, preferably from 2 to 6 carbon atoms. Cyclic moieties such as cycloalkyl, cycloalkenyl and cycloalkynyl are similar in nature but have at least 3 carbon atoms. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. Examples of unsaturated alkyl groups include vinyl, 2-propenyl, crotyl, 2-isopentenyl, 2-(butadienyl), 2,4-pentadienyl, 3-(1,4 pentadienyl), ethynyl, 1- and 3-propynyl, 3-butynyl, and the higher homologs and isomers. In the present application, cycloalkyl is also intended to include adamantyl groups and other bridge compounds. The terms alkoxy, alkylamino and alkylthio (or thioalkoxy) are used in their conventional sense, and refer to those alkyl groups attached to the remainder of the molecule via an oxygen atom, an amino group, or a sulfur atom, respectively. Therefore, terms such as alkoxy and thioalkyl comprise alkyl moieties as defined above, attached to the appropriate functionality.

Other suitable substituents which can be used in the many carbon rings of the present invention such as cycloaliphatic, aromatic, non-aromatic heterocyclic ring or benzyl group include, for example, —OH, halogen (—Br, —Cl, —I and —F) —O(aliphatic, substituted aliphatic, benzyl, substituted benzyl, phenyl, substituted phenyl, aromatic or substituted aromatic group), —CN, —NO$_2$, —COOH, —NH$_2$, —NH (aliphatic group, substituted aliphatic, benzyl, substituted benzyl, phenyl, substituted phenyl, aromatic or substituted aromatic group), —N(aliphatic group, substituted aliphatic, benzyl, substituted benzyl, phenyl, substituted phenyl, aromatic or substituted aromatic group)$_2$, —COO(aliphatic group, substituted aliphatic, benzyl, substituted benzyl, phenyl, substituted phenyl, aromatic or substituted aromatic group), —CONH$_2$, —CONH(aliphatic, substituted aliphatic group, benzyl, substituted benzyl, phenyl, substituted phenyl, aromatic or substituted aromatic group)), —SH, —S(aliphatic, substituted aliphatic, benzyl, substituted benzyl, phenyl, substituted phenyl, aromatic or substituted aromatic group) and —NH—C=NH)—NH2. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

The carbocycle susbtituent as defined by $R_1$ is intended to include cycloalkyl of 3-10 carbon atoms, and bicyclic and multicyclic bridge systems such as norbornanyl, adamantyl and bicyclo[2.2.2]octyl. The carbocycle substituent as defined in $R_1$ may also be further substituted with a heterocycle or heteroaryl ring such as pyridyl, pyrrolidinyl, and all those defined under X above.

Specific examples of $R_1$ substituents includes phenyl, pyridin-2-yl, 4-methylphenyl, 3-methyl-phenyl, 2-methylphenyl, 4-bromophenyl, 3-bromophenyl, 4-chlorophenyl, 3-chlorophenyl, 4-trifluoromethylphenyl, 3-trifluoromethylphenyl, 2-trifluoromethylphenyl, 2-methoxyphenyl, 3-pyridyl, 4-pyridyl, 2-methoxy-5-pyridyl, 2-ethoxy-5-pyridyl, 3,4-methylenedioxyphenyl, 4-fluorophenyl, 3-trifluoromethyl-1H-pyrazol-1-yl, 3-fluorophenyl, 4-methoxyphenyl, 3-methoxyphenyl, pyridin-4-yl, pyridin-3-yl, 5-methylpyridin-2-yl, 6-methylpyridin-2-yl, quinolin-4-yl, 3-methyl-1H-pyrazol-1-yl, 3,5-dimethyl-1H-pyrazol-1-yl, 4-trifluoromethylphenyl, 3-trifluoromethylphenyl, 3,4-methylenedioxyphenyl, 4-cyanophenyl, 4-(methylaminocarbonyl)phenyl, 1-oxidopyridin-4-yl, pyridin-2-yl, pyridin-3-yl, pyridin-4-yl, 4-methylpyridin-2-yl, 5-methyl-pyridin-2-yl, 6-methylpyridin-2-yl, 6-methoxypyridin-2-yl, 6-methoxypyridin-3-yl, 6-methylpyridin-3-yl, 6-ethylpyridin-3-yl, 6-isopropylpyridin-3-yl, 6-cyclopropylpyridin-3-yl, 1-oxidopyridin-3-yl, 1-oxidopyridin-2-yl, 3-cyanophenyl, 3-(methylaminocarbonyl)-phenyl, 4-(morpholin-4-ylcarbonyl)phenyl, 5-(morpholin-4-ylcarbonyl)pyridin-2-yl, 6-(morpholin-4-ylcarbonyl)pyridin-3-yl, 4-(4-methylpiperazin-1-yl-carbonyl)phenyl, 6-(azetin-1-yl)pyridin-3-yl, 5-cyanopyridin-2-yl, 6-cyanopyridin-3-yl, 5-(methoxy-methyl)pyridin-2-yl, 5-(1-hydroxy-1-methylethyl)pyridin-2-yl, 5-dimethylaminomethyl, 4-ethylaminocarbonylphenyl, 4-isopropylaminocarbonylphenyl, 4-tert-butylamino-carbonylphenyl, 4 dimethylaminocarbonyl-phenyl, 4-(azetidin-1-yl)carbonylphenyl, 4-(pyrrolidin-1-yl)carbonylphenyl, 4-(morpholin-4-yl)carbonylphenyl, 4-(dimethyl-aminocarbonyl)-2-methylphenyl, 2-methyl-4-(methylamino-carbonyl)phenyl, 3-methyl-4-(methylaminocarbonyl)phenyl, 4-(dimethylaminocarbonyl)$_3$-methylphenyl, 3-methyl-4-(pyrrolidin-1-ylcarbonyl)phenyl, 4-(dimethylaminocarbonyl)-3-fluorophenyl, 4-[(2,2,2-trifluoroethyl)aminocarbonyl]phenyl, 3-fluoro-4-methylaminocarbonyl-phenyl, 4-ethyl-aminocarbonyl-3-fluorophenyl, 3-methylaminocarbonylphenyl, 3-dimethyl-aminocarbonylphenyl, 5-dimethylaminocarbonyl-2-methoxyphenyl, 2-methoxy-5-methylaminocarbonylphenyl, 3-(methylaminocarbonylamino) phenyl, 6-(morpholin-4-yl)-pyridin-3-yl, 6-dimethylaminopyridin-3-yl, 6-isopropylaminopyrid-3-yl, 6-(pyrrolidin-1-yl)pyridin-3-yl, 6-cyclopropylaminopyridin-3-yl, 6-ethoxypyridin-3-yl, 6-(2-fluoroethoxy)pyridin-3-yl, 6-(2,2-difluoroethoxy)pyridin-3-yl, 6-(2,2,2-trifluoroethoxy)-pyridin-3-yl, 4-iodophenyl, 5-(pyrrolidin-1-ylcarbonyl)-2-pyridyl, 5-(morpholin-4-yl-carbonyl)-2-pyridyl, 5-dimethylaminocarbonyl-2-pyridyl, 4-methylaminocarbonyl-aminophenyl, 6-(1-hydroxy-1-methylethyl)pyridin-3-yl, 4-(1-hydroxy-1-methylethyl)-phenyl, 4-(methoxymethyl) phenyl, 3-fluoro-4-(methoxymethyl)phenyl, 4-(dimethylamino)phenyl, 4-(dimethylamino)-3-fluorophenyl, 1H-indazol-5-yl, 1-methyl-1H-indazol-5-yl, 2-methyl-1H-indazol-5-yl, 1,3-thiazol-2-yl, 5-ethyl-1,3-thiazol-2-yl, 5-(methylaminocarbonyl)-1,3-thiazol-2-yl, 1,3-thiazole-5-yl, 2-(methoxycarbonylamino)-1,3-thiazol-5-yl, 2-isopropyl-1,3-thiazol-5-yl, 5-(pyridin-3-yl)-1,3-thiazol-2-yl, 5-(morpholin-4-ylcarbonyl)-1,3-thiazol-2-yl, 5-aminocarbonyl-1,3-thiazol-2-yl, 5-dimethylaminocarbonyl-1,3-thiazol-2-yl, 5-(pyrrolidin-1-ylcarbonyl)-1,3-thiazol-2-yl, 5-allyl-1,3-thiazol-2-yl, 5-propyl-1,3-thiazol-2-yl, 5-ethylaminocarbonyl-1,3-thiazol-2-yl, 5-phenyl-1,3-thiazol-2-yl, 5-methyl-1,3-thiazol-2-yl, 5-hydroxymethyl-1,3-thiazol-2-yl, 5-(1-hydroxy-1-methylethyl)-1,3-thiazol-2-yl, 5-methoxymethyl-1,3-thiazol-2-yl, 5-(2-pyridyl)-1,3-thiazol-2-yl, 2-(pyrrolidin-1-yl)-1,3-thiazolyl, 2-(morpholin-4-yl)-1,3-thiazolyl, 2-methyl-1,3-thiazol-5-yl, 2-(1-hydroxy-1-methylethyl)-1,3-thiazol-5-yl, 2-(pyrrolidin-1-yl)-1,3-thiazol-5-yl, 2-ethoxy-1,3-thiazol-5-yl, 2-ethyl-1,3-thiazol-5-yl, 2-(pyrrolidin-1-ylmethyl)-1,3-thiazol-5-yl, 2-(morpholin-4-yl)-1,3-thiazol-5-yl, 2-methoxy-methyl-1,3-thiazol-5-yl, 2-isobutyl-1,3-thiazol-5-yl, 2-ethylaminocarbonyl-1,3-thiazol-5-yl, 2-(pyrrolidin-1-ylcarbonyl)-1,3-thiazol-5-yl, 2-(morpholin-4-ylcarbonyl)-1,3-thiazol-5-yl, 2-(3-pyridyl)-1,3-thiazol-5-yl, 2-(2-pyridyl)-1,3-thiazol-5-yl, 4-methyl-1,3-thiazol-2-yl, 1,3-benzo-thiazol-2-yl, pyrimidin-5-yl, pyrimidin-2-yl, pyridazin-4-yl, pyridazin-3-yl, pyrazin-2-yl, 2-methoxypyrimidin-5-yl, 2-ethoxypyrimidin-5-yl, 2-(2-fluoroethoxy)pyrimidin-5-yl, 2-methylpyrimidin-5-yl, 2-ethylpyrimidin-5-yl, 2-isopropylpyrimidin-5-yl, 2-cyclopropylpyrimidin-5-yl, pyrimidin-4-yl, 4-(pyrimidin-5-yl)phenyl, 4-(1,3-oxazol-2-yl)phenyl, 4-(1H-imidazol-1-yl)phenyl, 4-(morpholin-4-yl)phenyl, 5-(pyrazin-2-yl)pyridin-2-yl, 4-(1-methyl-1H-imidazol-5-yl)phenyl, 4-(4,6-dimethylpyrimidin-5-yl)phenyl, 6-bromopyridin-3-yl, 5-bromopyridin-2-yl, 4'-(methylsulfonyl)biphenylyl, 3'-(methylsulfonyl)biphenyl-4-yl, 3'-(methoxy-carbonyl)-biphenyl-4-yl, 4-(2,3-dihydro-1,4-benzodioxin-6-yl)phenyl, 4'-(dimethyl-amino)-biphenyl-4-yl, 4-(pyridin-3-yl)phenyl, 4-(1H-pyrazol-4-yl)phenyl, 4-(3,3'-bipyridin-6-yl, 4-(3,4'-bipyridin-6-yl, 5-(3-acetylphenyl)pyridin-2-yl, 5-[3-(dimethyl-amino)phenyl]pyridin-2-yl, 5-[3-(trifluoromethyl)phenyl]pyridin-2-yl, 5-[4-(methyl-sulfonyl)phenyl]pyridin-2-yl, 5-(4-methoxyphenyl)pyridin-2-yl, 5-(3-methoxy-phenyl)-pyridin-2-yl, 5-[3-(aminocarbonyl)-phenyl]pyridin-2-yl, 5-(4-fluoro-phenyl)pyridin-2-yl, 5-(3,4-difluorophenyl)pyridin-2-yl, 5-(3,5-dimethylisoxazol-4-yl)pyridin-2-yl, 5-(1-methyl-1H-pyrazol-4-yl)pyridin-2-yl, 5-(1H-pyrazol-4-yl)pyridin-2-yl, 5-(1-benzofuran-2-yl)pyridin-2-yl, 5-(1,3-benzodioxol-5-yl)pyridin-2-yl, 5-(2-formyl-phenyl)pyridin-2-yl, 4-(2'-formylbiphenyl-4-yl, 5-(1,3-oxazol-2-yl)pyridin-2-yl, 6-(1,3-oxazol-2-yl)pyridin-3-yl, 4-(1,3-thizol-2-yl)phenyl, 5-(1,3-thiazol-2-yl)pyridin-2-yl, 6-(1,3-thiazol-2-yl)pyridin-3-yl, 6-(1H-imidazol-1-yl)pyridin-3-yl], 5-(1H-imidazol-1-yl)pyridin-2-yl, 6-phenylpyridin-3-yl, 5-(pyrimidin-5-yl)pyridin-2-yl, 5-(pyrimidin-2-yl)pyridin-2-yl, 5-(3-aminocarbonylphenyl)pyridin-2-yl, 4-(1-methyl-1H-imidazol-4-yl)phenyl, 4-(1H-imidazol-4-yl)phenyl], 5-[2-(hydroxymethyl)phenyl]pyridin-2-yl, 2'-(hydroxymethyl)biphenyl-4-yl, 5-{2-[(dimethylamino)methyl]phenyl}pyridin-2-yl, 2'-[(dimethylamino)methyl]biphenylyl, 5-fluoromethylpyrazin-2-yl, 5-difluoro-methyl-pyrazin-2-yl, 5-methylpyrazin-2-yl, 2-methylpyrimidin-5-yl, 2-fluoromethylpyrimidin-5-yl, 2-difluoromethylpyrimidin-5-yl, 2-trifluoromethylpyrimidin-5-yl, 2-cyclopropylpyrimidin-5-yl, isothiazol-5-yl, 3-methylisothiazol-5-yl, 3-fluoromethylisothiazol-5-yl, 4-(dimethylamino-carbonyl)phenyl, 4-(methylaminocarbonyl)phenyl, 4-(morpholin-4-ylcarbonyl)phenyl, 4-(piperidin-1-ylcarbonyl)phenyl, 3-fluoro-4-(pyrrolidin-1-ylcarbonyl)phenyl, 5-(pyrrolidin-1-ylcarbonyl)pyridin-2-yl, 5-(dimethyl-aminocarbonyl)pyridin-2-yl, 5-(morpholin-4-yl-carbonyl)-pyridin-2-yl, quinolin-4-yl, 6methoxypyridin-3-yl, 6-(morpholin-4-yl)pyridin-3-yl, 4-(dimethyl-aminomethyl)phenyl, 5-(dimethylaminomethyl)pyridin-2-yl, 5-(dimethyl-aminocarbonyl)pyridin-2-yl, 4-[hydroxy(pyridin-3-yl)methyl]phenyl, 6-[(hydroxy-(pyridin-3-yl)methyl]pyridin-3-yl, 6-(dimethylaminocarbonyl)pyridin-3-yl, 4-(4-hydroxypiperidin-1-ylcarbonyl)phenyl, 4-(4 methoxypiperidin-1-ylcarbonyl)phenyl, 5-(4-methoxypiperidin-1-ylcarbonyl)-pyridin-2-yl, 6-(4-methoxypiperidin-1-ylcarbonyl)pyridin-3-yl, phenoxy, benzyloxy, 2-thienyl, 5-(methoxy-methyl)-1,3-thiazol-2-yl, 5-(morpholin-4-ylcarbonyl)-1,3-thiazol-2-yl, 2-isopropyl-1,3-thiazol-5-yl, 2-(methoxymethyl)-1,3-thiazol-5-yl, 5-(methoxymethyl)-1,3-thiazol-2-yl, 4-(pyrimidin-2-yl)phenyl, 4-(pyrimidin-4-yl)phenyl, and 5-(methoxymethyl)pyridin-2-yl.

The term $R_3$ and $R_4$ or $R_5$ and $R_6$ are cyclized to form a bridged bicyclic system having an ethylene bridge is intended to include the bicyclo[2.2.2]octyl system and all isomeric forms thereof, adamantyl and all isomeric forms thereof which may be optionally substituted with heterocycle, hetereoaryl, hydroxyl, amino, halogen as well as those substituents that provide stable molecules such as $C_1$-$C_5$-alkoxy, halogen, haloalkyl, and all those susbtituents as defined above.

The term $R_3$ and $R_6$ are cyclized to form a bridged bicyclic system having a methylene group or a heteroatom selected form the group consisting of N, O and S is intended to include norbornanyl and all those stable bridged systems having also the heteroatoms defined above. They also may be optionally substituted with heterocycle, hetereoaryl, hydroxyl, amino, halogen as well as those substituents that provide stable molecules such as $C_1$-$C_5$-alkoxy, halogen, haloalkyl, and all those substituents as defined above.

When $R_7$ and $R_8$ are independently selected from an alkoxy group such as OR, R may be selected from the group consisting of H, but-2-yn-1-yl, benzyl, pyridin-2-ylmethyl, pyridin-3-ylmethyl, propoxy and ethoxy.

Unless otherwise indicated, the compounds provided in the above formula are meant to include pharmaceutically acceptable salts, prodrugs thereof, enantiomers, diastereomers, racemic mixtures thereof, crystalline forms, noncrystalline forms, amorphous forms thereof and solvates thereof.

The term pharmaceutically acceptable salts is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts.

The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As noted above, some of the compounds of the present invention possess chiral or asymmetric carbon atoms (optical centers) or double bonds; the racemates, diastereomers, geometric isomers and individual optical isomers are all intended to be encompassed within the scope of the present invention.

Some of the compounds of formula I, II and III can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In addition to salt forms, the present invention provides compounds may be in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent.

The compounds of the present invention can be prepared in a number of ways well known to one skilled in the art of organic synthesis. A variety of 3-aminopyrrolidine intermediates can be obtained from commercial sources or synthesized using the methods described in Schemes 1-6. tert-Butyl trans-3-amino-4-hydroxypyrrolidine-1-carboxylate 1-4 can be synthesized starting from tert-butyl 2,5-dihydro-1H-pyrrole-1-carboxylate 1-1 (Scheme 1). Epoxidation of 1-1 using an oxidant such as m-chloroperoxybenzoic acid (mCPBA) followed by ring opening with benzylamine or sodium azide provides tert-butyl trans-3-benzylamino-4-hydroxypyrrolidine-1-carboxylate or tert-butyl trans-3-azido-4-hydroxypyrrolidine-1-carboxylate 1-3. Hydrogenation using a catalyst such as palladium on carbon or palladium hydroxide produces compound 1-4.

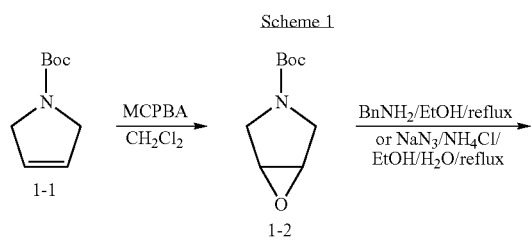

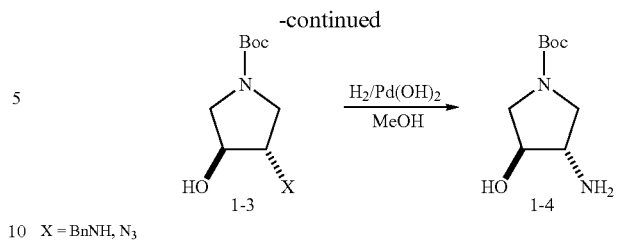

X = BnNH, N$_3$

Benzyl trans-3-amino-4-hydroxypyrrolidine-1-carboxylate 2-3 can be synthesized using the protocol outlined in Scheme 2. Epoxidation of benzyl 3-pyrroline-1-carboxylate 2-1 using an oxidant such as mCPBA followed by ring opening with ammonium hydroxide provides compound 2-3.

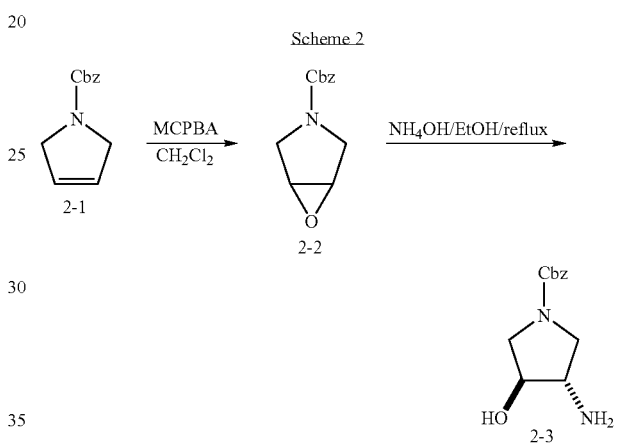

Introduction of an alkyl at 4-hydroxy on pyrrolidine can be accomplished using the sequence outlined in Scheme 3. Reaction of the intermediate 1-3 with N-(benzyloxycarbonyloxy)succinimide (CbzOSu) gives rise to 3-1. After alkylation of the hydroxyl group with an alkyl halide using sodium hydride, the benzyl and Cbz groups are removed by hydrogenation using a palladium catalyst such as palladium hydroxide to give the 3-alkoxypyrrolidine derivatives of formula 3-3.

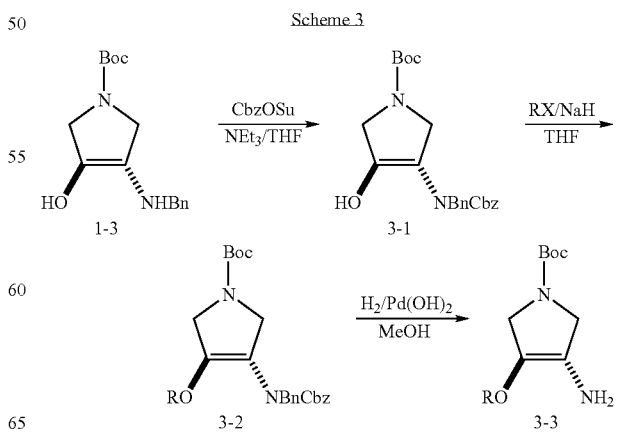

Alternatively, alkylation at 4-hydroxy on pyrrolidine can be accomplished using the method described in Scheme 4. Boc protection of the intermediate 2-3 followed by alkylation with an alkyl halide using sodium hydride as base produces the intermediate 4-2. Treatment of 4-2 with an acid such as HCl in dioxane or TFA affords compounds of formula 4-3.

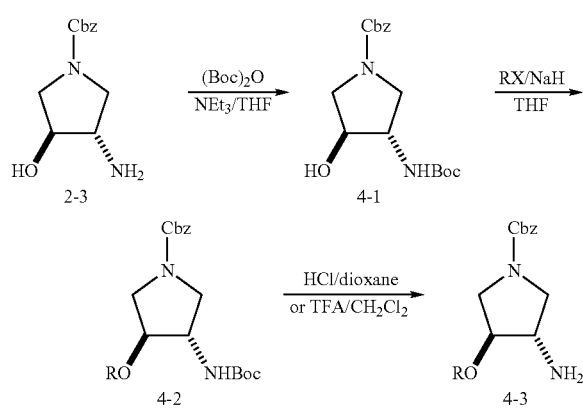

Spiropyrrolidine derivatives such as compound of formula 5-6 can be synthesized using the sequence depicted in Scheme 5. Cbz protection of the intermediate 1-4 followed by oxidation using an oxidant such as sulfur trioxide pyridine complex produces the ketone 5-2. Addition of allyl magnesium bromide to ketone 5-2 provides the tertiary alcohol 5-3. The olefin in 5-3 is converted to an alcohol by treatment with 9-BBN/$H_2O_2$. After treatment of the resulting alcohol with methanesulfonyl chloride, the reaction mixture is subjected to a reflux to give a ring closure product 5-5. Removal of the Cbz by hydrogenation affords compound 5-6.

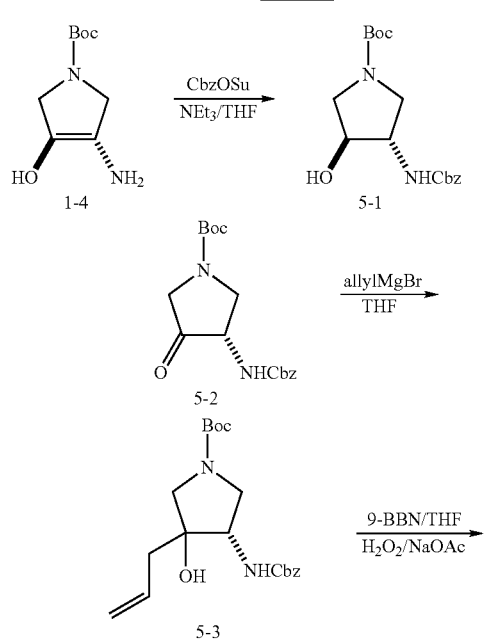

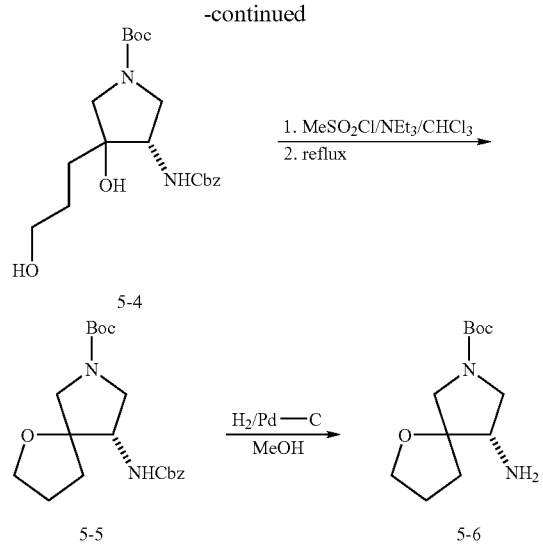

5-Alkyl substituted 3-aminopyrrolidine derivatives such as compounds of formula 6-5 can be prepared using the sequence shown in Scheme 6. Compound 6-1, which is synthesized following the procedures described in the literature (T. Rosen, et al. *J. Med. Chem.* 1988, 31, 1598-1611) is subjected to a Mitsunobu coupling with benzoic acid to give the ester 6-2. Hydrolysis of ester using $K_2CO_3$/MeOH produces the alcohol 6-3. Reaction of the alcohol with methanesulfonyl chloride followed by treatment of the resulting mesylate with sodium azide at an elevated temperature provides the azido compound 6-4. Conversion of the azido in 6-4 to an amino group by hydrogenation using a catalyst such as Pd-C yields compounds of formula 6-5.

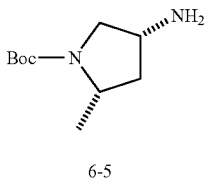

6-5

A variety of cyclohexanone derivatives can be synthesized using the protocols described in Schemes 7-19. Compounds of formula 7-2 can be prepared by addition of an aryl magnesium halide or arylhalide/BuLi to 1,4-cyclohexanedione 7-1. Alternatively, 7-2 can be synthesized by addition of an aryl magnesium halide, an arylhalide/BuLi or a heteroarylH/lithium tetramethylpiperidine to 1,4-cyclohexanedione mono-ethylene ketal 7-3 followed by acid treatment of the resulting ketal 7-4.

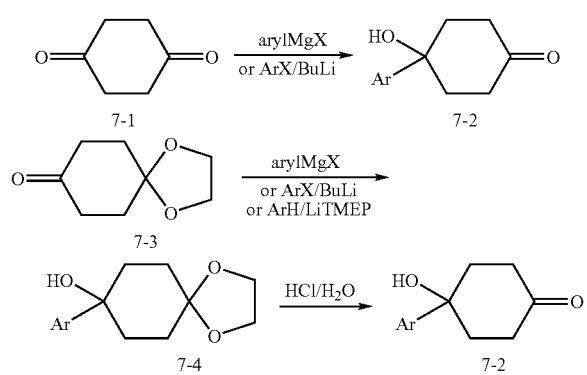

4-Arylcyclohexanone derivatives of formula 8-3 and 8-5 can be synthesized following the procedures shown in Scheme 8. The intermediate 7-4 is subjected to a treatment with a dehydrating agent such as thionyl chloride/pyridine followed by reduction of the resulting olefin by hydrogenation using a catalyst such as Pd-C or PtO$_2$. Treatment of the intermediate 7-4 with DAST converts the hydroxy group to a fluoro group. Removal of the ketal in 8-2 and 8-4 by treatment with an acid provides the ketones of formula 8-3 and 8-5.

Alternatively, compounds of formula 8-3 can be prepared using the procedures described in Scheme 9. Mono-protection of cyclohexan-1,4-diol 9-1 with tert-butyldimethylsilyl (TBDMS) followed by mesylation provides the mesylate 9-3. Displacement of the mesylate with a heteroaryl such as pyrazole, imidazole, triazole or tetrazole gives rise to the intermediate 9-4. Removal of the TBDMS group using TBAF followed by Swern oxidation affords compounds of formula 8-3.

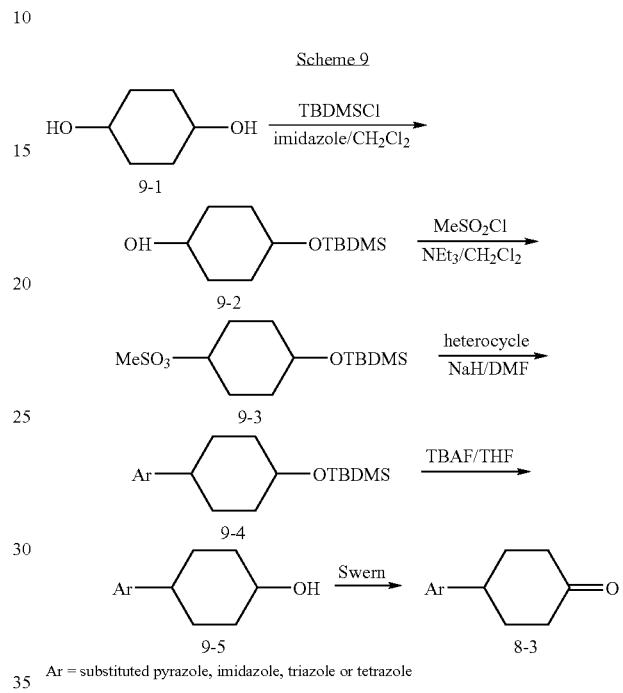

Ar = substituted pyrazole, imidazole, triazole or tetrazole

Alternatively, compounds of formula 8-3 can be synthesized according to Scheme 10. Reduction of ketone 7-3 using a reducing agent such as sodium borohydride produces the alcohol 10-1 which is converted to a mesylate 10-2 by treating with methanesulfonyl chloride. Displacement of the mesylate 10-2 with a heterocycle such as pyrazole, imidazole, triazole or tetrazole provides the intermediate 10-3 which is converted to compounds of formula 8-3 by treatment with an acid such as HCl.

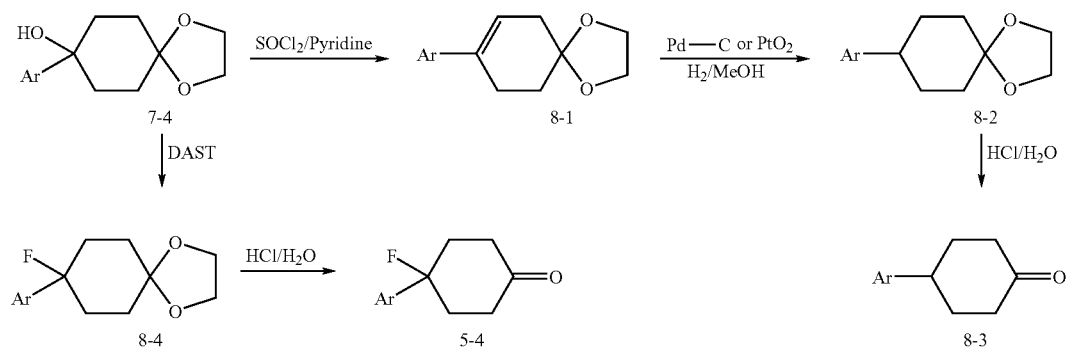

Scheme 10

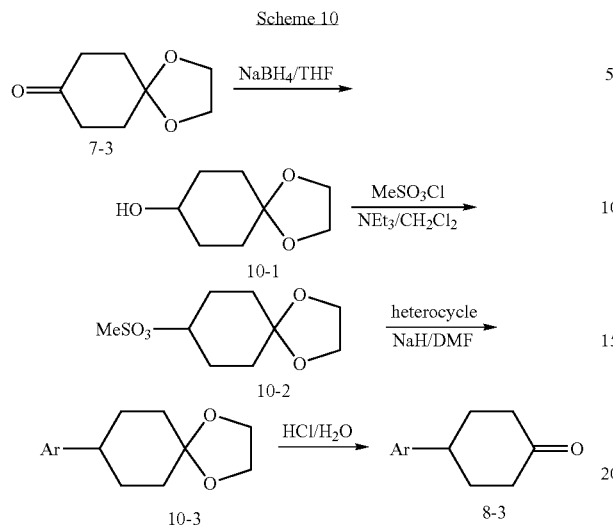

Ar = substituted pyrazole, imidazole, triazole or tetrazole

4-Hydroxy-4-(pyrimidin-2-yl)cyclohexanone 11-4 can be synthesized using a method shown in Scheme 11. 2-Chloropyrimidine 11-1 is subjected to a treatment with LDA/(Bu)₃SnH to give the stannylpyrimidine derivative 11-2. Treatment of 11-2 with n-butyllithium followed by quenching with 1,4-cyclohexanedione mono-ethylene ketal 7-3 provides the ketal intermediate 11-3. Deprotection of the ketal using an acid such as HCl affords the ketone 11-4.

Scheme 11

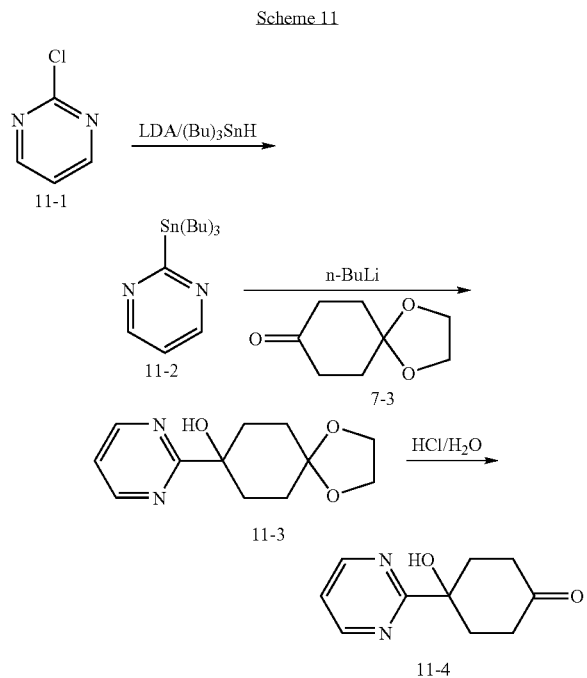

Spirocyclohexanone derivatives of formula 12-3 can be synthesized using the procedures outlined in Scheme 12. Treatment of R-substituted 2-bromobenzyl alcohol 12-1 with n-butyl lithium and addition of the resulting solution to 1,4-cyclohexanedione mono-ethylene ketal 7-3 produces the adduct 12-2. Treatment of 12-2 with TFA/CH₂Cl₂ results in a ring closure and simultaneous removal of the ketal to give the spiroketone 12-3.

Scheme 12

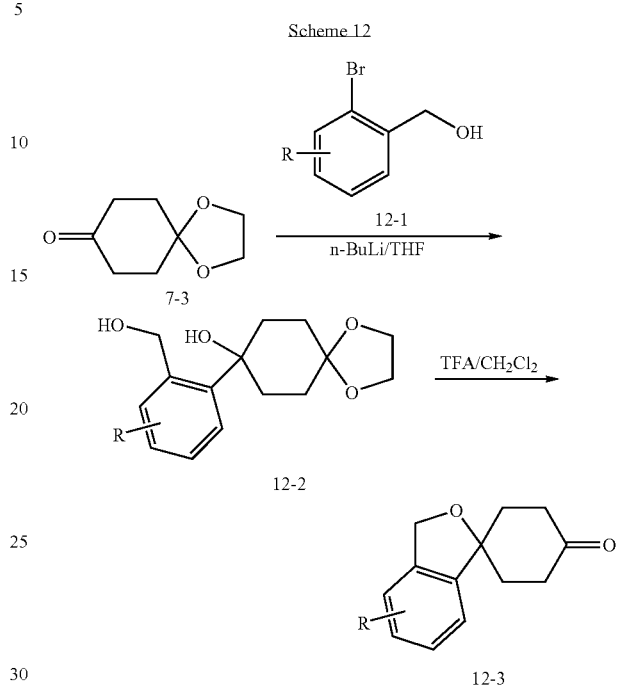

Spiroketones of formulae 13-6 and 13-8 can be obtained using the procedures described in Scheme 13. Following protection of the ketone in 13-1 using ethylene glycol/TMSCl, the diester 13-2 is reduced to a diol 13-3 using a reducing agent such as lithium aluminum hydride. The resulting diol is converted to a dimesylate 13-4 which is reacted with an indene derivative using LHMDS to give the spiroindene intermediate 13-5. Hydrogenation of 13-5 gives rise to the spiroindane derivative 13-7. Deprotection of the ketal in 13-5 and 13-7 using an acid such as HCl affords the corresponding ketones 13-6 and 13-8.

Scheme 13

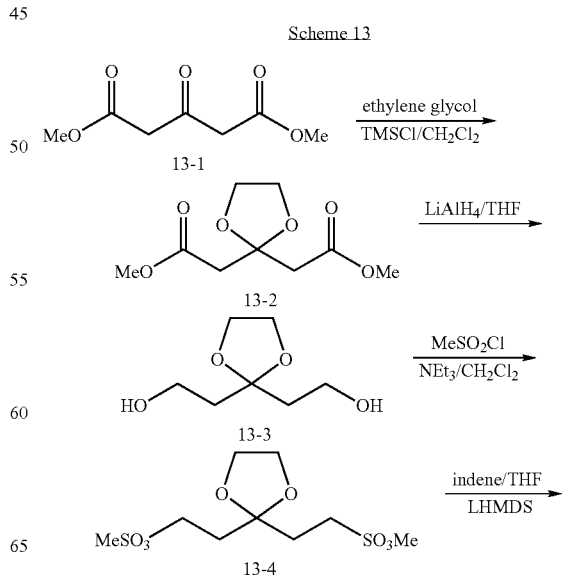

-continued

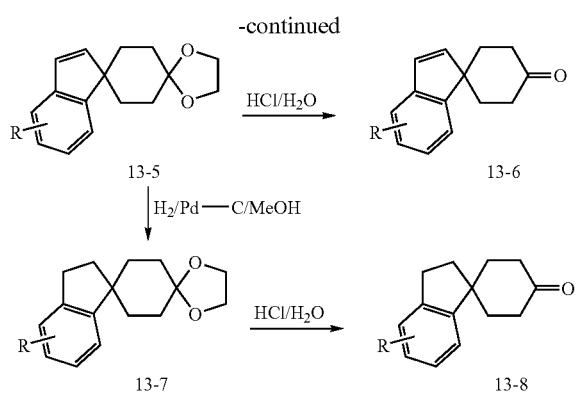

Scheme 14 describes the synthesis of compounds of formula 14-4. Treatment of R-substituted 4-cyanophenylbromide with n-butyl lithium followed by quenching with 1,4-cyclohexanedione mono-ethylene ketal 7-3 produces the intermediate 14-1. Following hydrolysis of the cyano group with a base, the resulting carboxylic acid is coupled with an amine using a coupling agent such as BOP to give the amide 14-3. Treatment of the ketal 14-3 with an acid provides the ketones of formula 14-4.

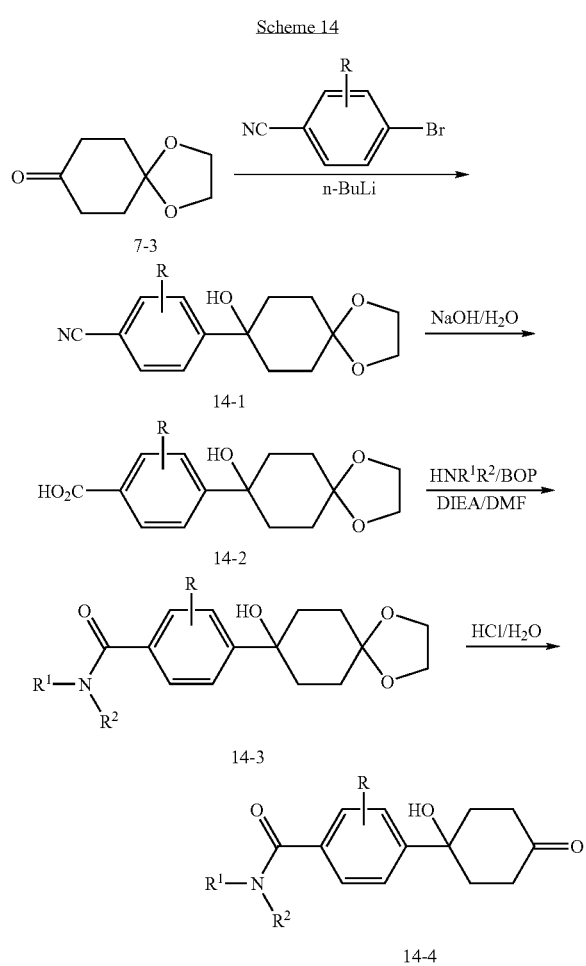

Compounds of formula 15-4 can be prepared as outlined in Scheme 15. Dehydration of the hydroxy intermediate 14-1 by treating with thionyl chloride/pyridine provides the olefin intermediate 15-1. Hydrolysis of the cyano in 15-1 using a base is followed by coupling of the resulting carboxylic acid with an amine, providing the amide intermediate 15-3. Compounds of formula 15-4 are then obtained by hydrogenation of 15-3 using a catalyst such as Pd-C followed by treatment with an acid.

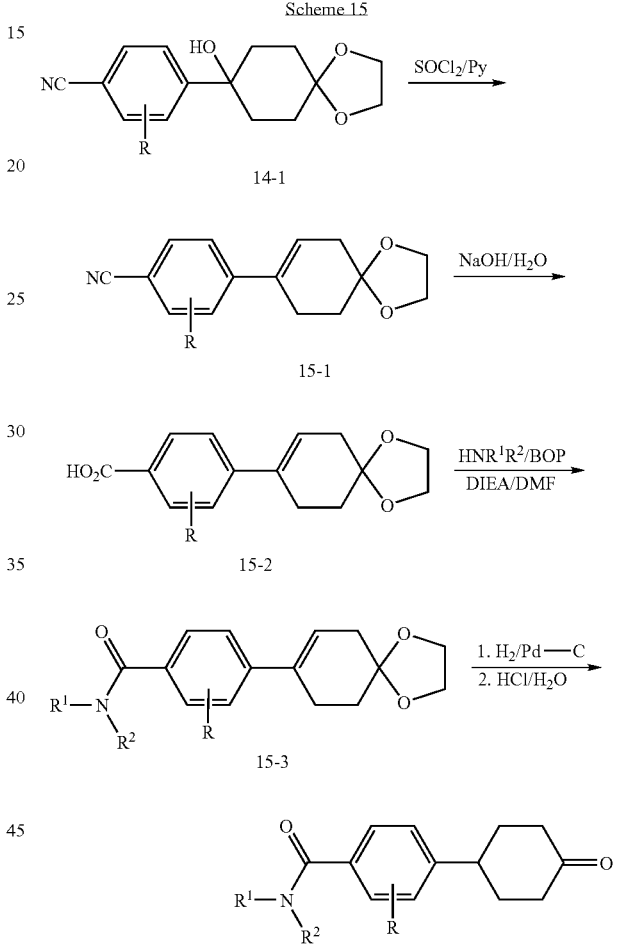

Introduction of a substituent on the aryl or heteroaryl at 4-position of cyclohexanone can be accomplished from the ketal intermediate 16-1 wherein X is a bromo or an iodo. Treatment of 16-1 with butyl lithium followed by quenching with an electrophile such as alkylhalide, aldehyde, ketone, isocyanate, chloroformate or carbonate, Suzuki coupling of 16-1 with a boronic acid or reaction of 16-1 with arylZnX (X=halide) produces the R-substituted aryl derivative 16-2. Alternatively, compounds of formula 16-2 can be generated by converting 16-1 to a boronic ester followed by Suzuki coupling of the resulting boronic ester with RX (X=Br, I). Treatment of the ketal 16-2 with an acid provides the ketone 16-4.

Scheme 16

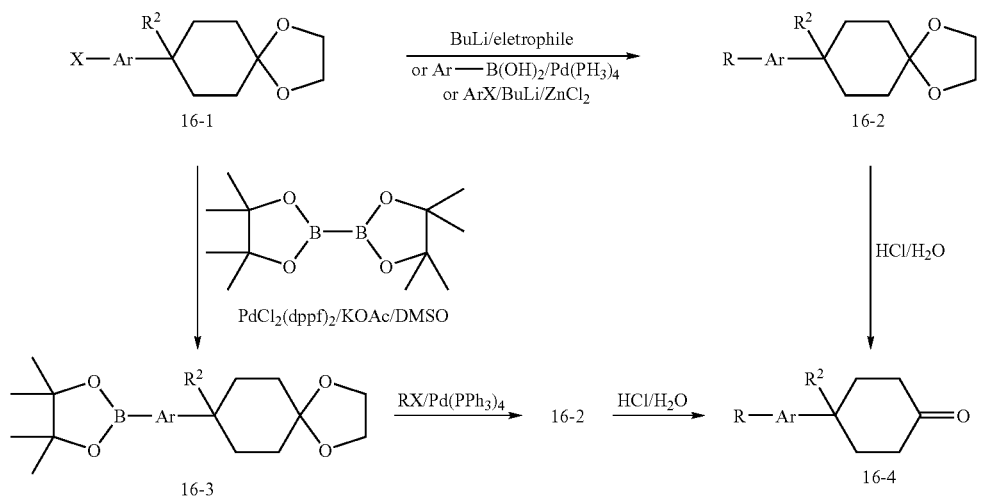

When the Ar in 16-4 is a thiazole residue, introduction of the R substituent can be accomplished following the procedures described in Schemes 17-19. 5-R-substituted 1,3-thiazol-2-yl derivatives of formula 17-5 can be obtained using a sequence depicted in Scheme 17. Treatment of 1,3-thiazole with n-butyl lithium followed by quenching with 1,4-cyclohexanedione mono-ethylene ketal 7-3 generates the intermediate 17-2. Lithiation at 5-position on the thiazole followed by quenching with an electrophile such as an alkylhalide, an isocyanate, carbon dioxide, an aldehyde or a ketone gives rise to the intermediate 17-4. Conversion of the ketal to the ketone 17-5 is accomplished by treatment with an acid.

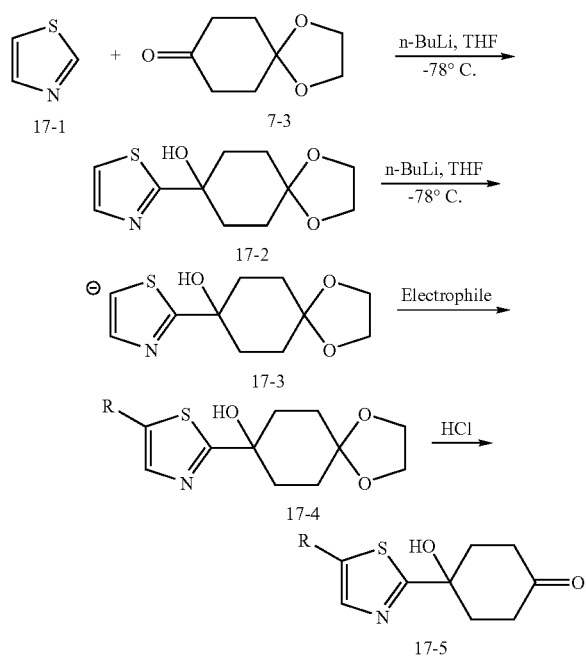

Synthesis of 2-R-substituted 1,3-thiazol-5-yl derivatives of formula 18-3 involves lithiation of 18-1 followed by quenching with 1,4-cyclohexanedione mono-ethylene ketal and conversion of the resulting ketal to a ketone.

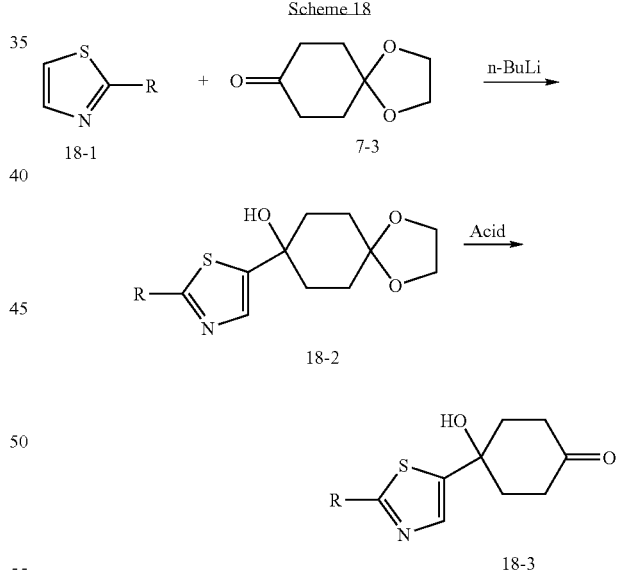

Alternatively, compounds of formula 18-3 can be obtained following a sequence outlined in Scheme 19. Lithiation of the 2-trimethylsilyl protected thiazole 19-1 followed by quenching with 7-3 gives rise to the intermediate 19-2. Following removal of the trimethylsilyl group using TBAF, lithiation of 19-3 followed by quenching with an electrophile such as alkylhalide, aldehyde, ketone, isocyanate, chloroformate or carbonate provides the 5-R-substituted thiazole derivative 19-4. Treatment of 19-4 with an acid affords the ketone 18-3.

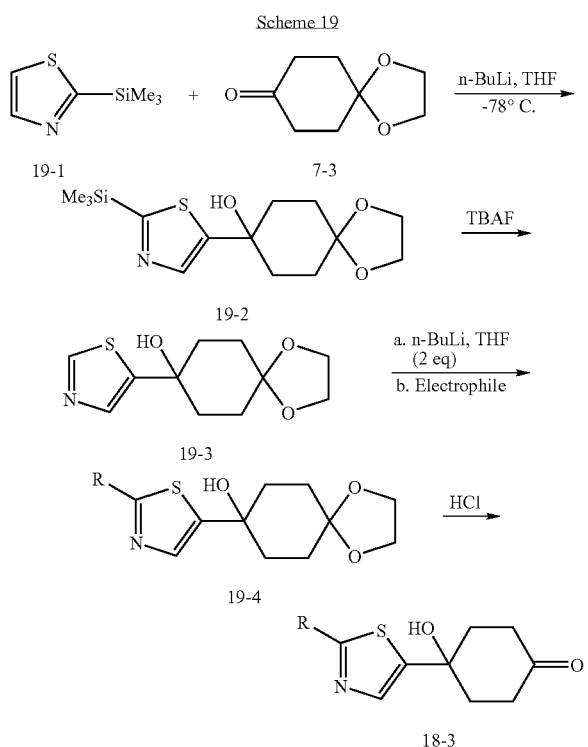

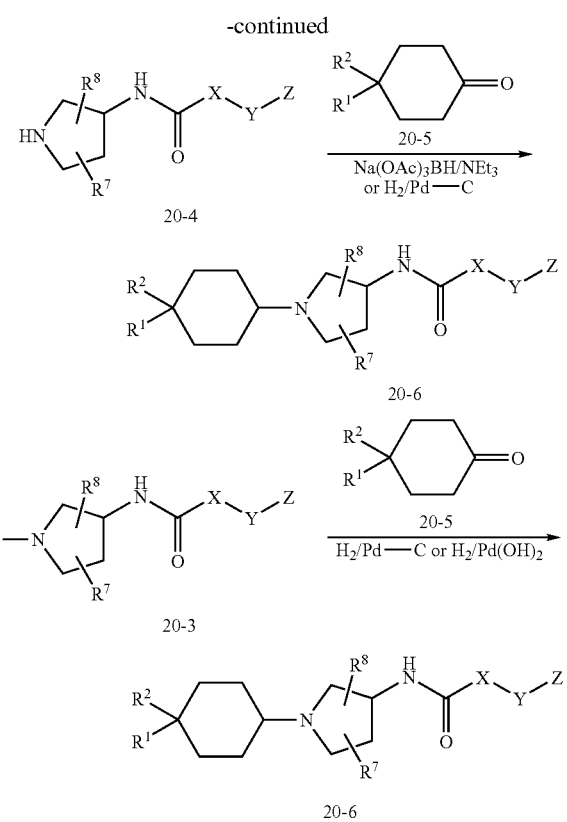

The final compounds of formula I can be obtained by assembling the 3-aminopyrrolidine intermediates with the cyclohexanone intermediates as shown in Scheme 20. Coupling of 3-aminopyrrolidine derivatives 20-1 with a carboxylic acid of formula 20-2 using a coupling agent such as BOP, chloroformate or EDC gives rise to the amide 20-3. After removal of the protecting group (P) on the pyrrolidine nitrogen using an acid or hydrogenation, reductive amination of the resulting pyrrolidine 20-4 with a ketone of formula 20-5 using a reducing agent such as sodium triacetoxyborohydride or catalytic hydrogenation provides the target compounds of formula 20-6. Alternatively, compounds of formula 20-6 can be obtained by reductive amination of 20-3 (P=Cbz, Bn) with a ketone of formula 20-5 via hydrogenation using a catalyst such as Pd-C or Pd(OH)2.

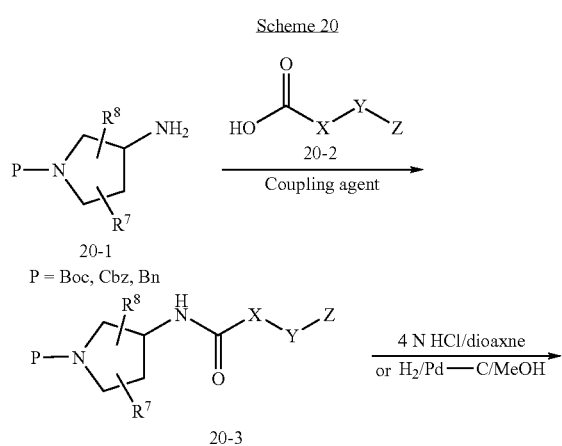

Alternatively, a variety of final compounds of formula I can be synthesized using the procedures outlined in scheme 21. Reductive amination of 3-tert-butoxycarbonylaminopyrrolidine 21-2 with the ketone 21-1 (M. Povarny et al. *Tetrahedron Lett.* 1984, 25, 1311-1312) using a reducing agent such as sodium triacetoxyborohydride provides the intermediate 21-3. Treatment of 21-3 with an acid in aqueous solution converts the ketal to a ketone and removes the Boc group simultaneously. The resulting amine is reacted with di-tert-butyl dicarbonate to give the Boc-protected amino ketone intermediate 21-4. Addition of arylMgX or ArX/BuLi to the ketone 21-4 gives rise to the alcohol 21-5. Removal of Boc using an acid such as 4 N HCl in dioxane followed by coupling of the resulting amine 21-6 with a carboxylic acid of formula 20-2 using a coupling agent such as BOP affords the target compounds of formula 21-7.

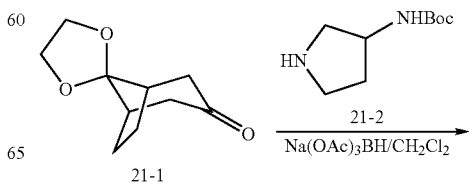

Alternatively, a variety of final compounds of formula I can be prepared using the method given in Scheme 22. Addition of arylMgX or ArX/BuLi to the ketone 21-1 (M. Povarny et al. *Tetrahedron Lett.* 1984, 25, 1311-1312) produces the alcohol 22-1. The ketal in 22-1 is converted to a ketone by treatment with an acid such as HCl in aqueous solution. The resulting ketone 22-2 is subjected to a reductive amination with the pyrrolidine intermediate 20-4 using a reducing agent such as sodium triacetoxyborohydride to give the target compounds of formula 22-3.

Alternatively, a variety of compounds of formula I can be synthesized according to Scheme 23. Swern oxidation of 5-norbornen-2-ol (23-1) (G. T. Wang et al. *J. Org. Chem.* 2001, 66, 2052-2056) followed by addition of arylMgX or ArX/BuLi to the resulting ketone 23-2 gives rise to the tertiary alcohol 23-3 (C. J. Collins, B. M. Benjamin, *J. Am. Chem. Soc.* 1967, 89, 1652-1661). The olefin in 23-3 is converted to an alcohol 23-4 by treatment with borane/hydrogen peroxide (C. J. Collins, B. M. Benjamin, *J. Org. Chem.* 1972, 37, 4358-4366). Swern oxidation of the alcohol provides the ketone 23-5 which is subjected to a reductive amination with a pyrrolidine derivative 20-4 using a reducing agent such as sodium triacetoxyborohydride to afford the target compounds of formula 23-6.

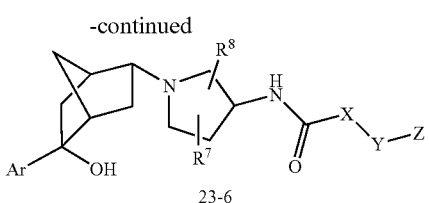

23-6

Alternatively, a variety of compounds of formula I can be synthesized using the protocol depicted in Scheme 24. Reaction of trans-4-aminocyclohexanol 24-1 with di-tert-butyl dicarbonate gives rise to trans-4-tert-butoxycarbonylaminocyclohexanol 24-2 which is subjected to a Swern oxidation to give the ketone 24-3. Reductive amination of the ketone 24-3 with a pyrrolidine derivative 20-4 using a reducing agent such as sodium triacetoxyborohydride provides the intermediate 24-4. After removal of the Boc in 24-4 using an acid such as 4 N HCl in dioxane, the resulting amine 24-5 is acylated with an aryl carboxylic acid chloride or aryl carboxylic acid using a coupling agent such as BOP affords the target compounds of formula 24-6.

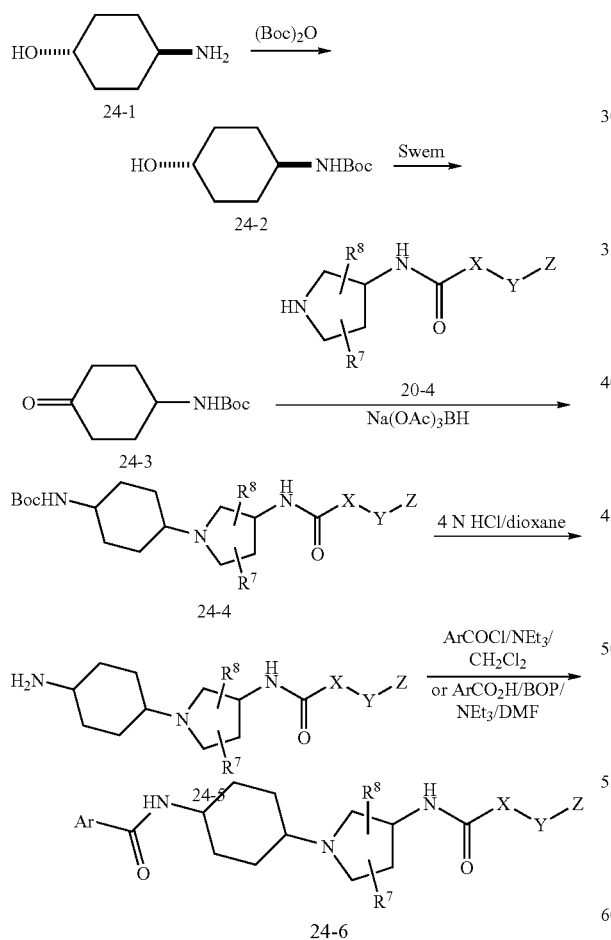

Alternatively, compounds of formula I can be generated via the sequence outlined in Scheme 25. Reduction of the ketone intermediate 7-2 using a reducing agent such as lithium aluminum hydride or sodium borohydride produces the cis diol 25-1. Selective mesylation can be achieved by treating 25-1 with one equivalent of methanesulfonyl chloride to give the mono-mesylate 25-2. Displacement of the mesylate with a 3-aminopyrrolidine derivative such as 21-2 provides the trans-1,4-disubstituted cyclohexane derivative 25-3. Removal of the Boc group using an acid followed by coupling of the resulting amine with a carboxylic acid of formula 20-2 affords the final compounds of formula 25-5.

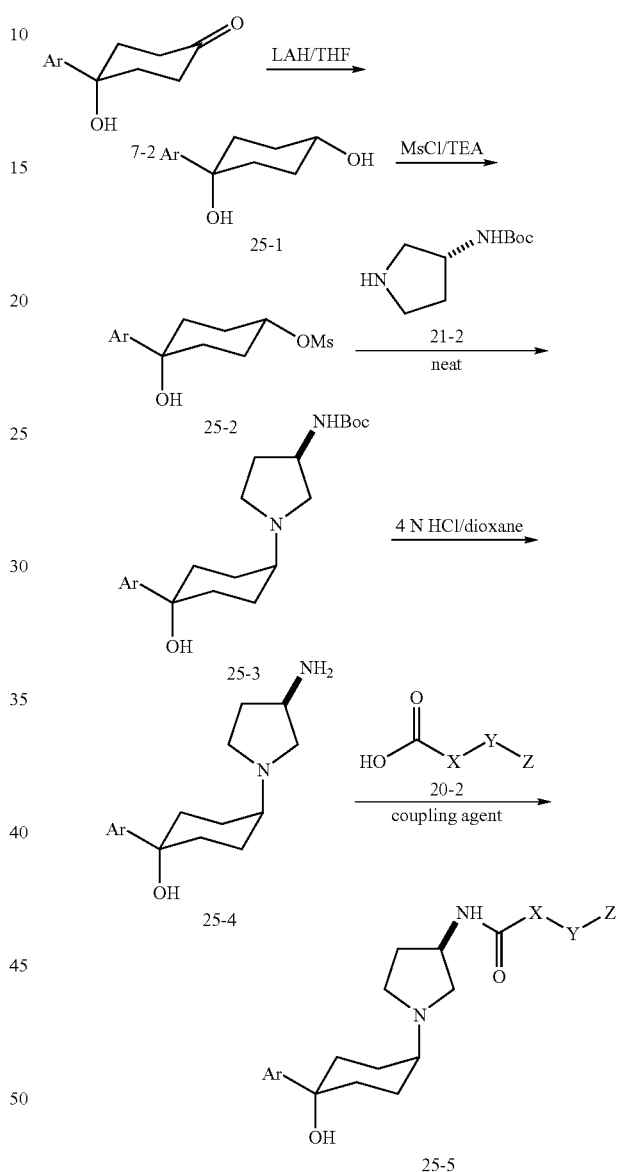

Alternatively, compounds of formula I can be synthesized as described in Schemes 26-27. The intermediate 26-2 can be obtained through three pathways (Scheme 26). Path-1 involves a Mitsunobu coupling of the alcohol 25-1 with the succinimide 26-1 which is prepared by treatment of D-asparagine with thionyl chloride/methanol (esterification) followed by cyclization using a base such as NaOH. Path-2 involves displacement of the mesylate intermediate 25-2 with the succinimide 26-1 in the presence of a base such as CsF. In path-3, the mesylate 25-2 is displaced with sodium azide and the resulting azido intermediate 26-3 is reduced to an amine (26-4) by hydrogenation. Ring opening of D-aspartic acid anhydride 26-5 with 26-4 followed by ring closure with carbonyldiimidazole provides the intermediate 26-2.

Scheme 26

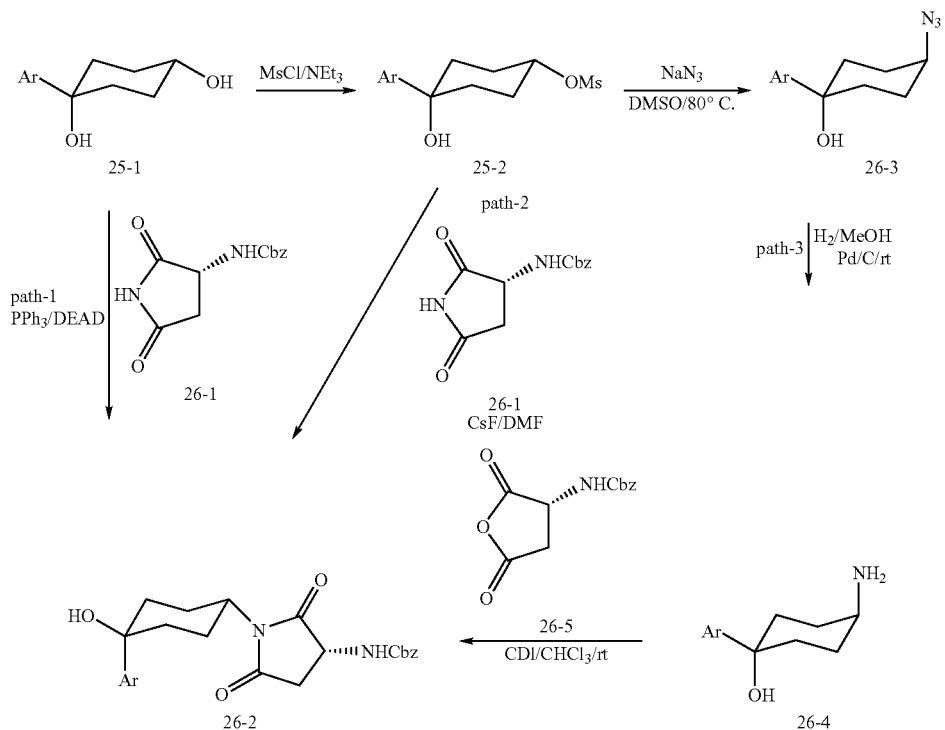

Transformation of the intermediate 26-2 to the final products 27-3 can be achieved using the method given in Scheme 27. Following removal of the Cbz group in 26-2 by hydrogenation, the succinimide 27-1 is reduced to a pyrrolidine by treatment with borane followed by decomplexation via hydrogenation. Coupling of the resulting amine 27-2 with a carboxylic acid of formula 20-2 using a coupling agent such as BOP, chloroformate or EDC provides the final compounds of formula 27-3, Scheme 27

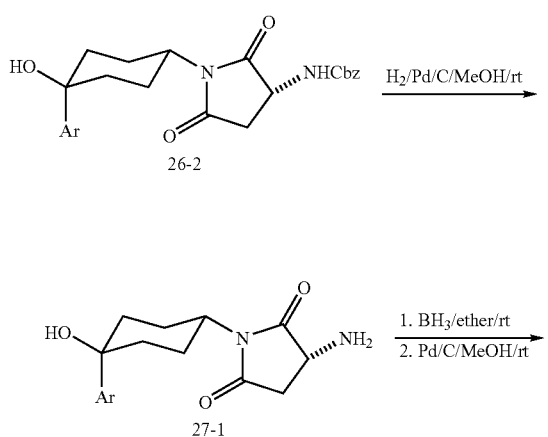

-continued

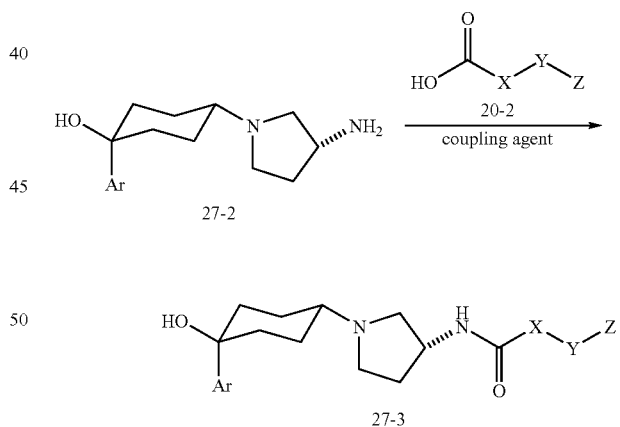

Alternatively, final compounds of formula I can be prepared using a protocol shown in Scheme 28. When the Ar residue on the cyclohexyl in 28-1 bears an iodo group, the iodo can be converted to a boronic acid ester. Coupling of the resulting boronic acid ester with ArX (X=Br, I) in the presence of $PdCl_2$(dppf) provides the R-substituted compounds of formula 28-2. Alternatively, compounds of formula 28-2 can be obtained by Suzuki coupling of a boronic acid with 28-1.

Scheme 28

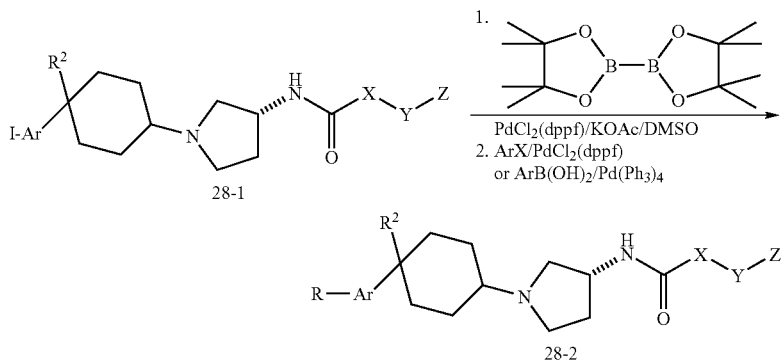

Alternatively, intermediates of formula 25-4 can be obtained according to Scheme 29. Reduction of N-Cbz protected D-aspartic acid dimethyl ester 29-1 using a reducing agent such as LAH followed by treating the resulting diol with methanesulfonyl chloride provides the dimesylate 29-2. Treatment of the amine intermediate 26-4 with the dimesylate 29-2 in the presence of NaI and Proton Sponge produces the pyrrolidine derivative 29-3. Removal of the Cbz group in 29-3 by hydrogenation using a catalyst such as Pd-C yields the intermediates of formula 25-4.

Scheme 29

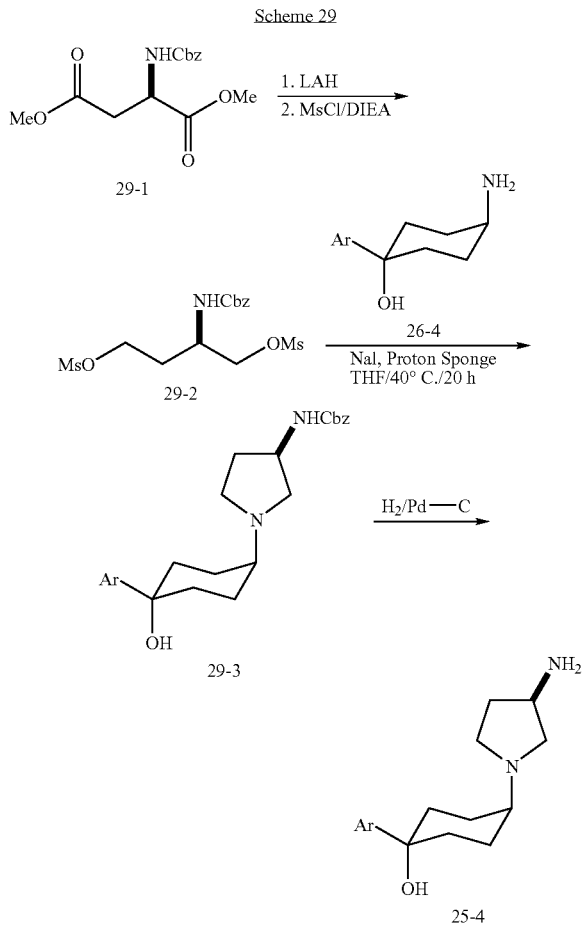

Alternatively, compounds of formula I can be prepared using the protocol outlined in Scheme 30. Reductive amination of a pyrrolidine derivative of formula 30-1 with a ketone derivative of formula 30-2 using a reducing agent such as sodium triacetoxyborohydride gives rise to the intermediate 30-3. Deprotection of the protecting group P (P=Boc or Cbz) followed by coupling of the resulting amine with a carboxylic acid of formula 20-2 affords compounds of formula 30-5.

The compounds of the present invention may be MCP-1 receptor modulators, e.g., antagonists, and may be capable of inhibiting the binding of MCP-1 to its receptor. Surprisingly, the compounds block T cell migration in vitro, and have dramatic effects on the recruitment of inflammatory cells in multiple models of inflammatory diseases. Therefore, the compounds of formula I are useful as agents for the treatment of inflammatory disease, especially those associated with lymphocyte and/or monocyte accumulation, such as arthritis, rheumatoid arthritis, multiple sclerosis, neuropathic pain, atherosclerosis and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

Modulation of chemokine receptor activity, as used in the context of the present invention, is intended to encompass antagonism, agonism, partial antagonism and/or partial agonism of the activity associated with a particular chemokine receptor, preferably the CCR2 receptor. The term composition as used herein is intended to include a product comprising the specified ingredients in the specified amounts, as well as any product which results, directly or indirectly, from combination of the specified ingredients in the specified amounts. By pharmaceutically acceptable it is meant the carrier, diluent or excipient must be compatible with the other ingredients of the formulation and not deleterious to the recipient thereof.

The compounds of formula I of the present invention, and compositions thereof are useful in the modulation of chemokine receptor activity, particularly CCR2. Accordingly, the compounds of the present invention are those which inhibit at least one function or characteristic of a mammalian CCR2 protein, for example, a human CCR2 protein. The ability of a compound to inhibit such a function can be demonstrated in a binding assay (e.g., ligand binding or promotor binding), a signalling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

The invention is illustrated by the following examples, which are not intended to be limiting in any way.

EXAMPLES

Reagents and solvents used below can be obtained from commercial sources such as Aldrich Chemical Co. (Milwaukee, Wis., USA). Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases.

Example 1

Step A

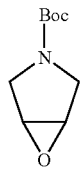

tert-Butyl 6-Oxa-3-azabicyclo[3.1.0]hexane-3-carboxylate. To a solution of 3-chloroperoxybenzoic acid (13.0 g, 75.3 mmol) in CH$_2$Cl$_2$ (50 mL) cooled in an ice bath was dropwise added a solution of tert-butyl 2,5-dihydropyrrole-carboxylate (5 g, 29.5 mmol) in CH$_2$Cl$_2$ (50 mL). The mixture was stirred in the ice bath for 30 minutes and at room temperature overnight. The solid was filtered off. The filtrate was washed twice with a solution of Na$_2$S$_2$O$_3$, NaHCO$_3$ and brine, dried over MgSO$_4$, and concentrated. Chromatography on silica gel eluting with 20% EtOAc in hexanes provided 4.75 g of the desired compound as an oil. MS calculated (M+H)+186, found 186.

Step B

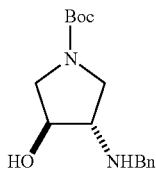

tert-Butyl(3S,4S)-3-(Benzylamino)-4-hydroxypyrrolidine-1-carboxylate. A solution of the epoxide (4.6 g, 24.9 mmol) of step A and benzylamine (5.2 g, 48.6 mmol) in ethanol was stirred at 85° C. overnight. The solvent was removed by concentration under reduced pressure to give a solid. The solid was washed with a mixed solvent of 50% EtOAc/hexanes to provide 6.2 g of the desired compound. MS calculated (M+H)$^+$ 293, found 293.

Step C

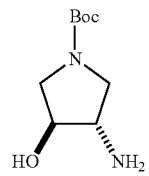

tert-Butyl(3S,4S)-3-Amino-4-hydroxypyrrolidine-1-carboxylate. A solution of the intermediate (5.4 g, 18.5 mmol) of step B, Pd(OH)$_2$/C (0.3 g) in MeOH (200 mL) was stirred under hydrogen at 55 psi overnight. The catalyst was filtered off and the filtrate was concentrated to give 3.7 g of the desired product as a solid. MS calculated (M+H)$^+$ 203, found 203.

Step D

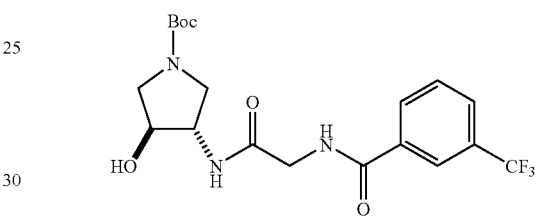

tert-Butyl(3S,4S)-3-Hydroxy-4-[({[3-(trifluoromethyl) benzoyl]amino}acetyl)-amino]pyrrolidine-1-carboxylate.
To a solution of 3-(trifluoromethyl)benzoyl chloride (21 g, 98.7 mmol) in toluene (400 mL) cooled in an ice bath was added a solution of glycine methyl ester hydrochloride (11.5 g, 94 mmol) and triethylamine (100 mL) in water (210 mL) and THF (65 mL). After being stirred at room temperature for 8 hours, the two phases were separated. The water layer was extracted with EtOAc. The combined organic phase was washed with NaHCO$_3$ and brine, dried over MgSO$_4$ and concentrated. The residue was taken up in MeOH (150 mL) and THF (300 mL). To it was added a solution of 2 N NaOH (300 mL). The mixture was stirred at room temperature overnight, acidified with concentrated HCl (pH=2), and extracted with EtOAc twice. The organic phase was washed with brine, dried over MgSO$_4$ and concentrated. Crystallization from EtOAc/hexanes provided 18 g of the desired product (3-trifluoromethylbenzoylamino)acetic acid as a solid. MS calculated (M+H)$^+$ 248, found 248.

To a solution of the carboxylic acid (3.2 g, 13 mmol) obtained above and the amino alcohol (2.02 g, 10 mmol) obtained from step C in DMF (15 mL) cooled in an ice bath was added NEt$_3$ (4.2 mL, 30 mmol) followed by BOP (5.8 g, 13 mmol). The mixture was stirred at room temperature overnight. Brine (100 mL) was added to the mixture. The solution was extracted with EtOAc twice. The organic phase was washed with NaHCO$_3$ and brine, dried over MgSO$_4$ and concentrated. Chromatography on silica gel eluting first with 70% EtOAc/hexanes and then with 20% MeOH/EtOAc provided 3.7 g of the desired product as a solid. MS calculated (M+H)$^+$ 432, found 332 (M+H-Boc)$^+$.

Step E

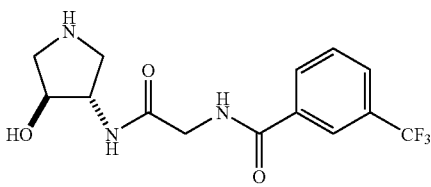

N-(2-{[(3S,4S)-4-Hydroxypyrrolidin-3-yl]amino}-2-oxoethyl)-3-(trifluoromethyl)benzamide. The product (3.7 g, 8.6 mmol) from step D was dissolved in $CH_2Cl_2$ (10 mL) and TFA (10 mL). After being stirred at room temperature for 40 minutes, the volatiles were removed by concentration under reduced pressure to give the desired product as an oil. MS calculated $(M+H)^+$ 332, found 446 $(M+H+TFA)^+$.

Step F

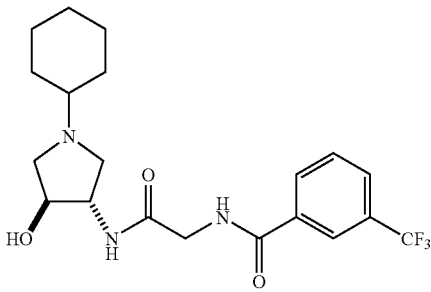

N-(2-{[(3S,4S)-1-Cyclohexyl-4-hydroxypyrrolidin-3-yl]amino}-2-oxoethyl)-3-(trifluoromethyl)benzamide. To a solution of the intermediate (444 mg, 1 mmol) of step E and cyclohexanone (196 mg, 2 mmol) in THF (5 mL) was added $NEt_3$ (0.42 mL, 3 mmol) followed by $Na(OAc)_3BH$ (424 mg, 2 mmol). The mixture was stirred at room temperature overnight and poured into a NaCl solution. The resulting solution was extracted with EtOAc twice. The combined EtOAc layers were washed with $NaHCO_3$ and brine, dried over $MgSO_4$ and concentrated. Purification on silica gel gave 324 mg of the desired product. MS calculated $(M+H)^+$ 414, found 414.

Example 2

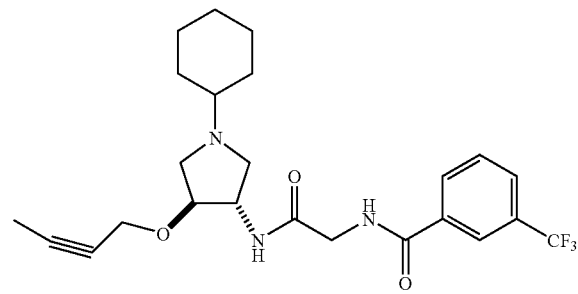

N-(2-{[(3S,4S)-4-(But-2-yn-1-yloxy)-1-cyclohexylpyrrolidin-3-yl]amino}-2-oxoethyl)-3-(trifluoromethyl)benzamide. To a solution of compound of Example 1 (41 mg, 0.1 mmol) in THF (3 mL) cooled in an ice bath was added NaH (16 mg, 0.4 mmol) followed by 2-butynyl bromide (9.6 μL, 0.11 mmol). After being stirred in the ice bath for 3 hours, saturated $NH_4Cl$ was added followed by EtOAc. The EtOAc layer was separated, washed with brine, dried over $MgSO_4$ and concentrated. Purification by reversed phase HPLC gave the title compound as a powder. MS calculated $(M+H)^+$ 466, found 466.

Example 3

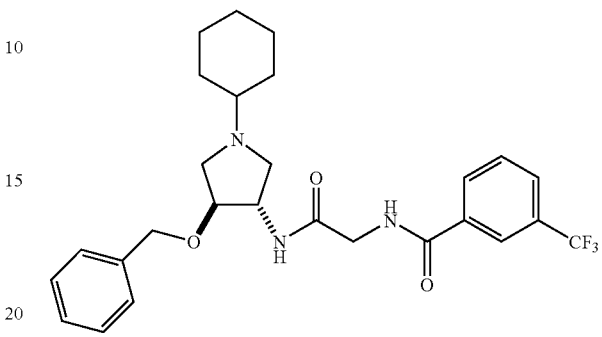

N-(2-{[(3S,4S)-4-(Benzyloxy)-1-cyclohexylpyrrolidin-3-yl]amino}-2-oxoethyl)-3-(trifluoromethyl)benzamide. The title compound was prepared by alkylation of compound of Example 1 with benzyl bromide following the procedure described in Example 2. MS calculated $(M+H)^+$ 504, found 504.

Example 4

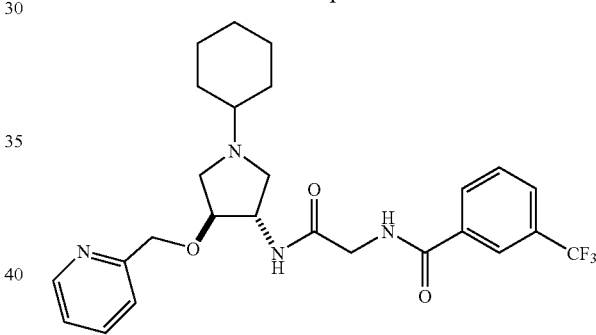

N-(2-{[(3S,4S)-1-Cyclohexyl-4-(pyridin-2-ylmethoxy)pyrrolidin-3-yl]amino}-2-oxoethyl)-3-(trifluoromethyl)benzamide. The title compound was prepared in a fashion similar to that for Example 3. MS calculated $(M+H)^+$ 505, found 505.

Example 5

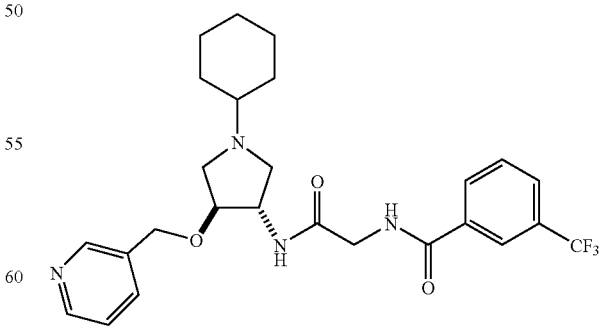

N-(2-{[(3S,4S)-1-Cyclohexyl-4-(pyridin-3-ylmethoxy)pyrrolidin-3-yl]amino}-2-oxoethyl)-3-(trifluoromethyl)benzamide. The title compound was prepared in a fashion similar to that for Example 3. MS calculated $(M+H)^+$ 505, found 505.

Example 6

Step A

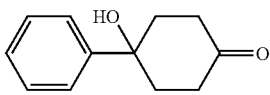

4-Hydroxy-4-phenylcyclohexanone. To a solution of 1,4-cyclohexanedione (6.72 g, 60 mmol) in THF (100 mL) cooled in an ice bath was added a 1 M solution of phenyl magnesium bromide in THF (20 mL, 20 mmol). The mixture was stirred at room temperature for 3 hours and quenched with an NH$_4$Cl solution. The resulting solution was extracted with EtOAc three times. The combined organic phase was washed with brine, dried over MgSO$_4$ and concentrated. Purification on silica gel eluting with 1:1 EtOAc/hexanes yielded 0.83 g (22%) of the title compound. MS calculated (M+H)$^+$ 190, found 173 (M+H—H$_2$O)$^+$.

Step B

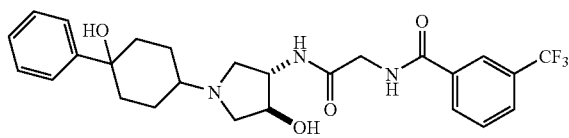

N-(2-{[(3S,4S)-4-Hydroxy-1-(4-hydroxy-4-phenylcyclohexyl)pyrrolidin-3-yl]amino}-2-oxoethyl)-3-(trifluoromethyl)benzamide. To a solution of the ketone of step A (198 mg, 1.1 mmol) and the pyrrolidine intermediate of step E in Example 1 (331 mg, 1 mmol) in THF was added Na(OAc)$_3$BH (424 mg, 2 mmol). The mixture was stirred at room temperature overnight and poured into a NaCl solution. The resulting solution was extracted with EtOAc twice. The combined EtOAc layers were washed with NaHCO$_3$ and brine, dried over MgSO$_4$ and concentrated. Purification on silica gel gave 150 mg of the fast moving isomer (trans isomer, MS calculated (M+H)$^+$ 506, found 506.) and 130 mg of the slow moving isomer (cis isomer, MS calculated (M+H)$^+$ 506, found 506.)

Example 7

Step A

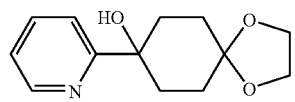

8-Pyridin-2-yl-1,4-dioxaspiro[4.5]decan-8-ol. To a solution of 2-bromopyridine (14 g, 88.6 mmol) in anhydrous ether (300 mL) cooled at –78° C. was slowly added a solution of 2.5 M butyl lithium (36 mL). After the addition, stirring was continued at –78° C. for 1 hour. To it was slowly added a solution of 1,4-cyclohexanedione mono-ethylene ketal (15 g, 96 mmol) in anhydrous ether (300 mL). When the addition was complete, the mixture was allowed to warm to 0° C. and stirring was continued for 1 hour. The reaction was quenched by the addition of an aqueous solution (100 mL) of ammonium chloride (4.5 g). The organic phase was separated and the aqueous phase was extracted with methylene chloride 4 times. The combined organic phases were dried over MgSO$_4$ and concentrated. Crystallization from EtOAc provided 7 g of the desired product. The mother liquid was purified on silica gel eluting with 10% MeOH/EtOAc to give 3 g of the desired product. MS calculated (M+)+236, found 236.0.

Step B

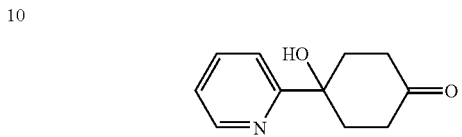

4-Hydroxy-4-pyridin-2-ylcyclohexanone. The above product was dissolved in THF (30 mL) and a 3 N solution of HCl in water (30 mL). The mixture was stirred at 50° C. for 3 hours. After cooling to room temperature, NaHCO$_3$ was added to the solution with stirring until no bubbling occurred. The organic phase was separated and the aqueous layer was extracted with THF three times. The combined organic phase was dried over MgSO$_4$ and concentrated. The residue was triturated with EtOAc to give 5.5 g of the title compound. MS calculated (M+H)$^+$ 192, found 192.

Step C

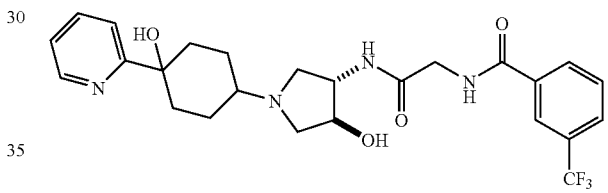

N-(2-{[(3S,4S)-4-Hydroxy-1-(4-hydroxy-4-pyridin-2-yl-cyclohexyl)pyrrolidin-3-yl]amino}-2-oxoethyl)-3-(trifluoromethyl)benzamide. Reductive amination of the ketone from step B with the pyrrolidine derivative from step E in Example 1 using a procedure analogous to that described for Example 6 provided the title compound. MS calculated (M+H)$^+$ 507; found 507.

The following compounds were prepared following the procedures described in Examples 6 and 7.

| Example # | R | MS (M + H)$^+$ |
| --- | --- | --- |
| 8 | 4-methylphenyl | 520 |
| 9 | 3-methylphenyl | 520 |
| 10 | 2-methylphenyl | 520 |
| 11 | 4-bromophenyl | 584 |
| 12 | 3-bromophenyl | 584 |
| 13 | 4-chlorophenyl | 539 |
| 14 | 3-chlorophenyl | 539 |
| 15 | 4-trifluoromethylphenyl | 574 |
| 16 | 3-trifluoromethylphenyl | 574 |
| 17 | 2-trifluoromethylphenyl | 574 |

-continued

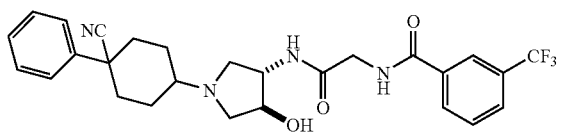

| Example # | R | MS (M + H)+ |
|---|---|---|
| 18 | 4-methoxyphenyl | 536 |
| 19 | 3-methoxyphenyl | 536 |
| 20 | 2-methoxyphenyl | 536 |
| 21 | Pyridin-3-yl | 507 |
| 22 | Pyridin-4-yl | 507 |
| 23 | 6-methoxypyridin-3-yl | 537 |
| 24 | 6-ethoxypyridin-3-yl | 551 |
| 25 | 3,4-methylenedioxyphenyl | 550 |

Example 26

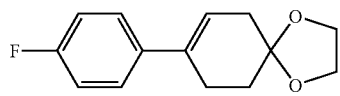

N-(2-{[(3S,4S)-1-(4-Cyano-4-phenylcyclohexyl)-4-hydroxypyrrolidin-3-yl]amino}-2-oxoethyl)-3-(trifluoromethyl)benzamide. The title compound was prepared by ion of 4-cyano-4-phenylcyclohexanone with the intermediate from step E in Example 1 using a procedure analogous to that described for Example 6. MS calculated (M+H)+ 515, found 515.

Example 27

Step A

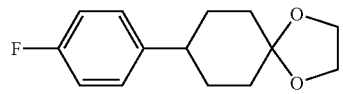

8-(4-Fluorophenyl)-1,4-dioxaspiro[4.5]dec-7-ene. To a solution of 1,4-cyclohexanedione mono-ethylene ketal (8.1 g, 50 mmol) in THF (20 mL) at 10° C. was added a 1 M solution of 4-fluorophenyl magnesium bromide in THF (65 mL, 65 mmol). The resulting mixture was stirred at room temperature for 2 hours before quenching with saturated NH4Cl solution. The solution was extracted with EtOAc 3 times. The combined organic phase was washed with brine, dried over MgSO4 and concentrated. The residue was taken up in toluene (80 mL). To it was added p-toluenesulfonic acid monohydrate (80 mg). The mixture was stirred at reflux with removal of water using a Dean-Stark trap for 2 hours. The resulting solution was washed with saturated NaHCO3 and brine, dried over MgSO4 and concentrated. Purification on silica gel eluting with 5%, 10% and then 15% EtOAc in hexanes provided the title compound (8.8 g, 75%) as a solid. MS calculated (M+H)+ 235, found 235.

Step B

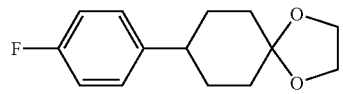

8-(4-Fluorophenyl)-1,4-dioxaspiro[4.5]decane. The intermediate from step A (8.8 g, 37.6 mmol) was dissolved in toluene and to it was added PtO2 (0.5 g). The resulting mixture was stirred under hydrogen at atmospheric pressure overnight. The catalyst was filtered off and the filtrate was removed under reduced pressure. Flash chromatography on silica gel eluting with 5% and then 10% EtOAc in hexanes provided the title compound (8.6 g, 98%) as an oil. MS calculated (M+H)+ 237, found 237.

Step C

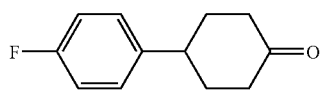

4-(4-Fluorophenyl)cyclohexanone. A solution of the intermediate from step B (8.6 g, 36.5 mmol) in toluene (40 mL), THF (20 mL) and 10% H2SO4 in water (25 mL) was stirred at reflux overnight. After cooling to room temperature, the organic layer was separated, washed with brine, dried over MgSO4 and concentrated. Flash chromatography on silica gel eluting with 5% and then 10% EtOAc in hexanes provided the title compound (6.0 g, 86%) as an oil. MS calculated (M+H)+ 193, found 193.

Step D

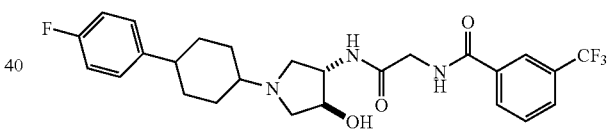

N-[2-({(3S,4S)-1-[4-(4-Fluorophenyl)cyclohexyl]4-hydroxypyrrolidin-3-yl}amino)-2-oxoethyl]-3-(trifluoromethyl)benzamide. The title compound was prepared by reductive amination of the ketone from step C with the intermediate from step E in Example 1 using a procedure analogous to that described for Example 6. MS calculated (M+H)+ 508, found 508.

Example 28

Step A

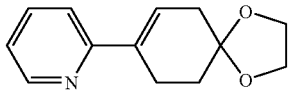

2-(1,4-Dioxaspiro[4.5]dec-7-en-8-yl)pyridine. The ketal (2 g, 8.5 mmol) obtained from step A, Example 7 was dissolved in pyridine (40 mL) and the solution was cooled in an ice bath. To it was added SOCl2 (3.1 mL, 42.5 mmol). The solution was allowed to warm to room temperature and stirring was continued overnight. The reaction was quenched by addition of ice and then water. The resulting solution was extracted with EtOAc three times. The combined EtOAc layer was dried over MgSO₄ and concentrated. Flash chromatography on silica gel eluting with 0 to 55% EtOAc/hexanes provided 1.54 g of the title compound. MS calculated (M+H)⁺ 218, found 218.

Step B

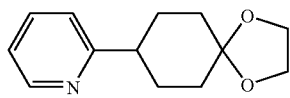

2-(1,4-Dioxaspiro[4.5]dec-8-yl)pyridine. The olefin (1.54 g, 7.1 mmol) obtained above was dissolved in MeOH (40 mL) and Pd/C (160 mg) was added. The system was hydrogenated at 53 psi for 3 hours. The catalyst was filtered off and the filtrate was concentrated to give the title compound. MS calculated (M+H)⁺ 220, found 220.

Step C

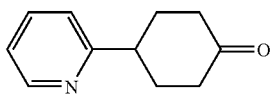

4-Pyridin-3-ylcyclohexanone. The above ketal was converted to ketone by treatment with aqueous HCl following the procedure described in step B, Example 7. MS calculated (M+H)⁺ 176, found 176.

Step D

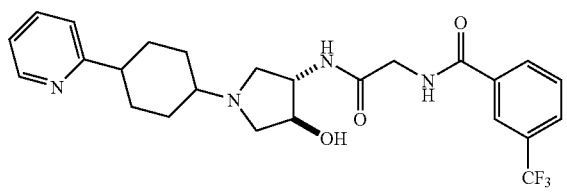

N-(2-{[(3S,4S)-4-Hydroxy-1-(4-pyridin-2-ylcyclohexyl)pyrrolidin-3-yl]amino}-2-oxoethyl)-3-(trifluoromethyl)benzamide. The title compound was prepared by reductive amination of the ketone obtained above with the pyrrolidine intermediate obtained from step E, Example 1 using a procedure analogous to that described for Example 6. MS calculated (M+H)⁺ 490, found 490.

Example 29

Step A

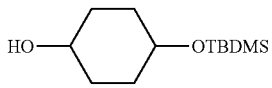

4-{[tert-Butyl(dimethyl)silyl]oxy}cyclohexanol. To a solution of 1,4-cyclohexanediol (5 g, 43 mmol), imidazole (2.92 g, 43 mmol) and NEt₃ (7 mL) in CH₂Cl₂ (100 mL) cooled in an ice bath was added tert-butyldimethylsilyl chloride (6.47 g, 43 mmol). The mixture was stirred at room temperature overnight. Water was added and the organic phase was separated. The aqueous layer was extracted with EtOAc. The combined organic phase was dried over MgSO₄ and concentrated. Chromatography on silica gel eluting with 3:1 EtOAc/hexanes provided the title compound (4.2 g, 42%) as an oil. MS calculated (M+H)⁺ 231, found 231.

Step B

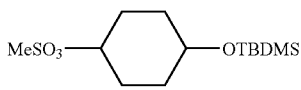

4-{[tert-Butyl(dimethyl)silyl]oxy}cyclohexyl methanesulfonate. To a solution of the silyl intermediate obtained from step A in CH₂Cl₂ (40 mL) cooled in an ice bath was added NEt₃ (6 mL) followed by methanesulfonyl chloride (1.8 mL). After being stirred at room temperature for 2 hours, the solution was diluted with water. The organic phase was separated and the water layer was extracted with EtOAc. The combined organic phase was dried over MgSO₄ and concentrated. Purification on silica gel eluting with 2:1 EtOAc/hexanes yielded the title compound (4.6 g, 82%) as an oil. MS calculated (M+H)⁺ 309, found 309.

Step C

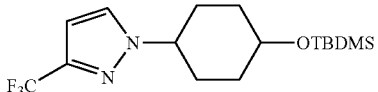

1-(4-{[tert-Butyl(dimethyl)silyl]oxy}cyclohexyl)-3-(trifluoromethyl)-1H-pyrazole. To a solution of 3-trifluoromethyl-1H-pyrazole (1.0 g, 7.35 mmol) in DMF (10 mL) cooled in an ice bath was added NaH (0.3 g, 60% in mineral oil). The mixture was stirred for 10 minutes before the mesylate (1.13 g, 3.68 mmol) of step B in DMF (5 mL) was added. Stirring was continued at room temperature for 1 hour and then at 100° C. overnight. After being cooled to room temperature, the solution was poured into ice water and extracted with EtOAc three times. The combined extract was washed with brine, dried over MgSO₄ and concentrated. Purification on silica gel eluting with 5:1 EtOAc/hexanes provided the title compound (0.56 g, 44%) as an oil. MS calculated (M+H)⁺ 349, found 349.

Step D

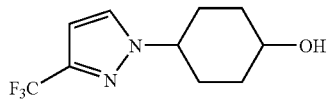

4-[3-(Trifluoromethyl)-1H-pyrazol-1-yl]cyclohexanol.
The intermediate (0.56 g, 1.6 mmol) from step C was dissolved in CH₂Cl₂ (10 mL) and to it was added a 1 M solution of TBAF in CH₂Cl₂ (5 mL). After being stirred at room temperature for 2 hours, the solution was diluted with CH₂Cl₂. The resulting solution was washed with brine, dried over MgSO₄ and concentrated. Purification on silica gel eluting with 2:1 EtOAc/hexanes provided the title compound (0.27 g, 71%) as an oil. MS calculated (M+H)+ 235, found 235.

Step E

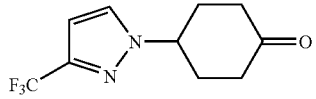

4-[3-Trifluoromethyl)-1H-pyrazol-1-yl]cyclohexanone. To a solution of oxalyl chloride (0.25 mL, 2.88 mmol) in THF (10 mL) cooled at −78° C. was added DMSO (0.3 mL, 4.23 mmol). The mixture was stirred for 20 minutes and to it was added a solution of the alcohol step D (0.27 g, 1.15 mmol) in THF (2 mL) followed by NEt3 (1 mL, 7.1 mmol). After being stirred at room temperature for 2 hours, the solution was diluted with EtOAc. The resulting solution was washed with brine, dried over MgSO4 and concentrated. Purification on silica gel eluting with 2:1 EtOAc/hexanes provided the title compound (0.22 g, 82%) as an oil. MS calculated (M+H)+ 233, found 233.

Step F

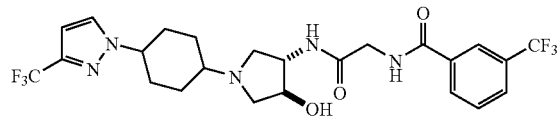

N-{2-[((3S,4S)-4-Hydroxy-1-{4-[3-(trifluoromethyl)-1H-pyrazol-1-yl]cyclohexyl}pyrrolidin-3-yl)amino]-2-oxoethyl}-3-(trifluoromethyl)benzamide. The title compound was prepared by reductive amination of the ketone from step E with the pyrrolidine intermediate from step E, Example 1 using a procedure analogous to that described for Example 6. MS calculated (M+H)+ 548, found 548.

The following compounds were prepared using the procedures analogous to those described for Examples 27-29.

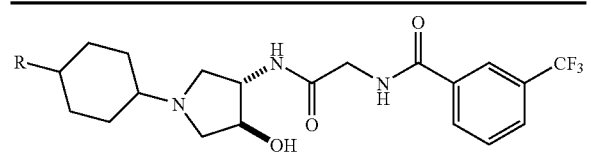

| Example # | R | MS (M + H)+ |
|---|---|---|
| 30 | 3-fluorophenyl | 508 |
| 31 | 4-chlorophenyl | 523 |
| 32 | 3-chlorophenyl | 523 |
| 33 | 4-bromophenyl | 568 |
| 34 | 3-bromophenyl | 568 |
| 35 | 4-methylphenyl | 504 |
| 36 | 3-methylphenyl | 504 |
| 37 | 2-methylphenyl | 504 |
| 38 | 4-methoxyphenyl | 520 |
| 39 | 3-methoxyphenyl | 520 |
| 40 | Pyridin-4-yl | 490 |
| 41 | Pyridin-3-yl | 490 |
| 42 | 5-methylpyridin-2-yl | 504 |
| 43 | 6-methylpyridin-2-yl | 504 |
| 44 | Quinolin-4-yl | 540 |
| 45 | 3-methyl-1H-pyrazol-1-yl | 494 |

-continued

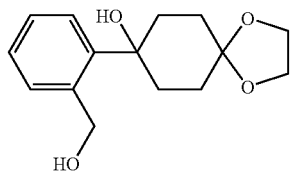

| Example # | R | MS (M + H)+ |
|---|---|---|
| 46 | 3,5-dimethyl-1H-pyrazol-1-yl | 508 |
| 47 | 4-trifluoromethylphenyl | 558 |
| 48 | 3-trifluoromethylphenyl | 558 |
| 49 | 3,4-methylenedioxyphenyl | 534 |

Example 50

Step A

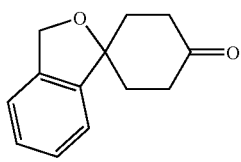

8-[2-(Hydroxymethyl)phenyl]-1,4-dioxaspiro[4.5]decan-8-ol. To a solution of 2-bromobenzyl alcohol (3.0 g, 16 mmol) in THF (40 mL) cooled at −78° C. was added a 2.5 M solution of n-BuLi in hexanes (14.1 mL). The mixture was stirred at −4° C. for 1 hour and cooled back to −78° C. To it was added a solution of 1,4-cyclohexanedione mono-ethylene ketal (2.5 g, 16 mmol) in THF (10 mL) over 15 minutes. Stirring was continued at −78° C. for 30 minutes and at −4° C. for 1 hour. The reaction was quenched by addition of a solution of NH4Cl in water. The resulting solution was extracted with EtOAc three times. The combined extract was washed with brine, dried over MgSO4 and concentrated. Purification on silica gel eluting with 5% MeOH/CH2Cl2 provided the title compound. MS calculated (M+H)+ 265, found 287 (M+Na)+.

Step B 3H,4'H-Spiro[2-benzofuran-1,1'-cyclohexan]-4'-one. The ketal was dissolved in 80% TFA/CH2Cl2. After being stirred at room temperature for 3.5 hours, the solution was concentrated. The residue was taken up in EtOAc. The resulting solution was washed with 1 N NaOH and brine, dried over MgSO4 and concentrated.

Step C

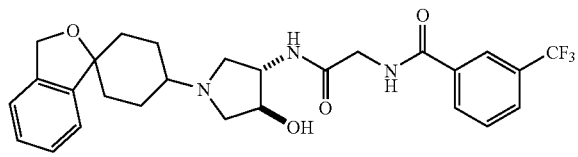

N-(2-{[(3S,4S)-4-Hydroxy-1-(3H-spiro[2-benzofuran-1,1'-cyclohexan]-4'-yl)pyrrolidin-3-yl]amino}-2-oxoethyl)-3-(trifluoromethyl)benzamide. The title compound was obtained by reductive amination of the ketone of step B with the intermediate from step E in Example 1 using a procedure analogous to that described for Example 6. MS (M+H)⁺ 518, found 518.

Example 51

Step A

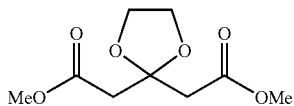

Dimethyl 2,2'-(1,3-Dioxolane-2,2-diyl)diacetate. To a solution of 4.2 g (24 mmol) of dimethyl 3-oxopentanedioate and 2.7 ml (48 mmol) of ethylene glycol in 50 mL of methylene chloride was added 12 mL (96 mmol) of TMSCl at room temperature. The reaction mixture was stirred at 50° C. for 3 days. The reaction was quenched with saturated NaHCO₃ aqueous solution. The aqueous layer was extracted with ether. The combined organic layers were washed with brine, dried over Na₂SO₄, evaporated under reduced pressure. Chromatography on silica gel gave the desired product, dimethyl 2,2'-(1,3-dioxolane-2,2-diyl)diacetate (2.6 g, 12 mmol, yield: 50%): MS (m/e): 219 (M+1)⁺.

Step B

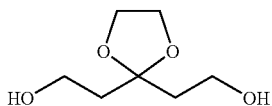

2,2'-(1,3-Dioxolane-2,2-diyl)diethanol. To a solution of 2.6 g (12 mmol) of dimethyl 2,2'-(1,3-dioxolane-2,2-diyl)diacetate in 100 mL of dry THF was added 1.4 g (36 mmol) of LAH at 0° C. The reaction mixture was then refluxed for 1 h, was quenched with 15% NaOH aqueous solution (3 mL) and water (3 mL). The mixture was stirred overnight, filtered through celite. The residue was washed twice with THF (100 mL×2). The combined organic phase was evaporated. Chromatography on silica gel afforded 1.3 g (8.0 mmol, yield: 66%) of 2,2'-(1,3-dioxolane-2,2-diyl)diethanol: MS (m/e): 163 (M+1)⁺.

Step C

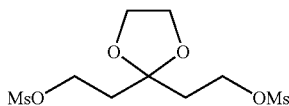

1,3-Dioxolane-2,2-diyldiethane-2,1-diyl dimethanesulfonate. To a solution of 2,2'-(1,3-dioxolane-2,2-diyl)diethanol (1.3 g, 8.0 mmol) in methylene chloride (100 mL) was added triethylamine (3.4 mL, 24 mmol) at room temperature. The solution was cooled down to −40° C. and then mesyl chloride (1.65 mL, 20 mmol) was added dropwise. The reaction mixture was stirred at −40° C. for 30 min, then warmed up to 0° C. gradually. The reaction was quenched with saturated aqueous NaHCO₃ solution. The aqueous layer was extracted with methylene chloride. The combined organic extracts were washed with brine, dried over Na₂SO₄, then evaporated to afford the crude product, 1,3-dioxolane-2,2-diyldiethane-2,1-diyl dimethanesulfonate: MS (m/e): 319 (M+1)⁺.

Step D

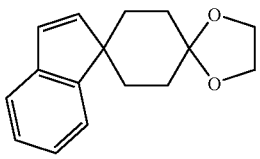

Dispiro[1,3-dioxolane-2,1'-cyclohexane-4',1"-indene]. To a solution of indene (0.5 g, 4.3 mmol) in THF (10 mL) cooled in an ice bath was added a 1 M solution of LDS in THF (8.6 mL, 8.6 mmol). After being stirred for 30 minutes, a solution of the above crude dimesylate in THF (5 mL) was added. The mixture was stirred at room temperature overnight and quenched by addition of cold water. The resulting solution was extracted with EtOAc twice. The combined extract was dried over MgSO₄ and concentrated. Purification on silica gel eluting with 1:5 EtOAc/hexanes provided 250 mg (26%) of the title compound. MS calculated (M+H)⁺ 243, found 243.

Step E

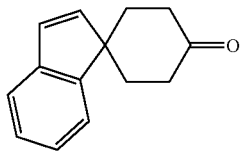

4H-Spiro[cyclohexane-1,1'-inden]-4-one. To a solution of the ketal of step D (0.24 g, 1 mmol) in THF (3 mL) was added a solution of 1N HCl (3 mL). After being stirred at room temperature overnight, the solution was diluted with EtOAc and a solution of saturated NaHCO₃. The organic phase was separated and the water layer was extracted with EtOAc twice. The combined organic phase was dried over MgSO₄ and concentrated. Purification on silica gel eluting with 1:5 EtOAc/hexanes provided 170 mg (86%) of the title compound. MS calculated (M+H)⁺ 199, found 199.

Step F

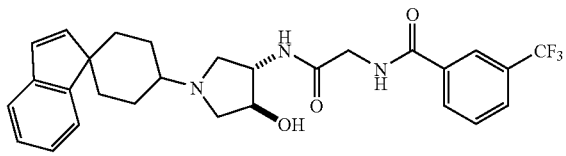

N-(2-{[(3S,4S)-4-Hydroxy-1-spiro[cyclohexane-1,1'-inden]-4-ylpyrrolidin-3-yl]amino}-2-oxoethyl)-3-(trifluoromethyl)benzamide. Reductive amination of the pyrrolidine intermediate from step E, Example 1 with the ketone of step E using a procedure analogous to that described for Example 6 afforded the title compound. MS calculated (M+H)⁺ 514, found 514.

Example 52

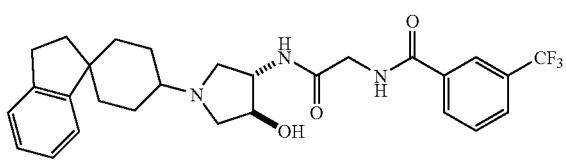

N-(2-{[(3S,4S)-1-(2',3'-Dihydrospiro[cyclohexane-1,1'-inden]-4-yl)-4-hydroxypyrrolidin-3-yl]amino}-2-oxoethyl)-3-(trifluoromethyl)benzamide. Hydrogenation of compound of Example 52 using Pd/C as a catalyst provided the title compound. MS calculated (M+H)⁺ 516; found 516.

Example 53

Step A

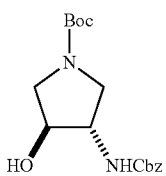

tert-Butyl(3S,4S)-3-{[(Benzyloxy)carbonyl]amino}-4-hydroxypyrrolidine-1-carboxylate. To a solution of 1.4 g of the amine obtained from step C in Example 1 (6.9 mmol) in THF (40 mL) was added 2.1 g of CbzSu (8.4 mmol) followed by Et3N (1.1 mL, 7.6 mmol). The reaction was stirred at room temperature overnight. Solvent was removed under vacuum. The residue was taken up in EtOAc/water. The two phases were separated and the water phase was extracted twice with EtOAc. The combined organic was dried over Na₂SO₄ and concentrated under vacuum. Column chromatography on silica gel eluting with 2:1 hexane/EtOAc provided 1.6 g (68%) of the title compound. MS found: 237.2 (M-Boc+1)⁺, 336.9 (M+1)⁺, 359.2 (M+Na)⁺.

Step B

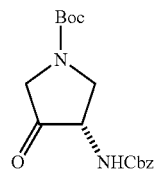

tert-Butyl(3S)-3-{[(Benzyloxy)carbonyl]amino}-4-oxopyrrolidine-1-carboxylate. To a solution of 0.7 mL of oxalyl chloride in THF (10 mL) cooled at −78° C. was added 1.5 mL of anhydrous DMSO. After stirring for 5 minutes a solution of 1.6 g of the alcohol intermediate of step A in 20 mL of anhydrous THF was added, which was followed by addition of 2.3 mL of triethylamine. The cold bath was removed. The reaction was stirred at room temperature for 0.5 h. The reaction mixture was quenched with 50/50 mL of EtOAc/water. Water phase was extracted twice with EtOAc. The combined organic phase was dried over Na₂SO₄ and concentrated under vacuum. Column chromatogrphy on silica gel using 2:1 hexane/EtOAc provided 1.44 g of the title compound. MS (M+H)⁺ 335.

Step C

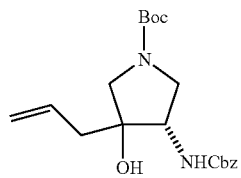

tert-Butyl(4S)-3-Allyl-4-{[(benzyloxy)carbonyl]amino}-3-hydroxypyrrolidine-1-carboxylate. To a solution of 1.44 g of the ketone of step B in 20 mL of anhydrous T° F. cooled at 0° C. was added a solution of 6.2 mL of 1 M allyl magnesium bromide. The color turned dark right away. After being stirred at room temperature overnight, the reaction mixture was quenched with 50/50 mL of EtOAc/water. Water phase was extracted twice with EtOAc. The combined organic phase was dried over Na₂SO₄ and concentrated under vacuum. Column chromatography on silica gel using 3:1~2:1 hexane/EtOAc as eluent provided 0.85 g of the title compound. MS (M+H)⁺ 377.

Step D

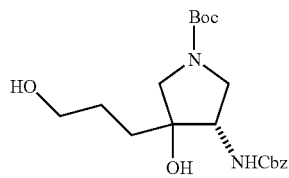

tert-Butyl(4S)-4-{[(Benzyloxy)carbonyl]amino}-3-hydroxy-3-(3-hydroxypropyl)pyrrolidine-1-carboxylate. To a solution of 0.85 g of allyl alcohol of step C in 20 mL of anhydrous THF was added a solution of 15 mL of 0.5 N 9-BBN. The reaction was stirred for 2 days. Water (0.5 mL) was added followed with 1 mL of 30% H₂O₂ and 1 mL of NaOAc/water. After being stirred for 1 h, the organic phase was separated. The water solution was neutralized with HCl and extracted with EtOAc twice. The combined organic phase was dried over Na$_2$SO$_4$. Solvent was removed under vacuum. Column chromatography on silica gel using pure EtOAc as eluent provided 0.80 g of the title compound. MS (M+H)$^+$ 395.

Step E

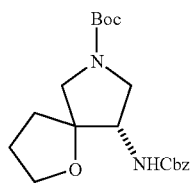

tert-Butyl(9S)-9-{[(Benzyloxy)carbonyl]amino}-1-oxa-7-azaspiro[4.4]nonane-7-carboxylate. To a solution of 0.80 g of the diol of step D in 15 mL of dichloromethane at 0° C. were added 0.2 mL of methanesulfonyl chloride and 0.8 mL of triethylamine. After being stirred for 1 hour, the mixture was refluxed at 60° C. overnight. Solvent was removed under vacuum. The residue was taken up in EtOAc/water and the two phases were separated. The water phase was extracted with EtOAc twice. The combined organic was dried over Na$_2$SO$_4$. Solvent was removed under vacuum. Column chromatography on silica gel using 15% EtOAc/hexane to 100% EtOAc as eluent provided 0.32 g of the title compound. MS (M+H)$^+$ 377.

Step F

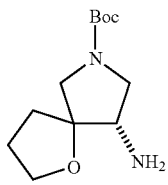

tert-Butyl(9S)-9-Amino-1-oxa-7-azaspiro[4.4]nonane-7-carboxylate. The sample obtained above (0.3 g) was dissolved in 10 mL of methanol. To it was added 0.2 g Pd/C. The mixture was stirred under 1 atm H$_2$ balloon overnight and filtered. Solvent was removed under vacuum to give 0.22 g crude product. Column chromatography on silica gel eluting with 2:1 EtOAc/MeOH provided 0.13 g (64%) of the title compound. MS found: 143.1 (M-Boc+1).

Step G

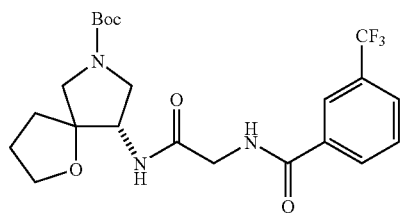

tert-Butyl(9S)-9-[({[3-(Trifluoromethyl)benzoyl]amino}acetyl)amino]-1-oxa-7-azaspiro[4.4]nonane-7-carboxylate. To a solution of the amine of step F (0.13 g, 0.54 mmol) and (3-trifluoromethylbenzoylamino)acetic acid (0.133 g, 0.54 mmol) in DMF (7 mL) in an ice bath was added BOP reagent (0.238 g, 0.54 mmol) followed by triethylamine (0.5 mL, 3.5 mmol). The reaction was stirred at room temperature overnight. Solvent was removed at 60° C. under full vacuum. The residue was taken up in EtOAc/NaHCO$_3$ aqueous solution. The two phases were separated and the water phase was extracted with EtOAc twice. The combined organic phase was dried over Na$_2$SO$_4$ and concentrated under vacuum. Column chromatography on silica gel eluting with EtOAc gave 0.18 g (70%) of the title compound as a mixture of two diastereomers. MS (M+H)$^+$ 472.

Step H

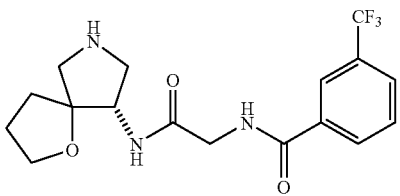

N-{2-[(9S)-1-Oxa-7-azaspiro[4.4]non-9-ylamino]-2-oxoethyl}-3-(trifluoromethyl)benzamide. The intermediate of step G (0.18 g) was mixed with 5 mL of 4 N HCl/dioxane. The solution was stirred for 2 h and concentrated under vacuum. MS (M+H)$^+$ 372.

Step I

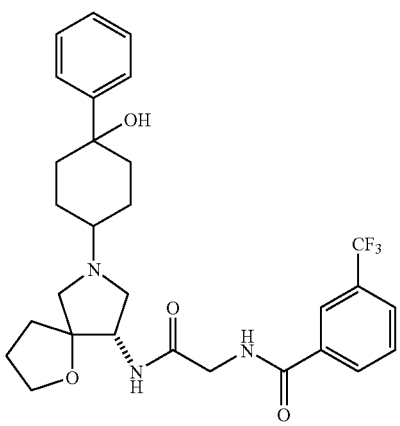

N-(2-{[(9S)-7-(4-Hydroxy-4-phenylcyclohexyl)-1-oxa-7-azaspiro[4.4]non-9-yl]amino}-2-oxoethyl)-3-(trifluoromethyl)benzamide. To a solution of the amine of step H (90 mg, 0.243 mmol) and 4-hydroxy-4-phenyl-cyclohexanone (43 mg, 0.226 mmol) in THF (5 mL) was added sodium triacetoxyborohydride (129 mg, 0.61 mmol) followed by Et$_3$N (0.29 ml, 2 mmol). The mixture was stirred at room temperature overnight. Solvent was removed under vacuum. The residue was taken up in EtOAc/NaHCO$_3$ aqueous solution. The two phases were separated and the water layer was extracted with EtOAc twice. The combined organic phase was dried (Na$_2$SO$_4$) and concentrated. Purification by prep-HPLC provided two isomers. MS: 546.4 (M+1)$^+$.

Example 54

Step A

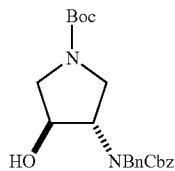

tert-Butyl(3S,4S)-3-{Benzyl[(benzyloxy)carbonyl]amino}-4-hydroxypyrrolidine-1-carboxylate. To a solution of the intermediate from step B in Example 1 (3.2 g, 11 mmol) and N-(benzyloxycarbonyloxy)succinimide (4.23 g, 11 mmol) in DMF (20 mL) was added NEt$_3$ (4.6 mL, 33 mmol). The mixture was stirred at room temperature overnight and diluted with water. The resulting solution was extracted with EtOAc three times. The combined extract was washed with brine three times, dried over MgSO$_4$ and concentrated. Purification on silica gel eluting with 30% EtOAc/hexanes provided the title compound (2.5 g, 53%) as an oil. MS calculated (M+H)$^+$ 427, found 449 (M+Na)$^+$.

Step B

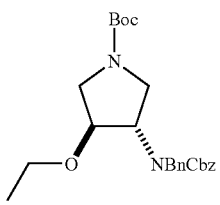

tert-Butyl(3S,4S)-3-{Benzyl[(benzyloxy)carbonyl]amino}-4-ethoxypyrrolidine-1-carboxylate. To a solution of the above intermediate (1 g, 2.3 mmol) in THF (6 mL) cooled in an ice bath was added NaH (184 mg, 4.6 mmol). After the mixture was stirred for 30 minutes, iodoethane (0.96 mL, 12 mmol) was added The mixture was stirred at room temperature overnight and quenched with a solution of NH$_4$Cl in water. The resulting solution was extracted with EtOAc three times. The combined extract was washed with brine, dried over MgSO$_4$ and concentrated. Purification on silica gel eluting with 10% EtOAc in hexanes provided the title compound (0.9 g, 90%) as an oil. MS (M+H)$^+$ 455, found 478 (M+Na)$^+$.

Step C

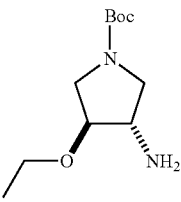

tert-Butyl(3S,4S)-3-Amino-4-ethoxypyrrolidine-1-carboxylate. The above intermediate (2.0 g, 4.5 mmol) was dissolved in MeOH. To it was added Pd(OH)$_2$ on carbon (0.2 g). The mixture was stirred under 55 psi overnight. The catalyst was filtered off and the filtrate was concentrated. MS calculated (M+H)$^+$ 231, found 231.

Step D

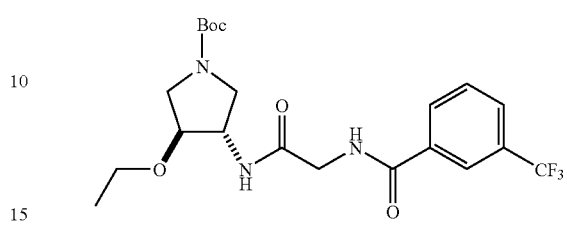

tert-Butyl(3S,4S)-3-Ethoxy-4-[({[3-(trifluoromethyl)benzoyl]amino}acetyl)amino]pyrrolidine-1-carboxylate. To a solution of the amine (1.0 g, 4.43 mmol) and (3-trifluoromethylbenzoylamino)acetic acid (1.09 g, 4.43 mmol) in DMF (20 mL) cooled in an ice bath was added BOP (1.96 g, 4.43 mmol) followed by NEt$_3$ (5 mL). The mixture was stirred at room temperature overnight and concentrated under reduced pressure. The residue was taken up in EtOAc. The resulting solution was washed with NaHCO$_3$ and brine, dried over MgSO$_4$ and concentrated. Purification on silica gel eluting with 2:1 EtOAc/hexanes provided the title compound (1.8 g, 88%) as a solid. MS (M+H)$^+$ 460, found 460.

Step E

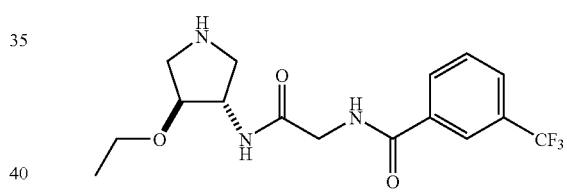

N-(2-{[(3S,4S)-4-Ethoxypyrrolidin-3-yl]amino}-2-oxoethyl)-3-(trifluoromethyl)benzamide. The above intermediate was dissolved in 4 N HCl in dioxane (20 mL). After being stirred at room temperature for 2 hours, the solvent was stripped off to give a solid. MS calculated (M+H)$^+$ 360, found 360.

Step F

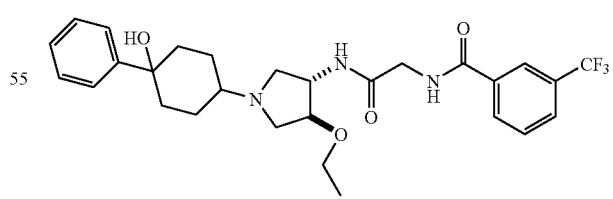

N-(2-{[(3S,4S)-4-Ethoxy-1-(4-hydroxy-4-phenylcyclohexyl)pyrrolidin-3-yl]amino}-2-oxoethyl)-3-(trifluoromethyl)benzamide. Reductive amination of the above amine with the ketone from step A in Example 6 using a procedure analogous to that described for Example 6 afforded the title compound. MS calculated (M+H)$^+$ 534, found 534.

Example 55

Step A

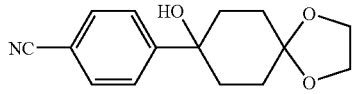

4-(8-Hydroxy-1,4-dioxaspiro[4.5]dec-8-yl)benzonitrile. A solution of 4-bromobenzonitrile (10 g, 0.055 mol) in 260 mL of dry THF and 70 mL of dry hexane under argon was cooled to −100° C. in a liquid nitrogen-Et$_2$O bath. n-Butyllithium (34.3 mL, 0.055 mol, 1.6 M solution in hexane) was added dropwise so that the internal temperature did not exceed −95° C. The orange solution was stirred an additional 10 min at −100° C. to −95° C. and then treated dropwise over 10 min with a solution of 1,4-cyclohexanedione monoethylene ketal (8.75 g, 0.055 mol) in 55 mL of dry THF, again carefully maintaining the temperature below −95° C. The reaction mixture was stirred for 10 min at −100° C. to −95° C., allowed to warm to 20° C. and poured into ice water (400 mL). The organic layer was separated, and the aqueous layer was extracted twice with Et$_2$O (200 mL). The combined organic extracts were dried over MgSO$_4$ and evaporated to give 14.1 g of white crystalline solid. Trituration with Et$_2$O afforded 9.9 g (70% yield) of white crystals: $^1$HNMR (CDCl$_3$) δ 1.6-2.2 (8H, m, cyclohexane), 3.97 (4H, s, ketal), 7.63 (4H, s, Ar); MS: 260 (M+1)$^+$.

Step B

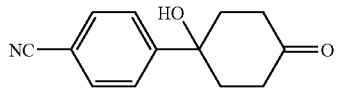

4-(1-Hydroxy-4-oxocyclohexyl)benzonitrile. 4-(8-Hydroxy-1,4-dioxaspiro[4.5]dec-8-yl)benzonitrile (520 mg, 2.0 mmol) was dissolved in the mixed solvent of 10 mL of THF and 10 mL of 1 N HCl aqueous solution at room temperature. The reaction mixture was then stirred at 60° C. for 1 h. The solution was cooled down to room temperature, adjusted to pH 7-8 with saturated NaHCO$_3$ aqueous solution. The organic layer was separated, and the aqueous layer was extracted twice with EtOAc (20 mL×2). The combined organic extracts were dried over MgSO$_4$ and evaporated to give an oil residue. Chromatography on silica gel (flash chromatography grade) with 40% ethyl acetate-hexane gave 410 mg (95%) of the desired product: $^1$H NMR (CDCl$_3$) δ 7.7 (2H, d, J=11.0 Hz), 7.42 (2H, d, J=10.7 Hz), 4.10 (H, s), 2.79-2.74 (2H, m), 2.63-2.49 (2H, m), 1.95-1.89 (2H, m), 1.67-1.59 (2H, m); MS: 216 (M+1)$^+$.

Step C

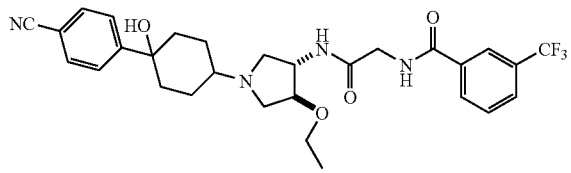

N-[2-({(3S,4S)-1-[4-(4-Cyanophenyl)-4-hydroxycyclohexyl]4-ethoxypyrrolidin-3-yl}amino)-2-oxoethyl]-3-(trifluoromethyl)benzamide. Reductive amination of the above ketone with the intermediate from Step E in Example 54 using sodium triacetoxyborohydride as reducing agent provided the title compound after chromatography. MS: 559 (M+1)$^+$.

Example 56

Step A

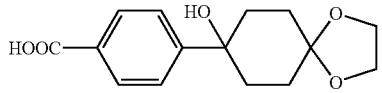

4-(8-Hydroxy-1,4-dioxaspiro[4.5]dec-8-yl)benzoic acid. A mixture of 4-(8-hydroxy-1,4-dioxaspiro[4.5]dec-8-yl)benzonitrile (7.5 g, 0.029 mol) in 190 mL of 2-methoxyethanol and 190 mL of 2.5 N NaOH was heated on the steam bath for 15 h. The solution was cooled in an ice bath, adjusted to pH 7-8 with concentrated HCl, and evaporated to driness. Water (375 mL) was added, and the pH was adjusted to 2 with HCl. The tan solid was filtered off and washed with water to give 7.6 g (94% yield) of 4-(8-hydroxy-1,4-dioxaspiro[4.5]dec-8-yl)benzoic acid: $^1$H NMR (CDCl$_3$) δ 1.6-2.3 (8 H, m, cyclohexane), 4.00 (4 H, s, ketal), 7.60 (2 H, s, Ar), 8.00 (2 H, Ar); MS: 279 (M+1)$^+$.

Step B

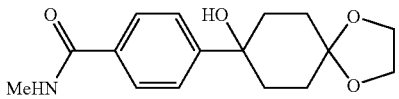

4-(8-Hydroxy-1,4-dioxaspiro[4.5]dec-8-yl)-N-methylbenzamide. 4-(8-Hydroxy-1,4-dioxaspiro[4.5]dec-8-yl)benzoic acid (560 mg, 2 mmol), methylamine (1.2 mL, 2.0 M THF solution), BOP reagent (1.07 g, 2.4 mmol) and 0.8 mL (6 mmol) of triethylamine were dissolved in 15 mL of DMF at room temperature. The reaction mixture was stirred at r.t. overnight. Direct chromatography on silica gel (flash chromatography grade) with 50% ethyl acetate-hexane gave 410 mg (70%) of the desired product: $^1$H NMR (CDCl$_3$) δ 7.76 (2 H, d, J=11.2 Hz), 7.56 (2 H, d, J=10.9 Hz), 5.01 (H, s), 3.90 (4 H, s), 3.37 (3 H, s), 2.80-2.75 (2 H, m), 2.60-2.45 (2 H, m), 1.95-1.90 (2 H, m), 1.63-1.52 (2 H, m); MS: 292 (M+1)$^+$.

Step C

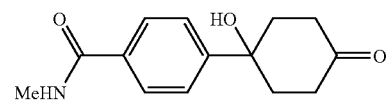

4-(1-Hydroxy-4-oxocyclohexyl)-N-methylbenzamide. 4-(8-Hydroxy-1,4-dioxaspiro[4.5]dec-8-yl)-N-methylbenzamide (410 mg, 1.4 mmol) was dissolved in the mixture solvent of 7 mL of THF and 7 mL of 1 N HCl aqueous solution at room temperature. The reaction mixture was then stirred at 60° C. for 1 h. The solution was cooled down to room temperature, adjusted to pH 7-8 with saturated NaHCO$_3$ aqueous solution. The organic layer was separated, and the aqueous layer was extracted twice with EA (20 mL×2). The combined organic extracts were dried over MgSO$_4$ and evaporated to give an oil residue. Chromatography on silica gel (flash chromatography grade) with 40% Ethyl acetate-hexane gave 410 mg (90%) of the desired product: $^1$H NMR (CDCl$_3$) δ 7.78 (2 H, d, J=11.2 Hz), 7.51 (2 H, d, J=10.9 Hz), 4.10 (H, s), 3.37 (3 H, s), 2.79-2.74 (2 H, m), 2.63-2.49 (2 H, m), 1.95-1.89 (2 H, m), 1.67-1.59 (2 H, m); MS: 248 (M+1)$^+$.

Step D

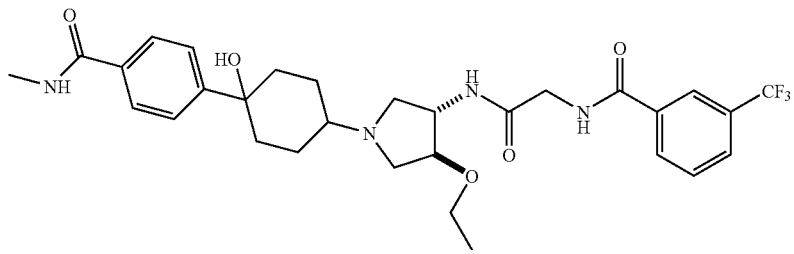

N-(2-{[(3S,4S)-4-Ethoxy-1-(4-hydroxy-4-{4-[(methylamino)carbonyl]phenyl}cyclohexyl)-pyrrolidin-3-yl]amino}-2-oxoethyl)-3-(trifluoromethyl)benzamide. The title compound was prepared by reductive amination of the above ketone with the intermediate from Step E in Example 54 using sodium triacetoxyborohydride as reducing agent followed by chromatography. MS (M+H)$^+$ 591.

Example 57

Step A

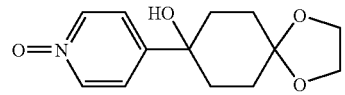

8-(1-Oxidopyridin-4-yl)-1,4-dioxaspiro[4.5]decan-8-ol. To a solution of 2.35 g (10 mmol) of 8-pyridin-4-yl-1,4-dioxaspiro[4.5]decan-8-ol (prepared following the procedure described in Example 7) in 20 mL of methylene chloride was added 2.6 g (15 mmol) of mCPBA. The reaction mixture was stirred at room temperature for 1.5 h. Direct chromatography on silica gel afforded the title compound (2.45 g, 98%).

Step B

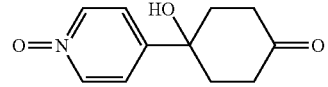

4-Hydroxy-4-(1-oxidopyridin-4-yl)cyclohexanone. The title compound was synthesized from 8-(1-oxidopyridin-4-yl)-1,4-dioxaspiro[4.5]decan-8-ol using the same typical deprotection procedure.

Step C

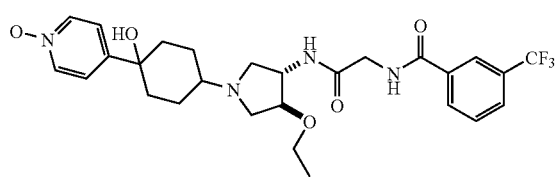

N-[2-({(3S,4S)-4-Ethoxy-1-[4-hydroxy-4-(1-oxidopyridin-4-yl)cyclohexyl]pyrrolidin-3-yl}amino)-2-oxoethyl]-3-(trifluoromethyl)benzamide. The title compound was prepared using the typical reductive amination procedure. MS (M+H)$^+$ 551.

The following compounds were prepared following the procedures analogous to those for Examples 54-57.

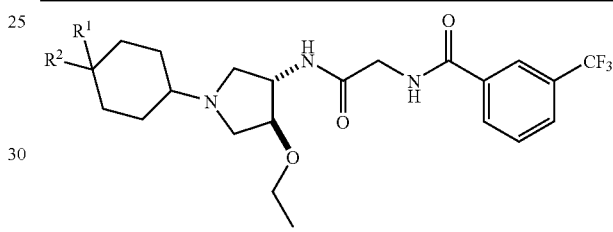

| Example # | R$^1$ | R$^2$ | MS (M + H)$^+$ |
|---|---|---|---|
| 58 | OH | 4-methylphenyl | 548 |
| 59 | OH | 4-methoxyphenyl | 564 |
| 60 | OH | 3-methoxyphenyl | 564 |
| 61 | OH | 4-fluorophenyl | 552 |
| 62 | OH | 3-fluorophenyl | 552 |
| 63 | OH | 4-chlorophenyl | 568 |
| 64 | OH | 3,4-methylenedioxyphenyl | 578 |
| 65 | OH | pyridin-2-yl | 535 |
| 66 | OH | pyridin-3-yl | 535 |
| 67 | OH | pyridin-4-yl | 535 |
| 68 | OH | 4-methylpyridin-2-yl | 549 |
| 69 | OH | 5-methylpyridin-2-yl | 549 |
| 70 | OH | 6-methylpyridin-2-yl | 549 |
| 71 | OH | 6-methoxypyridin-3-yl | 565 |
| 72 | OH | 1-oxidopyridin-3-yl | 551 |
| 73 | OH | 1-oxidopyridin-2-yl | 551 |
| 74 | OH | quinolin-4-yl | 585 |
| 75 | OH | 3-cyanophenyl | 559 |
| 76 | OH | 3-(methylaminocarbonyl)phenyl | 591 |
| 77 | H | pyridin-3-yl | 519 |
| 78 | H | pyridin-4-yl | 519 |
| 79 | H | pyridin-2-yl | 519 |
| 80 | H | 1-oxidopyridin-2-yl | 535 |
| 81 | H | 1-oxidopyridin-3-yl | 535 |
| 82 | H | 1-oxidopyridin-4-yl | 535 |
| 83 | H | 6-methoxypyridin-3-yl | 549 |
| 84 | H | 4-(morpholin-4-ylcarbonyl)phenyl | 631 |
| 85 | H | 5-(morpholin-4-ylcarbonyl)pyridin-2-yl | 632 |
| 86 | H | 6-(morpholin-4-ylcarbonyl)pyridin-3-yl | 632 |
| 87 | H | 4-(4-methylpiperazin-1-ylcarbonyl)phenyl | 644 |
| 88 | H | 3-methyl-1H-pyrazol-1-yl | 522 |
| 89 | H | 3-trifluoromethyl-1H-pyrazol-1-yl | 576 |

Example 90

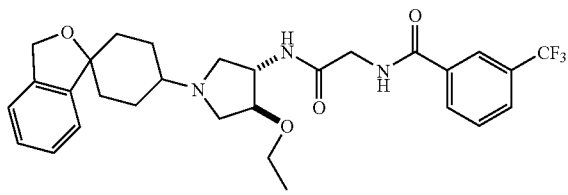

N-(2{[(3S,4S)-4-Ethoxy-1-(3H-spiro[2-benzofuran-1,1'-cyclohexan]4'-yl)pyrrolidin-3-yl]amino}-2-oxoethyl)-3-(trifluoromethyl)benzamide. The title compound was prepared using a sequence analogous to that described for Example 54. MS calculated (M+H)+ 546, found 546.

Example 91

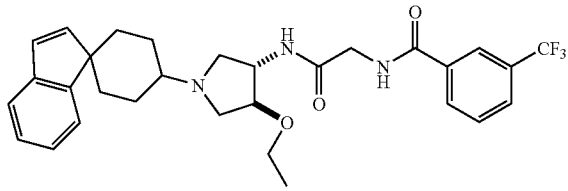

N-(2-{[(3S,4S)-4-Ethoxy-1-spiro[cyclohexane-1,1'-inden]-4-ylpyrrolidin-3-yl]amino}-2-oxoethyl)-3-(trifluoromethyl)benzamide. The title compound was prepared using a sequence analogous to that described for Example 52. MS calculated (M+H)+ 542, found 542.

Example 92

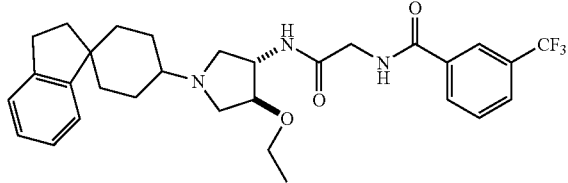

N-(2-{[(3S,4S)-1-(2',3'-Dihydrospiro[cyclohexane-1,1'-inden]-4-yl)-4-ethoxypyrrolidin-3-yl]amino}-2-oxoethyl)-3-(trifluoromethyl)benzamide. The title compound was prepared using a sequence analogous to that described for Example 54. MS calculated (M+H)+ 544, found 544.

Example 93

Step A

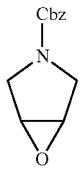

Benzyl 6-Oxa-3-azabicyclo[3.1.0]hexane-3-carboxylate. To a solution of 30 g (133 mmol) of benzyl 3-pyrroline-1-carboxylate in 700 mL of methylene chloride was added 57.2 g (200 mmol) of mCPBA. The reaction mixture was stirred at room temperature overnight and quenched with 250 mL of 20% NaHSO₃ aqueous solution. The organic phase was separated, and the aqueous layer was extracted with methylene chloride twice (100 mL×2). The combined extracts were washed with saturated NaHCO₃ aqueous solution twice (250 mL×2), brine, dried over Na₂SO₄, evaporated under reduced pressure. Chromatography on silica gel column with 40% EtOAc-Hexane provided the title compound (24 g, 83%). MS (M+H)+ 220.

Step B

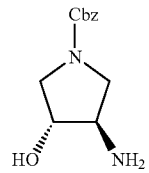

Benzyl (3S,4S)-3-Amino-4-hydroxypyrrolidine-1-carboxylate. To a solution of 20.7 g (94.4 mmol) of benzyl 6-oxa-3-azabicyclo[3.1.0]hexane-3-carboxylate in 80 mL of methanol was added 80 mL of ammonium hydroxide. The reaction mixture was stirred at 60° C. overnight. The concentration of the reaction mixture under reduced pressure gave an oil residue (22.3 g, 94.4 mmol), which was used directly for the next N-Boc-protection reaction. MS (M+H)+ 237.

Step C

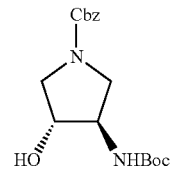

Benzyl(3S,4S)-3-[(tert-Butoxycarbonyl)amino]-4-hydroxypyrrolidine-1-carboxylate. To a solution of 22.3 g (94.4 mmol) of the above amino alcohol in 200 mL of THF was added 26.8 g (123 mmol) of di-tert-butyldicarbonate and 17.1 mL (123 mmol) of triethylamine at 0° C. The reaction mixture was stirred at room temperature overnight. The reaction was quenched with 100 mL of ethyl acetate and 100 mL of water. The organic phase was separated, and the aqueous layer was extracted with ethyl acetate twice (100 mL×2). The combined extracts were washed with saturated NaHCO₃ aqueous solution twice (250 mL×2), brine, dried over Na₂SO₄, evaporated under reduced pressure. Chromatography on silica gel column with 70% EtOAc-Hexane provided the title compound (27.3 g, 86%). MS (M+H)+ 337.

Step D

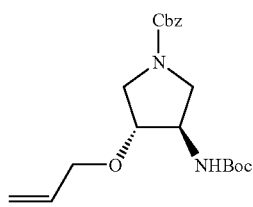

Benzyl (3S,4S)-3-(Allyloxy)-4-[(tert-butoxycarbonyl)amino]pyrrolidine-1-carboxylate. To a solution of 26 g (77 mmol) of benzyl 3-[(tert-butoxycarbonyl)amino]4-hydroxypyrrolidine-1-carboxylate in 120 mL of THF was added 5 g (211 mmol) of sodium hydride at 0° C. The reaction mixture was stirred at 0° C. for 1 h, then 10 mL (115 mmol) of allyl bromide was added. The reaction mixture was warmed up to room temperature and continuously stirred at room temperature overnight. Water (50 mL) was added to quench the reaction. The organic phase was separated, and the aqueous layer was extracted with ethyl acetate twice (100 mL×2). The combined extracts were washed with brine, dried over $Na_2SO_4$, evaporated under reduced pressure. Chromatography on silica gel column with 25% EtOAc-hexane provided the title compound (21.3 g, 73%). MS (M+H)$^+$ 377.

Step E

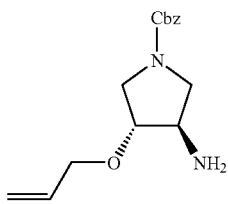

Benzyl(3S,4S)-3-(Allyloxy)-4-aminopyrrolidine-1-carboxylate. To a solution of 21.3 g (56.6 mmol) of benzyl 3-(allyloxy)-4[(tert-butoxycarbonyl)amino]pyrrolidine-1-carboxylate in 125 mL of THF was added 250 mL of 4 N HCl in dioxane solution. The reaction mixture was stirred at room temperature for 2 h, concentrated under reduced pressure to give an oil residue. This residue was redissolved in 200 mL of saturated $NaHCO_3$ aqueous solution. The mixture was adjusted to pH 7-8, then was extracted with ethyl acetate twice (100 mL×2). The combined extracts were washed with brine, dried over $Na_2SO_4$, evaporated under reduced pressure to give an oil residue. Chromatography on silica gel column with 5% MeOH-EtOAc provided the title compound (10.5 g, 68%). MS (M+H)$^+$ 277.

Step F

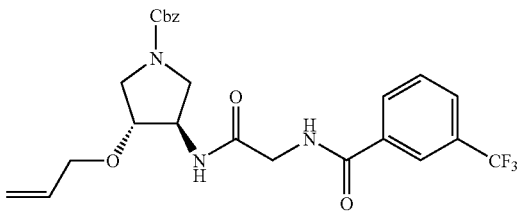

Benzyl(3S,4S)-3-(Allyloxy)-4-[({[3-(trifluoromethyl)benzoyl]amino}acetyl)amino]pyrrolidine-1-carboxylate. To a solution of 10 g (36 mmol) of benzyl 3-(allyloxy)-4-aminopyrrolidine-1-carboxylate in 150 mL of DMF was added 12 g (105 mmol) of N-methyl morpholine, 19 g (44 mmol) of BOP reagent and 10 g (39 mmol) of the glycine acid derivative at room temperature. The reaction mixture was stirred at room temperature overnight. Direct chromatography on silica gel column with 50% EtOAc-hexane provided the title compound (14.5 g, 79.8%). MS (M+H)+ 506.

Step G

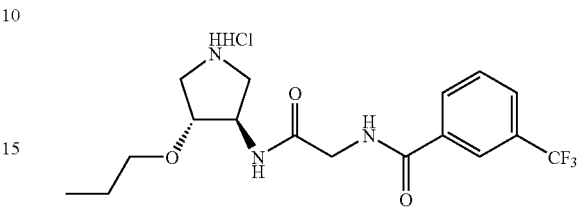

N-(2-Oxo-2-{[(3S,4S)-(4-propoxypyrrolidin-3-yl]amino}ethyl)-3-(trifluoromethyl)benzamide hydrochloride. To a solution of 3.7 g of benzyl 3-(allyloxy)-4-[({[3-(trifluoromethyl)benzoyl]amino}acetyl)amino]pyrrolidine-1-carboxylate in 35 mL of methanol was added 3.6 mL of 6 N HCl aqueous solution and 171 mg of Pd/C (10% on carbon). The reaction mixture was stirred at room temperature under hydrogen (40 psi) overnight. The mixture was filtered through celite and concentrated under reduced pressure to give the title compound (1.73 g, 58%). MS (M+H)$^+$ 374.

Step H

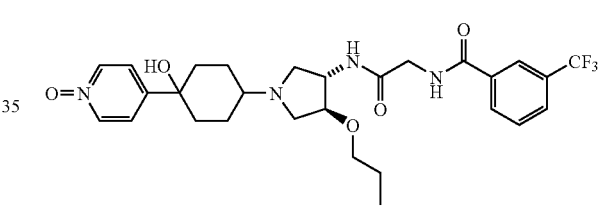

N-[2-({(3S,4S)-1-[4-Hydroxy-4-(1-oxidopyridin-4-yl)cyclohexyl]-4-propoxypyrrolidin-3-yl}amino)-2-oxoethyl]-3-(trifluoromethyl)benzamide. This compound was synthesized from N-(2-oxo-2-{[4-propoxypyrrolidin-3-yl]amino}ethyl)-3-(trifluoromethyl)benzamide hydrochloride and 4-hydroxy(1-oxidopyridin-4-yl)cyclohexanone according to typical reductive amination precedure. MS (m/e): 565 (M+1)$^+$.

The following compounds were prepared following the procedures described for Example 93.

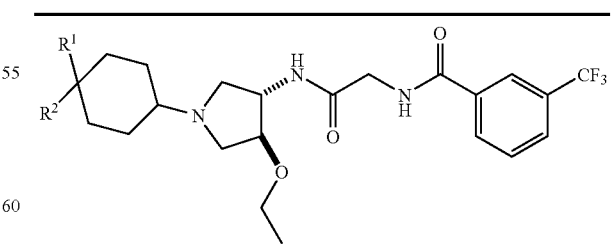

| Example # | R$^1$ | R$^2$ | MS (M + H)$^+$ |
|---|---|---|---|
| 94 | OH | phenyl | 548 |
| 95 | OH | 4-methoxyphenyl | 578 |
| 96 | OH | 3,4-methylenedioxyphenyl | 592 |

-continued

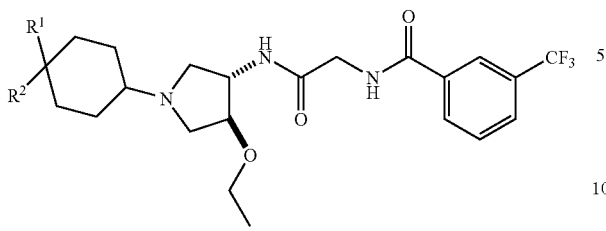

| Example # | R¹ | R² | MS (M + H)⁺ |
|---|---|---|---|
| 97 | OH | pyridin-2-yl | 549 |
| 98 | OH | pyridin-3-yl | 549 |
| 99 | OH | pyridin-4-yl | 549 |
| 100 | OH | quinolin-4-yl | 599 |
| 101 | OH | 6-methoxypyridin-3-yl | 579 |
| 102 | OH | 4-methylpyridin-2-yl | 563 |
| 103 | OH | 5-methylpyridin-2-yl | 563 |
| 104 | OH | 6-methylpyridin-2-yl | 563 |
| 105 | OH | 6-methoxypyridin-2-yl | 579 |
| 106 | OH | 1-oxidopyridin-3-yl | 565 |
| 107 | H | pyridin-3-yl | 533 |
| 108 | H | pyridin-4-yl | 533 |
| 109 | H | 3,5-dimethyl-1H-pyrazol-1-yl | 550 |
| 110 | H | 3-methyl-1H-pyrazol-1-yl | 536 |
| 111 | H | 1-oxidopyridin-3-yl | 549 |

Example 112

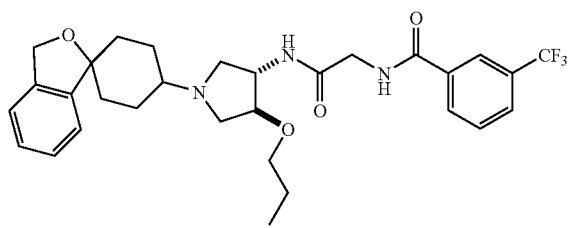

N-(2-Oxo-2-{[(3S,4S)-4-propoxy-1-(3H-spiro[2-benzofuran-1,1'-cyclohexan]-4'-yl)pyrrolidin-3-yl]amino}ethyl)-3-(trifluoromethyl)benzamide. The title compound was prepared using a sequence analogous to that described for Example 93. MS calculated (M+H)⁺ 560, found 560.

Example 113

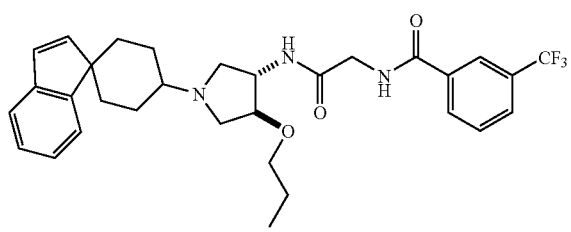

N-(2-Oxo-2-{[(3S,4S)-4-propoxy-1-spiro[cyclohexane-1,1'-inden]-4-ylpyrrolidin-3-yl]amino}ethyl)-3-(trifluoromethyl)benzamide. The title compound was prepared using a sequence analogous to that described for Example 93. MS calculated (M+H)⁺ 556, found 556.

Example 114

Step A

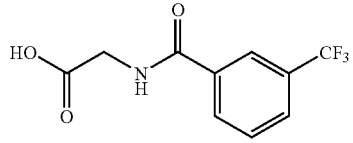

(3-Trifluoromethyl-benzoylamino)acetic acid. To a rapid stirring solution of glycine (15.014 g, 0.20 mol) in MeCN (400 mL) and 2 M NaOH (250 mL) at 0° C. was slowly added a solution of 3-(trifluoromethyl)-benzoyl chloride (41.714 g, 0.20 mol) in 75 mL of MeCN over 30 min. The cloudy yellow solution was stirred at 0° C. for 30 min. The reaction mixture was acidified with 3 M HCl to pH=3, followed by removal of MeCN on rotary evaporator. The resulting mixture was then extracted with EtOAc (400 mL×3). The combined organic layers were dried, filtered and concentrated to give a light yellow solid (48.53 g), which was triturated with toluene (500 mL). After filtration, the solid product was washed with cold toluene until the filtrate was colorless. After dried under high vacuum over the weekend, a white powder product: 44.60 g (90%) was afforded. MS (M+H⁺)=248.1. ¹H NMR (DMSO-d₆) δ 12.70 (br s, 1H), 9.17 (m, 1H), 8.20 (dd, 2H), 7.94 (dd, 1H), 7.78 (m, 1H), 3.97 (d, 2H).

Step B

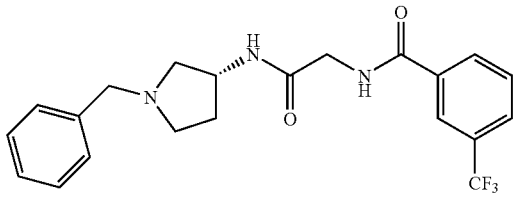

N-(2-{[(3R)-1-benzylpyrrolidin-3-yl]amino}-2-oxoethyl)-3-(trifluoromethyl)benzamide. To a solution of (3-Trifluoromethyl-benzoylamino)acetic acid (4.2 g, 17 mmol) and NMM (2.8 mL, 25.5 mmol) in dry THF (30 mL) at −10 to −15° C. under N₂, was slowly added isobutylchloroformate (2.4 mL, 17.85 mmol) via syringe. The reaction mixture gradually became pink. 15 min later, a solution of (3R)-1-benzylpyrrolidin-3-amine (3.0 g, 17 mmol) in THF (15 mL) was dropwise added to the above mixed anhydride over 20 min, maintaining reaction temperature <−10° C. The reaction mixture became a dark red color. 1 h later, the reaction mixture was allowed to warm to rt, and quenched with water (25 mL), extracted with EtOAc×3, dried, filtered and concentrated to give an orange solid. MeCN was added and concentrated to remove EtOAc. Then MeCN (15-20 mL) was added to afford a slurry, which was chilled in ice bath and stirred for 30 min. After filtration, the solid product was rinsed with cold MeCN (10-15 mL) until the filtrate was colorless After dried under high vacuum overnight, a pale yellow solid product: 5.0 g (73%) was afforded. MS (M+H⁺)=406.2; ¹H NMR (CDCl₃) δ 8.16 (s, 1H), 8.00 (dd, 1H), 7.78 (dd, 1H), 7.57 (m, 1H), 7.25 (m, 6H), 7.06 (m, 1H), 6.39 (m, 1H), 4.48 (m, 1H), 4.04 (d, 2H), 3.62 (d, 2H), 2.86 (m, 1H), 2.63 (m, 1H), 2.57 (m, 1H), 2.36 (m, 2H).

Step C

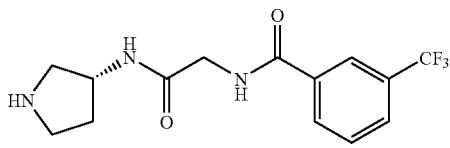

N-((R)-Pyrrolidin-3-ylcarbamoylmethyl)-3-trifluoromethyl-benzamide. To a Parr shaker flask containing compound of step B (14.0 g, 34.5 mmol) dissolved in MeOH (50 mL) was added Palladium hydroxide (2.8 g, 20 wt %). The suspension was shaken at rt under hydrogen (55 psi) overnight. The mixture was filtered through celite and concentrated to give the title compound as a white solid; yield 10.5 g, 97%; $^1$H NMR (CDCl$_3$) δ 9.06 (t, 1H), 8.20 (m, 3H), 7.94 (d, 1H), 7.75 (t, 1H), 4.23 (a, 1H), 3.89 (d, 2H), 3.00-3.22 (m, 4H), 2.82 (m, 1H), 2.05 (m, 1H), 1.73 (m, 1H); MS m/z=316.3 (M+H)$^+$.

Step D

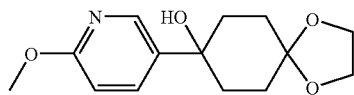

8-(6-Methoxy-pyridin-3-yl)-1,4-dioxa-spiro[4.5]decan-8-ol. In a dried 3-neck flask, 5-bromo-2-methoxypyridine (12.6 g, 67.2 mmol) was dissolved in dry THF (130 mL) and cooled to −78° C. under N$_2$. 2.5M n-BuLi in hexanes (28.2 mL, 70.4 mmol) was added dropwise and the mixture stirred at −78° C. for 50 min. To pyridine mixture was slowly added a solution of 1,4-cyclohexanedione mono-ethylene ketal (10.0 g, 64.0 mmol) in dry THF (25 mL). The resulting mixture was stirred at −78° C. for 80 min. The reaction was quenched with sat'd NH$_4$Cl and extracted with CH$_2$Cl$_2$ (3×). The combined extracts were dried (MgSO$_4$), filtered, and concentrated to give a yellow oil. Flash chromatography on silica gel eluting with 10% MeOH/CH$_2$Cl$_2$ afforded the title compound as a yellow solid; yield 16.5 g, 62.2 mmol, 97%; $^1$H NMR (CDCl$_3$) δ 8.26 (s, 1H), 7.72 (d, 1H), 6.69 (d, 1H), 3.96 (t, 4H), 3.91 (s, 3H), 2.21 (s, 1H), 2.08 (m, 4H), 1.82 (m, 2H), 1.66 (m, 2H); MS m/z=266.1 (M+H)$^+$.

Step E

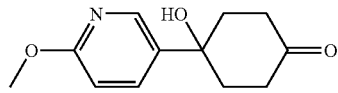

4-Hydroxy-4-(6-methoxy-pyridin-3-yl)-cyclohexanone. To a solution of the ketal of step D (11.5 g, 43.3 mmol) in THF (100 mL) was added 3N HCl (75 mL) and the solution stirred overnight at rt. The pH of the solution was adjusted to ~11 by the addition of 3N NaOH solution. After removal of most of the THF by rotary evaporation, the aqueous was extracted with CH$_2$Cl$_2$ (3×). The combined extracts were dried (MgSO$_4$), filtered, and concentrated to give the title compoun as a yellow solid; yield 8.2 g, 37.1 mmol, 86%; $^1$H NMR (CDCl$_3$) δ 8.26 (s, 1H), 7.75 (d, 1H), 6.73 (d, 1H), 3.91 (s, 31), 2.91 (m, 2H), 2.78 (s, 1H), 2.32 (m, 2H), 2.21(m, 4H); MS m/z=222.1.

Step F

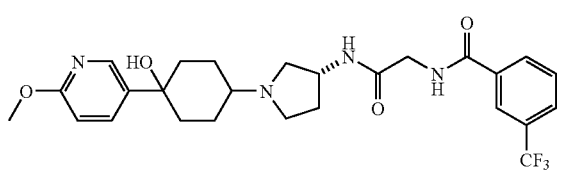

N-({(3R)-1-[4-Hydroxy-4-(6-methoxy-pyridin-3-yl)-cyclohexyl]-pyrrolidin-3-ylcarbamoyl}-methyl)-3-trifluoromethyl-benzamide. To a dry flask containing a solution of N-((3R)-pyrrolidin-3-ylcarbamoylmethyl)-3-trifluoromethyl-benzamide (5.0 g, 15.9 mmol) in dry CH$_2$Cl$_2$ (1.0 L) was added the ketone of step E (4.56 g, 20.6 mmol) followed by sodium triacetoxyborohydride (6.72 g, 31.7 mmol). The resulting mixture was stirred overnight at rt. The reaction was neutralized with 1N NaOH (250 mL) and extracted with CH$_2$Cl$_2$ (3×). The combined extracts were dried (MgSO$_4$), filtered, and concentrated to give a sticky solid. Flash chromatography over silica gel eluting with 1% NH$_4$OH/15% MeOH/EtOAc afforded the desired isomer as a white solid; yield (less polar isomer only) 3.68 g, 7.1 mmol, 45%; $^1$H NMR (CDCl$_3$) δ 8.28 (s, 1H), 8.09 (s, 1H), 7.97 (d, 1H), 7.75 (dd, 2H), 7.55 (m, 2H), 6.90 (d, 1H), 6.72 (d, 1H), 4.44 (m, 1H), 4.12 (s, 2H), 3.92 (s, 3H), 2.87 (m, 1H), 2.65 (m, 2H), 2.27 (m, 4H), 2.11 (bs, 1H), 1.93 (m, 2H), 1.64 (m, 5H); MS m/z=521.2 (M+H).

Example 115

Step A

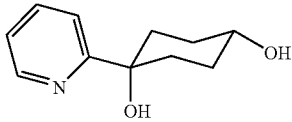

cis-1-Pyridin-2-ylcyclohexane-1,4-diol. To a solution of LAH (50 mL, 1.0 M in THF) in a 1 L 4-neckflask was added THF (150 mL), and then dropwise added a solution of 4-hydroxy-4-pyridin-2-yl-cyclohexanone (10.0 g, 52.3 mmol) in THF (100 mL) over 1.5 h. The reaction temperature was about 30° C. throughout. The reaction was completed as judged by HPLC analysis and HPLC also showed a 1:9 ratio of trans to cis diol. The reaction was quenched by slowly adding water (8 mL) and 15% NaOH (2 mL), and the mixture was filtered through Celite. The filtrate was concentrated to give a oil (10.1 g), which was chromatographed on silica gel (350 g), eluting with 1% TEA/5% IPA/hexane (400 mL) and then 1% TEA/15% IPA/10% tBME/hexane (6 L). The appropriate fractions were combined and concentrated in vacuo to give cis-1-pyridin-2-ylcyclohexane-1,4-diol (6.3 g, 63%) as a white solid. LCMS: 194.3 (M+H, 100%). $^1$H NMR (CDCl$_3$) δ 8.54 (dd, 1H), 7.72 (dd, 1H), 7.68 (dd, 1H), 7.39 (d, 1H), 5.09 (bs, 1H), 3.82-3.76 (m, 1H), 2.56-2.49 (m, 1H), 2.01-1.98 (m, 2H), 1.96-1.84 (m, 2H), 1.80-1.75 (m, 2H), 1.64-1.58 (m, 2H).

Step B

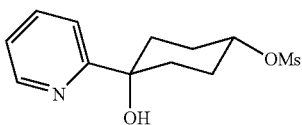

cis-4-Hydroxy-4-pyridin-2-ylcyclohexyl methanesulfonate. To a solution of the alcohol of step A (6.3 g, 32.6 mmol) and TEA (13.6 mL, 97.8 mmol) in THF (100 mL) at 0° C. was added mesyl chloride (3.78 mL. 48.9 mmol). After being stirred for 1.5 h, the reaction was completed as judged by LCMS. The reaction was quenched by adding 20% KHCO$_3$ (40 mL) and extracted with EtOAc (300 mL). The organic layer was washed with 10% KHCO$_3$, then saline solution, dried over sodium sulfate, and concentrated in vacuo. The residue was crystallized in toluene (100 mL) at 70° C. and the solid was air dried to yield crystalline solid (5.25 g, 59.4%). LCMS: 272.3 (M+H$^+$, 100%); $^1$H NMR (CDCl$_3$) δ 8.54 (d, 1H), 7.76 (dd, 1H), 7.35 (dd, 1H), 7.26 (dd, 1H), 5.20 (bs, 1H), 4.86-4.77 (m, 1H), 3.06 (s, 3H), 2.30-2.10 (m, 4H), 1.96-1.88 (m, 2H), 1.80-1.78 (m, 2H).

Step C

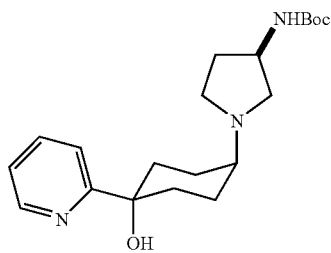

tert-Butyl[(3R)-1-(trans-4-hydroxy-4-pyridin-2-ylcyclohexyl)pyrrolidin-3-yl]carbamate. The 4-hydroxy-4-pyridin-2-ylcyclohexyl methanesulfonate (0.245 g, 0.9 mmol) and tert-butyl (3R)-pyrrolidine-3-ylcarbamate (1.6 g, 8.59 mmol) were weighed into a microwave oven tube. The neat reaction mixture was placed into the microwave oven for 15 minutes at 71° C. The mixture was chromatographed on silica gel, eluting with 1% NH$_4$OH in ethyl acetate/methanol (100/0 to 10/90), providing tert-butyl [(3R)-1-(4-hydroxy-4-pyridin-2-ylcyclohexyl)pyrrolidin-3-yl]carbamate. LC/MS: 362.2 (M+H, 100%). $^1$H NMR (CDCl$_3$) δ 8.52 (m, 1H), 7.70 (m, 1H), 7.43 (d, 1H), 7.19 (m, 1H), 4.86 (bs, 2H), 4.20 (bs, 1H), 2.82 (m, 1H), 2.68 (s, 1H), 2.56 (m, 1H), 2.40 (m, 1H), 2.31 (s, 1H), 2.27-2.17 (m, 3H), 2.04-1.98 (m, 2H), 1.78-1.74 (m, 3H), 1.61 (m, 2H), 1.46 (s, 9H).

Step D

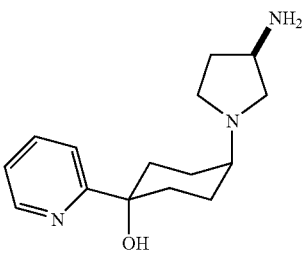

trans-4-[(3R)-3-Aminopyrrolidin-1-yl]-1-pyridin-2-ylcyclohexanol. To tert-butyl [(3R)-1-(4-hydroxypyridin-2-ylcyclohexyl)pyrrolidin-3-yl]carbamate (50 mg, 0.14 mmol) was added 4.0 M HCl in 1,4-dioxane (3 mL) at rt. After being stirred for 5 minutes, the product was precipitated out. To the mixture was added methanol (0.6 mL) and the solution became mostly clear with some gummy material present. The reaction was completed after 2½ hours as judged by HPLC and LCMS. This resulting mixture was concentrated to give 4-[(3R)-3-aminopyrrolidin-1-yl]-1-pyridin-2-ylcyclohexanol HCl salt (72 mg, 99%). LC/MS: 262.1 (M+H, 100%).

Step E

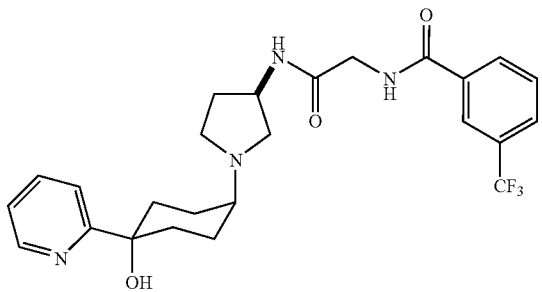

N-(2-{[(3R)-1-(4-Hydroxy-4-pyridin-2-ylcyclohexyl)pyrrolidin-3-yl]amino}-2-oxoethyl)-3-(trifluoromethyl)benzamide. To a solution of 4-[(3R)-3-aminopyrrolidin-1-yl]-1-pyridin-2-ylcyclohexanol (69 mg, 0.26 mmol) in anhydrous THF (5 mL) was added TEA (0.10 mL) and another solution of (3-trifluoromethyl-benzoylamino)-acetic (60 mg, 0.24 mmol), N-(3-dimethylaminopropyl)-N'-ethylcarbodiimide hydrochloride (50 mg, 0.26 mmol) in THF (5.0 mL) at rt, and then added DMF (0.07 mL) and additional TEA (0.05 mL) to get everything in solution. The reaction was stirred at rt overnight and was quenched with water (25 mL) and extracted with ethyl acetate (4×35 mL). The combined organic layers were dried over sodium sulfate, filtered, and solvent was removed under reduced pressure. The residue was chromatographed on silica gel, eluting with 1% NH$_4$OH in ethyl acetate/methanol (100/0 to 10/90), followed by purification on HPLC, eluting with 0.05% TFA in CH$_3$CN/water, to yield the TFA salt of N-(2-{[(3R)-1-(4-hydroxy-4-pyridin-2-ylcyclohexyl)pyrrolidin-3-yl]amino}-2-oxoethyl)-3-(trifluoromethyl)benzamide bis(trifluoroacetate) (68 mg, 57%). LRMS: 491 (M+H, 100%). $^1$HNMR: (CD$_3$OD) δ 8.20 (s, 1H), 8.12 (d, 1H), 7.85 (d, 1H), 7.67 (t, 1H), 6.96 (s, 2H), 4.37 (m, 1H), 4.01 (s, 2HH), 2.88 (m, 1H), 2.77 (m, 1H), 2.61 (m, 1H), 2.52 (m, 2H), 2.44 (q, 1H), 2.21 (m, 2H), 1.96 (m, 2H), 1.65 (m, 3H), 1.40 (m, 2H).

Example 116

Step A

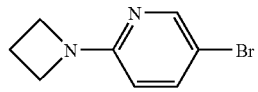

2-Azetidin-1-yl-5-bromopyridine. A mixture of azetidine HCl salt (590 mg, 6.3 mmol), 5-bromo-2-fluoropyridine (1.11 g, 6.3 mmol), Cs$_2$CO$_3$ (4.1 g, 12.6 mmol) and dry DMSO (7 mL) was stirred and heated at 95° C. for 20 h. The reaction mixture was cooled and filtered. The solid was treated with H$_2$O, extracted with CH$_2$Cl$_2$×3. The combined organic layers were dried, filtered to provide 1.15 grams (86%) of desired product as a light yellow solid. MS (M+H$^+$)

=213.0/215.0. ¹HNMR (CDCl₃) δ 8.18 (d, 1H), 7.50 (dd, 1H), 6.18 (d, 1H), 4.03 (t, 4H), 2.40 (q, 2H).

Step B

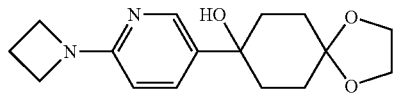

8-(6-Azetidin-1-ylpyridin-3-yl)-1,4-dioxaspiro[4.5]decan-8-ol. 2-azetidin-1-yl-5-bromopyridine (64 mg, 0.30 mmol) was dissolved in dry THF (1.5 mL) and cooled to −78° C., followed by the addition of n-BuLi (0.196 mL, 1.6 M in hexanes). Thirty minutes later, a solution of 1,4-cyclohexanedione mono-ethylene ketal (44.6 mg, 0.286 mmol) in dry THF (0.2 mL) was added dropwise at −78° C. with constant stirring. One hour later, the reaction was quenched with NH₄Cl (aq) and slowly warmed to rt. The aqueous layer was extracted with CH₂Cl₂×3, dried, filtered and concentrated to give a crude, which was purified by flash column chromatography (100% EtOAc) to provide 35 mg (43%) of white solid product. MS (M+H⁺)=291.1.

Step C

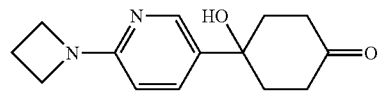

4-(6-Azetidin-1-ylpyridin-3-yl)-4-hydroxycyclohexanone. 8-(6-Azetidin-1-ylpyridin-3-yl)-1,4-dioxaspiro[4.5]decan-8-ol (35 mg) was dissolved in THF (1.2 mL), and then 3 M HCl (0.8 mL) was added at rt. The resulting solution was stirred at rt for 2 h, then basified with 6 N NaOH in ice bath to PH=10. The aqueous layer was extracted with CH₂Cl₂×3. The combined organic layers were dried, filtered and rotary evaporated to provide 28 mg (97%) of white solid product w/o further purification. MS (M+H⁺)=247.0.

Step D

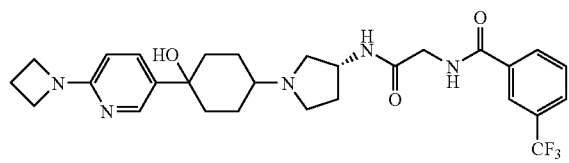

N-[2-({(3R)-1-[4-(6-Azetidin-1-ylpyridin-3-yl)-4-hydroxycyclohexyl]pyrrolidin-3-yl}amino)-2-oxoethyl]-3-(trifluoromethyl)benzamide. To a solution of 4-(6-azetidin-1-ylpyridin-3-yl)-4-hydroxycyclohexanone (115 mg, 0.467 mmol) and N-((R)-pyrrolidin-3-ylcarbamoylmethyl)-3-trifluoromethyl-benzamide (140.4 mg, 0.445 mmol) in dry CH₂Cl₂ (19 mL) was added Na(OAc)₃BH (198 mg, 0.934 mmol) in one portion under N₂ at rt. The reaction mixture was stirred under N₂ overnight (16 h) and treated with Na₂CO₃ (aq), extrated with CH₂Cl₂×3, dried, filtered and concentrated to give a crude, which was purified by column chromatography (20:80:0.5 MeOH(EtOAc/NH₄OH) to provide 60 mg (25%) of desired isomer product (top spot on TLC) as a white solid. MS (M+H⁺)=546.1. ¹HNMR (CD₃OD) δ 8.24 (m, 2H), 8.17 (m, 2H), 7.88 (m, 2H), 7.74 (m, 2H), 6.56 (d, 1H), 4.36 (m, 2H), 4.27 (m, 3H), 4.06 (m, 3H), 3.86 (m, 1H), 3.48 (m, 2H), 3.20 (m, 1H), 2.69 (m, 1H), 2.60 (m, 2H), 2.35-2.30 (m, 4H), 2.20-1.97 (m, 4H), 1.73 (m, 2H).

Example 117

Step A

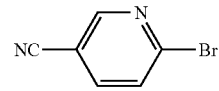

6-Bromonicotinonitrile. 6-Chloronicotinonitrile (13.8 g, 100 mmol) was heated at 145° C. in phosphorus tribromide (150 mL) for 32 h. After cooling, the mixture was concentrated in vacuo. To the residue was added phosphorus tribromide (150 mL), and the mixture was heated at 145° C. for another 32 h. After cooling, the mixture was concentrated in vacuo, and an ice-water mixture (500 mL) was added. Sodium bicarbonate was added to neutralize the mixture, and the product was extracted with ethyl acetate (3×250 mL). The combined organic extracts were washed with brine and dried over magnesium sulfate. The solvent was removed in vacuo, and the residue was chromatographed (hexanes-ethyl acetate) to give 14.9 g (81%) of 6-bromonicotinonitrile as a white solid: ¹H NMR (400 MHz, CDCl₃) δ7.66 (d, J=11.0 Hz, 1H), 7.80 (dd, J=3.1, 11.0 Hz, 1H), 8.67 (d, J=3.1 Hz, 1H); MS m/z 183.0, 185.0 (M+H⁺).

Step B

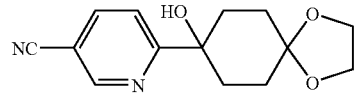

6-(8-Hydroxy-1,4-dioxaspiro[4.5]dec-8-yl)nicotinonitrile. A solution of 6-bromonicotinonitrile (2 g, 0.011 mol) in 50 mL of dry THF and 15 mL of dry hexane under argon was cooled to −100° C. in a liquid nitrogen-Et₂O bath. n-Butyllithium (7.5 mL, 0.011 mol, 1.6 M solution in hexane) was added rapidly dropwise so that the internal temperature did not exceed −95° C. The orange solution was stirred for an additional 10 min at −100° C. to −95° C. and then treated dropwise over 10 min with a solution of 1,4-cyclohexanedione monoethylene ketal (1.8 g, 0.011 mol) in 55 mL of dry THF, again carefully maintaining the temperature below −95° C. The reaction mixture was stirred for 10 min at −100° C. to −95° C., allowed to warm to 20° C. and poured into ice water (400 mL). The organic layer was separated, and the aqueous layer was extracted twice with Et₂O (200 mL). The combined organic extracts were dried over MgSO₄ and evaporated to give 2.8 g of white crystalline solid. Trituration with Et₂O afforded 1.9 g (67% yield) of white crystals: MS: 261 (M+1)⁺.

Step C

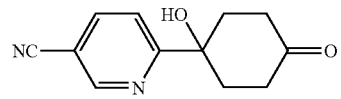

6-(1-Hydroxy-4-oxocyclohexyl)nicotinonitrile. The title compound was synthesized from 6-(8-hydroxy-1,4-dioxaspiro[4.5]dec-8-yl)nicotinonitrile using the sane typical deprotection procedure as for 4-(1-hydroxy-4-oxocyclohexyl)benzonitrile.

Step D

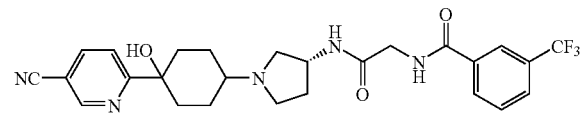

N-[2-({(3R)-1-[4-(5-cyanopyridin-2-yl)-4-hydroxycyclohexyl]pyrrolidin-3-yl}amino)-2-oxoethyl]-3-(trifluoromethyl)benzamide. The title compound was synthesized using a reductive amination procedure similar to that for Example 114. MS (M+H)$^+$ 516.

Example 118

Step A

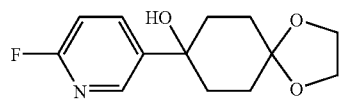

8-(6-Fluoropyridin-3-yl)-1,4-dioxaspiro[4.5]decan-8-ol. A solution of 5-bromo-2-fluoropyridine (2 g, 0.011 mol) in 50 mL of dry ether under nitrogen was cooled to −78° C. n-butyllithium (7.5 mL, 0.011 mol, 1.6 M solution in hexane) and TMEDA (2.5 g, 0.022 mol) were added dropwise. The orange solution was stirred for an additional 1 h at −78° C. and then treated dropwise over 10 min with a solution of 1,4-cyclohexanedione monoethylene ketal (1.8 g, 0.011 mol) in 20 mL of dry THF. The reaction mixture was stirred for 1 h, allowed to warm to 20° C. and poured into ice water (400 mL). The organic layer was separated, and the aqueous layer was extracted twice with EtOAc (20 mL×2). The combined organic extracts were dried over MgSO$_4$ and evaporated to give 2 g of white solid. Chromatography on silica gel afforded 1.7 g (67% yield) of white crystals: MS: 254 (M+1)$^+$.

Step B

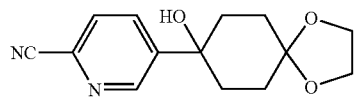

5-(8-Hydroxy-1,4-dioxaspiro[4.5]dec-8-yl)pyridine-2-carbonitrile. To a solution of 1.7 g (6.6 mmol) of 8-(6-fluoropyridin-3-yl)-1,4-dioxaspiro[4.5]decan-8-ol in 20 mL of DMF was added KCN (430 g, 6.6 mmol) and 18-crown-6 ether (1.8 g, 6.6 mmol). The reaction mixture was refluxed for 2 days. Direct chromatography on silica gel afforded the 5-(8-hydroxy-1,4-dioxaspiro[4.5]dec-8-yl)pyridine-2-carbonitrile (620 mg, 36%): MS (m/e): 261 (M+1)$^+$.

Step C

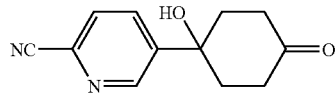

5-(1-Hydroxy-4-oxocyclohexyl)pyridine-2-carbonitrile. The title compound was synthesized from 5-(8-hydroxy-1,4-dioxaspiro[4.5]dec-8-yl)pyridine-2-carbonitrile using the same typical deprotection procedure as for 4-(1-hydroxy-4-oxocyclohexyl)benzonitrile.

Step D

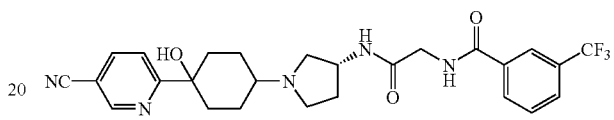

N-[2-({(3R)-1-[4-(6-cyanopyridin-3-yl)-4-hydroxycyclohexyl]pyrrolidin-3-yl}amino)-2-oxoethyl]-3-(trifluoromethyl)benzamide. The title compound was synthesized using a reductive amination procedure similar to that for Example 114. MS 516 (M+H)$^+$.

Example 119

Step A

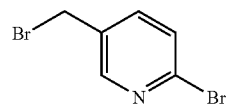

2-Bromo-5-bromomethylpyridine. 2-Bromo-5-methylpyridine (5.00 g, 29.1 mmoles) and N-bromosuccinimide (5.22 g, 29.3 mmoles) were dissolved in carbon tetrachloride (40 mL) under nitrogen. Benzoyl peroxide (0.35 g, 1.4 mmoles) was added and the mixture heated at reflux for four hours. The mixture was cooled to room temperature, filtered, and washed with NaHCO$_3$/H$_2$O. The mixture was adsorbed onto silica gel and then chromatographed. eluting with a gradient of hexane to 10% ethyl acetate/hexane. Pure fractions were combined and concentrated to provide the desired mono-brominated product as a pale yellow solid, 3.60 g (49%). LC/MS (positive ion) m/z=249.8, 251.8, 253.8, (M+H)$^+$. Step B

2-Bromo-5-(methoxymethyl)pyridine. 2-Bromo-5-bromomethyl-pyridine, 4 (3.58 g, 14.3 mmoles) was dissolved in methanol (20 mL) under nitrogen. Sodium methoxide (0.89 g, 15.7 mmoles, 95%) was added and the mixture stirred at room temperature. After 3 hours, the methanol was rotovapped off and the residue dissolved in dichloromethane and washed with water. The organic extract was adsorbed onto silica gel and chromatographed. The column was eluted with a gradient of hexane to 20% ethyl acetate/hexane. Pure fractions were combined and concentrated to provide the title compound as a colorless oil, 2.62 g (90%). LC/MS (positive ion) m/z=202.0, 204.0 (M+H)+. Step C

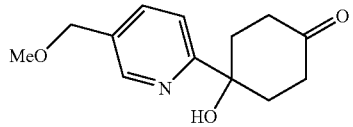

4-Hydroxy-4-[5-(methoxymethyl)pyridin-2-yl]cyclohexanone. A solution of 2-bromo-5-(methoxymethyl)pyridine (2.61 g, 12.9 mmoles) was dissolved in dry THF (40 mL) under nitrogen and cooled to −78° C. n-Butyllithium (6.20 mL, 15.5 mmoles, 2.5 M in hexane) was added dropwise over 10 minutes to form a black solution. After 15 minutes, a solution of 1,4-dioxa-spiro[4.5]decan-8-one (2.21 g, 14.1 mmoles) in THF was added dropwise over 2 minutes and the mixture was gradually warmed to room temperature over 3 hours. TLC (50% ethyl acetate/hexane) and LC/MS indicated complete conversion. Aqueous HCl (14 mL, 6.0 M) was added and the mixture was stirred for 3 hours at room temperature and then neutralized with NaHCO$_3$/H$_2$O. The mixture was extracted 3 times with ethyl acetate and the combined extracts were adsorbed onto silica gel and chromatographed. The column was eluted with a gradient of hexane to 40% ethyl acetate/hexane. Pure fractions were combined and concentrated to provide the title compound as a pale yellow solid, 1.00 g (33%). LC/MS (positive ion) m/z=236.1 (M+H)+.

Step D

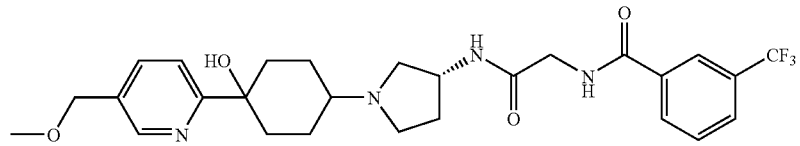

N-{2-[((3R)-1-{trans-4-hydroxy-4-[5-(methoxymethyl) pyridin-2-yl]cyclohexyl}pyrrolidin-3-yl)amino]-2-oxoethyl}-3-(trifluoromethyl)benzamide. N-{2-Oxo-2-[(3R)-pyrrolidin-3-ylamino]ethyl}-3-(trifluoromethyl)benzamide hydrochloride (100 mg, 0.284 mmoles) and 4-hydroxy-4-[5-(methoxymethyl)pyridin-2-yl]cyclohexanone (67.0 mg, 0.284 mmoles) were dissolved in 2-propanol (15 mL). Triethylamine (80 uL, 0.57 mmoles) and sodium triacetoxyborohydride (120 mg, 0.57 mmoles) were added and the mixture was stirred at room temperature overnight. The reaction mixture was adsorbed onto silica gel and chromatographed eluting with dichloromethane to 10% methanol/dichloromethane/0.5% ammonium hydroxide. Fractions were combined to give pure higher Rf isomer as a white solid (90 mg, 59%) and pure lower Rf isomer as a white solid (39 mg, 26%). Higher Rf product: LC/MS (positive ion) m/z=535.2 (M+H); lower Rf product: LC/MS (positive ion) m/z=535.2 (M+M)+.

Example 120

Step A

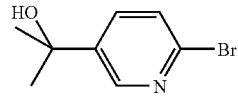

2-(6-Bromopyridin-3-yl)propan-2-ol. 2,5-Dibromopyridine 3.05 g (12.5 mmol) was dissolved in 20 mL of THF and 120 mL of anhydrous ether and cooled to −78° C. 5.0 mL n-butyllithium (2.5 M, 12.5 mmol) was slowly dropped through a syringe in 30 min. After being stirred at −78° C. for 30 minutes, acetone (2 ml, 20 mmol) was added. The reaction mixture was warmed up to room temperature during two hours and then quenched by 10 ml water. The mixture was extracted twice using EtOAc. The combined extracts were dried and concentrated. After crystallization using 20% EtOAc in hexane, 1.30 g of white crystals was obtained (48% yield), MS: 215.0, 217.0 (M++1).

Step B

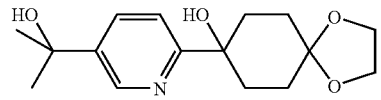

8-[5-(1-Hydroxy-1-methylethyl)pyridin-2-yl]-1,4-dioxaspiro[4,5]decan-8-ol. 2-(6-Bromopyridin-3-yl)propan-2-ol (1.08 g, 5 mmol) was dissolved in 10 mL of THF and 50 mL of anhydrous ether. After the solution was cooled to −78° C., 4.20 ml n-butyllithium (2.5 M, 11 mmol) was slowly dropped through a syringe in 10 min. After being stirred at −78° C. for 30 minutes, 1,4-cyclohexanedione mono-ethylene ketal (0.80 g, 5 mmol) was added. The reaction mixture was warmed up to room temperature during two hours and then quenched by addition of 5 mL of water. The mixture was extracted twice using EtOAc. The combined extracts were dried and concentrated. After flash column using 40-70% EtOAc in hexane, 0.48 g of white crystals were obtained (42% yield), MS: 294.1 (M++1).

Step C

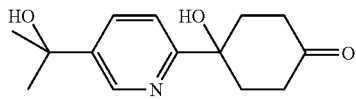

4-Hydroxy-4-[5-(1-hydroxy-1-methylethyl)methyl]pyridin-2-yl}-cyclohexanone. 8-[5-(1-hydroxy-1-methylethyl)pyridin-2-yl]-1,4-dioxaspiro[4,5]decan-8-ol (0.18 g, 2.9 mmol) was dissolved in 10 mL of THF and 10 mL of 2 N HCl solution was added. After being stirred for two hours, the reaction mixture was neutralized to pH-8-9 by saturated NaHCO$_3$ aqueous solution and extracted twice using EtOAc. The combined extracts were dried and concentrated to obtain 0.15 g of white solid (98% yield), MS: 250.2 (M$^+$+1).

Step D

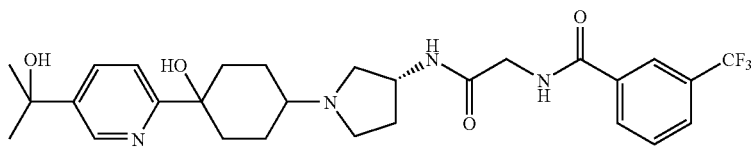

N-{2-[((3R)-1-{4-Hydroxy-4-[5-(1-hydroxy-1-methylethyl)pyridin-2-yl]cyclohexyl}pyrrolidin-3-yl)amino]-2-oxoethyl}-3-(trifluoromethyl)benzamide. The title compound was prepared from the ketone of step C following the procedure described for Example 114. MS 549 (M+H)$^+$.

Example 121

Step A

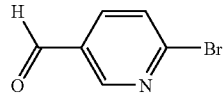

6-Bromo-pyridine-3-carbaldehyde. 2,5-Dibromopyridine 9.48 g (40 mmol) was dissolved in 60 mL of THF and 150 mL of anhydrous ether. After the solution was cooled to −78° C., 16 mL of n-butyllithium (2.5 M, 40 mmol) was slowly dropped through a syringe in 30 min. After being stirred at −78° C. for 30 minutes, N,N-dimethylformamide (3.5 g, 48 mmol) was added. The reaction mixture was warmed up to room temperature during two hours and then quenched by addition of 10 mL of water. The mixture was extracted twice using EtOAc. The combined extracts were dried and concentrated. After flash column using 30-40% EtOAc in hexane, 2.80 g of white solid was obtained (28% yield), MS: 186.0, 188.0 (M$^+$+1).

Step B

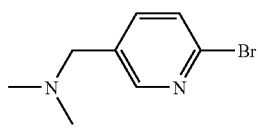

1-(6-Bromopyridin-3-yl)-N,N-dimethylmethanamine. To a solution of titanium tetraisopropoxide (6.4 g, 22 mmol) and 2.0 M of dimethylamine in methanol (22 mL, 44 mmol), 6-bromo-pyridine-3-carbaldehyde (2.10 g, 11 mmol) in 20 mL of methanol was added. After being stirred at r.t. for 5 hrs, sodium borohydride (0.43 g, 11 mmol) was added and the mixture was stirred overnight. The reaction was quenched by addition of 10 mL of water and extracted twice using EtOAc. The combined extracts were dried and concentrated. After flash column using 20-40% methanol in EtOAc and 0.5% NH$_4$OH, 1.15 g of oil was obtained (47% yield), MS: 214.0, 216.0 (M$^+$+1).

Step C

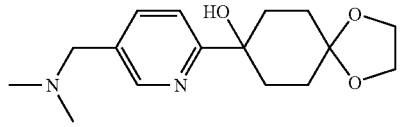

8-{5-[(Dimethylamino)methyl]pyridin-2-yl}-1,4-dioxaspiro[4,5]decan-8-ol. 1-(6-Bromopyridin-3-yl)-N,N-dimethylmethanamine (1.15 g, 5.4 mmol) was dissolved in 30 mL of THF and 80 mL of anhydrous ether. After the solution was cooled to −78° C. 2.60 mL of n-butyllithium (2.5 M, 6.40 mmol) was slowly dropped through a syringe in 10 min. After being stirred at −78° C. for 30 minutes, 1,4-cyclohexanedione mono-ethylene ketal (1.01 g, 6.4 mmol) was added. The reaction mixture was allowed to wram up to room temperature during two hours and then quenched by addition of 10 mL of water. The mixture was extracted twice using EtOAc. The combined extracts were dried and concentrated. After flash column using 20-40% methanol in EtOAc and 0.5% NH$_4$OH, 0.85 g of oil was obtained (54% yield), MS: 293.2.0 (M$^+$+1).

Step D

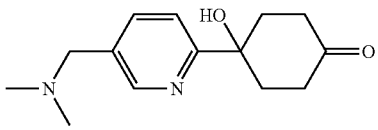

4-{5-[(Dimethylamino)methyl]pyridin-2-yl}-4-hydroxycyclohexanone. 8-{5-[(Dimethylamino)methyl]pyridin-2-yl}-1,4-dioxaspiro[4,5]decan-8-ol (0.85 g, 2.9 mmol) was dissolved in 10 mL of THF and 10 mL of 2 N HCl solution was added. After being stirred for two hours, the reaction mixture was neutralized to pH~8-9 by addition of a saturated NaHCO$_3$ aqueous solution and extracted twice using EtOAc. The combined extracts were dried and concentrated to obtain 0.37 g of white solid (51% yield), MS: 249.2 (M$^+$+1).

Step E

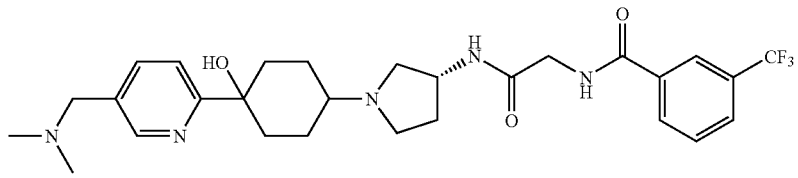

N-(2-{[(3R)-1-(4-{5-[(Dimethylamino)methyl]pyridin-2-yl}-4-hydroxycyclohexyl)pyrrolidin-3-yl]amino}-2-oxoethyl)-3-(trifluoromethyl)benzamide. The title compound was prepared from the ketone of step D following the procedure described for Example 114. MS 548 (M+H)+.

The following Examples were prepared following the procedures analogous to those described for Examples 114-121.

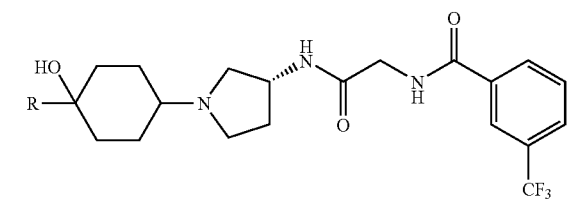

| Example # | R | MS (M + H)+ |
|---|---|---|
| 122 | pyridin-3-yl | 491 |
| 123 | pyridin-4-yl | 491 |
| 124 | 6-methylpyridin-2-yl | 505 |
| 125 | 5-methylpyridin-2-yl | 505 |
| 126 | 4-methylpyridin-2-yl | 505 |
| 127 | 1-oxidopyridin-3-yl | 507 |
| 128 | 1-oxidopyridin-4-yl | 507 |
| 129 | 1-oxidopyridin-2-yl | 507 |
| 130 | 6-methoxypyridin-2-yl | 521 |
| 131 | quinolin-4-yl | 541 |
| 132 | 4-cyanophenyl | 515 |
| 133 | 3-cyanophenyl | 515 |
| 134 | 4-(methylaminocarbonyl)phenyl | 547 |
| 135 | 4-(ethylaminocarbonyl)phenyl | 561 |
| 136 | 4-(isopropylaminocarbonyl)phenyl | 575 |
| 137 | 4-(tert-butylaminocarbonyl)phenyl | 589 |
| 138 | 4-(dimethylaminocarbonyl)phenyl | 561 |
| 139 | 4-[(azetidin-1-yl)carbonyl]phenyl | 573 |
| 140 | 4-[(pyrrolidin-1-yl)carbonyl]phenyl | 587 |
| 141 | 4-[(morpholin-4-yl)carbonyl]phenyl | 603 |
| 142 | 4-(dimethylaminocarbonyl)-2-methylphenyl | 575 |
| 143 | 2-methyl-4-(methylaminocarbonyl)phenyl | 561 |
| 144 | 3-methyl-4-(methylaminocarbonyl)phenyl | 561 |
| 145 | 4-(dimethylaminocarbonyl)-3-methylphenyl | 575 |
| 146 | 3-methyl-4-(pyrrolidin-1-ylcarbonyl)phenyl | 601 |
| 147 | 4-(dimethylaminocarbonyl)-3-fluorophenyl | 579 |
| 148 | 4-[(2,2,2-trifluoroethyl)aminocarbonyl]phenyl | 615 |
| 149 | 3-fluoro-4-(methylaminocarbonyl)phenyl | 565 |
| 150 | 4-(ethylaminocarbonyl)-3-fluorophenyl | 579 |
| 151 | 3-(methylaminocarbonyl)phenyl | 547 |
| 152 | 3-(dimethylaminocarbonyl)phenyl | 561 |
| 153 | 5-(dimethylaminocarbonyl)-2-methoxyphenyl | 591 |
| 154 | 2-methoxy-5-(methylaminocarbonyl)phenyl | 577 |
| 155 | 3-(methylaminocarbonylamino)phenyl | 562 |
| 156 | 6-(morpholin-4-yl)pyridin-3-yl | 576 |
| 157 | 6-dimethylaminopyridin-3-yl | 534 |
| 158 | 6-isopropylaminopyrid-3-yl | 549 |
| 159 | 6-(pyrrolidin-1-yl)pyridin-3-yl | 560 |
| 160 | 6-cyclopropylaminopyridin-3-yl | 546 |
| 161 | 6-ethoxypyridin-3-yl | 535 |
| 162 | 6-(2-fluoroethoxy)pyridin-3-yl | 553 |

-continued

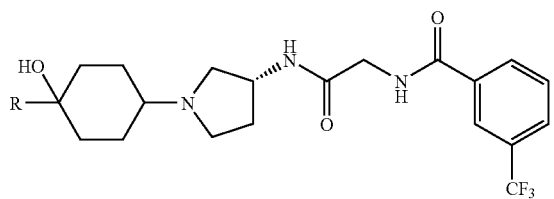

| Example # | R | MS (M + H)+ |
|---|---|---|
| 163 | 6-(2,2-difluoroethoxy)pyridin-3-yl | 571 |
| 164 | 6-(2,2,2-trifluoroethoxy)pyridin-3-yl | 589 |
| 165 | phenyl | 490 |
| 166 | 4-methylphenyl | 504 |
| 167 | 4-fluorophenyl | 508 |
| 168 | 3-fluorophenyl | 508 |
| 169 | 4-bromophenyl | 568 |
| 170 | 4-iodophenyl | 616 |
| 171 | 5-(pyrrolidin-1-ylcarbonyl)-2-pyridyl | 588 |
| 172 | 5-(morpholin-4-ylcarbonyl)-2-pyridyl | 604 |
| 173 | 5-dimethylaminocarbonyl-2-pyridyl | 562 |
| 174 | 4-methylaminocarbonylaminophenyl | 562 |
| 175 | 6-(1-hydroxy-1-methylethyl)pyridin-3-yl | 549 |
| 176 | 4-(1-hydroxy-1-methylethyl)phenyl | 548 |
| 177 | 4-(methoxymethyl)phenyl | 534 |
| 178 | 3-fluoro-4-(methoxymethyl)phenyl | 552 |
| 179 | 4-(dimethylaminomethyl)phenyl | 547 |
| 180 | 4-(dimethylaminomethyl)-3-fluorophenyl | 565 |
| 181 | 1H-indazol-5-yl | 530 |
| 182 | 1-methyl-1H-indazol-5-yl | 544 |
| 183 | 2-methyl-1H-indazol-5-yl | 544 |

Example 184

Step A

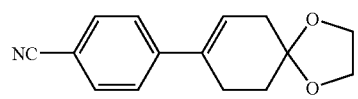

4-(1,4-Dioxaspiro[4.5]dec-7-en-8-yl)benzonitrile. To a solution of 4-(8-hydroxy-1,4-dioxaspiro[4.5]dec-8-yl)benzonitrile (7.8 g) in methylene chloride (100 mL) was added triethylamine (21 mL) at room temperature. The solution was cooled down to −40° C. and then mesyl chloride (4.7 mL) was added dropwise. The reaction mixture was stirred at −40° C. for 30 min, then warmed up to room temperature gradually and continuously stirred overnight. The reaction was quenched with sat. aqueous NaHCO$_3$ solution. The aqueous layer was extracted with methylene chloride. The combined organic extracts were washed with brine, dried with Na$_2$SO$_4$, then evaporated. The residue was purified by column (Hex/

EtOAc=5/1) to give the product 5.2 g as a white solid (yield: 71%): $^1$H NMR (CDCl$_3$) δ 7.62-7.55 (2H, m), 7.50-7.45 (2H, m), 6.17-6.13 (1H, m), 4.02 (4H, s), 2.68-2.62 (2H, m), 2.53-2.47 (2H, m), 1.96-1,92 (2H, m); MS: 242 (M+1)$^+$.

Step B

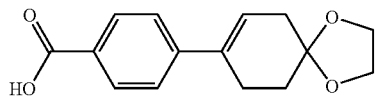

4-(1,4-Dioxaspiro[4.5]dec-7-en-8-yl)benzoic acid. A mixture of 4-(1,4-Dioxaspiro[4.5]dec-7-en-8-yl)benzonitrile (5.2 g, 0.021 mol) in 190 mL of 2-methoxyethanol and 190 mL of 2.5 N NaOH was heated on the steam bath for 15 h. The solution was cooled in an ice bath, adjusted to pH 7-8 with concentrated HCl, and evaporated to dryness. Water (375 mL) was added, and the PH was adjusted to 2 with HCl. The tan solid was filtered off and washed with water to give 5.3 g (94% yield) of 4-(1,4-dioxaspiro[4.5]dec-7-en-8-yl)benzoic acid: $^1$H NMR (CDCl$_3$) δ 8.06-8.01 (2H, m), 7.53-7.46 (2H, m), 6.18-6.14 (1H, m), 4.03 (4H, s), 2.73-2.67 (2H, m), 2.52-2.49 (2H, m), 2.00-1.93 (2H, m); MS: 260 (M+1)$^+$.

Step C

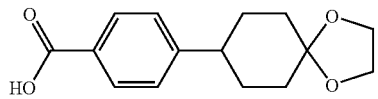

4-(1,4-Dioxaspiro[4.5]dec-8-yl)benzoic acid. To a solution of 5.3 g of 4-(1,4-dioxaspiro[4.5]dec-7-en-8-yl)benzoic acid in 30 mL of methanol was added 2.3 g of Pd/C (10% wt). The suspension was stirred under H$_2$ (balloon) for 1 h, filtered through celite pad and concentrated to dryness to give the desired product (5.2 g, yield: 97%) as a white solid: $^1$H NMR (CDCl$_3$) δ 8.06-8.01 (2H, m), 7.58-7.53 (2H, m), 4.02 (4H, s), 2.73-2.67 (2H, m), 2.70-2.61 (1H, m), 1.93-1.64 (8H, m); MS: 262 (M+1)$^+$.

4-(1,4-Dioxaspiro[4.5]dec-8-yl)-N,N-dimethylbenzamide. 564 mg (2 mmol) of 4-(1,4-dioxaspiro[4.5]dec-8-yl) benzoic acid, N,N-dimethylamine (1.2 mL, 2.0 M THF solution), BOP reagent (1.07 g, 2.4 mmol) and 0.8 mL (6 mmol) of triethylamine were dissolved in 15 mL of DMF at room temperature. The reaction mixture was stirred at r.t. overnight. Direct chromatography on silica gel (flash chromatography grade) with 50% Ethyl acetate-hexane gave 466 mg (80%) of the desired product, 4-(1,4-dioxaspiro[4.5]dec-8-yl)-N,N-dimethylbenzamide: $^1$H NMR (CDCl$_3$) δ 7.39 (2H, d, J=11.6 Hz), 7.29 (2H, d, J=10.6 Hz), 3.93 (4H, s), 3.17-2.99 (7H, m), 2.55-2.49 (4H, m), 2.13-2.10 (2H, m), 2.00-1.90 (2H, m); MS: 289 (M+1)$^+$.

Step E

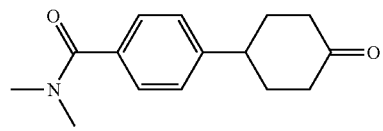

N,N-Dimethyl-4-(4-oxocyclohexyl)benzamide. 466 mg (1.6 mmol) of 4-(1,4-dioxaspiro[4.5]dec-8-yl)-N,N-dimethylbenzamide was dissolved in the mixture solvent of 8 mL of THF and 8 mL of 1N HCl aqueous solution at room temperature. The reaction mixture was then stirred at 60° C. for 1 h. The solution was cooled down to room temperature, adjusted to pH 7-8 with saturated NaHCO$_3$ aqueous solution. The organic layer was separated, and the aqueous layer was extracted twice with EtOAc (20 mL×2). The combined organic extracts were dried over MgSO$_4$ and evaporated to give an oil residue. Chromatography on silica gel (flash chromatography grade) with 40% Ethyl acetate-hexane gave 360 mg (90%) of the desired product, N,N-dimethyl-4-(4-oxocyclohexyl)benzamide. $^1$H NMR (CDCl$_3$) δ 7.39 (211, d, J=11.6 Hz), 7.29 (2H, d, J=10.6 Hz), 3.15-2.99 (7H, m), 2.56-2.49 (4H, m), 2.15-2.10 (2H, m), 2.01-1.94 (2H, m); MS: 245 (M+1)$^+$.

Step F

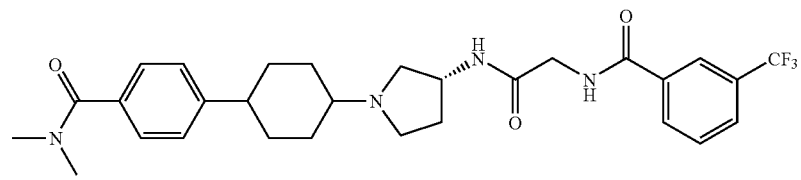

Step D

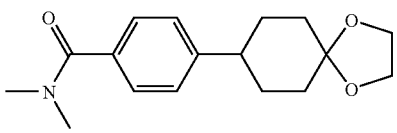

N,N-dimethyl-4-(4-{(3R)-3-[({[3-trifluoromethyl)benzoyl]amino}acetyl)amino]pyrrolidin-1-yl}cyclohexyl)benzamide. 100 mg (0.4 mmol) of N,N-dimethyl(4-oxocyclohexyl)benzamide and 126 mg (0.4 mmol) of N-{2-oxo-2-[(3R)-pyrrolidin-3-ylamino]ethyl}-3-(trifluoromethyl) benzamide were dissolved in 10 mL of methylene chloride. To the solution was added 170 mg (0.8 mmol) of sodium triacetoxyborohydride. The reaction mixture was stirred at room temperature for 2 h. Direct chromatography on silica gel gave the final desired product 45 mg (top spot on TLC and first peak on HPLC), yield: 22%. MS: 545 (M+1)$^+$.

The following Examples were prepared in a similar manner.

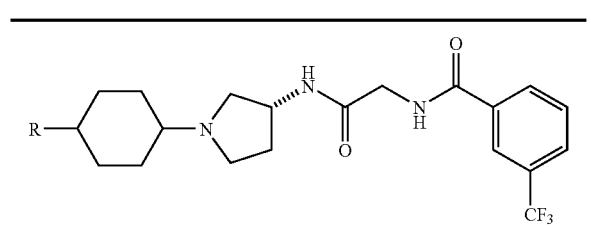

| Example # | R | MS (M + H)+ |
|---|---|---|
| 185 | 4-(methylaminocarbonyl)phenyl | 531 |
| 186 | 4-(morpholin-4-ylcarbonyl)phenyl | 587 |
| 187 | 4-(piperidin-1-ylcarbonyl)phenyl | 585 |
| 188 | 3-fluoro-4-(pyrrolidin-1-ylcarbonyl)phenyl | 589 |
| 189 | 5-(pyrrolidin-1-ylcarbonyl)pyridin-2-yl | 572 |
| 190 | 5-(dimethylaminocarbonyl)pyridin-2-yl | 546 |
| 191 | 5-(morpholin-4-ylcarbonyl)pyridin-2-yl | 588 |
| 192 | pyridin-2-yl | 475 |
| 193 | pyridin-3-yl | 475 |
| 194 | pyridin-4-yl | 475 |
| 195 | 1-oxidopyridin-2-yl | 491 |
| 196 | 1-oxidopyridin-3-yl | 491 |
| 197 | 1-oxidopyridin-4-yl | 491 |
| 198 | quinolin-4-yl | 525 |
| 199 | 6-methoxypyridin-3-yl | 505 |
| 200 | 6-(morpholin-4-yl)pyridin-3-yl | 560 |
| 201 | 4-(dimethylaminomethyl)phenyl | 531 |
| 202 | 5-(dimethylaminomethyl)pyridin-2-yl | 532 |
| 203 | 5-(dimethylaminomethyl)pyridin-2-yl | 546 |
| 204 | 4-[hydroxy(pyridin-3-yl)methyl]phenyl | 581 |
| 205 | 6-[(hydroxy(pyridin-3-yl)methyl]pyridin-3-yl | 582 |
| 206 | 6-(dimethylaminocarbonyl)pyridin-3-yl | 546 |
| 207 | 4-(4-hydroxypiperidin-1-ylcarbonyl)phenyl | 601 |
| 208 | 4-(4-methoxypiperidin-1-ylcarbonyl)phenyl | 615 |
| 209 | 5-(4-methoxypiperidin-1-ylcarbonyl)pyridin-2-yl | 616 |
| 210 | 6-(4-methoxypiperidin-1-ylcarbonyl)pyridin-3-yl | 616 |

Example 211

Step A

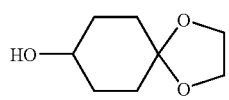

1,4-Dioxaspiro[4.5]decan-8-ol. 1,4-Cyclohexanedione mono-ethylene ketal (5.0 g, 32 mmol) in 20 mL of MeOH/water (1:1) was added NaBH$_4$ (1.21 g, 32 mmol). The mixture was stirred at room temperature overnight. The MeOH was removed via rotary evaporation. The aqueous layer was extracted with EtOAc (3×). The combined organic layers were dried (MgSO$_4$), and concentrated to give an oil which was stored on a high vacuum line overnight to afford 5.12 g of 1,4-dioxaspiro[4.5]decan-8-ol as as an oil. MS (EI) calcd: (M+H)$^+$=159.1; found: 159.2.

Step B

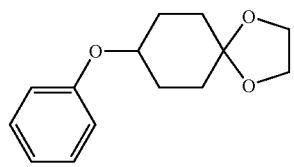

8-Phenoxy-1,4-dioxaspiro[4.5]decane. To a solution of 1,4-dioxaspiro[4.5]decan-8-ol (1.05 g, 6.63 mmol), phenol (0.75 g, 7.95 mmol), triphenylphosphine (1.91 g, 7.29 mmol) in CH$_2$Cl$_2$ (20 mL) was added disopropyl azodicarboxylate (1.57 mL, 7.95 mmol). After being stirred overnight at room temperature under N$_2$, the reaction mixture was concentrated. The residue was flash chromatographed using 10:90 hexane-EtOAc to give 1.09 g of 8-phenoxy-1,4-dioxaspiro[4.5]decane. MS (EI) calcd: (M+H)$^+$=235.1; found: 235.0.

Step C

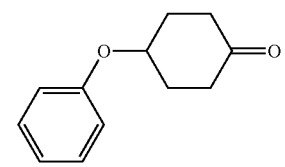

4-Phenoxycyclohexanone. A solution of 8-phenoxy-1,4-dioxaspiro[4.5]decane (1.05 g, 4.48 mmol) in 20 mL of THF/3N HCl (1:1) was stirred overnight at room temperature. The aqueous was extracted with EtOAc (3×). The combined organic layers were dried (MgSO$_4$), and concentrated to give 4-phenoxycyclohexanone as an oil. MS (EI) calcd: M+H =191.1; found: 191.0.

Step D

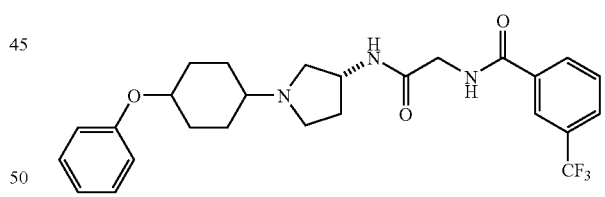

N-(2-Oxo-2-{[(3R)-1-(4-phenoxycyclohexyl)pyrrolidin-3-yl]amino}ethyl)-3-(trifluoromethyl)benzamide. To a mixture of 4-phenoxycyclohexanone (0.091 g, 0.475 mmol) and N-[2-oxo-2-({2-oxo-2-[(3R)-pyrrolidin-3-ylamino] ethyl}amino)ethyl]-3-(trifluoromethyl)benzamide in 2% AcOH/CH$_2$Cl$_2$ (10 mL) was added NaB(OAc)$_3$H (0.134 g, 0.634 mmol). After being stirred overnight at room temperature under N$_2$, the reaction mixture was diluted with EtOAc and washed with saturated Na$_2$CO$_3$. The aqueous was extracted with EtOAc (3×). The combined organic layers were dried (MgSO$_4$), concentrated and flash chromatographed (EtOAc to EtOAc:MeOH:Et$_3$N=9:1:0.1) to give 0.12 g of the title compound. MS (EI) calcd: (M+H)$^+$=490.2; found 490.0.

Example 212

Step A

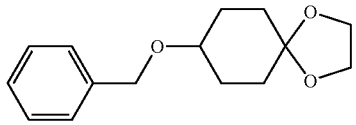

8-(Benzyloxy)-1,4-dioxaspiro[4.5]decane. To a mixture of 1,4-dioxaspiro[4.5]decan-8-ol (1.18 g, 7.46 mmol) and NaH (0.358 g, 8.96 mmol) in DMF (5 mL) at 0° C. was added benzyl bromide (1.06 mL, 8.95 mmol). After being stirred overnight under $N_2$, water and EtOAc were added. The aqueous layer was extracted with EtOAc (3×). The combined organic layers were dried (MgSO$_4$), concentrated and flash chromatographed using 10% EtOAc/hexane to give 1.524 g of the title compound. MS (EI) calcd: (M+1)$^+$=249.1; found: 249.2. $^1$H NMR (300 MHz, CDCl$_3$) δ (ppm) 7.35 (5H, m), 4.52 (2H, s), 3.95 (4H, m), 3.5 (1H, m), 1.95-1.50 (8H, m).

Step B

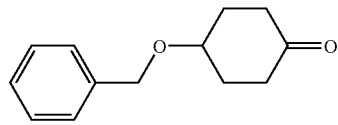

4-(Benzyloxy)cyclohexanone. The title compound was prepared from step A following the procedure as described in step C of Example 211. MS (EI) calcd: (M+H)$^+$=205.1; found: 205.0.

Step C

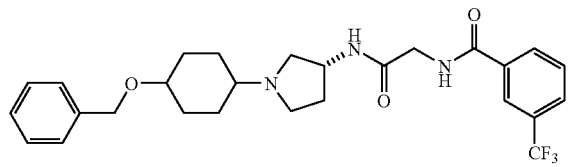

N-[2-({(3R)-1-[4-(Benzyloxy)cyclohexyl]pyrrolidin-3-yl}amino)-2-oxoethyl]-3-(trifluoromethyl)benzamide. The title compound was prepared from step B following the procedure described in step D of Example 211. MS (EI) calcd: (M+H)$^+$=504.2; found: 504.4.

Example 213

Step A

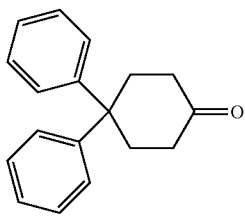

4,4-Diphenyl-cyclohexanone. To a Parr hydrogenation bottle was added 4,4-diphenyl-2-cyclohexen-1-one (0.91 g, 3.66), dissolved in methanol (20 mL), followed by the addition of 10% Pd/C (0.2 g). This mixture was hydrogenated at 50 psi overnight. After the catalyst was filtered and washed with methanol, the filtrate was concentrated in vacuo to give 0.90 g of 4,4-diphenyl-cyclohexanone. MS (EI) calcd: M+H=251.1; found: 251.1.

Step B

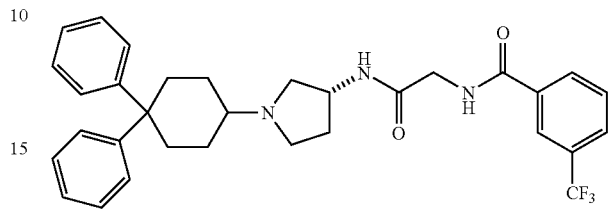

N-(2-{[(3R)-1-(4,4-Diphenyleyclohexyl)pyrrolidin-3-yl]amino}-2-oxoethyl)-3-(trifluoromethyl)benzamide. The title compound was prepared from step A following the procedure described in step D of Example 211. MS (EI) calcd: (M+H)$^+$=550.3; found: 550.5.

Example 214

Step A

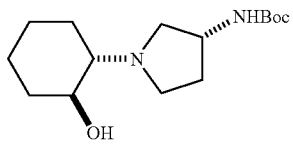

tert-Butyl [(3R)-1-(trans-2-Hydroxycyclohexyl)pyrrolidin-3-yl]carbamate. To a seal tube were added cyclohexene oxide (2.34 mL, 23.2), tert-butyl-(3R)-pyrrolidin-3-yl carbamate (2.16 mmol) and MeOH (2 mL). This mixture was sealed, heated at 60° C. and stirred overnight. The reaction mixture was concentrated to give 3.29 g of tert-butyl [(3R)-1-(2-hydroxycyclohexyl)pyrrolidin-3-yl]carbamate. MS (EI) calcd: (M+H)$^+$=285.2; found: 285.1.

Step B

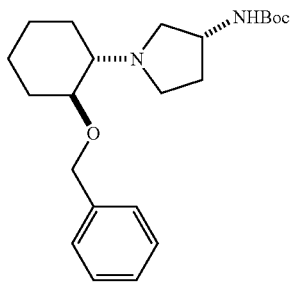

tert-Butyl{(3R)-1-[trans-2-(Benzyloxy)cyclohexyl]pyrrolidin-3-yl}carbamate. To a mixture of tert-butyl [(3R)-1-(trans-2-hydroxycyclohexyl)pyrrolidin-3-yl]carbamate (0.70 g, 2.46 mmol) and 60% NaH (0.108 g, 2.71 mmol) in DMF (5 mL) at 0° C. was added benzyl bromide (0.79 mL, 2.71 mmol). After being stirred overnight under N$_2$, water and EtOAc were added. The aqueous layer was extracted with EtOAc (3×). The combined organic layers were dried (MgSO$_4$), concentrated and flash chromatographed (EtOAc to 10% MeOH/EtOAc) to give 0.60 g of the title compound. MS (EI) calcd: (M+H)$^+$=375.3; found: 375.4.

Step C

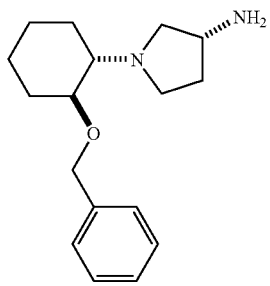

(3R)-1-[trans-2-(Benzyloxy)cyclohexyl]pyrrolidin-3-amine. The mixture of tert-butyl {(3R)-1-[2-(trans-benzyloxy)cyclohexyl]pyrrolidin-3-yl}carbamate (0.60 g, 1.602 mmol) in 4 N HCl/dioxane (10 mL) was stirred at room temperature for 1 hour. The solution was concentrated to give 0.55 g of the title compound as 2 HCl salt. MS (EI) calcd: (M+1)$^+$=275.2; found: 275.3.

Step D

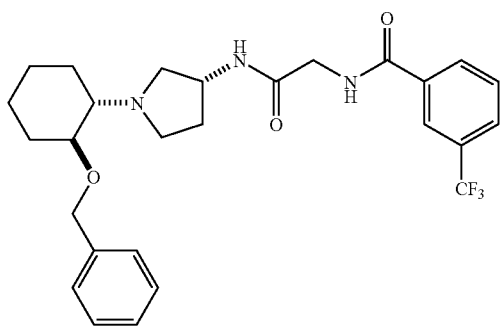

N-[2-({(3R)-1-[trans-2-(Benzyloxy)cyclohexyl]pyrrolidin-3-yl}amino)-2-oxoethyl]-3-(trifluoromethyl)benzamide. To a stirred solution of (3R)-1-[trans-2-(benzyloxy)cyclohexyl]pyrrolidin-3-amine 2 HCl salt (0.14 g, 0.45 mmol) and (3-trifluoromethyl-benzoylamino)-acetic acid (0.111 g, 0.45 mmol) in CH$_2$Cl$_2$ (5 mL) was added Et$_3$N (0.188 mL, 1.35 mmol) followed by EDC (0.0863 g, 0.45 mmol) and HOBt (0.069 g, 0.45 mmol). The mixture was stirred at room temperature overnight. Then the reaction mixture was diluted with EtOAc and washed with saturated Na$_2$CO$_3$ and brine. The organic layers was dried (MgSO$_4$), concentrated and flash chromatographed (EtOAc to 10% MeOH/EtOAc) to give 0.186 g of the title compound. MS (EI) calcd: M+1=504.2; found: 504.4.

Example 215

Step A

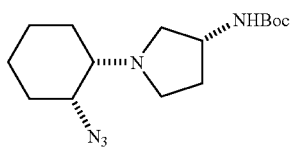

tert-Butyl [(3R)-1-(cis-2-Azidocyclohexyl)pyrrolidin-3-yl]carbamate. To the mixture of tert-butyl [(3R)-1-(2-hydroxycyclohexyl)pyrrolidin-3-yl]carbamate (3.29 g, 11.60 mmol), and Et$_3$N (3.23 mL, 23.17) in CH$_2$Cl$_2$ (20 mL) was added MsCl (1.08 mL, 12.86 mmol) at 0° C. After being stirred overnight under N$_2$, water and EtOAc were added. The aqueous layer was extracted with EtOAc (3×). The combined organic layers were dried (MgSO$_4$) and concentrated. The residue was mixed with NaN$_3$ in 20 mL DMF and stirred at 80° C. overnight under N$_2$. Then the reaction mixture was diluted with EtOAc and washed with water (3×). The organic layers was dried (MgSO$_4$) and concentrated to give 2.87 g of the title compound. MS (EI) calcd: (M+H)$^+$=310.2; found: 310.1.

Step B

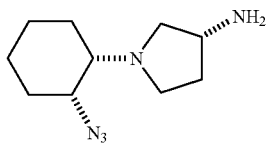

(3R)-1-(cis-2-Azidocyclohexyl)pyrrolidin-3-amine. The mixture of tert-butyl [(3R)-1-(cis-2-azidocyclohexyl)pyrrolidin-3-yl]carbamate (0.57 g, 1.842 mmol) in 4 N HCl/dioxane (10 mL) was stirred at room temperature for 1 hour. The solution was concentrated to give 0.48 g of the title compound as HCl salt. MS (EI) calcd: (M+H)$^+$=210.2; found: 210.2.

Step C

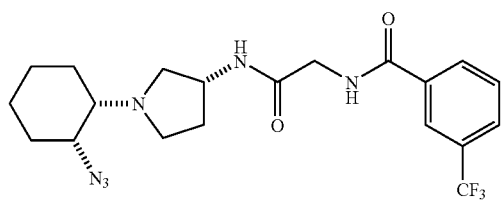

N-(2-{[(3R)-1-(cis-2-Azidocyclohexyl)pyrrolidin-3-yl]amino}-2-oxoethyl)-3-(trifluoromethyl)benzamide. To a stirred solution of (3R)-1-(cis-2-azidocyclohexyl)-pyrrolidin-3-amine (0.453 g, 1.842 mmol) and (3-trifluoromethyl-benzoylamino)-acetic acid (0.478 g, 1.934 mmol) in CH$_2$Cl$_2$ (15 mL) was added Et$_3$N (0.57 mL, 4.06 mmol) followed by EDC (0.389 g, 2.03 mmol) and HOBt (0.287 g, 2.13 mmol). The mixture was stirred at room temperature for 3 h. Then the reaction mixture was diluted with EtOAc and washed with saturated Na$_2$CO$_3$ and brine. The organic layer was dried (MgSO$_4$), concentrated and flash chromatographed (EtOAc to 10% MeOH/EtOAc) to give 0.745 g of the title compound. MS (EI) calcd: (M+H)$^+$=439.3; found: 439.4.

Step D

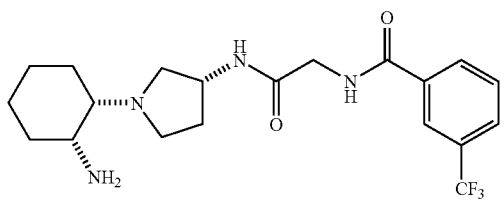

N-(2-{[(3R)-1-(cis-2-Aminocyclohexyl)pyrrolidin-3-yl]amino}-2-oxoethyl)-3-(trifluoromethyl)benzamide. To a Parr hydrogenation bottle was added N-(2-{[(3R)-1-(cis -2-azidocyclohexyl)pyrrolidin-3-yl]amino}-2-oxoethyl)-3-(trifluoromethyl)benzamide (0.745 g, 1.70 mmol), dissolved in methanol (20 mL), followed by the addition of 10% Pd/C (0.15 g). This mixture was hydrogenated at 50 psi for 3 h. After the catalyst was filtered and washed with methanol, the filtrate was concentrated in vacuo to give 0.70 g of N-(2-{[(3R)-1-(cis-2-aminocyclohexyl)pyrrolidin-3-yl]amino}-2-oxoethyl)-3-(trifluoromethyl)benzamide. MS (EI) calcd: (M+H)$^+$=413.2; found: 413.3.

Step E

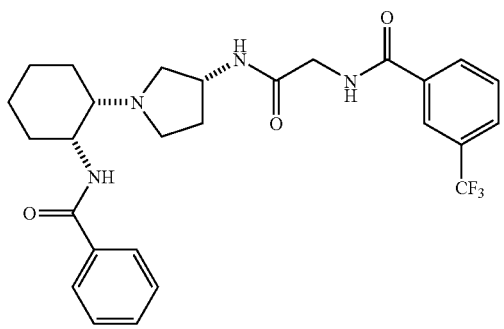

N-[2-({(3R)-1-[cis-2-(Benzoylamino)cyclohexyl]pyrrolidin-3-yl}amino)-2-oxoethyl]-3-(trifluoromethyl)benzamide. To a stirred solution of N-(2-{[(3R)-1-(cis-2-aminocyclohexyl)pyrrolidin-3-yl]amino}-2-oxoethyl)-3-(trifluoromethyl)benzamide (0.48 g, 0.6 mmol) and benzoic acid (0.088 g, 0.72 mmol) in CH$_2$Cl$_2$ (5 mL) was added Et$_3$N (0.25 mL, 1.8 mmol) followed by EDC (0.138 g, 0.72 mmol) and HOBt (0.097 g, 0.72 mmol). The mixture was stirred at room temperature overnight. Then the reaction mixture was diluted with EtOAc and washed with saturated Na$_2$CO$_3$ and brine. The organic layer was dried (MgSO$_4$), concentrated and flash chromatographed (EtOAc to 10% MeOH/EtOAc) to give 0.13 g of the title compound. MS (EI) calcd: (M+H)$^+$=517.2; found: 517.3.

Example 216

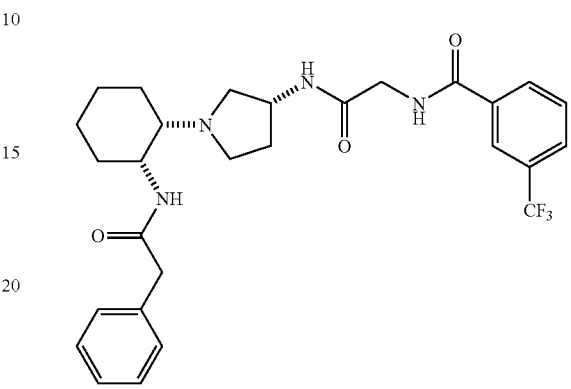

N-{2-Oxo-2-[((3R)-1-{cis-2-[(phenylacetyl)amino]cyclohexyl}pyrrolidin-3-yl)amino]ethyl}-3-(trifluoromethyl)benzamide. The title compound was prepared following the procedure described for Example 215. MS (EI) calcd: (M+H)$^+$=531.3; found: 531.3.

Example 217

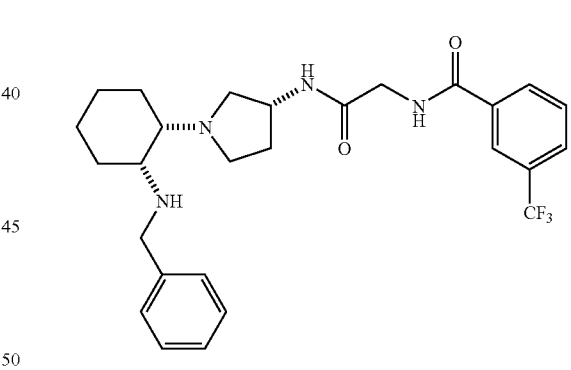

N-[2-({(3R)-1-[cis-2-(Benzylamino)cyclohexyl]pyrrolidin-3-yl}amino)-2-oxoethyl]3-(trifluoromethyl)benzamide. To a mixture of benzaldehyde (0.061 mL, 0.6 mmol) and N-(2-{[(3R)-1-(cis-2-aminocyclohexyl)pyrrolidin-3-yl]amino}-2-oxoethyl)-3-(trifluoromethyl)benzamide (0.278 g, 0.60 mmol) in CH$_2$Cl$_2$ (10 mL) was added NaB(OAc)$_3$H (0.128 g, 0.60 mmol). After being stirred overnight at room temperature under N$_2$, the reaction mixture was diluted with EtOAc and washed with saturated Na$_2$CO$_3$. The aqueous layer was extracted with EtOAc (3×). The combined organic layers were dried (MgSO$_4$), concentrated and flash chromatographed (EtOAc to EtOAc:MeOH:Et$_3$N=9:1:0.5) to give 0.21 g of the title compound. MS (EI) calcd: (M+H)$^+$=503.3; found: 503.4.

Example 218

Step A

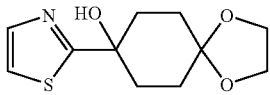

8-(1,3-Thiazol-2-yl)-1,4-dioxaspiro[4.5]decan-8-ol. A solution of n-butyllithium (8.1 mL of 1.6 M solution in hexane, 12.92 mmol) was added to thiazole (1.0 g, 11.75 mmol) in THF (10 mL) at −78° C. with stirring under $N_2$. After being stirred at −78° C. for 1 h, a solution of 1,4-cyclohexanedione mono-ethylene ketal (1.84 g, 11.75 mmol) in THF (10 mL) was added to the lithiated compound solution via syringe and stirred for 3 h at −78° C. Water (5 mL) was added, and the reaction mixture was warmed to room temperature and extracted using EtOAc (3×). The combined organic layers were dried ($MgSO_4$), filtered, concentrated in vacuo and chromatographed to yield 2.531 g of 8-(1,3-thiazol-2-yl)-1,4-dioxaspiro[4.5]decan-8-ol in 89% yield. MS (EI) calcd: $(M+H)^+$=242.1; found: 242.2.

Step B

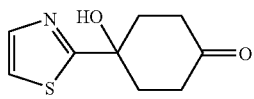

4-Hydroxy-4-(1,3-thiazol-2-yl)cyclohexanone. A solution of 8-(1,3-thiazol-2-yl)-1,4-dioxaspiro[4.5]decan-8-ol (1.0 g, 4.14 mmol) in 20 mL of THF/3 N HCl (1:1) was stirred for 1 h at 50° C. After cooling to room temperature, the mixture was treated with $Na_2CO_3$ to pH 8 and extracted with EtOAc (3×). The combined organic layers were washed with saturated NaCl solution, dried ($MgSO_4$), and concentrated to give 0.82 g of 4-hydroxy-4-(1,3-thiazol-2-yl)cyclohexanone in 99% yield. MS (EI) calcd: $(M+H)^+$=198.1; found: 198.2.

Step C

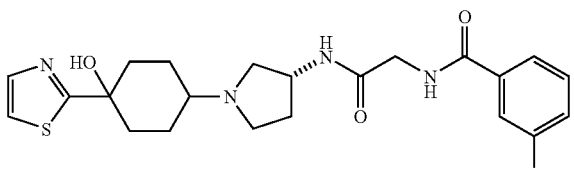

N-[2-({(3R)-1-[4-Hydroxy-4-(1,3-thiazol-2-yl)cyclohexyl]pyrrolidin-3-yl}amino) -2-oxoethyl]-3-(trifluoromethyl)benzamide. To a mixture of 4-hydroxy-4-(1,3-thiazol-2-yl)cyclohexanone (0.075 g, 0.38 mmol) and N-[2-oxo-2-({2-oxo-2-[(3R)-pyrrolidin-3-ylamino]ethyl}amino)ethyl]-3-(trifluoromethyl)benzamide (0.10 g, 0.317 mmol) in 2% AcOH($CH_2Cl_2$ (10 mL) was added $NaB(OAc)_3H$ (0.134 g, 0.634 mmol). After being stirred overnight at room temperature under $N_2$, the reaction mixture was diluted with EtOAc and washed with saturated $Na_2CO_3$. The aqueous was extracted with EtOAc (3×). The combined organic layers were dried ($MgSO_4$), concentrated and flash chromatographed [EtOAc to MeOH/EtOAc (1:9) then to 5% MeOH/EtOAc/$Et_3N$ (1:9:0.5)] to give 0.141 g of the title compound in 90% yield. MS (E) calcd: $(M+H)^+$=497.2; found: 497.3.

Example 219

Step A

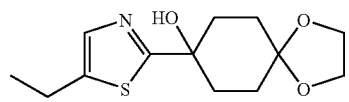

8-(5-Ethyl-1,3-thiazol-2-yl)-1,4-dioxaspiro[4.5]decan-8-ol. A solution of n-butyllithium (5.70 mL of 1.6 M solution in hexane, 9.12 mmol) was added to 8-(1,3-thiazol -2-yl)-1,4-dioxaspiro[4.5]decan-8-ol (1.00 g, 4.14 mmol) in THF (10 mL) at −78° C. with stirring under $N_2$. After being stirred at −78° C. for 1 h, ethyl iodide (0.736 mL, 9.12 mmol) was added to the lithiated compound solution via syringe at −78° C. The reaction mixture was allowed to warm to room temperature slowly and stirred overnight. Water and EtOAc were added. The aqueous layer was extracted with EtOAc (3×). The combined organic layers were washed with saturated NaCl, dried ($MgSO_4$), concentrated and flash chromatographed using 20% EtOAc/hexane to give 0.79 g of the title compound in 71% yield. MS (EI) calcd: $(M+H)^+$=270.1; found: 270.1.

Step B

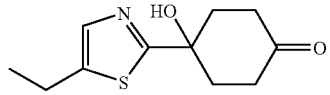

4-(5-Ethyl-1,3-thiazol-2-yl)-4-hydroxycyclohexanone. The title compound was prepared from the ketal of step A using a procedure similar to that described in step B of Example 218. MS (EI) calcd: $(M+H)^+$=226.1; found: 226.2.

Step C

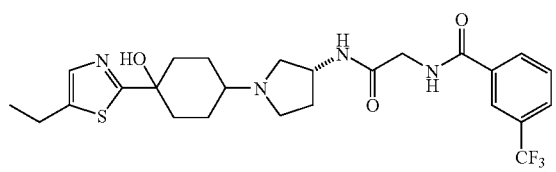

N-[2-({(3R)-1-[4-(5-Ethyl-1,3-thiazol-2-yl)-4-hydroxycyclohexyl]pyrrolidin-3-yl}amino)-2-oxoethyl]-3-(trifluoromethyl)benzamide. The title compound was prepared from the ketone of step B using a procedure similar to that described for Example 218. MS (EI) calcd: $(M+H)^+$=525.2; found: 525.2.

Example 220

Step A

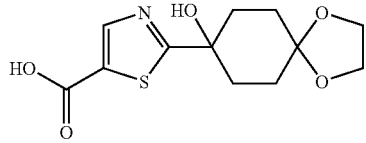

2-(8-Hydroxy-1,4-dioxaspiro[4.5]dec-8-yl)-1,3-thiazole-4-carboxylic acid. A solution of n-butyllithium (17.1 mL of 1.6 M solution in hexane, 27.35 mmol) was added to 8-(1,3-thiazol-2-yl)-1,4-dioxaspiro[4.5]decan-8-ol (3.00 g, 12.43 mmol) in THF (50 mL) at −78° C. with stirring under $N_2$. After being stirred at −78° C. for 1 h, dry ice (10 g, 227 mmol) was added to the lithiated compound solution and stirred for 2 h at −78° C. Water was added and the solution was warmed to room temperature. The mixture was then treated with 1N HCl to pH 3 to 4 and extracted with EtOAc (3×). The combined organic layers were washed with saturated NaCl solution, dried ($MgSO_4$), and concentrated and chromatographed EtOAc to 1% AcOH/EAOAc) to give 3.23 g of 2-(8-hydroxy-1,4-dioxaspiro[4.5]dec-8-yl)-1,3-thiazole-4-carboxylic acid. MS (EI) calcd: $(M+H)^+$=286.1; found: 286.0.

Step B

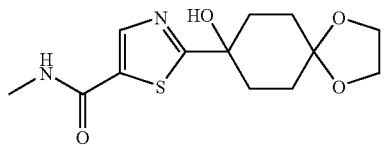

2-(8-Hydroxy-1,4-dioxspiro[45]dec-8-yl)-N-methyl-1,3-thiazole-4-carboxamide. To a stirred solution of 2-(8-hydroxy-1,4-dioxaspiro[4.5]dec-8-yl)-1,3-thiazole-4-carboxylic acid (0.30 g, 1.05 mmol) and methylamine (2M in THF, 2 mL, 4 mmol) in $CH_2Cl_2$ (10 mL) was added $Et_3N$ (0.5 mL, 3.6 mmol) followed by EDC (0.242 g, 1.262 mmol) and HOBt (0.193 g, 1.26 mmol). The mixture was stirred at room temperature overnight. Then the reaction mixture was diluted with EtOAc and washed with saturated $Na_2CO_3$ and brine. The organic layer was dried ($MgSO_4$), concentrated and flash chromatographed (50% EtOAc EtOAc) to give 0.16 g of the title compound in 50% yield. MS (EI) calcd: $(M+H)^+$=299.1; found: 299.0.

Step C

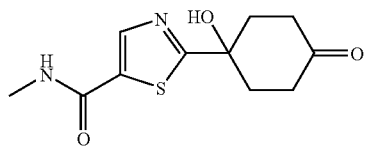

2-(1-Hydroxy-4-oxocyclohexyl)-N-methyl-1,3-thiazole-4-carboxamide. The title compound was prepared by conversion of the ketal of step B to a ketone using a procedure similar to that described in step B of Example 218. MS (EI) calcd: $(M+H)^+$=255.1; found: 255.0.

Step D

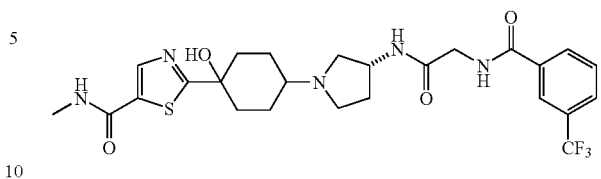

2-(1-Hydroxy-4-{(3R)-3-[({[3-(trifluoromethyl)benzoyl]amino}acetyl)amino]pyrrolidin-1-yl}cyclohexyl)-N-methyl-1,3-thiazole-5-carboxamide. The title compound was prepared from the ketone of step C using a procedure similar to that described for Example 218. MS (EI) calcd: $(M+H)^+$=554.2; found: 554.1.

Example 221

Step A

8-(1,3-Thiazol-5-yl)-1,4-dioxaspiro[4,5]decan-8-ol. 2-TMS-thiazole (2.5 g, 15.89 mmol) was added to a solution of n-butyllithium (11.9 mL of 1.6 M solution in hexane, 19.07 mmol) in THF (20 mL) at −78° C. with stirring under $N_2$. After being stirred at −78° C. for 0.5 h, a solution of 1,4-cyclohexanedione mono-ethylene ketal (2.48 g, 15.89 mmol) in THF (20 mL) was added to the lithiated compound solution via syringe and stirred for 1 h at −78° C. Water (5 mL) and EtOAc were added, and the reaction mixture was warmed to room temperature and extracted using EtOAc (3×). The combined organic layers were dried ($MgSO_4$), filtered, and crystallized from EtOAc to yield 3.4 g of 8-(1,3-thiazol-5-yl)-1,4-dioxaspiro[4,5]decan-8-ol in 90% yield. MS (EI) calcd: $(M+H)^+$=242.1; found: 242.1.

Step B

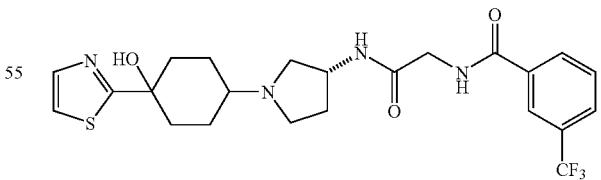

3-(Trifluoromethyl)-N-[2-({(3R)-1-[4-hydroxy-4-(1,3-thiazol-5-yl)cyclohexyl]pyrrolidin-3-yl}amino)-2-oxoethyl]benzamide. The title compound was prepared from 8-(1,3-thiazol-5-yl)-1,4-dioxaspiro[4,5]decan-8-ol using procedures similar to those described for Example 218. MS (EI): Calcd. $(M+H)^+$ 497.1, found: 497.1

Example 222

Step A

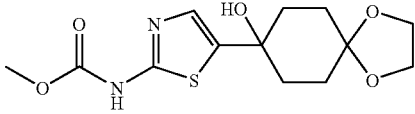

Methyl [5-(8-Hydroxy-1,4-dioxaspiro[4.5]dec-8-yl)-1,3-thiazol-2-yl]carbamate. A solution of n-butyllithium (10.0 mL of 1.6 M solution in hexane, 15.93 mmol) was added to methyl 1,3-thiazol-2-ylcarbamate (1.05 g, 6.64 mmol) in THF (10 mL) at −78° C. with stirring under $N_2$. After being stirred at −78° C. for 1 h, a solution of 1,4-cyclohexanedione mono-ethylene ketal (1.84 g, 11.75 mmol) in THF (10 mL) was added to the lithiated compound solution via syringe at −78° C. The reaction mixture was allowed to warm to room temperature slowly and stirred overnight. water and EtOAc were added. The aqueous layer was extracted with EtOAc (3×). The combined organic layers were washed with saturated NaCl, dried ($MgSO_4$), concentrated and flash chromatographed (50% EtOAc/hexane to 75% EtOAc/hexane) to give 0.744 g of the title compound in 51% yield. MS (EI) calcd: $(M+H)^+$=315.1; found: 315.0.

Step B

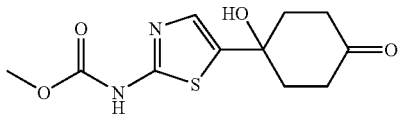

Methyl [5-(1-Hydroxy-4-oxocyclohexyl)-1,3-thiazol-2-yl]carbamate. The title compound was prepared from the ketal of step A using a procedure similar to that described in step B of Example 218. MS (EI) calcd: $(M+H)^+$=270.1; found: 270.0.

Step C

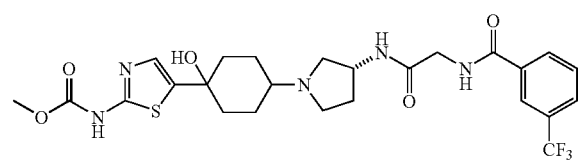

Methyl [5-(1-Hydroxy-4-{(3R)-3-[({[3-(trifluoromethyl)benzoyl]amino}acetyl)amino]pyrrolidin-1-yl}cyclohexyl)-1,3-thiazol-2-yl]carbamate. The tide compound was prepared from the ketone of step B using a procedure similar to that described for Example 218. MS (EI) calcd: $(M+H)^+$=569.2; found: 569.1.

Example 223

Step A

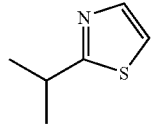

2-Isopropyl-1,3-thiazole. To a Parr hydrogenation bottle was added 2-isopropenyl-1,3-thiazole (1.8 g, 14.38), dissolved in methanol (25 mL), followed by the addition of $Pd(OH)_2$ (0.6 g). This mixture was hydrogenated at 50 psi for 48 hour. After the catalyst was filtered and washed with methanol, the filtrate was concentrated in vacuo to give 1.65 g of 2-isopropyl-1,3-thiazole in 92% yield. MS (EI) calcd: $(M+H)^+$=128.1; found: 128.0.

Step B

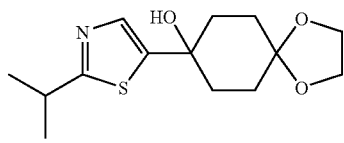

8-(2-Isopropyl-1,3-thiazol-5-yl)-1,4-dioxaspiro[4.5]decan-8-ol. The title compound was prepared from the intermediate of step A using a procedure similar to that described in step A of Example 221. MS (EI) calcd: $(M+H)^+$=284.1; found: 284.2.

Step C

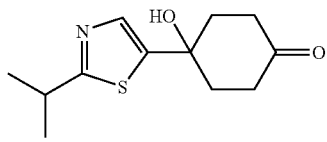

4-Hydroxy-4-(2-isopropyl-1,3-thiazol-5-yl)cyclohexanone. A solution of 8-(2-isopropyl-1,3-thiazol-5-yl)-1,4-dioxaspiro[4.5]decan-8-ol (0.714 g, 2.52 mmol) in 15 mL of THF/1N HCl (1:1) was stirred overnight at room temperature. The mixture was treated with $Na_2CO_3$ to PH 8 and extracted with EtOAc (3×). The combined organic layers were washed with saturated NaCl solution, dried ($MgSO_4$), and concentrated to give 0.65 g of 4-hydroxy-4-(2-isopropyl-1,3-thiazol-5-yl)cyclohexanone in 98% yield. MS (EI) calcd: $(M+H)^+$=240.1; found: 240.0.

Step D

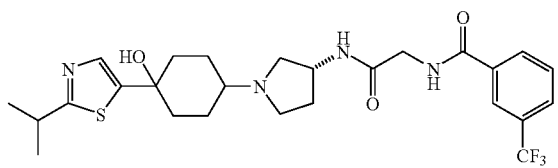

N-[2-({(3R)-1-[4-Hydroxy-4-(2 isopropyl-1,3-thiazol-5-yl)cyclohexyl]pyrrolidin -3-yl}amino)-2-oxoethyl]-3-(trifluoromethyl)benzamide. To a Parr hydrogenation bottle was added 4-hydroxy-4-(2-isopropyl-1,3-thiazol-5-yl)cyclohexanone (0.363 g, 1.52 mmol) and N-[2-oxo-2-({2-oxo-2-[(3R)-pyrrolidin-3-ylamino]ethyl}amino)ethyl]-3-(trifluoromethyl)benzamide (0.435 g, 1.38 mmol), dissolved in CH$_2$Cl$_2$ (20 mL), followed by the addition of 10% Pd(OH)$_2$ (0.8 g). This mixture was hydrogenated at 50 psi for 24 hour. After the catalyst was filtered and washed with methanol, the filtrate was concentrated in vacuo and chromatographed to give 0.345 g of title compound in 62% yield. MS (EI) calcd: (M+I)$^+$=539.2; found: 539.1.

Example 224

Step A

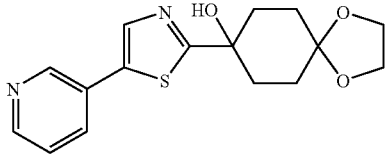

8-(5-Pyridin-3-yl-1,3-thiazol-2-yl)-1,4-dioxaspiro[4.5]decan-8-ol. A solution of n-butyllithium (7.8 mL of 1.6 M solution in hexane, 12.45 mmol) was added to 8-(1,3-thiazol-5-yl)-1,4-dioxaspiro[4,5]decan-8-ol (1.0 g, 4.15 mmol) in THF (20 mL) at −78° C. with stirring under N$_2$. After being stirred at −78° C. for 0.5 h, 12.5 mL of 0.5 M solution of ZnCl$_2$ (6.23 mmol) in THF was added. The resuting mixture was stirred at room temperature for 0.5 h and a mixture of 3-bromopyridine (0.40 mL, 4.15 mmol) and PdCl$_2$(PPh$_3$)$_2$ (0.11 g, 0.16 mmol) in 5 mL of THF was added via syringe. After refluxing overnight the reaction was quenched with 10 mL of saturated NH$_4$Cl solution. The aqueous layer was extracted using EtOAc (3×). The combined organic layers were dried (MgSO$_4$), filtered, concentrated in vacuo and chromatographed to yield 0.68 g of the title compound in 52% yield. MS (EI) calcd: (M+H)$^+$=319.1; found: 319.1.

Step B

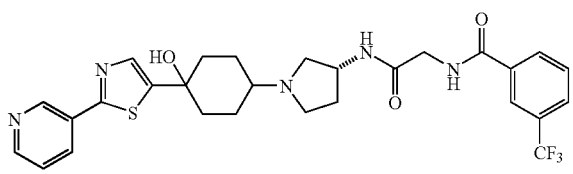

N-[2-({(3R)-1-[4-Hydroxy-4-(5-pyridin-3-yl-1,3-thiazol-2-yl]pyrrolidin-3-yl}amino)-2-oxoethyl]-3-(trifluoromethyl)benzamide. The title compound was prepared from the ketal of step A using procedures similar to those described for Example 218. MS (EI): Calcd. (M+H)+574.2, Found: 574.1

The following Examples were prepared using procedures analogous to those described for Examples 218-224.

| Example # | R | MS (M + H)$^+$ |
|---|---|---|
| 225 | 5-(morpholin-4-ylcarbonyl)-1,3-thiazol-2-yl | 610 |
| 226 | 5-aminocarbonyl-1,3-thiazol-2-yl | 540 |
| 227 | 5-dimethylaminocarbonyl-1,3-thiazol-2-yl | 568 |
| 228 | 5-(pyrrolidin-1-ylcarbonyl)-1,3-thiazol-2-yl | 594 |
| 229 | 5-allyl-1,3-thiazol-2-yl | 536 |
| 230 | 5-propyl-1,3-thiazol-2-yl | 538 |
| 231 | 5-ethylaminocarbonyl-1,3-thiazol-2-yl | 568 |
| 232 | 5-phenyl-1,3-thiazol-2-yl | 573 |
| 233 | 5-methyl-1,3-thiazol-2-yl | 511 |
| 234 | 5-hydroxymethyl-1,3-thiazol-2-yl | 527 |
| 235 | 5-(1-hydroxy-1-methylethyl)-1,3-thiazol-2-yl | 555 |
| 236 | 5-methoxymethyl-1,3-thiazol-2-yl | 541 |
| 237 | 5-(pyridin-2-yl)-1,3-thiazol-2-yl | 574 |
| 238 | 2-(pyrrolidin-1-yl)-1,3-thiazol-4-yl | 566 |
| 239 | 2-(morpholin-4-yl)-1,3-thiazol-4-yl | (M − H$_2$O + H)$^+$ = 564 |
| 240 | 2-methyl-1,3-thiazol-5-yl | 511 |
| 241 | 2-(1-hydroxy-1methylethyl)-1,3-thiazol-5-yl | 555 |
| 242 | 2-(pyrrolidin-1-yl)-1,3-thiazol-5-yl | 566 |
| 243 | 2-ethoxy-1,3-thiazol-5-yl | 541 |
| 244 | 2-ethyl-1,3-thiazol-5-yl | 525 |
| 245 | 2-(pyrrolidin-1-ylmethyl)-1,3-thiazol-5-yl | 580 |
| 246 | 2-(morpholin-4-yl)-1,3-thiazol-5-yl | 582 |
| 247 | 2-methoxymethyl-1,3-thiazol-5-yl | 541 |
| 248 | 2-isobutyl-1,3-thiazol-5-yl | 553 |
| 249 | 2-ethylaminocarbonyl-1,3-thiazol-5-yl | 568 |
| 250 | 2-(pyrrolidin-1-ylcarbonyl)-1,3-thiazol-5-yl | 594 |
| 251 | 2-(morpholin-4-ylcarbonyl)-1,3-thiazol-5-yl | 610 |
| 252 | 2-(pyridin-3-yl)-1,3-thiazol-5-yl | 574 |
| 253 | 2-(pyridin-2-yl)-1,3-thiazol-5-yl | 574 |
| 254 | 4-methyl-1,3-thiazol-2-yl | 511 |
| 255 | 1,3-benzothiazol-2-yl | 547 |

Example 256

Step A

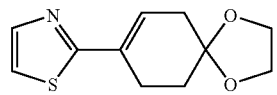

2-(1,4-Dioxaspiro[4.5]dec-7-en-8-yl)-1,3-thiazole. To a mixture of 8-(1,3-thiazol-2-yl)-1,4-dioxaspiro[4.5]decan-8-ol (0.8 g, 3.32 mmol) in pyridine (10 mL) at 0° C. was added thionyl chloride (2.5 mL, 34.3 mmol) under N$_2$. After being stirred for 2 h at 0° C. under N$_2$, water and EtOAc were added. The aqueous layer was extracted with EtOAc (3×). The combined organic layers were washed with saturated NaCl, dried (MgSO$_4$), concentrated and flash chromatographed using 10% EtOAc/hexane to give 0.27 g of the title compound in 36% yield. MS (EI) calcd: (M+1)⁺=224.1; found: 224.2.

Step B

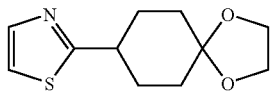

2-(1,4-Dioxaspiro[4.5]dec-8-yl)-1,3-thiazole. To a Parr hydrogenation bottle was added 2-(1,4-dioxaspiro[4.5]dec-7-en-8-yl)-1,3-thiazole (0.22 g, 0.99 mmol), dissolved in methanol (15 mL), followed by the addition of 10% Pd/C (0.08 g). This mixture was hydrogenated at 50 psi overnight. After the catalyst was filtered and washed with methanol, the filtrate was concentrated in vacuo to give 0.21 g of 2-(1,4-dioxaspiro[4.5]dec-8-yl)-1,3-thiazole in 95% yield. MS (EI) calcd: (M+1)⁺=226.1; found: 225.9.

Step C

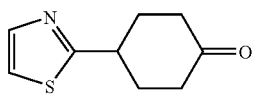

4-(1,3-Thiazol-2-yl)cyclohexanone. A solution of 2-(1,4-dioxaspiro[4.5]dec-8-yl) -1,3-thiazole (0.21 g, 0.93 mmol) in 10 mL of THF/3NHCl (1:1) was stirred for 2 h at 50° C. After cooling to room temperature, the mixture was treated with Na₂CO₃ to pH 8 and extracted with EtOAc (3×). The combined organic layers were washed with saturated NaCl solution, dried (MgSO₄), and concentrated to give 0.16 g of 4-(1,3-thiazol-2-yl)cyclohexanone in 95% yield. MS (EI) calcd: (M+H)⁺=182.1; found: 181.9.

Step D

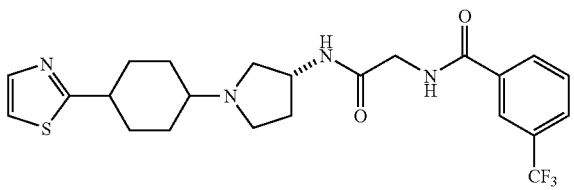

N-[2-Oxo-2-({(3R)-1-[4-(1,3-thiazol-2-yl)cyclohexyl]pyrrolidin-3-yl}amino)ethyl]-3-(trifluoromethyl)benzamide. To a mixture of 4-(1,3-thiazol-2-yl)cyclohexanone (0.069 g, 0.38 mmol) and N-[2-oxo-2-({2-oxo-2-[(3R)-pyrrolidin-3-ylamino]ethyl}amino)ethyl]-3-(trifluoromethyl)benzamide (0.10 g, 0.32 mmol) in 2% AcOH/CH₂Cl₂ (10 mL) was added NaB(OAc)₃H (0.134 g, 0.634 mmol). After being stirred overnight at room temperature under N₂, the reaction mixture was diluted with EtOAc and washed with saturated Na₂CO₃. The aqueous layer was extracted with EtOAc (3×). The combined organic layers were dried (MgSO₄), concentrated and flash chromatographed [EtOAc to MeOH/EtOAc (1:9) then to 5% MeOH/EtOAc/Et₃N (1:9: 0.5)] to give 0.129 g of the title compound in 85% yield. MS (EI) calcd: (M+H)⁺=480.2; found: 480.3.

Example 257

Step A

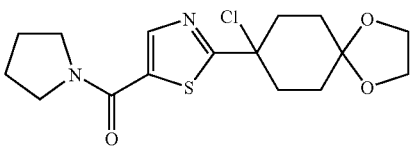

2-(8-Chloro-1,4-dioxaspiro[4.5]dec-8-yl)-5-(pyrrolidin-1-ylcarbonyl)-1,3-thiazole. To a mixture of 8-[5-(pyrrolidin-1-ylcarbonyl)-1,3-thiazol-2-yl]-1,4-dioxaspiro[4.5]decan-8-ol (0.2 g, 3.32 mmol) in pyridine (3 mL) at 0° C. was added thionyl chloride (0.5 mL, 6.86 mmol) under N₂. The mixture was warmed to room temperature and stirred overnight. After the reaction solution was concentrated, water and EtOAc were added. The aqueous layer was extracted with EtOAc (2×). The combined organic layers were washed with saturated NaCl, dried (MgSO₄), concentrated and flash chromatographed (50% EtOAc/hexane to EtOAc) to give 0.10 g of the title compound in 53% yield. MS (EI) calcd: (M+1)⁺=356.1; found: 357.0.

Step B

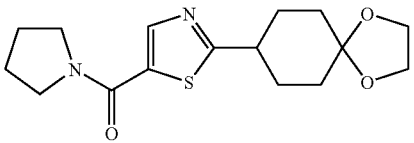

2-(1,4-Dioxaspiro[4.5]dec-8-yl)-5-(pyrrolin-1-ylcarbonyl)-1,3-thiazole. To a Parr hydrogenation bottle was added 2-(8-chloro-1,4-dioxaspiro[4.5]dec-8-yl)-5-(pyrrolidin-1-ylcarbonyl)-1,3-thiazole (0.095 g, 0.266 mmol), dissolved in methanol (10 mL), followed by the addition of 10% Pd/C (0.02 g). This mixture was hydrogenated at 50 psi overnight. After the catalyst was filtered and washed with methanol, the filtrate was concentrated in vacuo to give 0.083 g of 2-(1,4-dioxaspiro[4.5]dec-8-yl)-5-(pyrrolidin-1-ylcarbonyl)-1,3-thiazole in 97% yield. MS (EI) calcd: (M+H)⁺=322.1; found: 322.0.

Step C

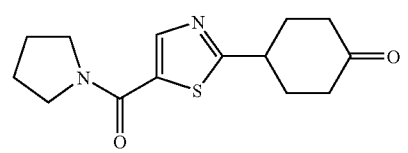

4-[5-(Pyrrolidin-1-ylcarbonyl)-1,3-thiazol-2-yl]cyclohexanone. The title compound was prepared from the ketal of step B using a procedure similar to that described in step C of Example 256. MS (EI) calcd: (M+H)⁺=279.1; found: 279.0.

Step D

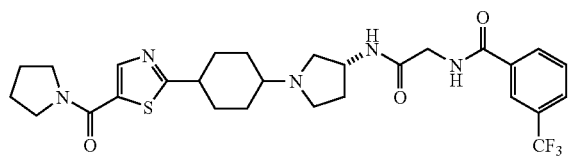

N-{2-Oxo-2-[((3R)-1-{4-[5-(pyrrolidin-1-ylcarbonyl)-1,3-thiazol-2-yl]cyclohexyl}pyrrolidin-3-yl)amino]ethyl}-3-(trifluoromethyl)benzamide. The title compound was prepared from the ketone of step C using a procedure similar to that described for Example 256. MS (EI) calcd: $(M+H)^+$ =578.2; found: 578.1.

The following Examples were prepared in a similar way.

Example 258

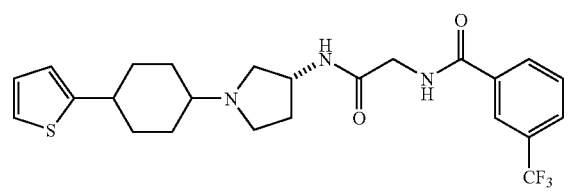

N-[2-Oxo-2-({(3R)-1-[4-(2-thienyl)cyclohexyl]pyrrolidin-3-yl}amino)ethyl]-3-(trifluoromethyl)benzamide. MS (EI): Calcd. $(M+H)^+$ 479.2, Found: 479.3

Example 259

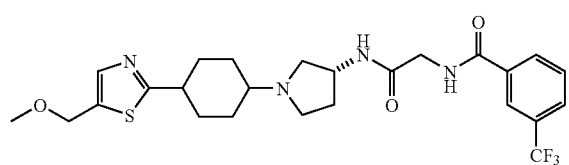

3-(Trifluoromethyl)-N-{2-[((3R)-1-{4-[5-(methoxymethyl)-1,3-thiazol-2-yl]cyclohexyl}pyrrolidin-3-yl)amino]-2-oxoethyl}benzamide. MS (EI): Calcd.: $(M+H)^+$ 525.2, Found: 525.2

Example 260

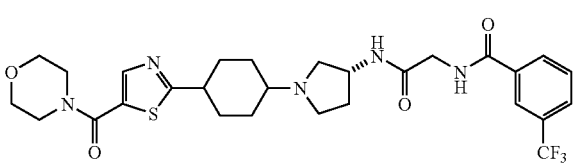

3-(Trifluoromethyl)-N-{2-[((3R)-1-{4-[5-(morpholin-4-ylcarbonyl)-1,3-thiazol-2-yl]cyclohexyl}pyrrolidin-3-yl)amino]-2-oxoethyl}benzamide. MS (EI): Calcd.: $(M+H)^+$ 594.2, Found: 594.2

Example 261

Step A

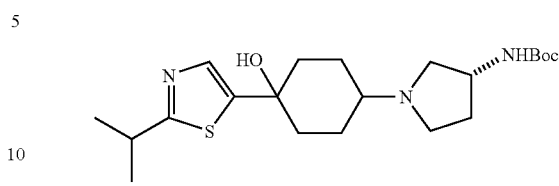

tert-Butyl{(3R)-1-[4-Hydroxy-4-(2-isopropyl-1,3-thiazol-5-yl)cyclohexyl]pyrrolidin-3-yl}carbamate. To a Parr hydrogenation bottle was added 4-hydroxy-4-(2-isopropyl-1,3-thiazol-5-yl)cyclohexanone (0.50 g, 2.09 mmol) and tert-butyl (3R)-pyrrolidin-3-ylcarbamate (0.373 g, 2.0 mmol), dissolved in $CH_2Cl_2$ (20 mL), followed by the addition of 10% Pd/C (0.12 g). This mixture was hydrogenated at 35 psi for 24 hour. After the catalyst was filtered and washed with methanol, the filtrate was concentrated in vacuo and chromatographed using $MeOH/EtOAc/Et_3N$ (1:9:0.1) to give 0.62 g of title compound in 76% yield. MS (EI) calcd: $(M+1)^+$ =409.2; found: 410.2.

Step B

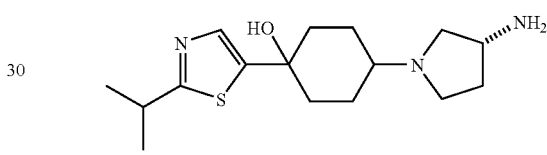

4-[(3R)-3-Aminopyrrolidin-1-yl]-1-(2-isopropyl-1,3-thiazol-5-yl)cyclohexanol. The mixture of tert-butyl {(3R)-1-[4-hydroxy-4-(2-isopropyl-1,3-thiazol-5-yl)cyclohexyl]pyrrolidin-3-yl}carbamate (0.50 g, 1.22 mmol) in 4 N HCl/dioxane (10 mL) was stirred at room temperature for 1 hour. The solution was concentrated to give 0.397 g of the title compound as 2 HCl salt. MS (EI) calcd: $(M+1)^+$=309.2; found: 310.2.

Step C

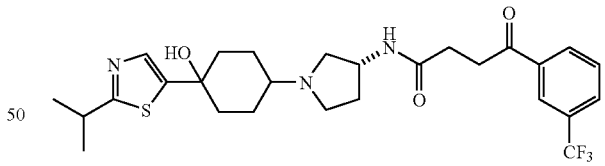

N-{(3R)-1-[4-Hydroxy-4-(2-isopropyl-1,3-thiazol-5-yl)cyclohexyl]pyrrolidin-3-yl}-4-oxo-4-[3-(trifluoromethyl)phenyl]butanamide. To a stirred solution of 4[(3R)-3-aminopyrrolidin-1-yl]-1-(2-isopropyl-1,3-thiazol-5-yl)cyclohexanol 3HCl salt (0.233 g, 0.557 mmol) and 4-oxo-4-[3-(trifluoromethyl)phenyl]butanoic acid (0.15 g, 0.61 mmol) in DMF (5 mL) was added $Et_3N$ (0.34 mL, 2.44 mmol) followed by BOP (0.296 g, 0.67 mmol). The mixture was stirred overnight at room temperature. Then the reaction mixture was diluted with EtOAc and washed with saturated $Na_2CO_3$ and brine. The organic layer was dried ($MgSO_4$), concentrated and flash chromatographed (EtOAc to 10% MeOH/EtOAc) to give 0.075 g of the title compound. MS (EI) calculated: MS (EI) calcd: $(M+H)^+$=538.2; found: 538.1.

The following Examples were prepared in a similar manner.

Example 262

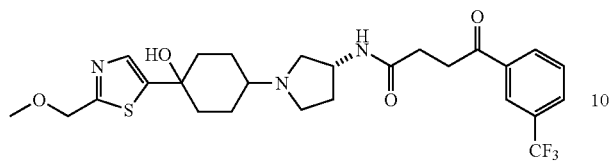

4-[3-(Trifluoromethyl)phenyl]-N-((3R)-1-{4-hydroxy-4-[5-(methoxymethyl)-1,3-thiazol -2-yl]cyclohexyl}pyrrolidin-3-yl)-4-oxobutanamide. MS (EI): Calcd. (M+H)$^+$ 540.2, found: 540.2.

Example 263

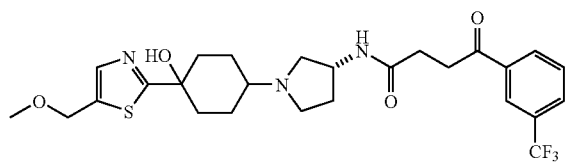

4-[3-(Trifluoromethyl)phenyl]-N-((3R)-1-{4-hydroxy-4-[5-(methoxymethyl)-1,3-thiazol-2-yl]cyclohexyl}pyrrolidin-3-yl)-4-oxobutanamide. MS (EI): Calcd. (M+H)$^+$ 540.2, found: 540.2

Example 264

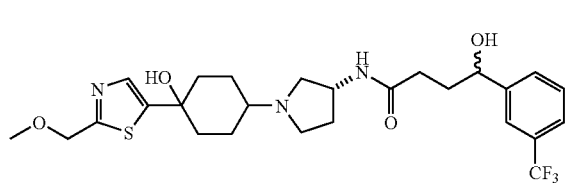

N-((3R)-1-{4-Hydroxy-4-[5-(methoxymethyl)-1,3-thiazol-2-yl]4-hydroxy-cyclohexyl}pyrrolidin-3-yl)-4-[3-(trifluoromethyl)phenyl]butanamide. To a solution of N-((3R)-1-{4-hydroxy-4-[5-(methoxymethyl)-1,3-thiazol-2-yl]cyclohexyl}pyrrolidin-3-yl)-4 oxo-4-[3-(trifluoromethyl)phenyl]butanamide (19.2 mg, 0.036 mol) in methanol (1.0 mL) was added sodium tetrahydroborate (2.7 mg, 0.071 mol) and the mixture was stirred for 1 h. The mixture was purified by prep. HPLC, eluting with H$_2$O/CH$_3$CN/0.05% TEA to provide the desired compound as a mixture of two diastereomers (10 mg, 99.7% pure). LCMS: 542.2 (M+H$^+$, 100%); $^1$H NMR: (CD$_3$OD) δ 7.70 (s, 1H), 7.63-7.53 (m, 4H), 4.80-4.77 (m, 1H), 4.65 (s, 2H), 4.4 (m, 1H), 3.96-3.93 (m, 1H), 3.84-3.72 (m, 1H), 3.57-3.49 (m, 1H), 3.38 (s, 3), 3.24-3.12 (m, 0.5H), 3.10-3.06 (m, 0.5H), 2.53-2.51 (m, 0.5H), 2.36-2.31 (m, 4.5H), 2.19 (s, 2H), 2.09-1.99 (m, 6H), 1.92-1.86 (m, 2H).

Example 265

Step A

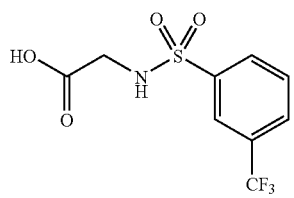

(3-Trifluorophenyl)sulfonyl]aminoacetic acid. To a solution of glycine (0.75 g, 10 mmol) in water (30 mL) and THF (30 mL) at 0° C. was added 3-(trifluoromethyl)benzenesulfonyl chloride (2.44 g, 10 mmol) portionwise over a period of 5 min. After addition was complete, the reaction mixture was stirred for an additional 0.5 h at room temperature followed by further cooling in an ice bath. Upon acidification of the reaction mixture with concentrated HCl to pH 1, the crude product was extracted with ethyl acetate. The organic extracts were combined, washed with saline solution (50 mL), dried over sodium sulfate, concentrated in vacuo, formed as thick precipitate white solid. The product was recrystallized from aqueous ethanol to give the desired compound ([(3-trifluorophenyl)sulfonyl]aminoacetic acids, 58%) as a white crystalline solid with the following characteristics: LCMC: 282.2 (M−H)$^−$.

Step B

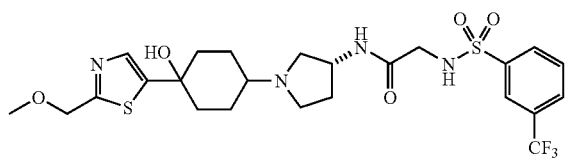

N-((3R)-1-{4-[5-(Methoxymethyl)-1,3-thiazol-2-yl]-4-hydroxycyclohexyl}pyrrolidin-3-yl)-2-({[3-trifluoromethyl)phenyl]sulfonyl}amino)acetamide. To a solution of ({[3-trifluoromethyl)phenyl]sulfonyl}amino)acetic acid (64 mg, 0.22 mmol) and 4-[(3R)-3-aminopyrrolidin-1-yl]-1-[5-(methoxymethyl)-1,3-thiazol-2-yl]cyclohexanol dihydrochloride (72 mg, 0.19 mmol) in DMF (5 mL) at 0° C. was added TEA (38 mg, 0.38 mmol) and BOP (benzotriazol-1-yloxy)tris(dimethylamino)phosphonium hexafluorophosphate (99 mg, 0.22 mmol). The reaction mixture was stirred for 2 h, and quenched with water (5 mL) and extracted with ethyl acetate (2×25 mL). The organic extracts were combined, washed with saline solution (10 mL), dried over sodium sulfate, concentrated in vacuo. The residue was chromatographed on silica gel, eluting with 1% ammonium hydroxide in ethyl acetate/methanol (100/0 to 90/10). The appropriate fractions were combined to provide two isomers of the desired compound in 1 to 1 ratio with the following characteristics: MS: 577.4 (M+H$^+$, 100%).

Example 266

Step A

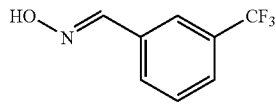

3-(Trifluoromethyl)benzaldehyde oxime. To a flask containing 3-trifluorobenzaldehyde (1.74 g, 10 mmol) and hydroxylamine hydrochloride (0.76 g, 11 mmol) in methanol (25 mL) was added TEA (0.65 g, 11 mmol). The reaction mixture was heated to reflux for 3 h, neutralized to pH 6.0, and extracted with ethyl acetate (3×20 mL). The organic extracts were combined, washed with saline solution (20 mL), dried over sodium sulfate, concentrated in vacuo to give 3-(trifluoromethyl)benzaldehyde oxime (1.9 g) as a colorless oil. LCMS: 190.2 (M+H$^+$, 100%).

Step B

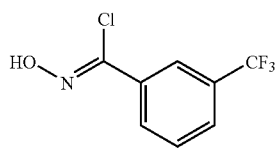

N-Hydroxy-3-(trifluoromethyl)benzenecarboximidoyl chloride. To a dried flask containing 3-(trifluoromethyl)benzaldehyde oxime (1.89 g, 10 mol) in methylene chloride (100 mL) was added N-chlorosuccinimide (1.40 g, 10.5 mmol) slowly at 0° C. The reaction mixture was warmed to 45° C. for 2 h, poured over ice, diluted with H$_2$O (20 mL), and extracted with EtOAc (100 mL). The organic phase was washed with H$_2$O (2×25 mL) and saline solution (25 mL), dried over sodium sulfate, concentrated in vacuo to give N-hydroxy-3-(trifluoromethyl)benzenecarboximidoyl chloride (2 g, 90% o). LCMS: 224.4 (M+H)$^+$.

Step C

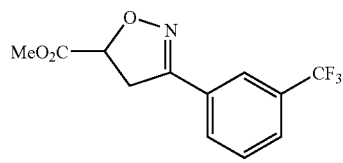

Methyl 3-[3-(Trifluoromethyl)phenyl]-4,5-dihydroisoxazole-5-carboxylate. To a flask containing N-hydroxy-3-(trifluoromethyl)benzenecarboximidoyl chloride (2.0 g, 8.9 mmol) and methyl acrylate (0.7 g, 8 mmol) in methylene chloride (100 mL) at 0° C. under an inert atmosphere was added TEA (0.90 g, 8.8 mmol). The reaction mixture was slowly warmed to ambient temperature, stirred for 20 h, quenched with water (30 mL), and extracted with methylene chloride (2×50 mL). The organic extracts were combined, washed with saline solution (50 mL), dried over sodium sulfate, concentrated in vacuo, and chromatographed on silica gel, eluting with methylene chloride/methanol (100/1 to 95/5). The appropriate fractions were combined and concentrated in vacuo to give methyl 3-[3-(trifluoromethyl)phenyl] 4,5-dihydroisoxazole-5-carboxylate (2.3 g, 100%): LCMS: 274.2 (M+H$^+$, 100%); $^1$H NMR: (CDCl$_3$) δ 8.03 (s, 1H), 7.92 (d, 1H), 7.71 (d, 1H), 7.59 (dd, 1H), 5.28 (dd, 1H), 3.86 (s, 3H), 3.71 (dd, 2H).

Step D

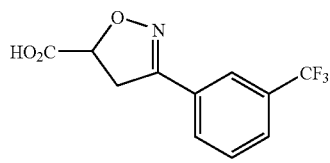

3-[3-(Trifluoromethyl)phenyl]-4,5-dihydroisoxazole-5-carboxylic acid. To a solution of methyl 3-[3-(trifluoromethyl)phenyl]4,5-dihydroisoxazole-5-carboxylate (2.3 g, 8.4 mmol) in THF (10 mL) was added 2 M of sodium hydroxide in water (10 mL) at 0° C. The reaction mixture was slowly warmed to ambient temperature, stirred for 2 h, neutralized with 2 N HCl to pH 7, and extracted with ethyl acetate (2×50 mL). The organic extracts were combined, washed with saline solution (50 mL), dried over sodium sulfate, concentrated in vacuo. The residue was chromatographed on silica gel, eluting with methylene chloride/methanol (95/5 to 80/20). The appropriate fractions were combined and concentrated in vacuo to give 3-[3-(trifluoromethyl)phenyl]-4,5-dihydroisoxazole-5-carboxylic acid (2.18 g, 100%) as a white crystalline solid. LCMS: 258.2 (M–H$^-$, 100%).

Step E

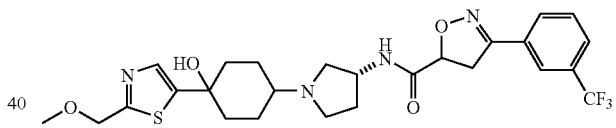

N-((3R)-1-{4-Hydroxy-4-[2-(methoxymethyl)-1,3-thiazol-5-yl]cyclohexyl}pyrrolidin-3-yl)-3-[3-(trifluoromethyl)phenyl]4,5-dihydroisoxazole-5-carboxamide. To a solution of 4[(3R)-3-aminopyrrolidin-1-yl]-1-[2-(methoxymethyl)-1,3-thiazol-4-yl]cyclohexanol dihydrochloride (90.0 mg, 0.234 mmol) in DMF (5 mL) was added 3-[3-(trifluoromethyl) phenyl]-4,5-dihydroisoxazole-5-carboxylic acid (60.7 mg, 0.234 mmol), N-(3-dimethylaminopropyl)-N'-ethylcarbodiimide hydrochloride (49.4 mg, 0.258 mmol) and TEA (28.4 mg, 0.281 mmol). The reaction mixture was stirred at rt for 2 h, and quenched with water (5 mL) and extracted with ethyl acetate (2×25 mL). The organic extracts were combined, washed with saline solution (10 mL), dried over sodium sulfate, concentrated in vacuo. The residue was chromatographed on silica gel, eluting with 1% ammonium hydroxide in ethyl acetate/methanol (100/0 to 90/10). The appropriate fractions were combined to provide the cis and trans isomers in 1 to 1 ratio. Each isomer was further purified by HPLC eluted with H$_2$O/CH$_3$CN/TFA (10/90/0.05 to 1001010.05) to provide the TFA salt of N-((3R)-1-{4-hydroxy-4-[2-(methoxymethyl)-1,3-thiazol-5-yl]cyclohexyl}pyrrolidin-3-yl)-3-[3-(trifluoromethyl)phenyl]-4,5-dihydroisoxazole-5-carboxamide (total 40 mg, 31%) as white solids. LCMS: 553

(M+H+, 100%). Each fraction shows two peaks (1 to 1) on anal. HPLC and greater than 95% purity.

Example 267

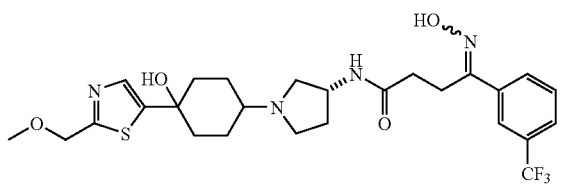

(4Z) and (4E)-4-(Hydroxyimino)-N-((3R)-1-{4-hydroxy-4-[5-(methoxymethyl) -1,3-thiazol-2-yl]cyclohexyl}pyrrolidin-3-yl)-4-[3-(trifluoromethyl)phenyl]butanamide. To a solution of N-((3R)-1-{4-hydroxy-4-[5-(methoxymethyl)-1,3-thiazol-2-yl]cyclohexyl}pyrrolidin-3-yl)-4-oxo-4-[3-(trifluoromethyl)phenyl]butanamide (19.2 mg, 0.036 mmol) in methanol (1.0 mL) was added hydroxylamine hydrochloride (9.9 mg, 0.14 mmol) and TEA (14 mg, 0.14 mmol). After refluxed for 4 h, the mixture was concentrated and the residue was purified by prep HPLC, eluting with H$_2$O/CH$_3$CN/0.05% TFA, to provide the desired compounds as the TFA salt (15 mg, 97% pure). LCMS: 555.2 (M+H+); $^1$H NMR: (CD$_3$OD) δ 7.98 (s, 1H), 7.92 (m, 1H), 7.67-7.55 (m, 3H), 4.64 (s, 2H), 4.31 (m, 1H), 3.86-3.66 (m, 2H), 3.50-3.45 (m, 1H), 3.44 (s, 3H), 3.20 (m, 0.5H), 3.11 (m, 2H), 2.98 (m, 0.5H), 2.51 (m, 3H), 2.33 (m, 2H), 2.16 (s, 2H), 1.97 (m 4H), 1.84 (m, 2H).

Example 268

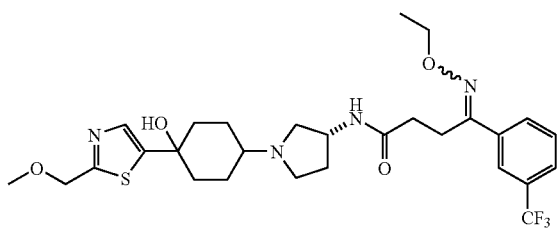

(4Z) and (4E)-4-(Ethoxyimino)-N-((3R)-1-{4-hydroxy-4-[5-(methoxymethyl)-1,3-thiazol-2-yl]cyclohexyl}pyrrolidin-3-yl)-4-[3-(trifluoromethyl)phenyl]butanamide. The title compound was prepared in a manner similar to that for Example 267. MS (M+H)+ 583.2.

Example 269

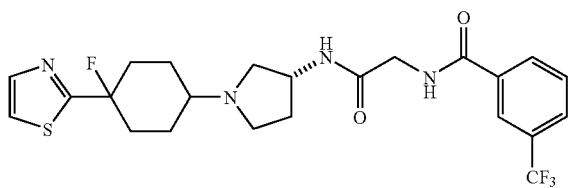

N-[2-({(3R)-1-[4-Fluoro-4-(1,3-thiazol-2-yl)cyclohexyl]pyrrolidin-3-yl}amino)-2-oxoethyl]-3-(trifluoromethyl)benzamide. DAST (0.2 mL, 1.5 mmol) was added to N-[2-({(3R)-1-[4-hydroxy-4-(1,3-thiazol-2-yl)cyclohexyl]pyrrolidin-3-yl}amino)-2-oxoethyl]-3-(trifluoromethyl)benzamide (0.06 g, 0.12 mmol) in CH$_2$Cl$_2$ (5 mL) at −78° C. with stirring under N$_2$. The solution was allowed to warm to 0° C. slowly and stirred for 1 h. Water and EtOAc were added. The aqueous layer was extracted with EtOAc (3×). The combined organic layers were washed with saturated NaCl, dried (MgSO$_4$), concentrated and purified by flash chromatography and reverse-phase HPLC to give 0.020 g of the title compound in 31% yield. MS (EI) calcd: (M+H)+=499.2; found: 499.1.

The following Examples were prepared in a similar manner.

Example 270

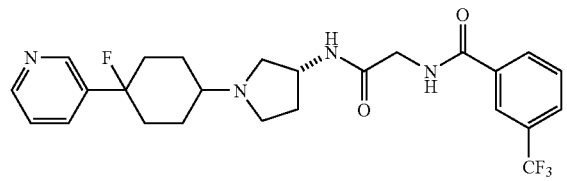

N-(2-{[(3R)-1-(4-Fluoro-4-pyridin-3-ylcyclohexyl)pyrrolidin-3-yl]amino}-2-oxoethyl)-3-(trifluoromethyl)benzamide. MS (M+H)+ 493.2.

Example 271

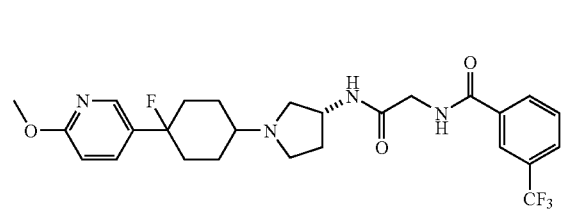

N-[2-({(3R)-1-[4-Fluoro-4-(6-methoxypyridin-3-yl)cyclohexyl]pyrrolidin-3-yl}amino)-2-oxoethyl]-3-(trifluoromethyl)benzamide. MS (M+H)+ 523.2

Example 272

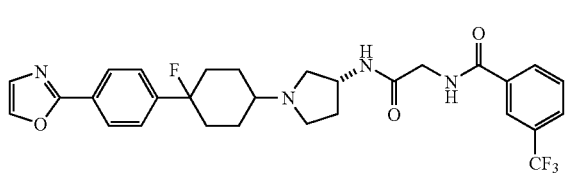

N-[2-({(3R)-[(1-{4-Fluoro-4-[6-(1,3-oxazol-2-yl)pyridin-3-yl]cyclohexyl}pyrrolidin-3-yl)amino]-2-oxoethyl}-3-(trifluoromethyl)benzamide. MS (M+H)+ 560.

Example 273

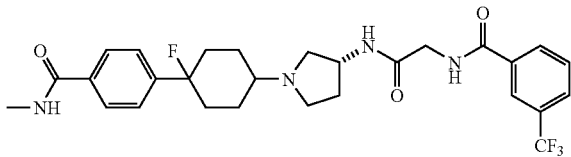

N-(2-{[(3R)-1-(4-Fluoro-4-{4-[(methylamino)carbonyl]phenyl}cyclohexyl)-pyrrolidin-3-yl]amino}-2-oxoethyl)-3-(trifluoromethyl)benzamide. MS calculated (M+H)+ 549, found 549.

Example 274

Step A

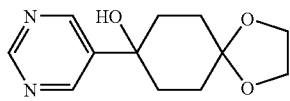

8-Pyrimidin-5-yl-1,4-dioxaspiro[4,5]decan-8-ol. A solution of n-butyllithium (4.32 mL of 1.6 M solution in hexane, 6.92 mmol) was added to 5-bromopyrimidine (1.0 g, 6.29 mmol) in THF (10 mL) at −78° C. with stirring under N₂. After being stirred at −78° C. for 1 h, a solution of 1,4-cyclohexanedione mono-ethylene ketal (0.982 g, 6.29 mmol) in THF (10 mL) was added to the lithiated compound solution via syringe and stirred for 4 h at −78° C. Water (5 mL) was added, and the reaction mixture was warmed to room temperature and extracted using EtOAc (3×). The combined organic layers were dried (MgSO₄), filtered, concentrated in vacuo and chromatographed to yield 0.18 g of 8-pyrimidin-5-yl-1,4 dioxaspiro[4,5]decan-8-ol in 12% yield. MS (E) calcd: (M+H)+=237.1; found: 237.2.

Step B

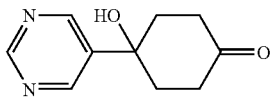

4-Hydroxy-4-pyrimidin-5-ylcyclohexanone. A solution of 8-pyrimidin-5-yl-1,4-dioxaspiro[4,5]decan-8-ol (0.14 g, 0.59 mmol) in 10 mL of THF/1 N HCl (1:1) was stirred for 24 h at room temperature. The mixture was treated with Na₂CO₃ to pH 8 and extracted with EtOAc (3×). The combined organic layers were washed with saturated NaCl solution, dried (MgSO₄), and concentrated to give 0.11 g of 4-hydroxy-4-pyrimidin-5-ylcyclohexanone in 79% yield. MS (EI) calcd: (M+H)+=192.1; found: 192.1.

Step C

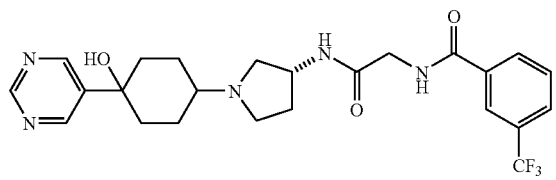

N-(2-{[(3R)-1-(4-Hydroxy-4-pyrimidin-5-ylcyclohexyl)pyrrolidin-3-yl]amino}-2-oxoethyl)-3-(trifluoromethyl)benzamide. The title compound was prepared from the ketone of step B using a procedure similar to that described for Example 218. MS (EI) calcd: (M+H)+=492.2; found: 492.2.

Example 275

Step A

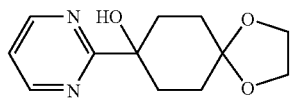

8-Pyrimidin-2-yl-1,4-dioxaspiro[4.5]decan-8-ol. To a solution of 2-stannyl pyrimidine (200 mmol, 80 g), prepared as previously described in the literature (Tetrahedron, 1994, 50, 275-284), in THF (1 L) was added n-butyllithium (240 mmol, 150 mL) at −78° C. The reaction was stirred for 30 min at −78° C. and 1,4-dioxa-spiro[4.5]decan-8-one (200 mmol, 30 g) was added. The reaction was allowed to stir overnight while warming to ambient temperature. The reaction was then quenched using NH₄Cl and extracted using EtOAc (3×400 mL). The organic layers were combined and dried over MgSO₄ and concentrated in vacuo. The crude was taken to the next step.

Step B

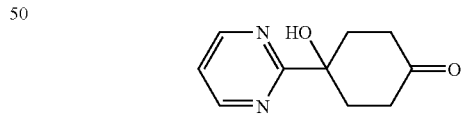

4-Hydroxy-4-pyrimidin-2-ylcyclohexanone. To the product from step A (190 mmol, 44 g) in THF (200 mL) was added HCl solution (300 mmol, 100 mL). The reaction was stirred over 2 days after which the reaction was washed using diethyl ether. The aqueous layer was then quenched using NaOH (50%) to obtain a pH of 11. The aqueous layer was extracted using EtOAc (6×300 mL). The organic layer was combined and dried over MgSO₄ and concentrated in vacuo. The residue was purified via flash chromatography to afford the desired ketone (18 g, 49%). MS [M+H]+ 193.1

Step C

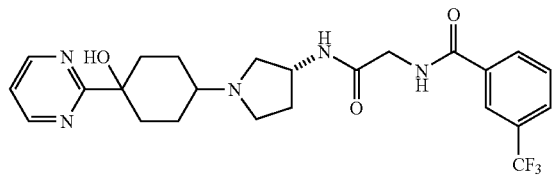

N-{[(R)-1-(4-Hydroxy-4-pyrimidin-2-yl-cyclohexyl)-pyrrolidin-3-ylcarbamoyl]-methyl}-3-trifluoromethyl-benzamide. To the product from step C (62 mmol, 12 g) in CH$_2$Cl$_2$ (500 mL) was added N-((3R)-pyrrolidin-3-ylcarbamoylmethyl)-3-trifluoromethylbenzamide (60 mmol, 20 g) followed by sodium triacetoxyborohydride (100 mmol, 30 g). The reaction was stirred for 2 h and then quenched using NaOH (2 M) to obtain a pH of 11. The reaction mixture was extracted using CH$_2$Cl$_2$ (3×300 mL). The organic layers were combined and dried over MgSO$_4$ and subsequently concentrated in vacuo. The residue was purified via flash chromatography to separate the two diastereomers and then HPLC to afford the desired amine diastereomer. MS [M+H]$^+$ 492.1.

Example 276

Step A

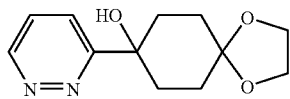

8-Pyridazin-3-yl-1,4-dioxaspiro[4.5]decan-8-ol. To a solution of pyridazine (17.7 mmol, 1.28 mL) in THF (60 mL) was added 2,2,6,6, lithium tetramethylpiperidine (71 mmol, 10 g) at −78° C. The reaction was then stirred for 6 min and 1,4-dioxa-spiro[4.5]decan-8-one (71 mmol, 11 g) was added. The reaction was stirred for 5 h at −78° C. at which point the reaction was quenched using a solution of ethanol, hydrochloric acid and THF (30 mL, 1:1:1). The reaction was allowed to warm to ambient temperature and the reaction mixture was extracted using EtOAc. The organic layers were combined and dried over MgSO$_4$. The residue was then purified using flash chromatography to afford the desired alcohol (44%, 1.84 g). MS [M+H]$^+$ 237.1.

Step B

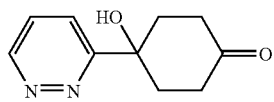

4-Hydroxy-4-pyridazin-3-ylcyclohexanone. To the product from step A (7.79 mmol, 1.84 g) in THF (15 mL) was added HCl (45 mmol, 15 mL). The reaction was stirred overnight and subsequently quenched using Na$_2$CO$_3$. The reaction was then extracted using EtOAc (3×100 mL). The organic layers were combined, dried and concentrated in vacuo to afford the desired ketone (780 mg, 52%). MS [M+H]$^+$ 193.1.

Step C

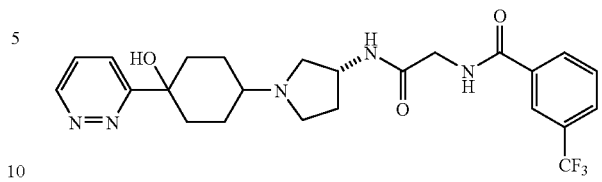

N-[2-({(3R)-1-[4-Hydroxy-4-pyridazin-3-yl cyclohexyl] pyrrolidin-3-yl}amino)-2-oxoethyl]-3-(trifluoromethyl)benzamide. To the product from step B (1.19 mmol, 215 mg) in CH$_2$Cl$_2$ (10 mL) was added N-((3R)-pyrrolidin-3-ylcarbamoylmethyl)-3-trifluoromethyl-benzamide (1.19 mmol, 375 mg). Subsequently sodium triacetoxyborohydride (2.38 mmol, 504 mg) was added and the reaction was stirred for 4 h and then quenched using NaOH (1M). The aqueous layer was extracted using CH$_2$Cl$_2$ and the organic layer was then washed using brine and then dried over MgSO$_4$. The organic layers were concentrated in vacuo to afford the desired amine diastereomer after flash chromatography and HPLC (17%, 10 mg) [M+H]$^+$ 492.1.

Example 277

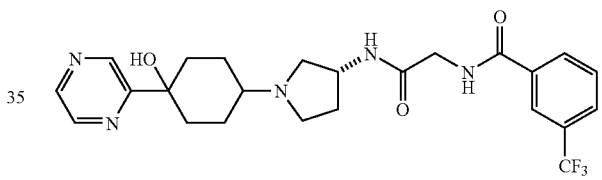

N-(2-{[(3R)-1-(4-Hydroxy-4-pyrazin-2-ylcyclohexyl)pyrrolidin-3-yl]amino}-2-oxoethyl)-3-(trifluoromethyl)benzamide. The title compound was prepared in a similar fashion as described for Example 276. MS [M+H]$^+$ 492.1.

Example 278

Step A

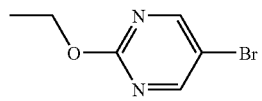

5-Bromo-2-ethoxypyridine. To EtOH (15 mL) was added sodium hydride (14 mmol, 330 mg) at 0° C. very slowly. The reaction was stirred for 30 min and 5-bromo-2-chloropyrimidine (3.2 mmol, 620 mg) was added. The reaction was allowed to warm to ambient temperature overnight and then quenched using water and extracted with EtOAc. The organic layers were combined and concentrated in vacuo to afford the desired bromide (470 mg, 72%). MS [M+2]$^+$ 203.4.

Step B

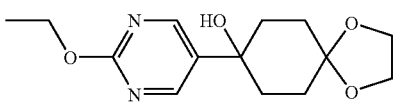

8-(2-Ethoxypyrimidin-5-yl)-1,4-dioxaspiro[4.5]decan-8-ol. To the product from step A (2.3 mmol, 471 mg) in THF (20 mL) was cooled to −78° C. and z-butyllithium (2.8 mmol, 1.7 mL) was added dropwise into the solution. The reaction was stirred for 10 min at −78° C. and 1,4-dioxa-spiro[4.5]decan-8-one (3.5 mmol, 540 mg) was added. The reaction was allowed to warm to room temperature over 12 hrs after which the reaction was quenched using NH$_4$Cl and was then extracted with EtOAc (3×30 mL). The organic layers were dried over MgSO$_4$ and then concentrated in vacuo to afford the crude desired ketal (22%, 184 mg) which was carried to the next step.

Step C

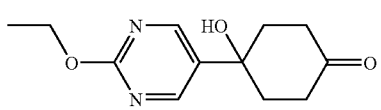

4-(2-Ethoxypyrimidin-5-yl)-4-hydroxycyclohexanone. To the product from step B (0.3 mmol, 184 mg) was added a solution of HCl in water (30 mmol, 10 mL). The reaction was stirred overnight. Subsequently the reaction was quenched using NaOH (1N) to pH 11. The reaction was then extracted using EtOAc (2×30 mL). The organic layers were dried and concentrated in vacuo. The residue was purified via HPLC to afford the desired ketone (70%, 100 mg). MS [M+H]$^+$ 237.1.

Step D

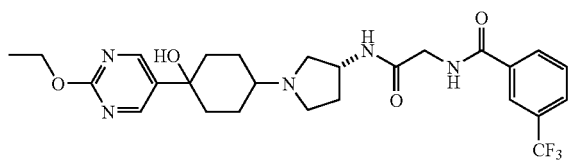

N-(2-{[(3R)-1-(4-Hydroxy-4-pyrazin-2-ylcyclohexyl)pyrrolidin-3-yl]amino}-2-oxoethyl)-3-(trifluoromethyl)benzamide. To the ketone from step C (0.4 mmol, 100 mg) in CH$_2$Cl$_2$ (10 mL) was added N-((3R)-pyrrolidin-3-ylcarbamoylmethyl)-3-trifluoromethylbenzamide (0.4 mmol, 100 mg) followed by sodium tracetoxyborohydride (0.8 mmol, 200 mg). The reaction was stirred overnight and then quenched using NaOH (1N). The reaction was extracted using EtOAc (3×10 mL). The organic layers were combined and dried over MgSO$_4$ and then concentrated in vacuo. The residue was purified via HPLC to afford the desired amine diastereomer (18%, 40 mg). MS [M+H]$^+$ 536.1.

Example 279

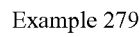
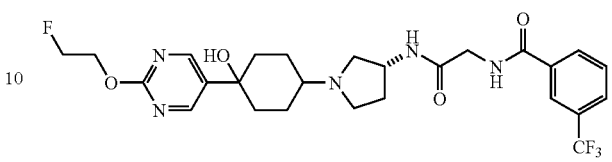

N-{2-[((3R)-1-{4-[2-(2-Fluoroethoxy)pyrimidin-5-yl]-4-hydroxycyclohexyl}pyrrolidin-3-yl)amino]-2-oxoethyl}-3-(trifluoromethyl)benzamide. The title compound was prepared in a similar fashion as described for Example 278. MS [M+H]$^+$ 554.2.

Example 280

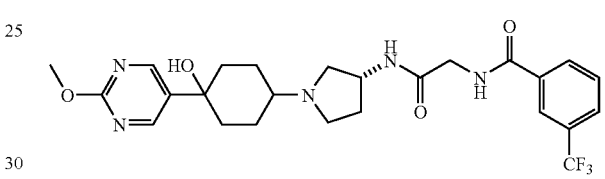

N-[2-({(3R)-1-[4-Hydroxy-4-(2-methoxypyrimidin-5-yl)cyclohexyl]pyrrolidin-3-yl}amino)-2-oxoethyl]-3-(trifluoromethyl)benzamide. The title compound was prepared in a fashion similar to that described for Example 278. MS (M+H)$^+$ 522.

Example 281

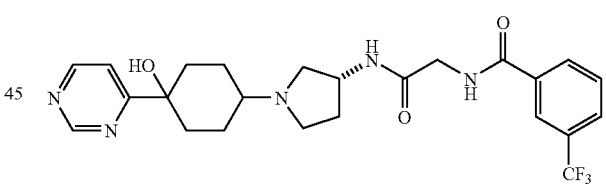

N-(2-{[(3R)-1-(4-Hydroxy-4-pyrimidin-4-ylcyclohexyl)pyrrolidin-3-yl]amino}-2-oxoethyl)-3-(trifluoromethyl)benzamide. The title compound was prepared in a fashion similar to that described for Example 276. MS [M+H]$^+$ 492.2.

Example 282

Step A

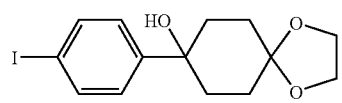

8-(4-Iodo-phenyl)-1,4-dioxa-spiro[4.5]decan-8-ol. To a solution of 1,4 diiodobenzene (16.5 g, 50 mmol) in THF (350 mL) at −78° C. was added n-BuLi (2.5 M, 24 mL) over 1 hour. After being stirred for an additional 30 minutes, a solution of 1,4-dioxa-spiro[4.5]decan-8-one (7.8 g, 50 mmol) in THF (30 mL) was added in and the resulting mixture was sired for 3 hours. To the mixture was added TMSCl (5.4 g, 50 mmol) and the resulting mixture was allowed to warm to rt and stirred at rt for 18 hours. The reaction mixture was neutralized to pH 6.0, and extracted with ethyl acetate (3×50 mL). The organic extracts were combined, washed with saline solution (2×50 mL), dried over sodium sulfate, concentrated in vacuo. The residue was chromatographed on silica gel, eluting with hexane/ethyl acetate (95/5 to 100/0). The appropriate fractions were combined to give 8-(4-Iodo-phenyl)-1,4-dioxaspiro[4.5]decan-8-ol (12 g, 66.6%) with LCMS: 361.2 (M+H$^+$, 100%) and {[8-(4-iodophenyl)-1,4-dioxaspiro[4.5]dec-8-yl]oxy}(trimethyl)silane (6 g, 27%) with LCMS: 433.1 (M+H$^+$, 100%).

Step B

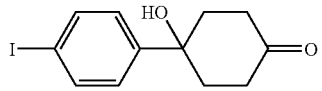

4-Hydroxy-4-(4-iodophenyl)cyclohexanone. To a solution of 8-(4-iodo-phenyl)-1,4 dioxa-spiro[4.5]decan-8-ol (2 g) in acetone (10 mL) was added 5% HCl (20 mL) and the mixture was stirred at rt for 14 hours. The reaction mixture was neutralized with 1N NaOH to pH 7, concentrated on rotvap, and then extracted with ethyl acetate (2×50 mL). The organic extracts were combined, washed with saline solution (2×50 mL), dried over sodium sulfate, concentrated in vacuo to provide 4-hydroxy-4-(4-iodophenyl)cyclohexanone (1.7 g, 98%). LCMS: 317.3 (M+H$^+$, 100%).

Step C

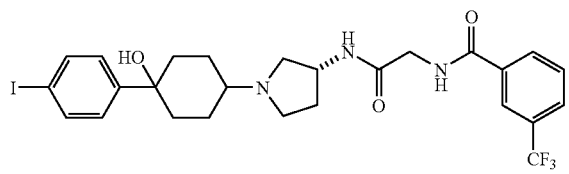

N-[2-({(3R)-1-[4-Hydroxy-4-(4-iodophenyl)cyclohexyl]pyrrolidin-3-yl}amino)-2 oxoethyl]-3-(trifluoromethyl)benzamide. To a solution of 4-hydroxy-4-(4-iodophenyl)cyclohexanone (624 mg, 2 mmol) in CH$_2$Cl$_2$ (10 mL) was added N-((3R)-pyrrolidin-3-ylcarbamoylmethyl)-3-trifluoromethylbenzamide (730 mg, 2 mmol) and then NaBH(OAc)$_3$ (666 mg, 3 mmol). After stirred for 1 h, the reaction was quenched with 10% NaHCO$_3$, and extracted with EtOAc. The organic extracts were combined, washed with saline solution, dried over sodium sulfate, concentrated in vacuo. The residue was chromatographed on silica gel, eluting with 1% NH$_4$OH in ethyl acetate/methanol (100/0 to 10/90) to yield the major isomer (544 mg, 44.2%) and the minor isomer (446 mg, 36.3% yield). For the major isomer, LCMS: 615.2 (M+H$^+$, 100%); $^1$H NMR: (CDCl$_3$) δ 8.09, (s, 1H); 7.98, (d, 1H); 7.77, (d, 1H); 7.67, (d, 21); 7.57, (t, 1H); 7.28, (d, 2H); 7.22, (t, 1H, NH); 6.44, (d, 1H, NH); 4.49, (m, 1H); 4.12, (m, 2H); 2.87, (m, 1H); 2.64, (m, 2H); 2.38, (m, 1H); 2.25, (m, 4H); 1.93, (m, 2H); 1.54-1.70, (m, 6H).

Step D

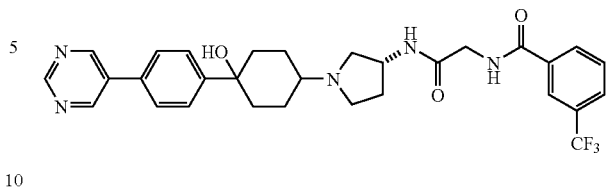

N-[2-({(3R)-1-[4-Hydroxy-4-(4-pyrimidin-5-ylphenyl)cyclohexyl]pyrrolidin-3-yl}amino)-2-oxoethyl]-3-(trifluoromethyl)benzamide. To a solution of N-[2-({(3R)-1-(4-hydroxy-4-(4-iodophenyl)cyclohexyl)pyrrolidin-3-yl}amino)-2-oxoethyl]-3-(trifluoromethyl)benzamide (61 mg, 0.1 mmol) and pyrimidin-5-ylboronic acid (26 mg, 0.2 mmol) in THF (5 mL) was added 2 M NaHCO$_3$ (5 mL) and the mixture was degassed with N$_2$ for 3 times. To it was added Pd(0) (PPh$_3$)$_4$ (5.7 mg, 5%) and the resulting mixture was heated to reflux under N$_2$ for 4 hours. The mixture was diluted with ethyl acetate (50 mL) and the organic layer was washed with saline solution (2×10 mL), dried over sodium sulfate, and concentrated in vacuo. The residue was chromatographed on silica gel, eluting with 1% NH$_4$OH in ethyl acetate/methanol (100/0 to 90/10), followed by purification on HPLC, eluting with 0.05% TFA in AcCN/water, to yield the TFA salt of N-[2-({(3R)-1-[4-hydroxy -4-(4-pyrimidin-5-ylphenyl)cyclohexyl]pyrrolidin-3-yl}amino)-2-oxoethyl]-3-(trifluoromethyl)benzamide (28.5 m, 41%). LCMS: 568.4 (M+H$^+$, 100%). For the neutral molecule, $^1$HNMR: (CD$_3$OD) δ 9.15 (s, 1H), 9.08 (s, 1H), 8.22 (s, 1H), 8.14 (d, 1H), 7.86 (d, 1H), 7.76-7.67 (m, 51), 4.45-4.40 (m, 1H), 4.05 (s, 2H), 2.86 (t, 2H), 2.60-2.53 (m, 2H), 2.42-2.38 (m, 2H), 2.32-2.68 (m, 2H), 2.05-2.01 (m, 2H), 1.75-1.72 (m, 2H), 1.67-1.63 (m, 3H); $^{19}$F NMR: (CDCl$_6$) δ −64.58.

Example 283

Step A

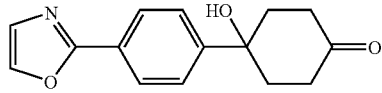

4-Hydroxy-4-[4-(1,3-oxazol-2-yl)phenyl]cyclohexanone. To a solution of oxazole (240 mg, 3.5 mmol) in THF (5 mL) at −78° C. was added n-BuLi (1.6 M, 2.6 mL). After the mixture was stirred for 1 hour, a solution of zinc chloride in THF (0.5 M, 8.2 mL) was added in and the resulting mixture was allowed to warm to 0° C. over 1 hour. To the mixture was added 8-(4-iodo-phenyl)-1,4-dioxa-spiro[4.5]decan-8-ol (1.35 g, 3.5 mmol) and the resulting mixtue was degassed with N$_2$ for 3 times. To a suspension of PdCl$_2$(PPh$_3$)$_2$ (122 mg, 5%) in THF (2 mL) was added nBuLi (1.6 M, 0.26 mL) and the mixture was added into the above mixture. The resulting mixture was heated to reflux under N$_2$ for 4 hours. The resulting mixture was diluted with ethyl acetate (50 mL). The organic layer was filtered through Celite and the filtrate was washed with saline solution (2×10 mL), dried over sodium sulfate, and concentrated in vacuo. The residue was dissolved in THF (2.5 mL) and was treated with 5% HCl (22.5 mL) at rt for 24 h. The mixture was neutralized with 1 N NaOH to pH 7, concentrated on rotvap, and then extracted with EtOAc (2×50 mL). The organic extracts were combined, washed with saline solution (2×50 mL), dried over sodium sulfate, concentrated in vacuo. The resulting residue was chromatographed on silica gel, eluting with hexane/ethyl acetate (100/0 to 100/0), to provide the desired compound (0.56 g, 62% for the two steps). LCMS: 258.2 (M+H⁺, 100%). ¹H NMR: (CDCl₃) δ 8.06 (d, 2H), 7.73 (s, 1H), 7.63 (d, 2H), 2.99-2.91 (m, 2H), 2.42-2.30 (m 4H), 2.22-2.05 (m, 2H).

Step B

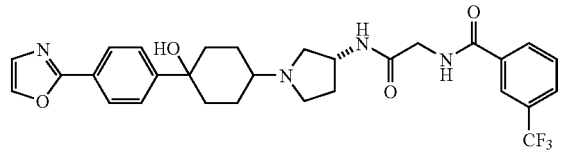

N-[2-({(3R)-1-[4-Hydroxy-4-(4-oxazol-2-ylphenyl)cyclohexyl]pyrrolidin-3-yl}amino)-2-oxoethyl]-3-(trifluoromethyl)benzamide. The title compound was prepared from the ketone of step A using a procedure similar to that for Example 282. MS (M+H)⁺ 557.3.

Example 284

Step A

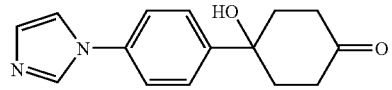

4-Hydroxy-4-[4-(1H-imidazol-1-yl)phenyl]cyclohexanone. To a solution of imidazole (102 mg, 1.5 mmol) and 8-(4-iodo-phenyl)-1,4-dioxa-spiro[4.5]decan-8-ol (316 mg, 1 mmol) in DMF (1 mL) was added CuI (19 mg, 0.1 mmol) and Cs₂CO₃ (488 mg, 1.5 mmol) and the mixture was stirred at 190° C. under microwave for 10 min. The mixture was diluted with ethyl acetate (50 mL) and water (10 mL). The organic layer was filtered through celite and the filtrate was washed with saline solution (2×10 mL), dried over sodium sulfate, and concentrated in vacuo. The residue was dissolve in THF (1 mL) and was treated with 5% HCl (9 mL) at rt for 14 h. The mixture was neutralized with 1N NaOH to pH 7, concentrated on rotvap, and then extracted with EtOAc (2×50 mL). The organic extracts were combined, washed with saline solution (2×50 mL), dried over sodium sulfate, concentrated in vacuo. The resulting residue was chromatographed on silica gel, eluting with hexane/ethyl acetate (100/0 to 0/100), to provide the desired compound (180 mg, 70% for the two steps). LCMS: 257.2 (M+H⁺, 100%); ¹H NMR: (CDCl₃) δ 7.82 (s, 1H), 7.64 (d, 2H), 7.40 (s, 1H), 7.28 (s, 1H), 7.21 (s, 1H), 2.99-2.91 (m, 2H), 2.43-2.28 (m 4H), 2.23-2.18 (m, 2H).

Step B

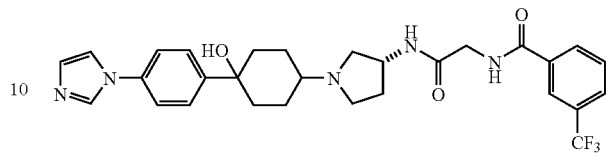

N-[2-({(3R)-1-[4-Hydroxy-4-(4-1H-imidazol-1-ylphenyl)cyclohexyl]pyrrolidin-3-yl}amino)-2-oxoethyl]-3-(trifluoromethyl)benzamide. The title compound was prepared from the ketone of step A using a procedure analogous to that for Example 282. MS (M+H)⁺ 556.3.

Example 285

Step A

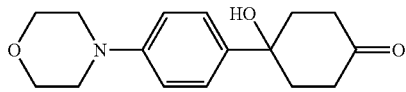

4-Hydroxy-4-(4-morpholin-4-ylphenyl)cyclohexanone. To an oven-dried flask was charged with Pd₂(dba)₃ (4.6 mg, 0.005 mmol), (o-biphenyl)P(t-Bu)₂ (6.0 mg, 0.02 mmol, 2 mol %), and NaOt-Bu (135 mg, 1.4 mmol). The flask was evacuated and backfilled with nitrogen and then capped with a rubber septum. Toluene (0.5 mL), the aryl iodide (360 mg, 1.0 mmol), morpholine (102 mg, 1.2 mmol), and additional toluene (0.5 mL) were added. The mixture was stirred at room temperature until the starting aryl iodide had been completely consumed as judged by TLC analysis. The mixture was diluted with ether (20 mL), filtered through Celite, and concentrated in vacuo. The crude residue was dissolve in THF (1 mL) and was treated with 5% HCl (9 mL) at rt for 14 h. The mixture was neutralized with 1 N NaOH to pH 7, concentrated on rotvap, and then extracted with EtOAc (2×50 mL). The organic extracts were combined, washed with saline solution (2×50 mL), dried over sodium sulfate, concentrated in vacuo. The resulting residue was chromatographed on silica gel, eluting with hexane/ethyl acetate (100/0 to 0/100), to provide the desired compound (100 mg, 36% for the two steps). LCMS: 276.2 (M+H⁺, 100%). ¹H NMR: (CDCl₃) δ 7.42 (d, 2H), 6.88 (d, 2H), 3.99-3.94 (m, 4H), 3.86-3.84 (m, 4H), 3.16-3.13 (m, 4H).

Step B

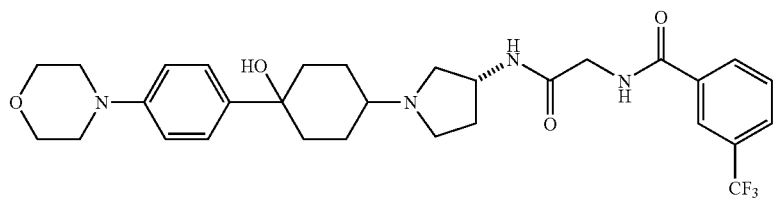

N-[2-({(3R)-1-[4-Hydroxy 4-(4-morpholin-4-ylphenyl)cyclohexyl]pyrrolidin-3-yl}amino)-2-oxoethyl]-3-(trifluoromethyl)benzamide. The title compound was prepared from the ketone of step A using a procedure similar to that described for Example 282. MS (M+H)+ 575.3.

Example 286

Step A

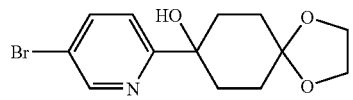

8-(5-Bromopyridin-2-yl)-1,4-dioxaspiro[4.5]decan-8-ol. To a solution of 2,5-dibromopyridine (4.10 g, 17 mmol) in anhydrous toluene (250 mL) at −78° C. was dropwise added n-BuLi (1.6 M, 12 mL). After stirred at −78° C. for 2.5 hours, a solution of 1,4-dioxa-spiro[4.5]decan-8-one (2.73 g, 17 mmol) in methylene chloride (25 mL) was added into the reaction mixture, and the resulting mixture was stirred for additional one hour and allowed to warm up to rt slowly. The reaction mixture was poured into aqueous NaHCO$_3$ (200 mL) and then extracted with EtOAc (2×50 mL). The organic extracts were combined, washed with saline solution (2×50 mL), dried over MgSO$_4$, concentrated in vacuo. The resulting solid was titrated with ether and the filtrate was collected. The ether was removed and the solid was chromatographed on silica gel, eluting with hexane/ethyl acetate (2 to 1), to give 8-(5-bromopyridin-2-yl)-1,4-dioxaspiro[4.5]decan-8-ol (4.27 g) as pale yellow solid. LCMS: 316.10/314.10 (M+H+, 100%). $^1$H NMR: δ 8.6 (s, 1H), 7.82 (d, 1H), 7.38 (d, 1H), 4.6 (s, 1H), 4.0 (m, 4H), 2.2 (m, 4H), 1.7 (m, 4H).

Step B

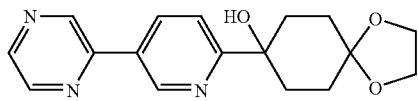

8-(5-Pyrazin-2-ylpyridin-2-yl)-1,4-dioxaspiro[4.5]decan-8-ol. To a solution of 8-(5-bromopyridin-2-yl)-1,4-dioxaspiro[4.5]decan-8-ol (0.50 g, 1.59 mmol) in THF (7.5 mL) was dropwise added isopropyl magnesium chloride (2 M in THF, 1.8 mL) at rt. After stirred for 1 hour, the solution was degassed with N$_2$ three times. To another degassed solution of THF (2.5 mL) at rt was added nickel acetylacetonate (20 mg, 0.080 mmol) and 1,2-bis(diphenylphosphino)-ethane (32 mg, 0.080 mmol) under N$_2$ flush. After stirred for 10 mins, 2-chloropyrazine (0.155 mL, 1.59 mmol) was added in, and the resulting mixture was stirred for 30 minutes. The mixture was then transferred to a freshly prepared solution of the Grignard reagent prepared previously. The mixture was stirred at rt for 18 hours, and was quenched with saturated NH$_4$Cl solution. The aqueous solution was extracted with ethyl acetate, and the combined organic phase was washed with saline solution (2×50 mL), dried over MgSO$_4$, concentrated in vacuo. The residue was chromatographed on SiO$_2$, eluted with hexane/ethyl acetate (1 to 1), and the appropriate fractions were collected to provide 8-(5-pyrazin-2-ylpyridin-2-yl)-1,4-dioxaspiro[4.5]decan-8-ol (95 mg, 19%) as an oil. LCMS: 314.2 (M+H+, 100%).

Step C

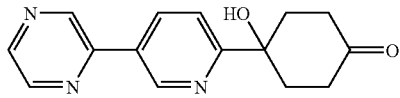

4-Hydroxy-4-(5-pyrimidin-5-ylpyridin-2-yl)cyclohexanone. To a solution of 8-(5-pyrazin-2-ylpyridin-2-yl)-1,4-dioxaspiro[4.5]decan-8-ol (95 mg, 0.30 mol) in THF (2.0 mL) was added 10% HCl (2 mL). The reaction mixture was heated at 40° C. for 60 minutes, and was cooled to rt. The mixture was neutralized with solid NaHCO$_3$, extracted with ethyl acetate. The organic extracts were combined, washed with saline solution, dried over MgSO$_4$, concentrated in vacuo. The residue was chromatographed on silica gel, eluting with hexane/ethyl acetate (1:1), providing the desired product as a white solid (32 mg, 40%). LCMS: 270.2 (M+H+, 100%); $^1$H NMR: δ 9.22 (s, 1H), 9.10 (s, 1H), 8.72 (d, 1H), 8.60 (d, 1H), 8.40 (d, 1H), 7.56 (d, 1H), 5.36 (s, 1H), 3.04 (m, 2H), 2.44 (dd, 2H), 2.36 (m, 2H), 2.10 (m, 2H).

Step D

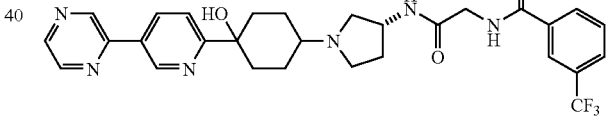

N-[2-({(3R)-1-[4-Hydroxy-4-(5-(pyrazin-2-yl)pyridin-2-yl)cyclohexyl]pyrrolidin -3-yl}amino)-2-oxoethyl]-3-(trifluoromethyl)benzamide. The title compound was prepared from the ketone of step C using a procedure similar to that described for Example 282. MS (M+H)+ 569.3.

Example 287

Step A

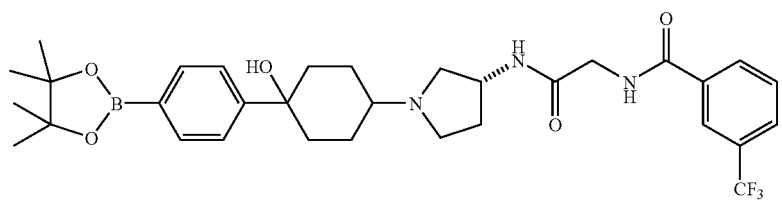

N-{2-[((3R)-1-{4-Hydroxy-4-[4-(4,4,5,5-tetramethyl-1,3,2-dioxaborolan-2-yl)phenyl]cyclohexyl}pyrrolidin-3-yl)amino]-2-oxoethyl}3-(trifluoromethyl)benzamide. A flask was charged with the bis(pinacolato)diboron (538 mg, 2.1 mmol), KOAc (589 mg. 6 mmol), and the PdCl₂(dppf) (49 mg, 0.06 mmol) under N₂. A solution of the N-[2-({(3R)-1-[4-hydroxy-4-(4-iodophenyl)cyclohexyl]pyrrolidin-3-yl}amino)-2-oxoethyl]-3-(trifluoromethyl)benzamide (1.23 g, 2 mmol) in DMSO (12 mL) in an addition funnel, degassed by bubbling N₂ through it; was then added to the flask and the mixture was heated to 70° C. After 1 h, the reaction was quenched with water, extracted with CH₂Cl₂, concentrated to provide the desired compound (190 mg, 15%). LCMS: 616.2 (M+H⁺, 100%).

Step B

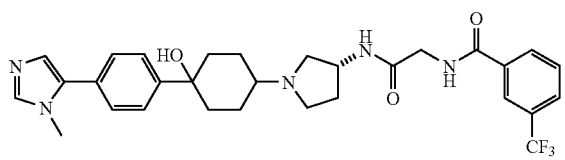

N-{2-[((3R)-1-{4-Hydroxy-4-[4-(1-methyl-1H-imidazol-5-yl)phenyl]cyclohexyl}pyrrolidin-3-yl)amino]-2-oxoethyl}-3-(trifluoromethyl)benzamide. To a degassed solution of the mixture of N-{2-[((3R)-1-{trans-4-hydroxy-4-[4-(4,4,5,5-tetramethyl-1,3,2-dioxaborolan-2-yl)phenyl]cyclohexyl}pyrrolidin-3-yl)amino]-2-oxoethyl}-3-(trifluoromethyl)benzamide (60 mg, 0.1 mmol), 5-bromo-1-methylimidazole (63 mg, 0.39 mmol), and aqueous Na₂CO₃ (0.5 mL) in DMF (0.5 mL) was added PdCl₂(dppf) (4 mg, 0.005 mmol)). After stirred at 80° C. for 18 h, the reaction was completed 66% as judged by LCMS. The crude was purified by prep LCMS and the appropriate fractions were combined and dried in a freeze drier to yield di-TFA salt of N-{2-[((3R)-1-{4-hydroxy-4-[4-(1-methyl-1H-imidazol -5-yl)phenyl]cyclohexyl}pyrrolidin-3-yl)amino]-2-oxoethyl}-3-(trifluoromethyl)benzamide (8 mg, 14%) as white powder. LCMS: 570.2 (M+H⁺, 100%); ¹⁹F NMR (CD₃OD) δ −64.6 (aryl-CF₃); −77.50 (TFA); ¹H NMR (CD₃OD) δ 9.02, (s, 1H); 8.18, (s, 1H); 8.12, (d, 1H); 7.81, (d, 2H); 7.78, (d, 1H); 7.63, (t, 1H); 7.55, (s, 1H); 7.32, (d, 2H); 4.40, (m, 1H); 4.11, (s, 2H); 3.90, (m, 1H) 3.83, (s, 3H); 3.48, (m, 2H); 3.20, (m, 1H); 2.70, (m, 1H); 2.37, (m, 3H); 2.24, (m, 2H); 2.01, (m, 2H); 1.82, (m, 3H).

The following compounds were prepared using procedures similar to those described for Examples 282-287.

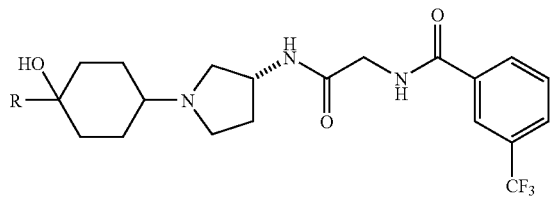

| Example # | R | MS (M + H)⁺ |
| --- | --- | --- |
| 288 | 4-(4,6-dimethylpyrimidin-5-yl)phenyl | 596.4 |
| 289 | 6-bromopyridin-3-yl | 569.3 |
| 290 | 5-bromopyridin-2-yl | 569.3 |
| 291 | 4'-(methylsulfonyl)biphenyl-4-yl | 644.4 |
| 292 | 3'-(methylsulfonyl)biphenyl-4-yl | 644.4 |
| 293 | 3'-(methoxycarbonyl)biphenyl-4-yl | 624.3 |
| 294 | 4-(2,3-dihydro-1,4-benzodioxin-6-yl)phenyl | 624.3 |
| 295 | 4'-(dimethylamino)biphenyl-4-yl | 609.4 |
| 296 | 4-(pyridin-3-yl)phenyl | 567.3 |
| 297 | 4-(1H-pyrazol-4-yl)phenyl | 556.3 |
| 298 | 3,3'-bipyridin-6-yl | 568.2 |
| 299 | 3,4'-bipyridin-6-yl | 568.2 |
| 300 | 5-(3-acetylphenyl)pyridin-2-yl | 609.3 |
| 301 | 5-[3-(dimethylamino)phenyl]pyridin-2-yl | 610.4 |
| 302 | 5-[3-(trifluoromethyl)phenyl]pyridin-2-yl | 634.3 |
| 303 | 5-[4-(methylsulfonyl)phenyl]pyridin-2-yl | 645.2 |
| 304 | 5-(4-methoxyphenyl)pyridin-2-yl | 597.3 |
| 305 | 5-(3-methoxyphenyl)pyridin-2-yl | 597.3 |
| 306 | 5-[3-(aminocarbonyl)phenyl]pyridin-2-yl | 610.3 |
| 307 | 5-(4-fluorophenyl)pyridin-2-yl | 585.4 |
| 308 | 5-(3,4-difluorophenyl)pyridin-2-yl | 603.3 |
| 309 | 5-(3,5-dimethylisoxazol-4-yl)pyridin-2-yl | 585.4 |
| 310 | 5-(1-methyl-1H-pyrazol-4-yl)pyridin-2-yl | 571.4 |
| 311 | 5-(1H-pyrazol-4-yl)pyridin-2-yl | 557.3 |
| 312 | 5-(1-benzofuran-2-yl)pyridin-2-yl | 607.2 |
| 313 | 5-(1,3-benzodioxol-5-yl)pyridin-2-yl | 611.3 |
| 314 | 5-(2-formylphenyl)pyridin-2-yl | 595.3 |
| 315 | 4-(2'-formylbiphenyl-4-yl | 594.3 |
| 316 | 5-(1,3-oxazol-2-yl)pyridin-2-yl | 558.4 |
| 317 | 6-(1,3-oxazol-2-yl)pyridin-3-yl | 558.4 |
| 318 | 4-(1,3-thizol-2-yl)phenyl | 573.2 |
| 319 | 5-(1,3-thiazol-2-yl)pyridin-2-yl | 5742 |
| 320 | 6-(1,3-thiazol-2-yl)pyridin-3-yl | 5742 |
| 321 | 6-(1H-imidazol-1-yl)pyridin-3-yl] | 557.4 |
| 322 | 5-(1H-imidazol-1-yl)pyridin-2-yl | 557.4 |
| 323 | 6-phenylpyridin-3-yl | 567.3 |
| 324 | 5-(pyrimidin-5-yl)pyridin-2-yl | 569.3 |
| 325 | 5-(pyrimidin-2-yl)pyridin-2-yl | 569.3 |
| 326 | 5-(3-aminocarbonyl)phenyl)pyridin-2-yl | 620.3 |
| 327 | 4-(1-methyl-1H-imidazol-4-yl)phenyl | 570.3 |
| 328 | 4-(1H-imidazol-4-yl)phenyl] | 556.4 |
| 329 | 5-[2-(hydroxymethyl)phenyl]pyridin-2-yl | 597.4 |
| 330 | 2'-(hydroxymethyl)biphenyl-4-yl | 596.2 |
| 331 | 5-{2-[(dimethylamino)methyl]phenyl}pyridin-2-yl | 624.3 |
| 332 | 2'-[(dimethylamino)methyl]biphenyl-4-yl | 623.3 |

Example 333

Step A

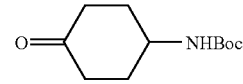

tert-Butyl (4-oxocyclohexyl)carbamate. To a solution of trans-4-aminocyclohexanol HCl salt (5 g, 33 mmol) and 1-methylmorpholine (9 mL, 82 mmol) in acetonitrile (35 mL) and water (30 mL) in an ice bath was added di-tert-butyl dicarbonate (7.2 g, 33 mmol). The mixture was stirred at room temperature overnight and EtOAc was added. The organic phase was separated. The aqueous layer was extracted with EtOAc twice. The combined organic phase was washed with brine, dried over MgSO₄ and concentrated.

To a solution of oxalyl chloride (2.33 mL, 26.7 mmol) in methylene chloride (50 mL) cooled at −60° C. was added a solution of DMSO (4 mL, 56 mmol) in methylene chloride (5 mL) followed by a solution of trans-4-tert-butoxycarbonylaminocyclohexanol (5 g, 23 mmol) obtained above in methylene chloride (20 mL). After stirring at −60° C. for 20 minutes, triethylamine (16.1 mL, 116 mmol) was added. The mixture was allowed to warm to room temperature and stirring was continued for 30 minutes. Water was added. The organic phase was separated and the aqueous layer was extracted with methylene chloride twice. The combined organic phase was washed with brine, dried over MgSO₄ and concentrated. Flash chromatography eluting with a gradient of 3% to 5% to 10% MeOH(CH₂Cl₂ provided 4.5 g (90%) of the title compound. MS (M+H)⁺ 214, found 236 (M+Na)⁺.

Step B

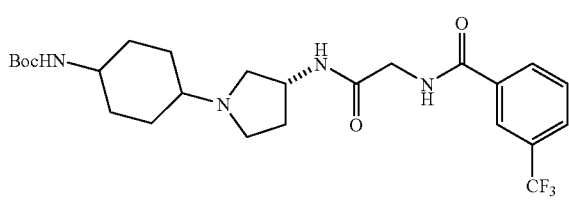

tert-Butyl (4{(3R)-3-[({[3-(trifluoromethyl)benzoyl]amino}acetyl)amino]pyrrolidin-1-yl}cyclohexyl)carbamate. To a solution of the ketone of step A (0.4 g, 1.9 mmol) and the pyrrolidine intermediate obtained in step C, Example 114 (0.4 g, 1.3 mmol) in THF (15 mL) was added sodium triacetoxyborohydride (0.4 g, 1.9 mmol). The reaction was stirred at room temperature overnight and quenched by addition of aqueous NaHCO₃. The resulting solution was extracted with EtOAc three times. The combined organic phase was washed with with NaHCO₃ and brine, dried over MgSO₄ and concentrated. Flash chromatography eluting with a gradient of 0-20% MeOH/CH₂Cl₂ provided 300 mg of the title compound. MS calculated (M+H)⁺ 513, found 513.

Step C

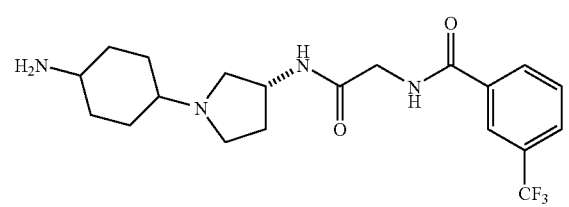

N-(2-{[1-((3R)-4-Aminocyclohexyl)pyrrolidin-3-yl]amino}-2-oxoethyl)-3-(trifluoromethyl)benzamide. The intermediate of step B (256 mg, 0.5 mmol) was dissolved in a solution of 4 N HCl in dioxane (10 mL). After being stirred at room temperature for 1 hour, the solution was concentrated to give a solid. MS calculated (M+H)⁺ 413, found 413.1.

Step D

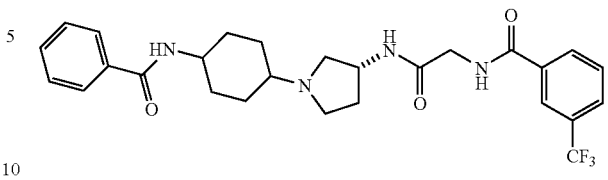

N-[2-({(3R)-1-[4-(Benzoylamino)cyclohexyl]pyrrolidin-3-yl}amino)-2-oxoethyl]-3-(trifluoromethyl)benzamide. To a solution of the amine of step C (80 mg, 0.18 mmol) in methylene chloride (2 mL) was added benzoyl chloride (25 μL, 0.21 mmol) followed by triethylamine (62 μL, 0.45 mmol). After being stirred at room temperature for 2 hours, the solution was concentrated. Flash chromatography eluting with 0-20% MeOH(CH₂Cl₂ provided the title compound. MS calculated (M+H)⁺ 517, found 517.1.

The following Examples were prepared using procedures analogous to those described for Example 333.

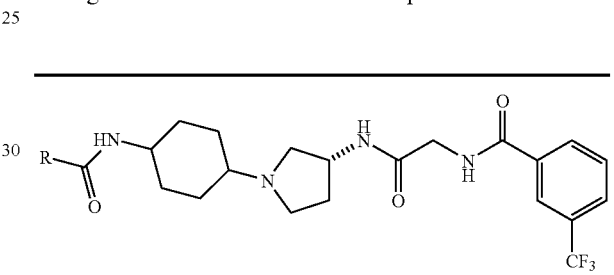

| Example # | R | MS (M + H)⁺ |
|---|---|---|
| 334 | pyridin-2-yl | 518 |
| 335 | pyridin-3-yl | 518 |
| 336 | pyridin-4-yl | 518 |
| 337 | 6-methylpyridin-2-yl | 532 |
| 338 | 5-methylpyridin-2-yl | 532 |
| 339 | 4-methylpyridin-2-yl | 532 |
| 340 | 6-methoxypyridin-2-yl | 548 |
| 341 | quinolin-4-yl | 568 |

Example 342

Step A

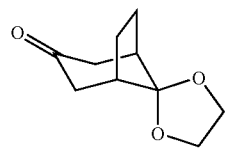

3H-Spiro[bicyclo[3.2.1]octane-8,2'-[1,3]dioxolan]-3-one. The title compound was prepared following the procedures described in the literature (M. Povarny et al. *Tetrahedron Lett.* 1984, 25, 1311-1312 and references cited therein). MS calculated (M+H)⁺ 183, found 183.0.

Step B

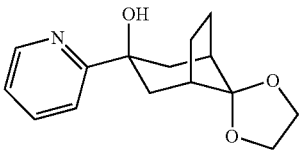

3-Pyridin-2-ylspiro[bicyclo[3.2.1]octane-8,2'-[1,3]dioxolan]-3-ol. To a solution of 2-bromopyridine (0.04 mL, 0.422 mmol) in ether (2 mL) cooled at −78° C. was added a 2.5 M solution of butyl lithium in hexanes (0.17 mL, 0.425 mmol). After stirring at −78° C. for 1 hour, a solution of the ketone obtained in Step A (70 mg, 0.384 mmol) in ether (2 mL) was added. Stirring was continued at −78° C. for 2 hours and the reaction was allowed to warm to 0° C. before it was quenched with a solution of ammonium chloride. The resulting solution was extracted with ether 3 times. The combined ether layers were dried over MgSO$_4$ and concentrated. Chromatography on silica gel eluting with 50% EtOAc/hexanes provided 58 mg (60%) of the title compound. MS calculated (M+H)$^+$ 262, found 262.1.

Step C

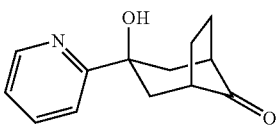

3-Hydroxy-3-pyridin-2-ylbicyclo[3.2.1]octan-8-one. The ketal (58 mg, 0.22 mmol) obtained in Step B was dissolved in MeOH (2 mL) and 10% HCl (1 mL). After being stirred at room temperature overnight, the solution was refluxed for 10 min and neutralized by addition of NaOH solution after cooling to room temperature. The resulting solution was condensed on a rotovap under reduced pressure to give the crude product which was used for the next reaction without purification. MS calculated (M+H)$^+$ 218, found 218.0.

Step D

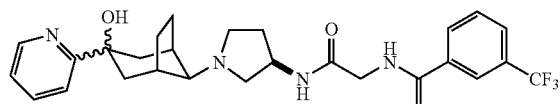

N-(2-{[(3R)-1-(3-Hydroxy-3-pyridin-2-ylbicyclo[3.2.1]oct-8-yl)pyrrolidin-3-yl]amino}-2-oxoethyl)-3-(trifluoromethyl)benzamide. Reductive amination of the ketone obtained above with the pyrrolidine derivative obtained in Step B, Example 1 using a procedure analogous to that described in Step D, Example 1 provided the title compound as a mixture (2:3) of two isomers. MS calculated (M+H)$^+$ 517, found 517.1.

Example 343

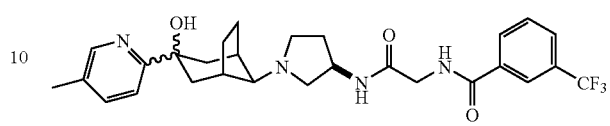

N-[2-({(3R)-1-[3-Hydroxy-3-(5-methylpyridin-2-yl)bicyclo[3.2.1]oct-8-yl]pyrrolidin-3-yl}amino)-2-oxoethyl]-3-(trifluoromethyl)benzamide. The title compound was prepared using procedures analogous to those described for Example 342. MS calculated (M+H)$^+$ 531, found 531.2.

Example 344

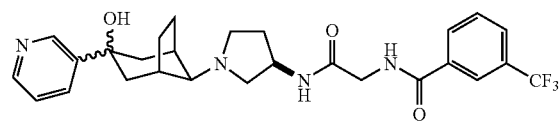

N-(2-{[(3R)-1-(3-Hydroxy-3-pyridin-3-ylbicyclo[3.2.1]oct-8-yl)pyrrolidin-3-yl]amino}-2-oxoethyl)-3-(trifluoromethyl)benzamide. The title compound was prepared using procedures analogous to those described for Example 342. MS calculated (M+H)$^+$ 517, found 517.1.

Example 345

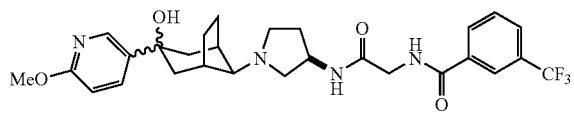

N-[2-({(3R)-1-[3-Hydroxy-3-(6-methoxypyridin-3-yl)bicyclo[3.2.1]oct-8-yl]pyrrolidin-3-yl}amino)-2-oxoethyl]-3-(trifluoromethyl)benzamide. The title compound was pared using procedures analogous to those described for Example 342. MS calculated M+H)$^+$ 547, found 547.2.

Example 346

Step A

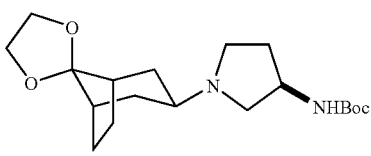

tert-Butyl [(3R)-1-spiro[bicyclo[3.2.1]octane-8,2'-[1,3]dioxolan]-3-ylpyrrolidin-3-yl]carbamate. To a solution of the ketone (0.1 g, 0.55 mmol) obtained in step A, Example 342 and (3R)-(+)-3-(tert-butoxycarbonylamino)pyrrolidine (0.1 g, 0.55 mmol) in methylene chloride (4 mL) was added sodium triacetoxyborohydride (0.13 g, 0.60 mmol). The reaction was stirred at room temperature overnight and quenched with aqueous sodium bicarbonate solution. The resulting solution was extracted with EtOAc 3 times. The combined EtOAc layer was dried over MgSO_4 and concentrated. Flash chromatography on silica gel eluting with 30% EtOAc/hexane, EtOAc and then 10% MeOH/CH_2Cl_2 provided two isomers of the title compound. MS calculated (M+H)$^+$ 353, found 353.1.

Step B

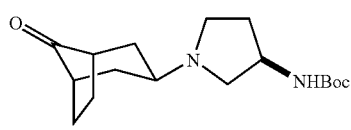

tert-Butyl [(3R)-1-(8-oxobicyclo[3.2.1]oct-3-yl)pyrrolidin-3-yl]carbamate. Isomer 1 obtained above (30 mg, 0.085 mmol) was dissolved in MeOH (1 mL) and 2 N HCl solution (0.5 mL). The solution was stirred at room temperature overnight and reflux at 110° C. for 2 hours. After being cooled to room temperature, the solution was neutralized with NaOH solution. To it was added a solution of di-tert-butyl dicarbonate (50 mg) in THF (2 mL) followed by triethylamine (0.05 mL). After being stirred at room temperature overnight, the solution was diluted with EtOAc. The organic phase was separated and the water layer was extracted with EtOAc twice. The combined organic phase was dried over MgSO_4 and concentrated. Flash chromatography on silica eluting with a gradient of CH_2Cl_2, 5%, 10% and 20% MeOH(CH_2Cl_2 provided 10 mg of the title compound. MS calculated (M+H)$^+$ 309, found 309.0.

Step C

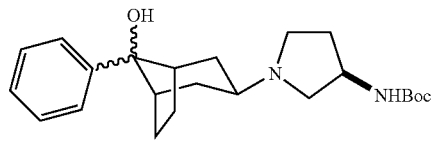

tert-Butyl [(3R)-1-(8-hydroxy-8-phenylbicyclo[3.2.1]oct-3-yl)pyrrolidin-3-yl]carbamate. To a solution of the ketone obtained in Step B (65 mg, 0.21 mmol) in THF (2 mL) cooled in an ice bath was added a 1 M solution of phenyl magnesium bromide in THF (0.25 mL). After being stirred at −78° C. for 3 hours, the reaction was quenched with aqueous ammonium chloride. The resulting solution was extracted with EtOAc 3 times. The combined EtOAc layers were dried over MgSO_4 and concentrated. Flash chromatography on silica gel eluting with 5%, 10% and 50% MeOH(CH_2Cl_2 provided 27 mg of the title compound as a mixture of two isomers (7:3). MS calculated (M+H)$^+$ 387, found 387.1.

Step D

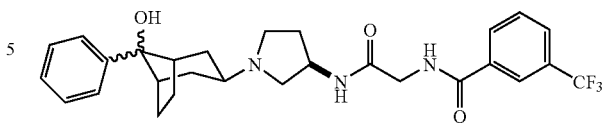

N-(2-{[(3R)-1-(8-Hydroxy-8-phenylbicyclo[3.2.1]oct-3-yl)pyrrolidin-3-yl]amino}-2-oxoethyl)-3-(trifluoromethyl)benzamide. The alcohol obtained in Step C (27 mg, 0.07 mmol) was dissolved in 2 mL 4 N HCl in dioxane. After being stirred at room temperature for 1 hour, the solution was concentrated. The residue was taken up in DMF (1 mL). To it was added the carboxylic acid obtained in Step A, Example 1 (25 mg, 0.1 mmol) followed by BOP (45 mg, 0.1 mmol) and triethylamine (0.05 mL, 0.36 mmol). The mixture was stirred at room temperature for 5 hours and diluted with EtOAc. The resulting solution was washed with sodium bicarbonate and brine, dried over MgSO_4 and concentrated. Reversed HPLC purification provided 22 mg of the title compound as a mixture of two isomers (7:3). MS calculated (M+H)$^+$ 516, found 516.1.

Following the procedures described above, isomer 2 from Step A was converted to the title compound as a single isomer. MS calculated (M+H)$^+$ 516, found 516.0.

Example 347

Step A

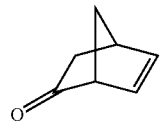

Bicyclo[2.2.1]hept-2-en-5-one. The title compound was prepared following the procedure described in the literature (G. T. Wang et al. *J. Org. Chem.* 2001, 66, 2052-2056).

Step B

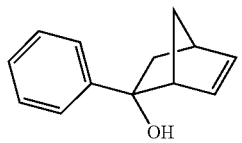

2-Phenylbicyclo[2.2.1]hept-5-en-2-ol. The title compound was prepared following the procedure described in the literature (C. J. Collins, B. M. Benjamin, *J. Am. Chem. Soc.* 1967, 89, 1652-1661).

Step C

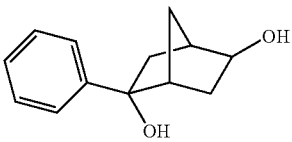

2-Phenylbicyclo[2.2.1]heptane-2,5-diol. The title compound was prepared following the procedure described in the literature (C. J. Collins, B. M. Benjamin, *J. Org. Chem.* 1972, 37, 4358-4366).

Step D

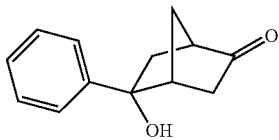

5-Hydroxy-5-phenylbicyclo[2.2.1]heptan-2-one. The title compound was prepared by Swern oxidation of the alcohol obtained above. MS calculated (M+H)+ 203, found 203 & 225 (M+Na)+.

Step E

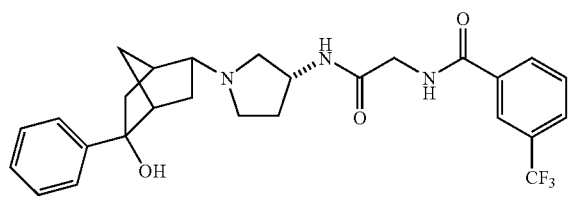

N-(2-{[(3R)-1-(5-Hydroxy-5-phenylbicyclo[2.2.1]hept-2-yl)pyrrolidin-3-yl]amino}-2-oxoethyl)-3-(trifluoromethyl)benzamide. To a solution of the ketone obtained in Step D, Example 45 (0.28 g, 1.38 mmol) and the pyrrolidine intermediate obtained in Step B, Example 1 (0.43 g, 1.38 mmol) in THF (15 mL) was added acetic acid (0.1 mL). After being stirred at 50° C. for 30 minutes, the solution was concentrated. The residue was taken up in THF (5 mL). To it was added sodium triacetoxyborohydride (300 mg, 1.42 mmol). After being stirred at room temperature overnight, the reaction was quenched with aqueous NaHCO3. The solution was extracted with EtOAc 3 times. The combined organic phase was washed with brine, dried over MgSO4 and concentrated. Purification by reversed phase HPLC provided the title compound as a TFA salt. MS calculated (M+H)+ 502, found 502.

Example 348

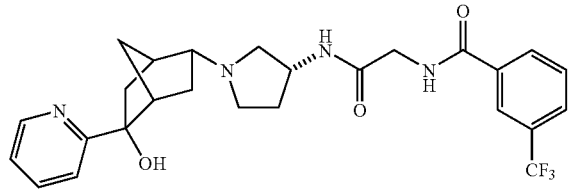

N-(2-{[(3R)-1-(5-Hydroxy-5-pyridin-2-ylbicyclo[2.2.1]hept-2-yl)pyrrolidin-3-yl]amino}-2-oxoethyl)-3-(trifluoromethyl)benzamide. The title compound was prepared following the procedures described for Example 347. MS calculated (M+H)+ 503, found 503.

Example 349

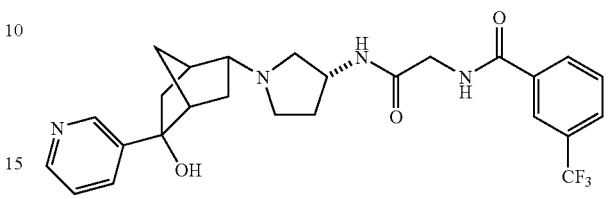

N-(2-{[(3R)-1-(5-Hydroxy-5-pyridin-3-ylbicyclo[2.2.1]hept-2-yl)pyrrolidin-3-yl]amino}-2-oxoethyl)-3-(trifluoromethyl)benzamide. The title compound was prepared following the procedures described for Example 347. MS calculated (M+H)+ 503, found 503.

Example 350

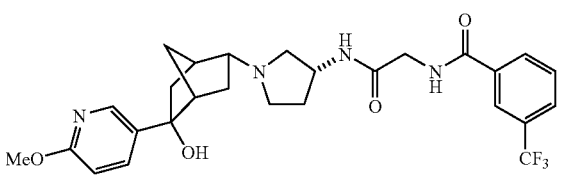

N-[2-({(3R)-1-[5-Hydroxy-5-(6-methoxypyridin-3-yl)bicyclo[2.2.1]hept-2-yl]pyrrolidin-3-yl}amino)-2-oxoethyl]-3-(trifluoromethyl)benzamide. The title compound was prepared following the procedures described for Example 347. MS calculated (M+H)+ 533, found 533.

Example 351

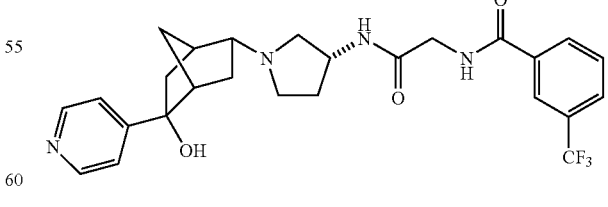

N-(2-{[(3R)-1-(5-Hydroxy-5-pyridin-4-ylbicyclo[2.2.1]hept-2-yl)pyrrolidin-3-yl]amino}-2-oxoethyl)-3-(trifluoromethyl)benzamide. The title compound was prepared following the procedures described for Example 347. MS calculated (M+H)+ 503, found 503.

Example 352

Step A

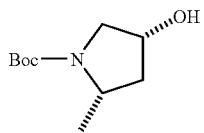

tert-Butyl (2S,4R)-4-Hydroxy-2-methylpyrrolidine-1-carboxylate. The title compound was prepared following the procedures described in the literature (T. Rosen, et al. *J. Med. Chem.* 1988, 31, 1598-1611).

Step B

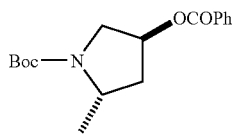

tert-Butyl (2S,4S)-4-(Benzoyloxy)-2-methylpyrrolidine-1-carboxylate. To a solution of the alcohol of step A (0.81 g, 4.0 mmol), benzoic acid (0.74 g, 6.0 mmol) and triphenylphosphine (2.11 g, 8.0 mmol) in toluene (20 mL) was added DIAD (1.67 mL, 8.0 mmol). After being stirred at room temperature for 4 hours, the solution was concentrated. The residue was purified by flash chromatography eluting with 0%, 5% and 20% EtOAc/hexanes provided 1.0 g of the title compound. MS calculated (M+H)+ 308, found 308.1.

Step C

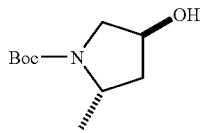

tert-Butyl (2S,4S)-4-Hydroxy-2-methylpyrrolidine-1-carboxylate. To a solution of the ester of step B (1.0 g, 3.48 mmol) in MeOH (30 mL) was added K$_2$CO$_3$ (1.2 g, 8.7 mmol). After being stirred at room temperature for 4 hours, the solution was concentrated. The residue was taken up in ether. The resulting solution was washed with brine, dried over MgSO$_4$ and concentrated. Flash chromatography eluting with a gradient of 0% to 20% to 40% EtOAc/hexanes provided 0.56 g of the title compound. MS calculated (M+H)+ 202, found 202.1.

Step D

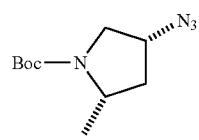

tert-Butyl (2S,4R)-4-Azido-2-methylpyrrolidine-1-carboxylate. To a solution of the alcohol of step C (0.55 g, 2.73 mmol) in methylene chloride (30 mL) cooled in an ice bath was added triethylamine (0.51 mL, 3.69 mmol) followed by methanesulfonyl chloride (0.29 mL, 3.69 mmol). After being stirred in the ice bath for 30 minutes, the reaction was continued by stirring at room temperature for 40 minutes. The solution was washed with water, dried over MgSO$_4$ and concentrated.

The residue obtained above was dissolved in DMF (15 mL) and NaN$_3$ (1.06 g, 16.3 mmol) was added. The mixture was stirred at 50° C. overnight and diluted with tert-butyl methyl ether. The resulting solution was washed with brine, 5% citric acid and saturated NaHCO$_3$ solutions, dried over MgSO$_4$ and concentrated to give 0.58 g of the title compound. MS calculated (M+H)+ 227, found 227.2.

Step E

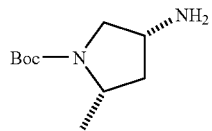

tert-Butyl (2S,4R)-4-Amino-2-methylpyrrolidine-1-carboxylate. To a solution of the azido compound obtained above (0.58 g, 2.56 mmol) in MeOH (30 mL) was added 5% Pd/C (100 mg). The mixture was stirred under hydrogen (balloon) for 3 hours. The catalyst was filtered off and the filtrate was concentrated to give 0.5 g of the title compound. MS calculated (M+H)+ 201, found 201.1.

Step F

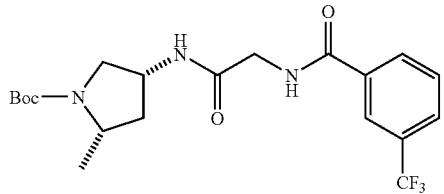

tert-Butyl (2S,4R)-2-Methyl-4-[({[3-(trifluoromethyl)benzoyl]amino}acetyl)amino]pyrrolidine-1-carboxylate. To a solution of the amine of step D (0.5 g, 2.5 mmol), the carboxylic acid obtained in step A, Example 114 and triethylamine (0.7 mL, 5.0 mmol) in methylene chloride (25 mL) cooled in an ice bath was added EDC (0.53 g, 2.75 mmol). After being stirred at room temperature overnight, the solution was concentrated. The residue was purified on silica gel eluting with a gradient of 0-4% MeOH(CH$_2$Cl$_2$ provided 0.6 g of the title compound. MS calculated (M+H)+ 430, found 430.1.

Step G

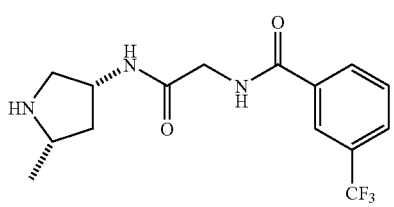

N-(2-{[(3R,5S)-5-Methylpyrrolidin-3-yl]amino}-2-oxo-ethyl)-3-(trifluoromethyl)benzamide. The intermediate of step F (0.6 g, 1.4 mmol) was dissolved in MeOH (3 mL) and a solution of 4 N HCl in dioxane (3 mL). After being stirred at room temperature for 4 hours, the solution was concentrated to give 0.56 g of the title compound. MS calculated (M+H)+ 330, found 330.2.

Step H

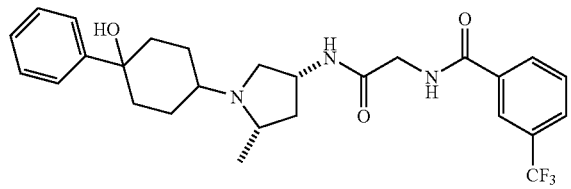

N-(2-{[(3R,5S)-1-(4-Hydroxy-4-phenylcyclohexyl)-5-methylpyrrolidin-3-yl]amino}-2-oxoethyl)-3-(trifluoromethyl)benzamide. The title compound was prepared by reductive amination of the amine of step G with 4-hydroxy-4-phenylketone using a procedure analogous to that described for Example 114. MS calculated (M+H)+ 504, found 504.1.

The following Examples were prepared using procedures analogous to those described for Example 352.

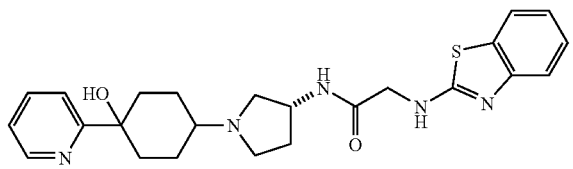

| Example # | R | MS (M + H)+ |
|---|---|---|
| 353 | 4-methylphenyl | 518 |
| 354 | pyridin-2-yl | 505 |
| 355 | 5-methylpyridin-2-yl | 519 |
| 356 | pyridin-3-yl | 505 |
| 357 | 6-methoxypyridin-3-yl | 535 |
| 358 | pyridin-4-yl | 505 |

Example 359

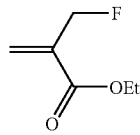

2-(1,3-Benzothiazol-2-ylamino)-N-[(3R)-1-(4-hydroxy-4-pyridin-2-ylcyclohexyl)pyrrolidin-3-yl]acetamide. The mixture of 2-amino-N-[(3R)-1-(4-hydroxy-4-pyridin-2-ylcyclohexyl)pyrrolidin-3-yl]acetamide (0.080 g, 0.25 mmol), Et3N (0.35 mL, 2.5 mmol) and 2-chloro-benzothiazole (0.424 g, 2.5 mmol) in isopropanol was stirred overnight at 90° C. The reaction mixture was concentrated and chromatographed to provide 55 mg of the title compound in 49% yield. MS (EI) calculated: (M+)+=452.2; found: 452.2.

Example 360

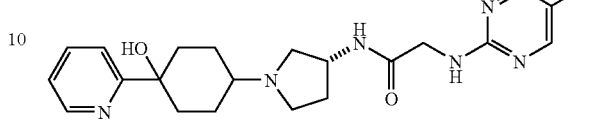

N-[(3R)-1-(4-hydroxy-4-pyridin-2-ylcyclohexyl)pyrrolidin-3-yl]-2-{[5-(trifluoromethyl)pyrimidin-2-yl]amino}acetamide. The title compound was prepared in a manner similar to that for Example 359. MS (EI) calcd: (M+H)+=465.2; found: 465.1.

Example 361

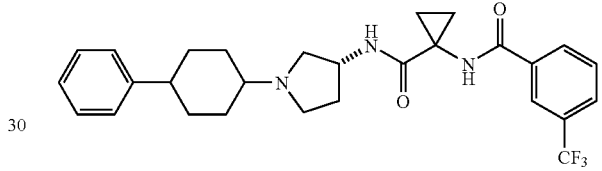

N-[1-({[(3R)-1-(4-Phenylcyclohexyl)pyrrolidin-3-yl]amino}carbonyl)cyclopropyl]-3-(trifluoromethyl)benzamide. The tide compound was prepared using procedures analogous to those for Example 114. MS (EI): Calcd. (M+H)+ 500.2, found: 500.4. 1H NMR (CDCl3) δ=8.61 (1H, d), 8.21 (1H, s), 8.15 (1H, d), 7.78 (1H, s), 7.75 (1H, d), 7.58 (1H, dd), 7.22 (5H, m), 4.81 (1H, m), 3.8 (1H, m), 3.62 (1H, dd), 3.17 (1H, m), 2.92 (2H, m), 2.8 (1H, m), 2.48 (1H, m), 2.18 (2H, m), 2.1 (2H, m), 1.75 (3H, m), 1.55 (4H, m), 1.18 (2H, m).

Example 362

Step A

Ethyl 2-(Fluoromethyl)acrylate. To a solution of ethyl 2-(hydroxymethyl)acrylate (5 g, 38 mmol) in 50 mL of methylene chloride was added DAST (6.0 mL, 46.1 mmol) at −78° C. The reaction mixture was stirred at −78° C. for 1 h, then warmed up to room temperature and continuously stirred overnight. 20 mL of saturated NaHCO3 aqueous solution and 20 mL of ethyl acetate were added to quench the reaction. The organic layer was separated, and the aqueous layer was extracted twice with EtOAc (20 ml×2). The combined organic extracts were dried over MgSO4 and evaporated to give an oil residue (2.8 g, yield: 56%). MS (m/z): 131 (M+1)+.

Step B

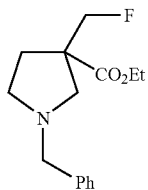

Ethyl 1-benzyl-3-(fluoromethyl)pyrrolidine-3-carboxylate. To a solution of N-benzyl-1-methoxy-N-[(trimethylsilyl)methyl]methanamine (2.5 g, 21 mmol) and ethyl 2-(fluoromethyl)acrylate (5.0 g, 21 mmol) in methylene chloride (30 mL) was added TFA (0.15 ml, 2.1 mmol) at 0° C. The reaction mixture was stirred at 0° C. overnight. 20 mL of saturated NaHCO$_3$ aqueous solution and 20 mL of ethyl acetate were added to quench the reaction. The organic layer was separated, and the aqueous layer was extracted twice with EtOAc (20 mL×2). The combined organic extracts were dried over MgSO$_4$ and evaporated to give an oil residue. Chromatography on silica gel with 10% EtOAc-Hexane afforded 1.27 g (4.8 mmol, yield: 23%) of ethyl 1-benzyl-3-(fluoromethyl)pyrrolidine-3-carboxylate: $^1$H NMR (400 MHz, CDCl$_3$) δ 7.39-7.20 (5H, m), 4.62-4.44 (2H, m), 4.18-4.21 (2H, m), 3.62 (2H, s), 2.81-2.72 (2H, m), 2.60-2.50 (2H, m), 2.22 (2H, s), 1.25 (311, t, J=6.7 Hz); MS (m/e): 266 (M+1)$^+$.

Step C

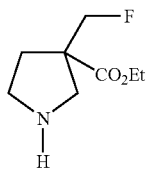

Ethyl 3-(fluoromethyl)pyrrolidine-3-carboxylate. To a solution of 1.27 g (4.8 mmol) of ethyl 1-benzyl-3-(fluoromethyl)pyrrolidine-3-carboxylate in 20 mL of methanol was added 500 mg of Pd/C (10% on carbon) and 1.5 g (24 mmol) of HCOONH$_4$. The reaction mixture was refluxed for 1 h, filtered through celite pad and evaporated to give a residue. The residue was then dissolved in ethyl acetate, the resulting solution was washed with saturated NaHCO$_3$ aqueous solution, brine, dried over Na$_2$SO$_4$, evaporated to give the final crude product (426 mg, 2,4 mmol, yield: 50%): MS (m/e): 176 (M+H)$^+$.

Step D

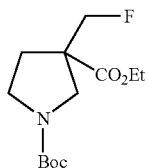

1-tert-Butyl 3-Ethyl 3-(fluoromethyl)pyrrolidine-1,3-dicarboxylate. To a solution of ethyl 3-(fluoromethyl)pyrrolidine-3-carboxylate (2.4 mmol) in 20 mL of methylene chloride was added 786 mg of (Boc)$_2$O (3.6 mmol) and 0.67 ml (4.8 mmol) of triethylamine at room temperature. The reaction mixture was stirred overnight. Direct chromatography on silica gel gave 562 mg (2.0 mmol, yield: 85%) of the desired product, 1-tert-butyl 3-ethyl 3-(fluoromethyl)pyrrolidine-1,3-dicarboxylate: $^1$H NMR (400 MD, CDCl$_3$) δ 4.65-4.42 (2H, m), 4.28-4.19 (2H, m), 3.80-3.72 (1H, m), 3.56-3.40 (3H, m), 2.40-2.20 (1H, m), 2.08-1.93 (1H, m), 1.45 (9H, s), 1.1.32-1.25 (3H, m); MS (m/e): 276 (M+1)$^+$.

Step E

1-(tert-Butoxycarbonyl)-3-(fluoromethyl)pyrrolidine-3-carboxylic acid. To a solution of 562 mg of 1-tert-butyl 3-ethyl 3-(fluoromethyl)pyrrolidine-1,3-dicarboxylate (2.0 mmol) in 10 mL of THF and 5 mL of water was added 420 mg of LiOH.H$_2$O (10 mmol at room temperature. The reaction mixture was stirred for 5 h. The reaction mixture was quenched with 1N HCl aqueous solution and adjusted to pH 34, extracted with ethyl acetate twice (20 mL×2). The combined extracts were washed with brine, dried with Na$_2$SO$_4$, evaporated to give the final product (530 mg, 2.0 mmol), 1-(tert-butoxycarbonyl)-3-(fluoromethyl)pyrrolidine-3-carboxylic acid: $^1$H NMR (400 MHz, CDCl$_3$) δ 4.70-4.22 (2H, m), 3.81-3.75 (1H, m), 3.60-3.41 (3H, m), 2.41-2.30 (1H, m), 2.10-1.99 (1H, m), 1.47 (9H, s); MS (m/e): 248 (M+1)$^+$.

Step F

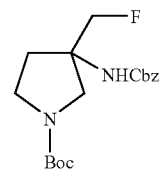

tert-Butyl 3-{[(benzyloxy)carbonyl]amino}-3-(fluoromethyl)pyrrolidine-1-carboxylate. To a solution of 530 mg (2.0 mmol) of 1-(tert-butoxycarbonyl)-3-(fluoromethyl)pyrrolidine-3-carboxylic acid in toluene (30 mL) was added 0.69 mL (3.2 mmol) of DPPA and 0.3 6 mL (2.6 mmol) of triethylamine. The reaction mixture was stirred at 110° C. for 4 h. Then 0.33 mL (3.2 mmol) of benzyl alcohol was added and the reaction was stirred overnight at 110° C. The mixture was cooled down and evaporated to give a residue. The residue was dissolved in methylene chloride, washed with 5% citric acid aqueous solution, saturated K$_2$CO$_3$ aqueous solution, brine, dried over Na$_2$SO$_4$, evaporated. Chromatography on silica gel afforded 540 mg (1.53 mmol, yield: 73%) of the desired product, tert-butyl 3-{[(benzyloxy)carbonyl]amino}-3-(fluoromethyl)pyrrolidine-1-carboxylate: $^1$H NMR (400 MHz, CDCl$_3$) δ 7.40-7.35 (5H, m), 5.10 (2H, s), 4.94 (1H, s), 4.70-4.50 (2H, m), 3.60-3.40 (4H, m), 2.40-2.00 (2H, m), 1.45 (9H, s); MS (m/e): 353 (M+1)$^+$.

Step G

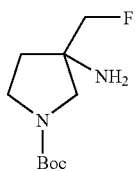

tert-Butyl 3-Amino-3-(fluoromethyl)pyrrolidine-1-carboxylate. To a solution of 540 mg (1.53 mmol) of tert-butyl 3-{[(benzyloxy)carbonyl]amino}-3-(fluoromethyl)pyrrolidine-1-carboxylate in 10 mL of methanol was added 330 mg (10% on carbon) of Pd/C. The suspension was stirred at room temperature under $H_2$ (balloon) for 2 h. The reaction mixture was filtered through celite pad, evaporated to give 337 mg (1,52 mmol, yield: 99%) of the crude product, tert-butyl 3-amino-3-(fluoromethyl)pyrrolidine-1-carboxylate: MS (m/e): 219 (M+1)$^+$.

Step H

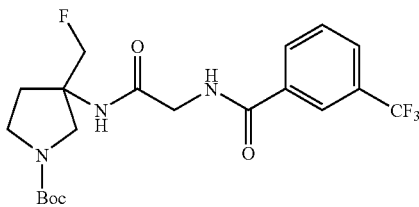

tert-Butyl 3-(Fluoromethyl)-3-[({[3-(trifluoromethyl)benzoyl]amino}acetyl)amino]pyrrolidine-1-carboxylate. 337 mg (1.52 mmol) of tert-butyl 3-amino-3-(fluoromethyl)pyrrolidine-1-carboxylate, 457 mg (1.85 mmol) of {[3-(trifluoromethyl)benzoyl]amino}acetic acid, BOP reagent (817 mg, 1.85 mmol) and 0.64 mL (4.6 mmol) of triethylamine were dissolved in 15 mL of DMF at room temperature. The reaction mixture was stirred at r.t. overnight. Direct chromatography on silica gel (flash chromatography grade) with 50% ethyl acetate-hexane gave 578 mg (1.29 mmol, 84%) of tert-butyl 3-(fluoromethyl)-3-[({[3-(trifluoromethyl)benzoyl]amino}acetyl)amino]pyrrolidine-1-carboxylate: $^1$H NMR (400 MHz, CDCl$_3$) δ 8.15-8.12 (1H, m), 8.05-7.98 (1H, m), 7.81-7.77 (1H, m), 7.63-7.58 (1H, m), 6.64-6.62 (1H, m), 4.20-4.16 (2H, m), 3.61-3.57 (2H, m), 3.55-3.42 (1H, m), 2.98-2.94 (2H, m), 2.90-2.86 (2H, m), 1.62-1.60 (2H, m), 1.45 (9H, s); MS (m/e): 448 (M+1)$^+$.

Step I

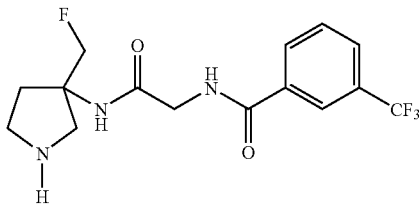

N-(2-{[3-(Fluoromethyl)pyrrolidin-3-yl]amino}-2-oxoethyl)-3-(trifluoromethyl)benzamide. To a solution of 578 mg (1.29 mmol) of tert-butyl 3-(fluoromethyl)-3-[({[3-(trifluoromethyl)benzoyl]amino}acetyl)amino]pyrrolidine-1-carboxylate in 5 mL of THF was added 2 mL of 4 N HCl dioxane solution. The reaction mixture was stirred at room temperature for 1 h and evaporated to give the yellow solid, N-(2-{[3-(fluoromethyl)pyrrolidin-3-yl]amino}-2-oxoethyl)-3-(trifluoromethyl)benzamide HCl salt: MS (m/e): 347 (M+1)$^+$.

Step J

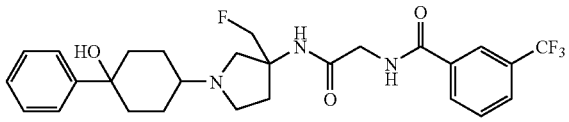

N-(2-{[3-(Fluoromethyl)-1-(4-hydroxy-4-phenylcyclohexyl)pyrrolidin-3-yl]amino}-2-oxoethyl)-3-(trifluoromethyl)benzamide. 100 mg (0.53 mmol) of 4-hydroxy-4-phenylcyclohexanone and 184 mg (0.53 mmol) of N-(2-{[3-(fluoromethyl)pyrrolidin-3-yl]amino}-2-oxoethyl)-3-(trifluoromethyl)benzamide were dissolved in 10 mL of methylene chloride. To the solution was added 221 mg (1.06 mmol) of sodium triacetoxyborohydride. The reaction mixture was stirred at room temperature for 2 h. Direct chromatography on silica gel gave the final desired product 41 mg (top spot on TLC and first peak on HPLC, yield: 16.7%, MS: 522 (M+1)$^+$) and the other isomer 51 mg (second peak on HPLC, yield: 20%, MS: 522 (M+1)$^+$).

Example 363

Step A

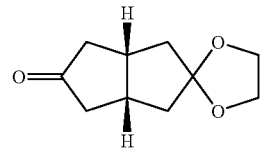

(3a'R,6a'S)-Tetrahydro-1'H-spiro[1,3-dioxolane-2,2'-pentalen]-5'(3'H)-one. cis-Tetrahydropentalene -2,5(1H,3H)-dione (5 g, 36 mmol) and ethylene glycol (2.3 g, 36 mmol) were dissolved in toluene. To the resulting solution was added PTSA (684 mg, 3.6 mmol). The reaction mixture was refluxed for 12 h meanwhile the resulting water was removed away. Direct chromatography on silica gel gave 2.0 g (11 mmol, yield: 31%) of the desired product, (3a'R,6a'S)-tetrahydro-1'H-spiro[1,3-dioxolane-2,2'-pentalen]-5'(3'H)-one: MS (m/e): 183 (M+1)$^+$.

Step B

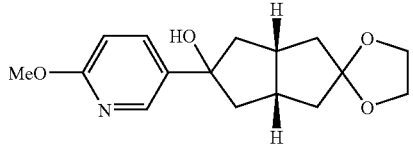

(3a'R,6a'S)-5'-(6-Methoxypyridin-3-yl)hexahydro-1'H-spiro[1,3-dioxolane-2,2'-pentalen]-5'-ol. A solution of 5-bromo-2-methoxypyridine (1 g, 5.3 mmol) in 50 mL of dry THF under nitrogen was cooled to −78° C. n-Butyllithium (3.5 mL, 5.6 mmol, 1.6 M solution in hexane) was added dropwise. The orange solution was stirred for an additional 1 h at −78° C. and then treated dropwise over 10 min with a solution of 1,4-cyclohexanedione monoethylene ketal (960 mg, 5.3 mmol) in 20 mL of dry IT. The reaction mixture was stirred for 1 h, allowed to warm to 20° C. and poured into ice water (400 mL). The organic layer was separated, and the aqueous layer was extracted twice with EtOAc (20 mL×2). The combined organic extracts were dried over MgSO$_4$ and evaporated. Chromatography on silica gel afforded 1.08 g (3.7 mmol, yield: 70%) of white crystals, (3a'R,6a'S)-5'-(6-methoxypyridin-3-yl)hexahydro-1'H-spiro[1,3-dioxolane-2, 2'-pentalen]-5'-ol: MS: 292 (M+1)$^+$.

Step C

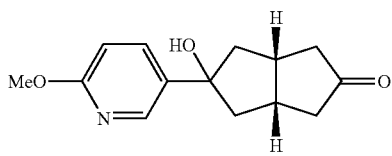

(3aR,6aS)-5-hydroxy-5-(6-methoxypyridin-3-yl)hexahydropentalen-2(1H)-one. The title compound was synthesized from (3a'R,6a'S)-5'-(6-methoxypyridin-3-yl)hexahydro -1'H-spiro[1,3-dioxolane-2,2'-pentalen]-5'-ol using the typical deprotection procedure.

Step D

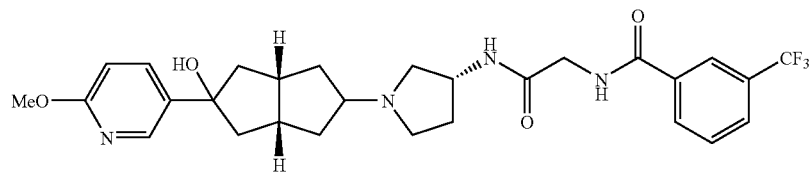

N-[2-({(3R)-1-[(3aR,6aS)-5-Hydroxy-5-(6-methoxypyridin-3-yl)octahydropentalen-2-yl]pyrrolidin-3-yl}amino)-2-oxoethyl]-3-(trifluoromethyl)benzamide. The title compound was synthesized according to the same reductive amination procedure as described for Example 114. MS (M+H)$^+$ 547.

Example 364

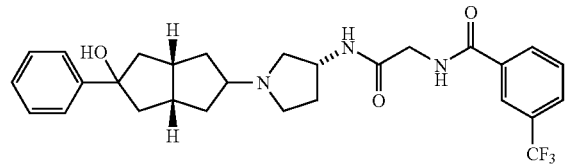

N-[2-({(3R)-1-[(3aR,6aS)-5-Hydroxy-5-phenyloctahydropentalen-2-yl]pyrrolidin -3-yl}amino)-2-oxoethyl]-3-(trifluoromethyl)benzamide. The title compound was prepared in a manner similar to that described for Example 363. MS (M+H)$^+$ 516.

Example 365

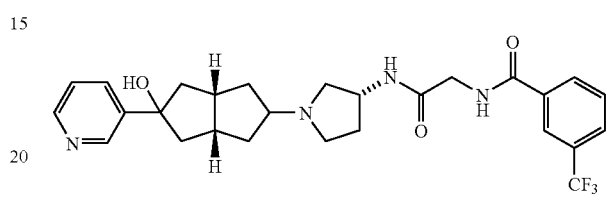

N-[2-({(3R)-1-[(3aR,6aS)-5-Hydroxy-5-pyridin-3-yloctahydropentalen-2-yl]pyrrolidin-3-yl}amino)-2-oxoethyl]-3-(trifluoromethyl)benzamide. The title compound was prepared in a fashion similar to that described for Example 363. MS (M+H)$^+$ 517.

Example 366

Step A

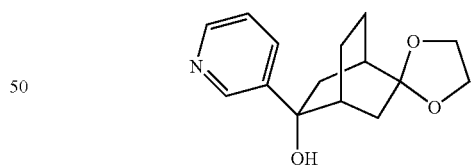

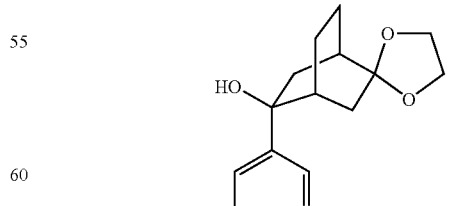

5-Pyridin-3-ylspiro[bicyclo[2.2.2]octane-2,2'-[1,3]dioxolan]-5-ol. A solution of 3-bromopyridine (1.13 g, 7.13 mmol) was dissolved in dry ether under nitrogen, cooled to −78° C. and then n-butyllithium (4.50 mL, 7.13 mmol, 1.6 M in hexane) was added dropwise. After thirty minutes, a solution of 5H-spiro[bicyclo[2.2.2]octane-2,2'-[1,3]dioxolan]-5-one (0.65 g, 3.56 mmol, *J. Org. Chem.* 1991, 56, 1052-1058) in ether was added dropwise and the mixture stirred for two hours at −78° C. The mixture was then warmed to 0° C. and diluted with ethyl acetate. The organic extract was washed with NaHCO$_3$/H$_2$O and brine and then dried over MgSO$_4$, filtered and concentrated. The residue was chromatographed on silica gel using ethyl acetate as eluent to provide two isomeric products as white solids: higher Rf product, 0.294 g (32%); lower Rf product, 0.220 g (24%). Higher Rf product: $^1$H NMR (CDCl$_3$) δ 8.87 (s, 1H), 8.49 (d, 1H), 7.91 (dt, 1H), 7.27 (m, 1H), 3.92 (m, 4H), 2.69 (dt, 1H), 2.20 (m, 1H), 1.85-2.15 (m, 3H), 1.60-1.83 (m, 4H), 1.50 (m, 1H). Lower Rf product: $^1$H NMR (CDCl$_3$) δ 8.80 (s, 1H), 8.50 (d, 1H), 7.86 (dt, 1H), 7.29 (m, 1H), 3.90-4.10 (m, 4H), 2.44 (dt, 1H), 2.33 (dd, 1H), 2.15-2.27 (m, 2H), 2.00 (m, 1H), 1.75-1.88 (m, 2H), 1.70 (m, 1H), 1.51 (m, 2H), 1.34 (m, 1H).

Step B

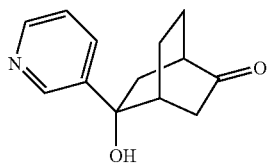

5-Hydroxy-5-pyridin-3-ylbicyclo[2.2.2]octan-2-one. Alcohol of step A (higher Rf isomer, 0.290 g, 1.11 mmol) was dissolved in THF (10 mL) under nitrogen. Hydrochloric acid (2.0 mL, 4.0 M aqueous solution, 8.0 mmol) was added and the mixture stirred for 4 hours at room temperature. The mixture was then diluted with NaHCO$_3$/H$_2$O and extracted twice with ethyl acetate. The extracts were washed with brine, dried over MgSO$_4$, filtered and concentrated to provide a light yellow solid, 0.204 g (85%). The crude product 2 was used directly for the next step without further purification. $^1$H NMR (CDCl$_3$) δ 8.74 (s, 1H), 8.52 (d, 1H), 7.72 (dt, 1H), 7.30 (dd, 1H), 2.66 (dt, 1H), 2.53 (m, 2H), 2.41 (t, 1H), 2.18 (t, 1H), 2.13 (d, 1H), 2.09 (m, 1H), 1.99 (m, 1H), 1.89 (m, 1), 1.62 (m, 2H). Step C

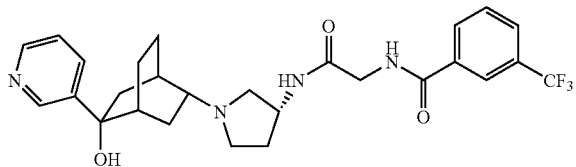

N-(2-{[(3R)-1-(5-Hydroxy-5-pyridin-3-ylbicyclo[2.2.2]oct-2-yl)pyrrolidin-3-yl]amino}-2-oxoethyl)-3-(trifluoromethyl)benzamide. N-{2-Oxo-2-[(3R)-pyrrolidin-3-ylamino]ethyl}-3-(trifluoromethyl)benzamide hydrochloride (100 mg, 0.284 mmol) and 5-hydroxy-5-pyridin-3-ylbicyclo[2.2.2]octan-2-one (62.0 mg, 0.284 mmol) were dissolved in dry THF (10 mL). Triethylamine (80 uL, 0.57 mmol) and sodium triacetoxyborohydride (120 mg, 0.57 mmol) were added and the mixture was stirred at room temperature overnight. TLC indicated conversion to desired products in about a 1:1 ratio of isomers. Adsorbed reaction mixture onto silica gel and chromatographed eluting with dichloromethane to 10% methanol/dichloromethane/0.5% ammonium hydroxide. Fractions were combined to give pure higher Rf isomer and pure lower Rf isomer: Higher Rf product: LC/MS (positive ion) m/z=517.1 (M+H)$^+$; Lower Rf product: LC/MS (positive ion) m/z=517.2 (M+H)$^+$.

Example 367

Step A

3-Methylisothiazole. The title compound was prepared according to the procedures in the literature (Lucchesini, F.; Picci, N.; Pocci, M., *Heterocycles*, 1989, 29, 97). At 0° C., 3-butyn-2-one (2.5 mL, 0.032 mol) and hydroxylamine-O-sulfonic acid (3.67 g, 0.0324 mol) were mixed in Water (15 mL, 0.83 mol). After being stirred for 30 min, solid sodium bicarbonate (3.0 g, 0.036 mol) was slowly added (30 minutes) by portion. A solution of sodium hydrogen sulfide dihydrate (3.3 g, 0.036 mol) in water (25 mL, 1.4 mol) was dropwise added to the above reaction mixture. Ice bath was then removed. Stirring was continued for another 4 hr at rt. The mixture was extracted with ether. The extract was dried and concentrated. Chromatography on silica gel eluting with ether/hexane (1/3) provided 1.37 g (48.2%) of the title compound.

Step B

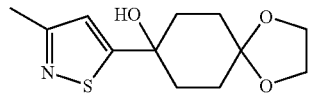

8-(3-Methyl-isothiazol-5-yl)-1,4-dioxa-spiro[4.5]decan-8-ol. At −78° C., 1.5 M of n-butyllithium in hexane (6.7 mL) was slowly added to a solution of 3-methylisothiazole (1.0 g, 0.010 mol) in tetrahydrofuran (15 mL) over a period of 20 min. After being stirred for another 30 min, 1,4-dioxa-spiro [4.5]decan-8-one (1.56 g, 0.00999 mol) in tetrahydrofuran (5 mL) was added within 10 min. The reaction mixture was stirred for another 2 hour at −78° C. and allowed to warm up overnight to room temperature. After quenching with with brine, the mixture was extracted with EtOAc. The organic layer was dried and concentrated. Chromatography on silica gel eluting with hexane/EtOAc (1:5~1:1) provided 1.8 g (70.6%) of the title compound. MS (M+H)$^+$ 256.

Step C

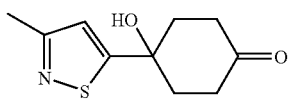

4-Hydroxy-4-(3-methyl-isothiazol-5-yl)-cyclohexanone. 8-(3-Methyl-isothiazol-5-yl)-1,4-dioxa-spiro[4.5]decan-8-ol (0.76 g, 0.0030 mol) was dissolved in tetrahydrofuran (10 mL), and a solution of 3.0 M of hydrogen chloride in water (5.0 mL) was added. The mixture was stirred overnight. Solid potassium carbonate was added to neutralize the acid and EtOAc was added to extract the product. The extract was dried and concentrated to give a crude product which was used directly for next step.

Step D

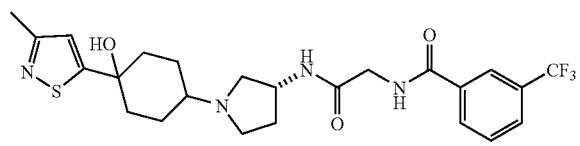

N-[2-({(3R)-1-[4-Hydroxy-4-(3-methylisothiazol-5-yl) cyclohexyl]pyrrolidin-3-yl}amino)-2-oxoethyl]-3-(trifluoromethyl)benzamide. The title compound was prepared from the ketone of step D using a procedure analogous to that for Example 114. MS (M+H)+ 511.

Example 368

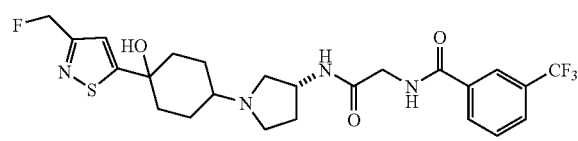

N-{2-[((3R)-1-{4-[3-(Fluoromethyl)isothiazol-5-yl]-4-hydroxycyclohexyl}pyrrolidin-3-yl)amino]-2-oxoethyl}-3-(trifluoromethyl)benzamide. The title compound was prepared using procedures analogous to those described for Example 367. MS (M+H)+ 529.

Example 369

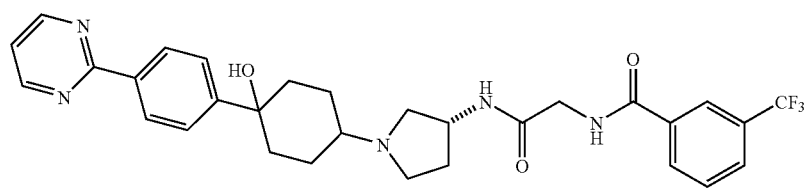

N-(2-{[(3R)-1-(4-Hydroxy-4-isothiazol-5-ylcyclohexyl) pyrrolidin-3-yl]amino}-2-oxoethyl)-3-(trifluoromethyl)benzamide. The title compound was prepared using procedures analogous to those described for Example 367. MS (M+H)+ 497.

Example 370

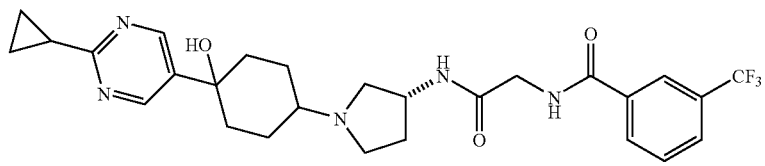

N-[2-({(3R)-1-[4-Hydroxy-4-(4-pyrimidin-2-ylphenyl) cyclohexyl]pyrrolidin-3-yl}amino)-2-oxoethyl]-3-(trifluoromethyl)benzamide. The title compound was prepared in a manner similar to that for Example 282. MS 568 (M+H)+.

Example 371

N-[2-({(3R)-1-[4-(2-Cyclopropylpyrimidin-5-yl)-4-hydroxycyclohexyl]pyrrolidin-3-yl}amino)-2-oxoethyl]-3-(trifluoromethyl)benzamide. The title compound was prepared in a manner analogous to that for Example 276. MS 532 (M+H)+.

Example 372

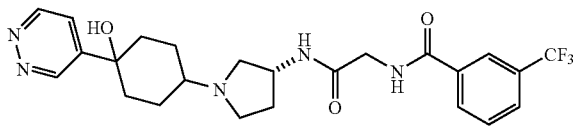

N-(2-{[(3R)-1-(4-Hydroxy-4-pyridazin-4-ylcyclohexyl) pyrrolidin-3-yl]amino}2-oxoethyl)-3-(trifluoromethyl)benzamide. The title compound was prepared in a fashion similar to that for Example 276. MS 492 (M+H)$^+$.

Pharmaceutical Applications of the Compounds of the Invention

The capacity of the novel compounds of the invention to antagonize CCR2 function can be determined using a suitable screen (e.g., high through-put assay). For example, an agent can be tested in an extracellular acidification assay, calcium flux assay, ligand binding assay or chemotaxis assay (see, for example, Hesselgesser et al., J Biol. Chem. 273(25):15687-15692 (1998); WO 00/05265 and WO 98/02151).

In a practical assay, a CCR2 protein which can be isolated or recombinantly derived is used which has at least one property, activity or functional charateristic of a mammalian CCR2 protein. The specific property can be a binding property (to, for example, a ligand or inhibitor), a signalling activity (e.g., activation of a mammalian G protein, induction of rapid and transient increase in the concentration of cytosolic free calcium [$Ca^{++}$]i, cellular response function (e.g., stimulation of chemotaxis or inflammatory mediator release by leukocytes), and the like.

In one embodiment, a composition containing a CCR2 protein or variant thereof is maintained under conditions suitable for binding. The CCR2 receptor is contacted with a compound to be tested, and binding is detected or measured.

In alternate embodiments, the assay is a cell-based assay and cells are used which are stably or transiently transfected with a vector or expression cassette having a nucleic acid sequence which encodes the CCR2 receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation can be detected directly or indirectly. For example, the agent can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The CCR2 antagonist activity of test agents (e.g., the 3,4 disubstituted pyrrolidine compounds of formula I, II or III of the invention) can be reported as the inhibitor concentration required for 50% inhibition ($IC_{50}$ values) of specific binding in receptor binding assays using $^{125}$I-labeled MCP-1, as ligand, and Peripheral Blood Mononuclear Cells (PBMCs) prepared from normal human whole blood via density gradient centrifugation. Specific binding is preferably defined as the total binding (e.g., total cpm on filters) minus the non-specific binding. Non-specific binding is defined as the amount of cpm still detected in the presence of excess unlabeled competitor (e.g., MCP-1).

The human PBMCs described above can be used in a suitable binding assay. For example, 200,000 to 500,000 cells can be incubated with 0.1 to 0.2 nM $^{125}$I-labeled MCP-1, with or without unlabeled competitor (10 nM MCP-1) or various concentrations of compounds to be tested. $^{125}$I-labeled MCP-1, can be prepared by suitable methods or purchased from commercial vendors (Perkin Elmer, Boston Mass.), The binding reactions can be performed in 50 to 250 μl of a binding buffer consisting of 1M HEPES pH 7.2, and 0.1% BSA (bovine serum albumin), for 30 min at room temperature. The binding reactions can be terminated by harvesting the membranes by rapid filtration through glass fiber filters (Perkin Elmer) which can be presoaked in 0.3% polyethyleneimine or Phosphate Buffered Saline (PBS). The filters can be rinsed with approximately 600 μl of binding buffer containing 0.5 M NaCl or PBS, then dried, and the amount of bound radioactivity can be determined by counting on a Gamma Counter (Perkin Elmer).

The capacity of compounds to antagonize CCR2 function can also be determined in a leukocyte chemotaxis assay using suitable cells. Suitable cells include, for example, cell lines, recombinant cells or isolated cells which express CCR2 and undergo CCR2 ligand-induced (e.g., MCP-1) chemotaxis. The assay in use, utilizes human peripheral blood mononuclear cells, in a modified Boyden Chamber (Neuro Probe). 500,000 cells in serum free DMEM media (In Vitrogen) are incubated with or without the inhibitors and warmed to 37° C. The chemotaxis chamber (Neuro Probe) is also prewarmed. 400 ul of warmed 10 nM MCP-1 is added to the bottom chamber in all wells expect the negative control which has DMEM added. An 8 micron membrane filter (Neuro Probe) is place on top and the chamber lid is closed. Cells are then added to the holes in the chamber lid which are associated with the chamber wells below the filter membrane. The whole chamber is incubated at 37° C., 5% CO2 for 30 minutes. The cells are then aspirated off, the chanber lid opened, and the filter gently removed. The top of the filter is washed 3 times with PBS and the bottom is left untouched. The filter is air dried and stained with Wright Geimsa stain (Sigma). Filters are counted by microscopy. The negative control wells serve as background and are subtracted from all values. Antagonist potency can be determined by comparing the number of cell that migrate to the bottom chamber in wells which contain antagonist, to the number of cells which migrate to the bottom chamber in MCP-1 control wells.

When the binding assay protocol is used, the compounds of the present invention have IC50 in the range of about 0.01 to about 500 (nM). In chemotaxis assays the compounds of the invention have IC50's in the range of about 1 to about 3000 (nM).

The compounds of the invention are administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is a mammal, male or female, in whom modulation of chemokine receptor activity is desired. The term modulation is intended to encompass antagonism, agonism, partial antagonism and/or partial agonism.

In the present specification, the term therapeutically effective amount means the amount of the subject compound that will elicit the biological or medical response of a tissue, system, animal or human that is being sought by the researcher, veterinarian, medical doctor or other clinician.

The compounds of the invention are administered in therapeutic effective amounts to treat a disease for example such as rheumatoid arthritis. A therapeutically effective amount of a compound is that amount which results in the inhibition of one or more of the processes mediated by the binding of a chemokine to a receptor such as CCR2 in a subject with a disease associated with aberrant leukocyte recruitment and/or activation. Typical examples of such processes include leukocyte migration, integrin activation, transient increases in the concentration of intracellular free calcium $[Ca^{2+}]i$ and granule release of proinflammatory mediators. Alternatively, a therapeutically effective amount of a compound is the quantity required to achieve a desired therapeutic and/or prophylactic effect, such as an amount which results in the prevention of or a decrease in the symptoms associated with a disease associated with aberrant leukocyte recruitment and/or activation.

Additional diseases or conditions of human or other species which can be treated with the inhibitors or modulators of chemokine receptor function of the invention, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, restenosis, certain hematologic malignancies, cytokine-induced toxicity (e.g., septic shock, endotoxic shock), polymyositis, dermatomyositis.

The compounds represented in Formula I, II and III of the invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the metabolic stability, rate of excretion, drug combination, and length of action of that compound the species, age, sex, health, medical condition, and weight of the recipient; the nature and extent of the symptoms; the kind of concurrent treatment; the frequency of treatment; the specific route of administration, the renal and hepatic function of the patient, and the desired effect. A physician or veterinarian can determine and prescribe the effective amount of the drug required to prevent, counter, or arrest the progress of the specific disorder for which treatment is necessary.

Generally, the daily oral dosage of each active ingredient, when used for the indicated effects, will range between about 0.0001 to 1000 mg/kg of body weight, preferably between about 0.001 to 100 mg/kg of body weight per day, and most preferably between about 0.1 to 20 mg/kg/day. For intravenous use, the most preferred doses will range from about 0.1 to about 10 mg/kg/minute during a constant rate infusion. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The compounds of the instant invention can also be administered in intranasal form via topical use of suitable intranasal vehicles, or via transdermal routes, using transdermal skin patches. When administered in the form of a transdermal delivery system, the dosage administration-will, of course, be continuous rather than intermittent throughout the dosage regimen.

The compounds of the invention are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water, and the like. Additionally, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be provided to a patient in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or poly-ethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, and crosslinked or amphipathic block copolymers of hydrogels.

Dosage forms for the compounds of the invention suitable for administration may contain from about 0.1 milligram to about 100 milligrams of active ingredient per dosage unit. In these pharmaceutical compositions the active ingredient will ordinarily be present in an amount of about 0.5-95% by weight based on the total weight of the composition.

Gelatin capsules can also be used as dosage forms and may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

When using liquid dosage forms for oral administration they can contain coloring and flavoring to increase patient acceptance.

Generally, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in the field of pharmacology.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical compositions and methods of the present invention may further comprise other therapeutically active compounds which are usually applied in the treatment of the above mentioned pathological conditions.

Representative useful pharmaceutical dosage-forms for administration of the compounds of this invention can be illustrated as follows:

Capsules

A large number of unit capsules can be prepared by filling standard two-piece hard gelatin capsules each with 50 milligrams of powdered active ingredient, 100 milligrams of lactose, 25 milligrams of cellulose, and 3 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 75 milligrams of the active ingredient. The capsules should be washed and dried.

Tablets

Tablets may be prepared by conventional procedures so that the dosage unit is 75 milligrams of active ingredient, 0.15 milligrams of colloidal silicon dioxide, 4 milligrams of magnesium stearate, 250 milligrams of microcrystalline cellulose, 9 milligrams of starch and 75 milligrams of lactose. Appropriate coatings well known to one skilled in the art may be applied to increase palatability or delay absorption.

Injectable

A parenteral composition suitable for administration by injection may be prepared by stirring 1.0% by weight of active ingredient in 8% by volume propylene glycol and water. The solution should be made isotonic with sodium chloride and sterilized.

Suspension

An aqueous suspension can be prepared for oral administration so that each 5 mL contain 75 mg of finely divided active ingredient, 150 mg of sodium carboxymethyl cellulose, 3.75 mg of sodium benzoate, 0.75 g of sorbitol solution, U.S.P., and 0.015 mL of vanillin.

Example 373

This example describes a procedure to evaluate the efficacy of CCR2 antagonists for treatment of rheumatoid arthritis.

An animal model of rheumatoid arthritis can be induced in rodents by injecting them with type II collagen in selected adjuvants. Three series of rodent groups consisting 15 genetically-susceptible mice or rats per group are injected subcutaneously or intra-dermally with type II collagen emulsified in Complete Freund's Adjuvant at days 0 and 21. One series of rodents additionally receives phosphate buffered saline (PBS) and Tween 0.5% i.p. at the initial sensitization, and at different dosing schedules thereafter. A second series consists of groups of rodents receiving different doses of the CCR2 antagonist(s) given either intra-peritoneally, intravenously, sub-cutaneously, intramuscularly, orally, or via any other mode of administration at the initial sensitization, and at different dosing schedules thereafter. A third series of rodents, serving as positive control, consists of groups treated with either mouse IL-10 i.p., or anti-TNF antibodies i.p. at the initial sensitization, and at different dosing schedules thereafter.

Animals are monitored from weeks 3 til 8 for the development of swollen joints or paws, and graded on a standard disease severity scale. Disease severity is confirmed by histological analysis of joints.

All publications, patents, and patent applications including all cited art and bibliographic references cited herein are hereby incorporated by reference in their entirety for all purposes.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes many equivalents may be made without departing from the spirit or scope of the claimed invention.

What is claimed is:

1. A compound which is N-(2-{[(3R)-1-(4-hydroxy-4-pyrimidin-4-ylcyclohexyl)pyrrolidin-3-yl]amino}-2-oxoethyl)-3-(trifluoromethyl)benzamide, a racemic mixture thereof, or a pharmaceutically acceptable salt thereof.

2. A compound which is N-(2-{[(3R)-1-(4-hydroxy-4-pyrimidin-4-ylcyclohexyl)pyrrolidin-3-yl]amino}-2-oxoethyl)-3-(trifluoromethyl)benzamide, or a pharmaceutically acceptable salt thereof.

3. A composition comprising a compound of claim 1, a racemic mixture thereof, or a pharmaceutically acceptable salt thereof, and a pharmaceutically acceptable carrier.

4. A method of treating multiple sclerosis in a patient, comprising administering to said patient a therapeutically effective amount of a compound of claim 1, a racemic mixture thereof, or a pharmaceutically acceptable salt thereof.

* * * * *